US011326161B2

(12) United States Patent
Church et al.

(10) Patent No.: US 11,326,161 B2
(45) Date of Patent: May 10, 2022

(54) METHODS AND SYSTEMS OF MOLECULAR RECORDING BY CRISPR-CAS SYSTEM

(71) Applicant: President and Fellows of Harvard College, Cambridge, MA (US)

(72) Inventors: George M. Church, Brookline, MA (US); Seth Lawler Shipman, Boston, MA (US); Jeffrey D. Macklis, Brookline, MA (US); Jeffrey Matthew Nivala, Allston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 89 days.

(21) Appl. No.: 15/999,616

(22) PCT Filed: Feb. 16, 2017

(86) PCT No.: PCT/US2017/018071
§ 371 (c)(1),
(2) Date: Aug. 20, 2018

(87) PCT Pub. No.: WO2017/142999
PCT Pub. Date: Aug. 24, 2017

(65) Prior Publication Data
US 2021/0230588 A1    Jul. 29, 2021

Related U.S. Application Data

(60) Provisional application No. 62/395,738, filed on Sep. 16, 2016, provisional application No. 62/296,812, filed on Feb. 18, 2016.

(51) Int. Cl.
*C12N 15/113* (2010.01)
*C12N 9/22* (2006.01)
*G06N 3/12* (2006.01)

(52) U.S. Cl.
CPC .............. *C12N 15/113* (2013.01); *C12N 9/22* (2013.01); *G06N 3/123* (2013.01); *C12N 2310/122* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2009/0029477 A1 | 1/2009 | Meller et al. | |
| 2015/0133315 A1 | 5/2015 | Jacobson et al. | |
| 2017/0360048 A1* | 12/2017 | Nunez ............... | C12N 15/79 |
| 2019/0055543 A1* | 2/2019 | Tran ............... | A01K 67/0275 |

FOREIGN PATENT DOCUMENTS

| | | | |
|---|---|---|---|
| CN | 104080462 A | 10/2014 | |
| CN | 104520429 A | 4/2015 | |
| CN | 104995302 A | 10/2015 | |
| WO | WO-2016205728 A1 * | 12/2016 | ........... C12N 15/102 |

OTHER PUBLICATIONS

Heidi Ledford Nature News 10.1038, pp. 1-3, 2017, 22288 (Year: 2017).*
Yosef et al. Nucleic Acids Research 40, 5569-5576 (Year: 2012).*
Vorontsova et al. Nucleic Acids Research 43, 10848-10860 (Year: 2015).*
Arslan et al. Nucleic Acids Research vol. 42, 7884-789 (Year: 2014).*
Arslan et al. Nucleic Acids Research vol. 42, supplementary data, pp. 1-14 (Year: 2014).*
Diez-Villasenor et al. "CRISPR-spacer integration reporter plasmids reveal distinct genuine acquisition specificities among CRISPR-Cas 1-E variants of *Escherichia coli*." RNA Biol May 2013 vol. 10 No. 5 pp. 792-802. Especially p. 793 col. 2 para 2, p. 794, fig 1, p. 795 fig 2, p. 796 col. 1 para 3, p. 798 col. 1 para 1.
Fernandez-Rodriguez et al. "Memory and Combinatorial Logic Based on DNA Inversions: Dynamics and Evolutionary Stability." ACS Synth Biol Dec. 18, 2015 vol. 4 No. 12 pp. 1361-1372. Especially abstract, p. 1362 col. 2 para 3, p. 1363 fig 1A.
Kleinstiver et al. "Engineered CRISPR-Cas9 nucleases with altered PAM specificities." Nature Jul. 23, 2015 pp. 481-485. Especially abstract, p. 481 col. 2 para 2.
Nunez et al. "Cas1-Cas2 complex formation mediates spacer acquisition during CRISPR-Cas adaptive immunity." Nat Struc Mol Biol Jun. 2014 vol. 21 No. 6 pp. 528-534. Especially p. 529 col. 1 para 1.
Shipman et al. "Molecular recordings by directed CRISPR spacer acquisition." Science Epub Jun. 9, 2016 vol. 353 No. 6298 p. 463 and online doi: 10.1126/science.aaf1175 pp. aaf1175-1 to aaf1175-10. Especially entire article.
Farzadfard, Fahim et al., "Genomically encoded analong memory with precise in vivo DNA writing in living cell populations", Science, vol. 346, No. 6211, Nov. 14, 2014 (Nov. 14, 2014), pp. 825, 1256272-1 to 1256272-8.
Shipman, Seth L. et al., "CRISPR-Cas encoding of a digital movie into the genomes of a population of living bacteria", Nature, vol. 547, No. 7663, Jul. 12, 2017 (Jul. 12, 2017), pp. 345-349.
Silas, Sukrit et al., "Direct CRISPR spacer acquisition from RNA by a natural reverse transcriptase-Cas1 fusion protein" Science (New York, N.Y.) Feb. 26, 2016, vol. 351, No. 6276, pp. 932, aad4234-1 to aad4234-12.

(Continued)

*Primary Examiner* — Brian Whiteman
(74) *Attorney, Agent, or Firm* — Banner & Witcoff, Ltd.

(57) ABSTRACT

This invention provides methods of altering a cell including providing the cell with a nucleic acid sequence encoding a Cas1 protein and/or a Cas2 protein of a CRISPR adaptation system, providing the cell with a CRISPR array nucleic acid sequence including a leader sequence and at least one repeat sequence, wherein the cell expresses the Cas1 protein and/or the Cas2 protein and wherein the CRISPR array nucleic acid sequence is within genomic DNA of the cell or on a plasmid. Also provided are methods and systems for nucleic acid storage and in vivo molecular recordings of events into a cell.

24 Claims, 108 Drawing Sheets
Specification includes a Sequence Listing.

(56) References Cited

OTHER PUBLICATIONS

Perli, Samuel D. et al., "Continuous genetic recording with self-targeting CRISPR-Cas in human cells", Science, vol. 353, No. 6304, Aug. 18, 2016 (Aug. 18, 2016), pp. aag0511-1 toaag0511-10.
Shipman, Seth L. et al., "Supplementary Material for: Molecular recordings by directed CRISPR spacer acquisition", vol. 353, No. 6298, Jun. 9, 2016 (Jun. 9, 2016), pp. 1-16.

* cited by examiner

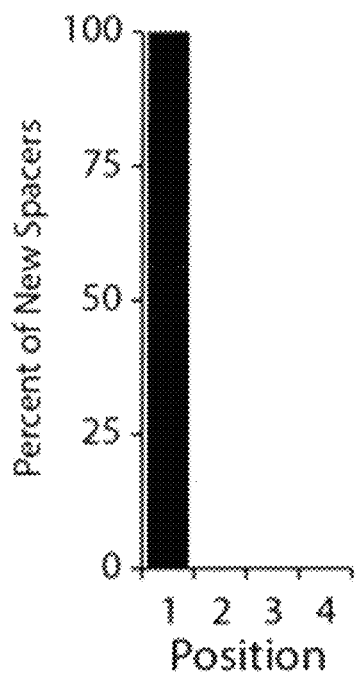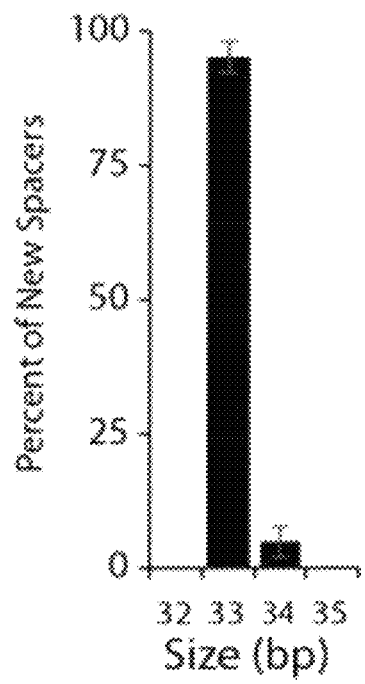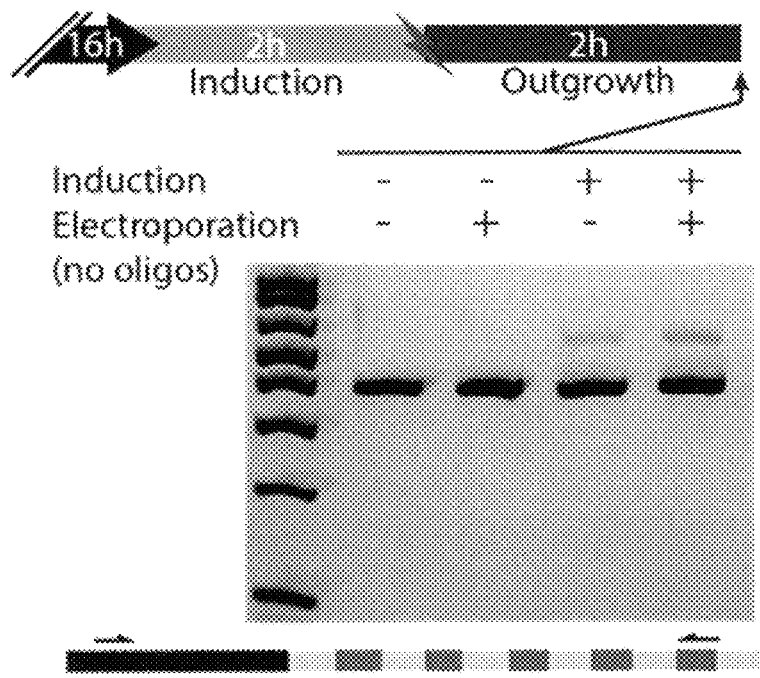

FIG. 2D  DNA/RNA
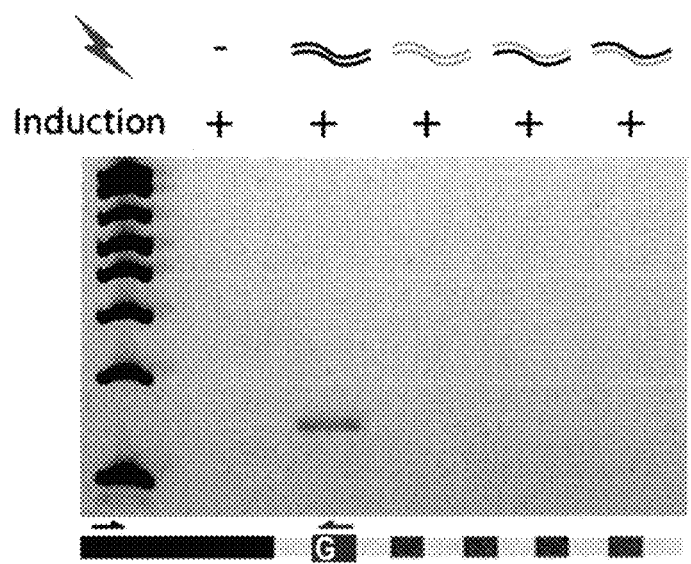
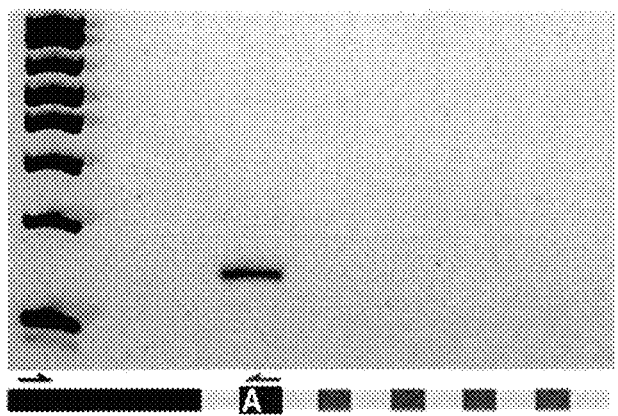

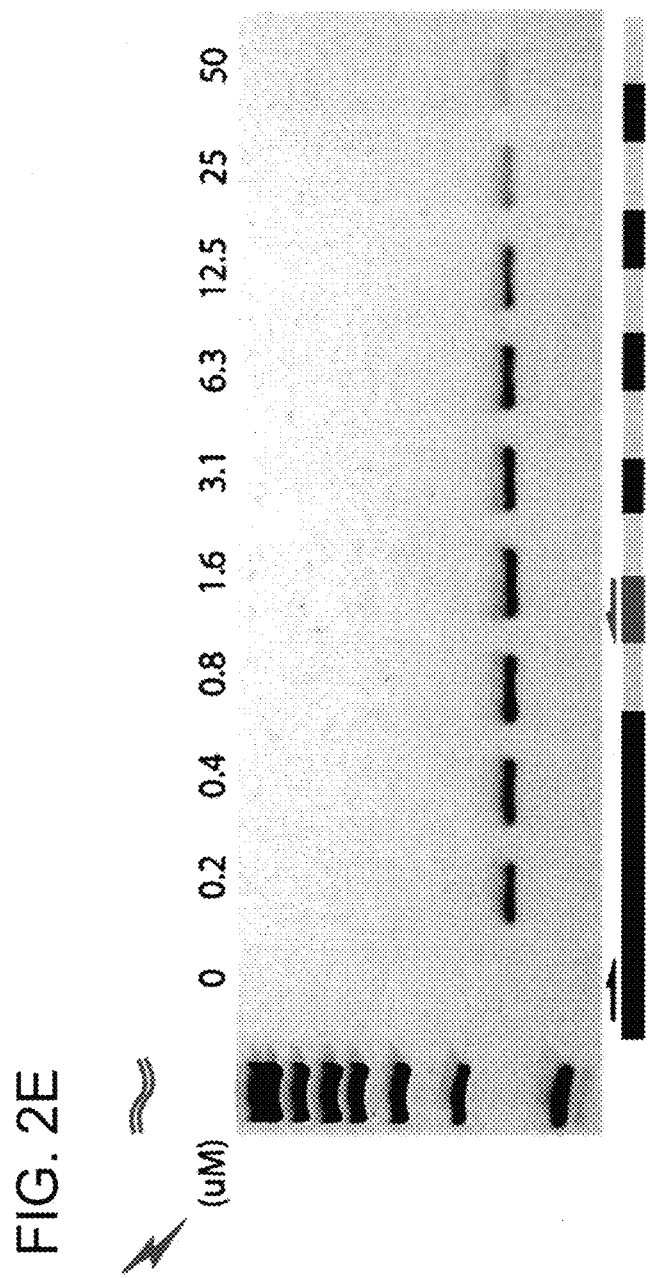

FIG. 3A
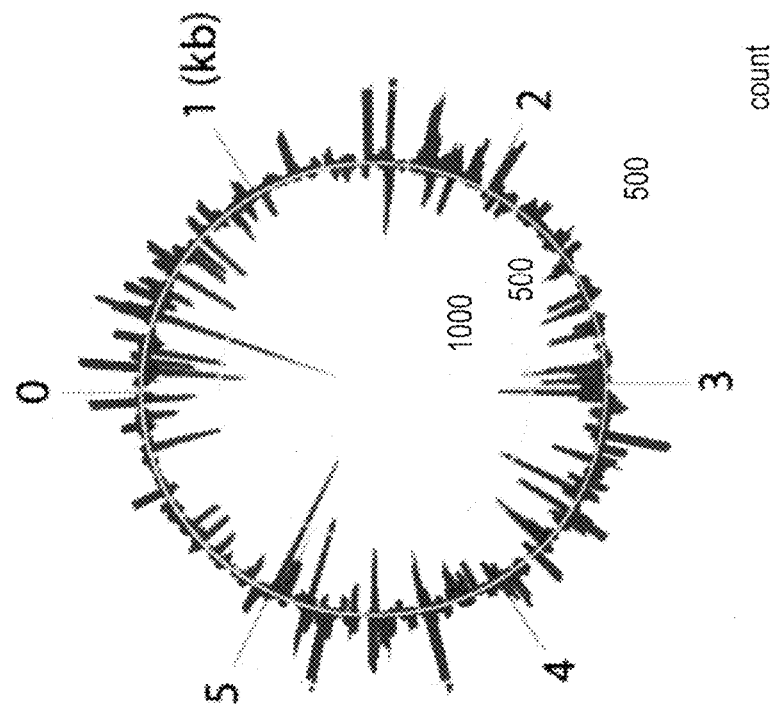
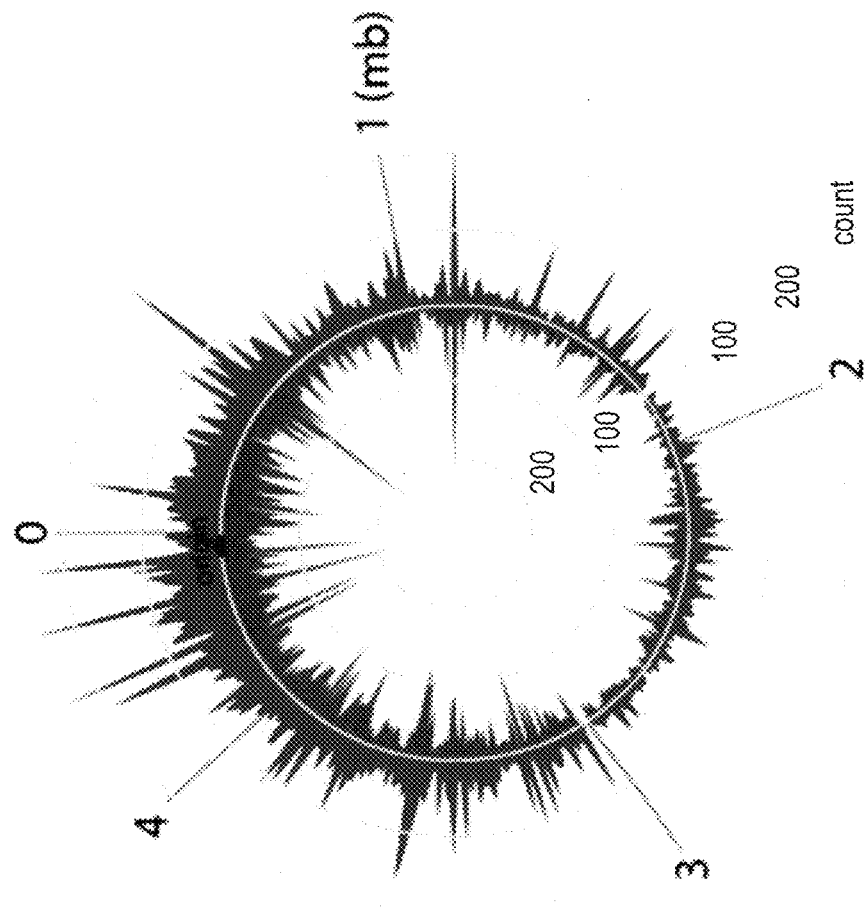

FIG. 4E psH
CTCCCGCCTGTAGAAGTCACCATTGTTGTCACCACGACATCATTCCGTCGCGTTATCCAGCT
CAGCGCCACATCTTCAGTGGTAACAACACGTGCTGCTGTAGTAAGGCACCGCAATAGGTCCA psM
CCACACTTCCCGGTAACCCAGAAACCACGTATCCCGTAAACCGCAGGTCCAGCAACAGG
GGTTGCAAGGGCCATTCCCCTCTTTCCCCATAGCCATTTGTCCAGCCCACCCTTGTCCC psL
AAATGGACTCCTTAACATTCTTGTACCACGGTATTACAATTCAAGCCTCATCAGCCCTGAAC
TTTACCTGAGGAATTGTAAGAACATGCTGCCATAATCTTAAGTTCGACTAGTCGGGACTTC psL/H
CTCCCGCCTGTAGAACATTCTTGTACCACGGTATTACAATTCAAGCCTGTGCGTTATCCAGCT
CAGCGCCGGACATCTTCTTAAGAACATGCTGCCATAATCTTAAGTTCGACACGCAATAGGTCCA psH/L
AAATGGACTCCTTAAGTCACCATTGTTGTCACCACGACATCATTCCGATCAGCCCTGAAC
TTTACCTGAGGAATTCAGTGGTAACAACAGTGCTGCTGTAGTAAGGCTAGTCGGGACTTC

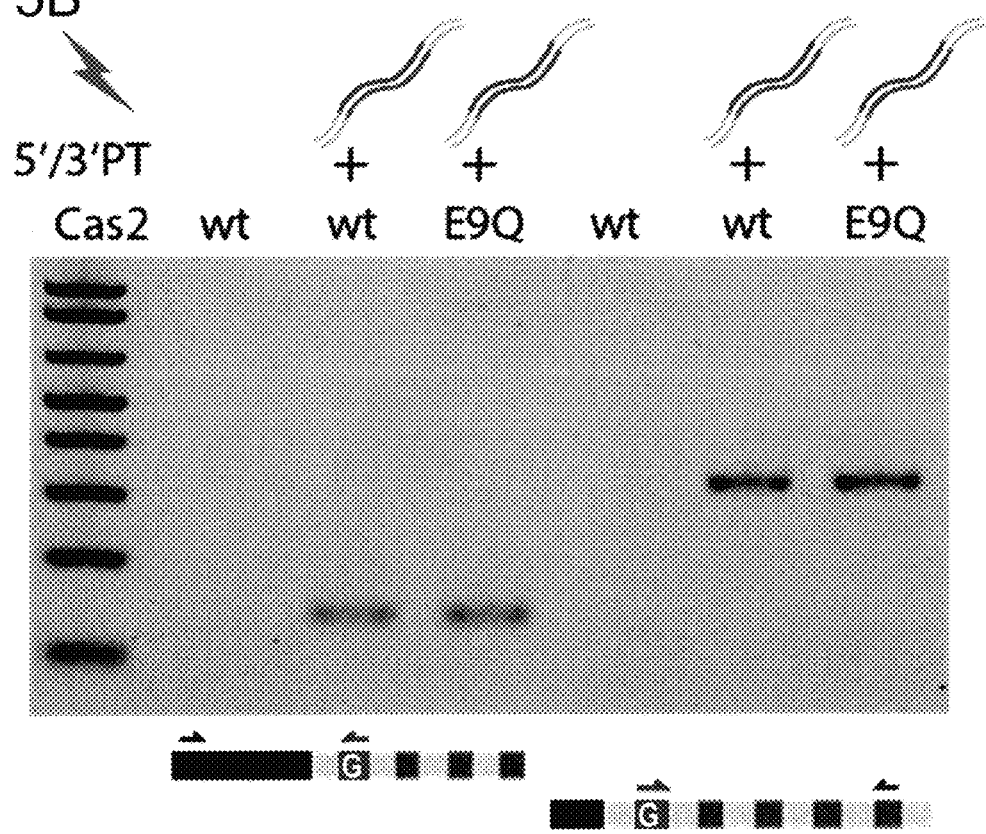

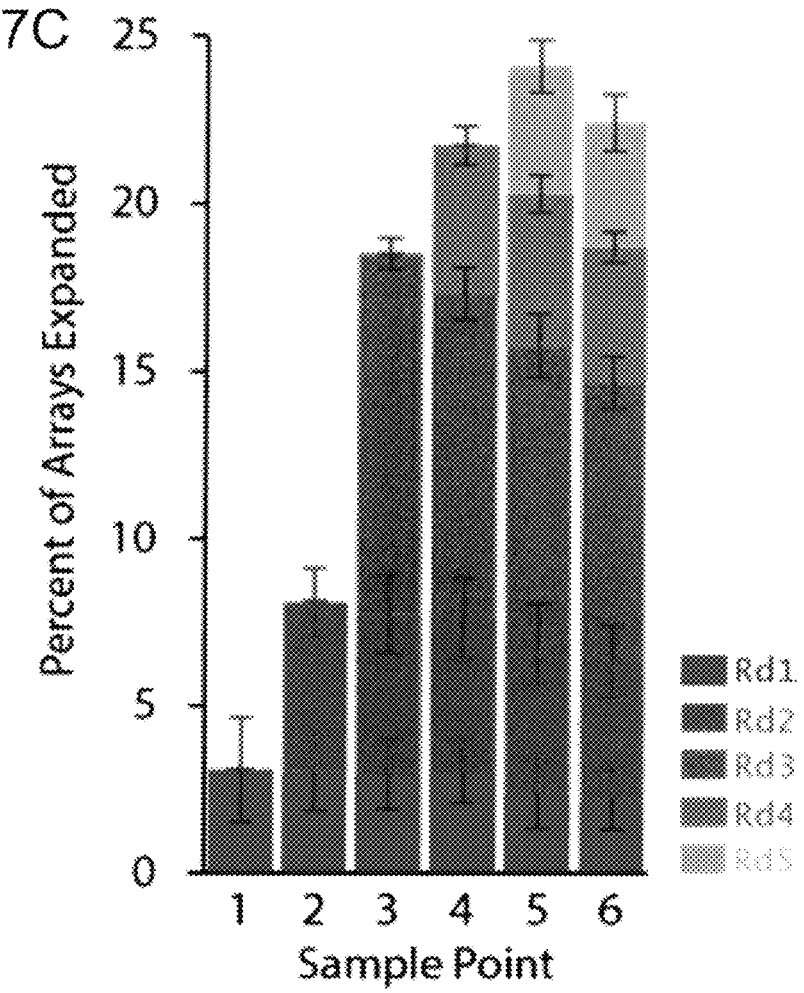
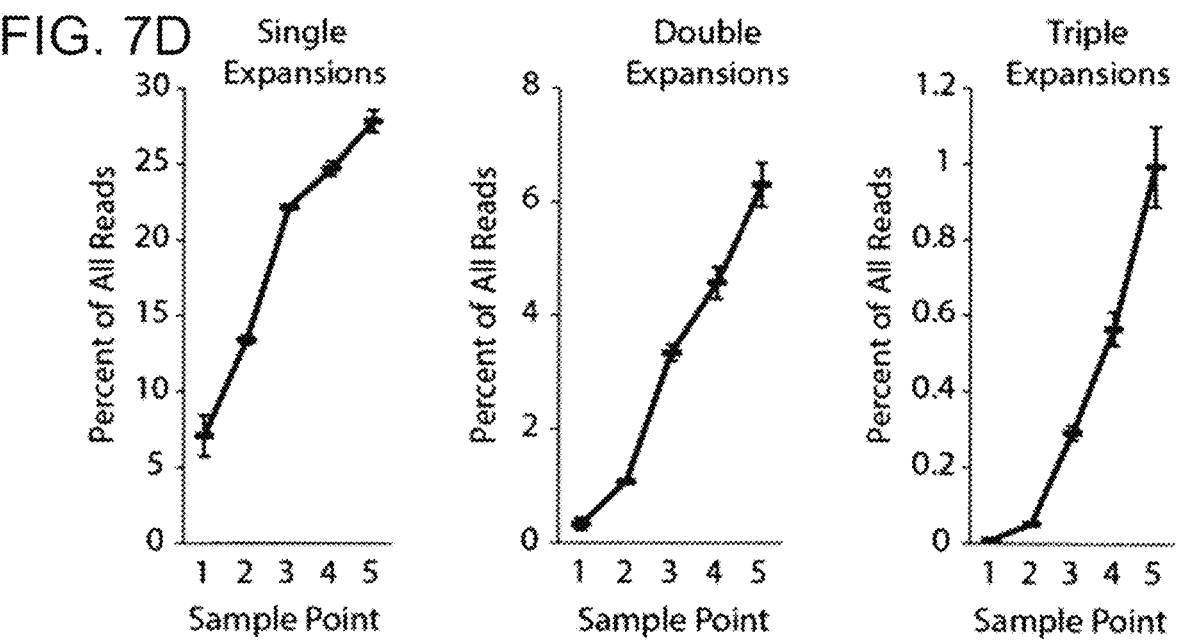

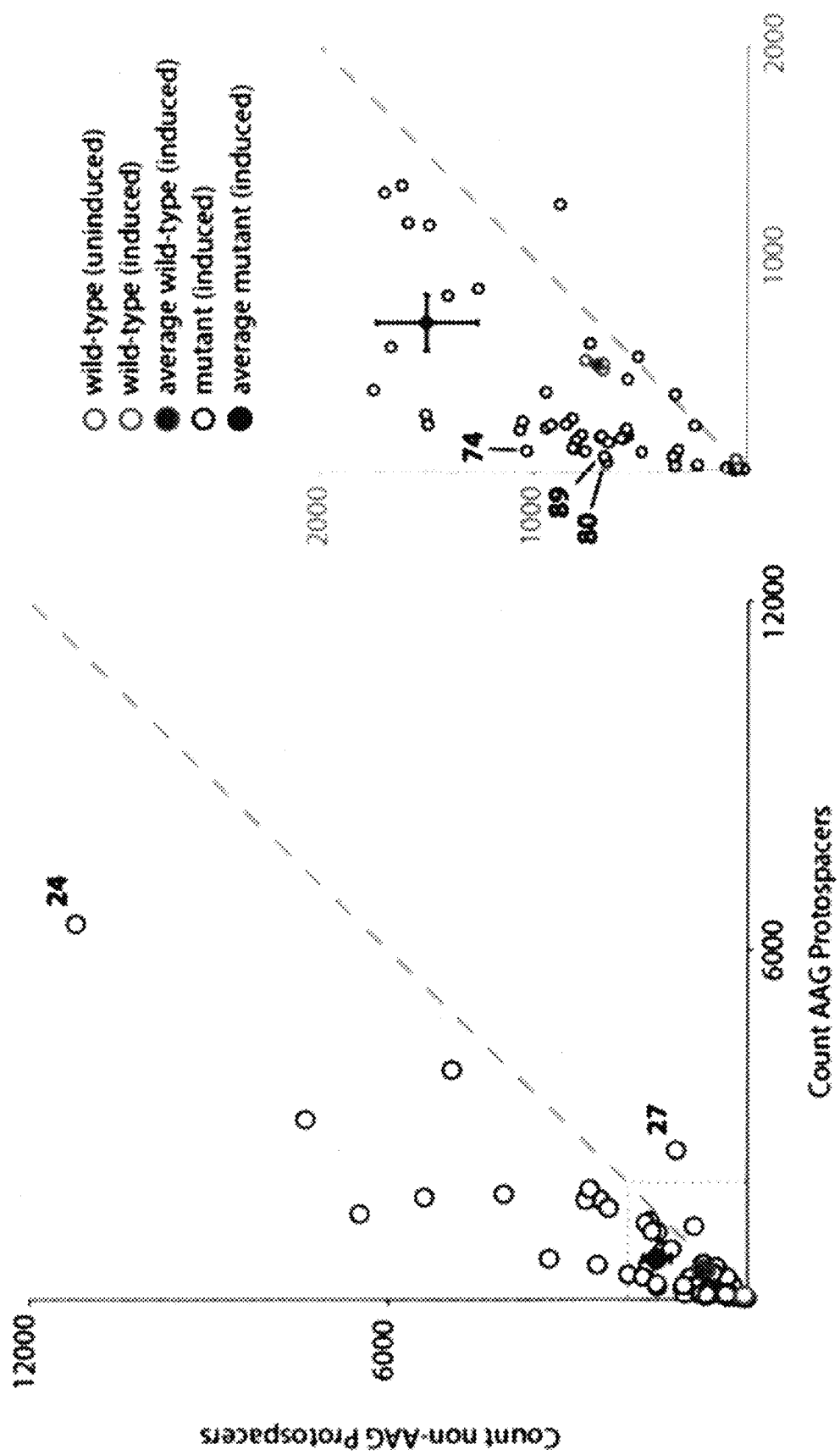

FIG. 8E
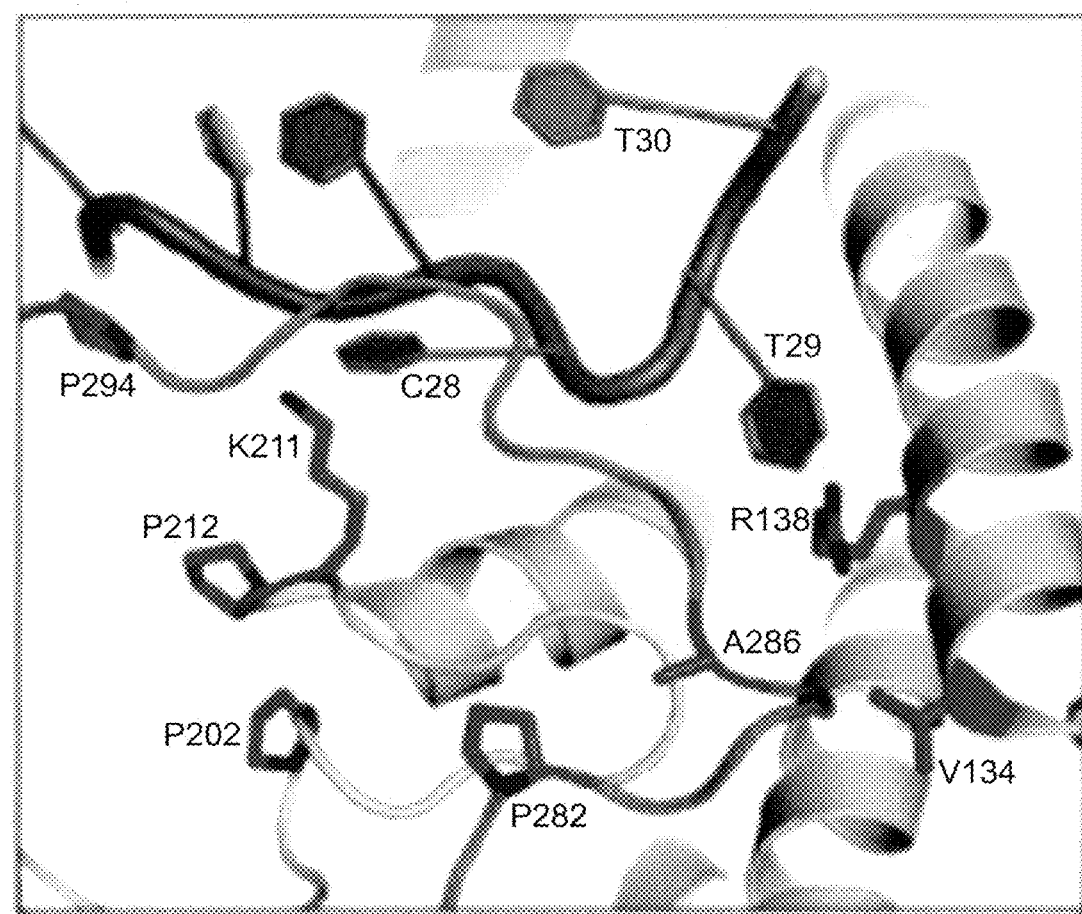
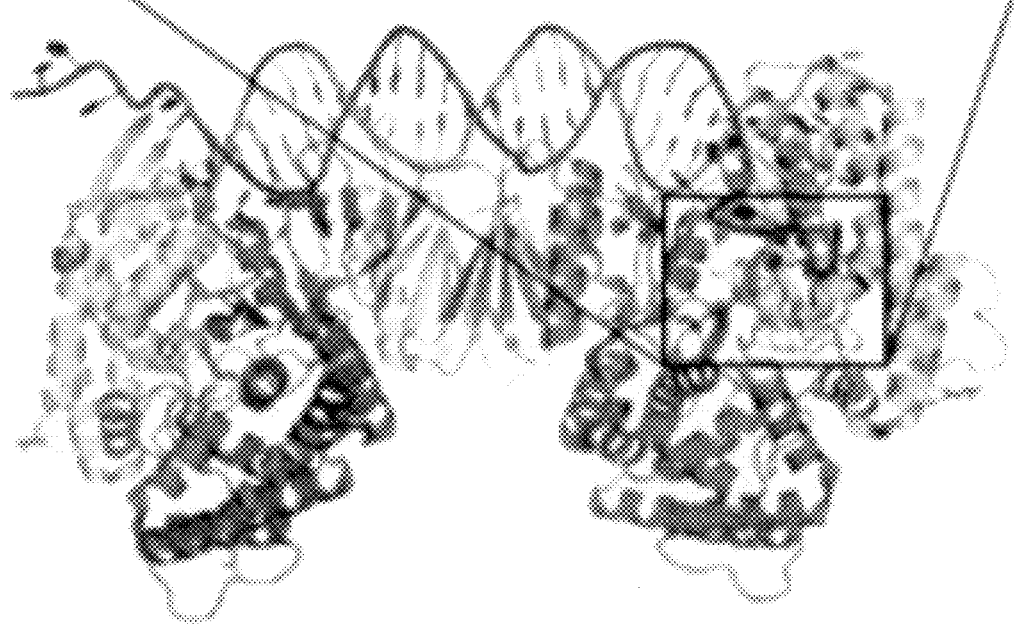

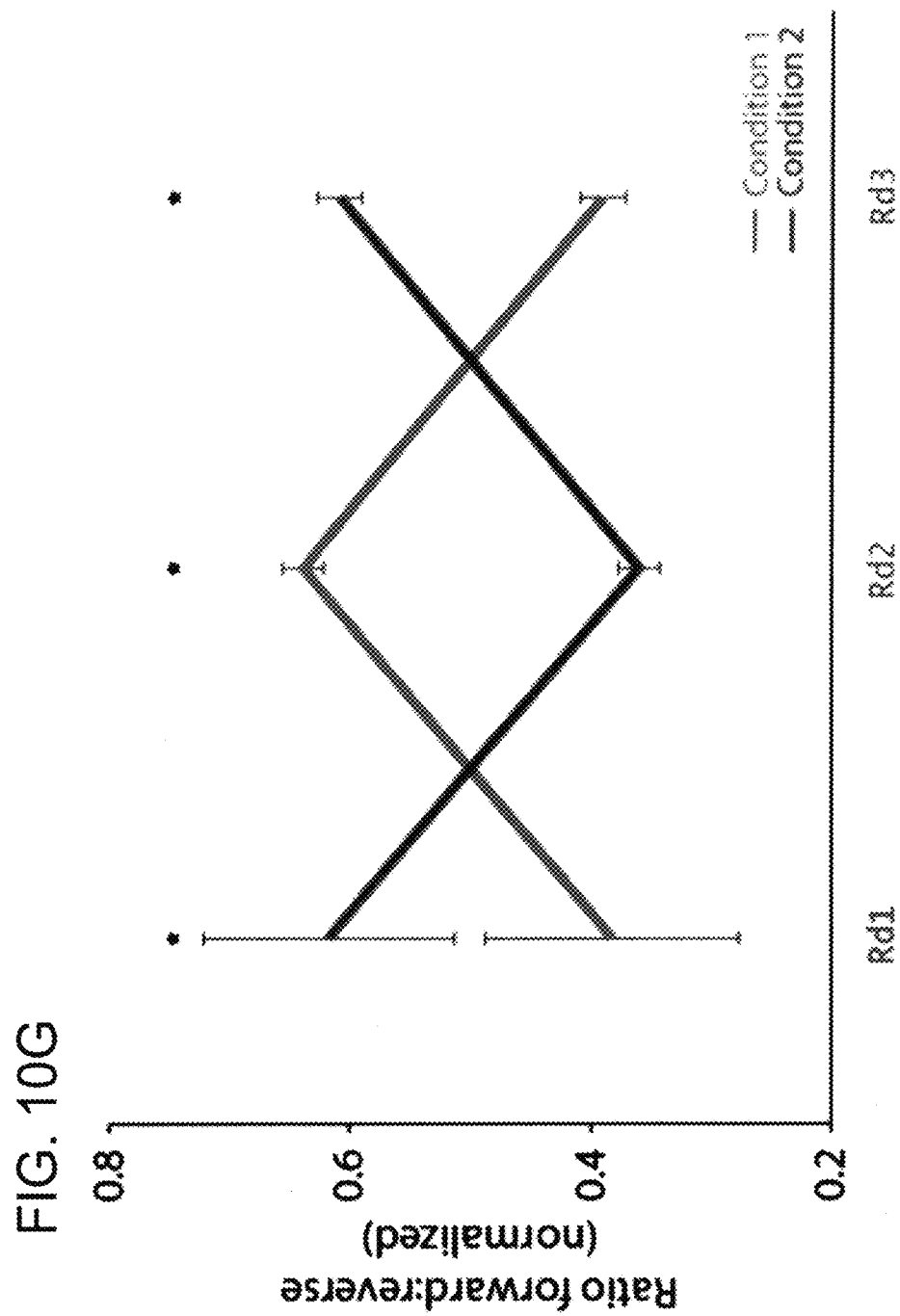

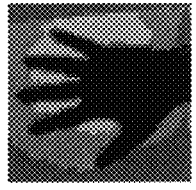
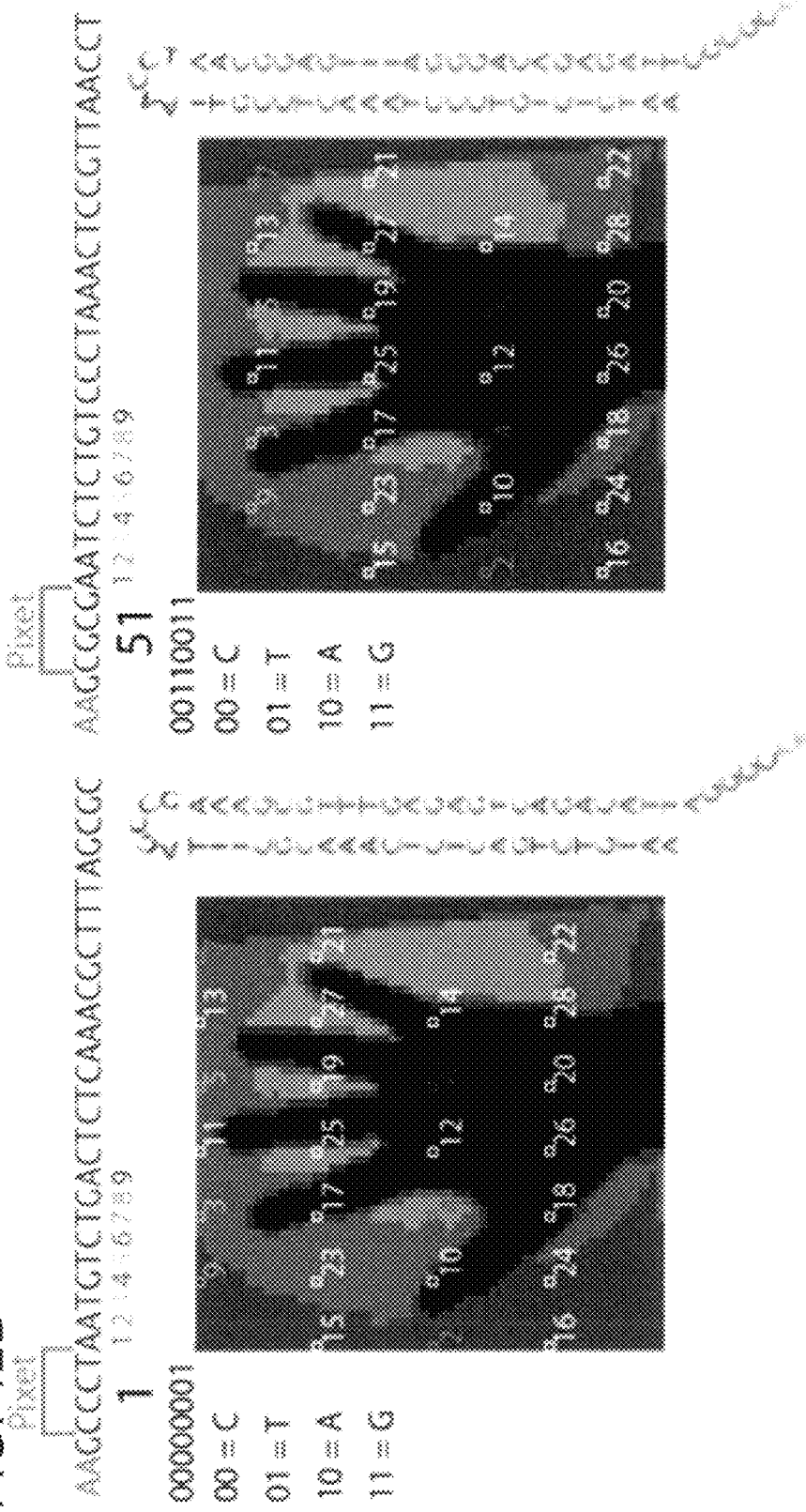
FIG. 12B  FIG. 12C
FIG. 12D

FIG. 12G
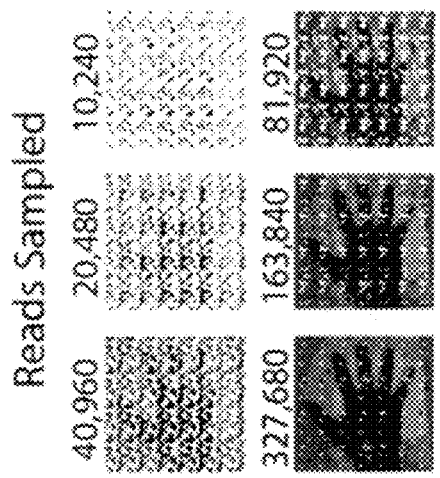
FIG. 12H
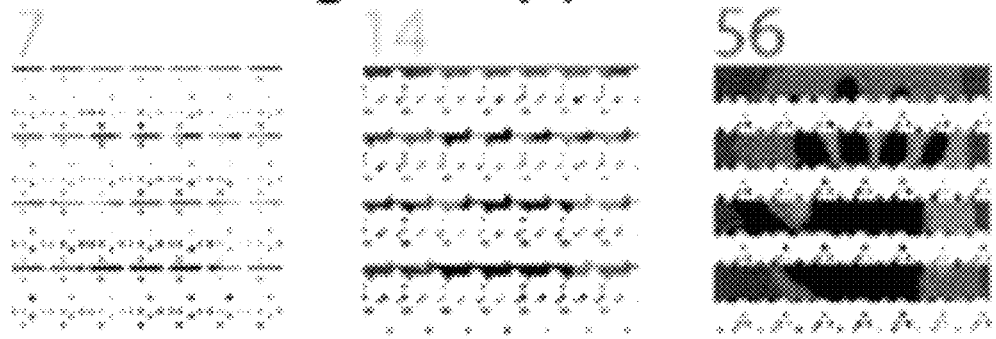
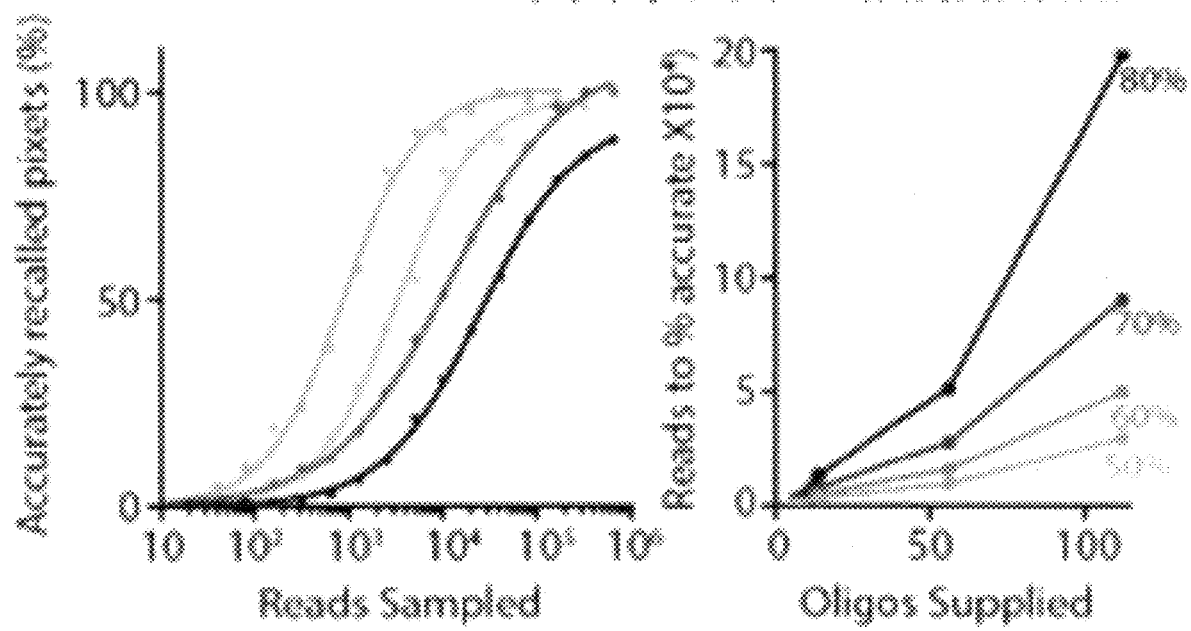

No PAM
CCCCAATTTACTACTCGTTCTGGTGTTTCTCGT
GGGGTTAAATGATGAGCAAGACCACAAAGAGCA

Full PAM
AAGCCCAATTTACTACTCGTTCTGGTGTTTCTCGT
TTCGGGTTAAATGATGAGCAAGACCACAAAGAGCA Top PAM
AAGCCCAATTTACTACTCGTTCTGGTGTTTCTCGT
GGGGTTAAATGATGAGCAAGACCACAAAGAGCA Bottom PAM
CCCCAATTTACTACTCGTTCTGGTGTTTCTCGT
TTCGGGTTAAATGATGAGCAAGACCACAAAGAGCA

|  | 2nd Base | | | | |
|---|---|---|---|---|---|
| 1st Base | T | C | A | G | 3rd Base |
| T | 1 | 2 | 3 | 4 | T |
|  | 5 | 6 | 7 | 8 | C |
|  | 9 | 10 | 11 | 12 | A |
|  | 13 | 14 | 15 | 16 | G |
| C | 17 | 18 | 19 | 20 | T |
|  | 21 | 1 | 2 | 3 | C |
|  | 4 | 5 | 6 | 7 | A |
|  | 8 | 9 | 10 | 11 | G |
| A | 12 | 13 | 14 | 15 | T |
|  | 16 | 17 | 18 | 19 | C |
|  | 20 | 21 | 1 | 2 | A |
|  | 3 | 4 | | 5 | G |
| G | 6 | 7 | 8 | 9 | T |
|  | 10 | 11 | 12 | 13 | C |
|  | 14 | 15 | 16 | 17 | A |
|  | 18 | 19 | 20 | 21 | G |

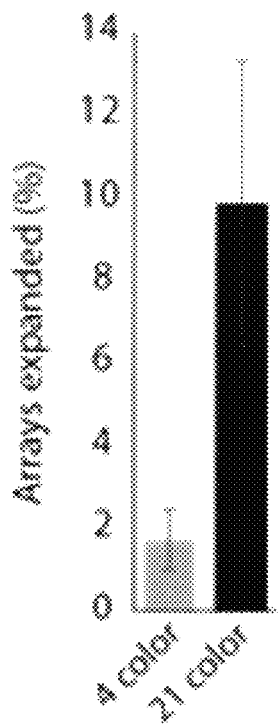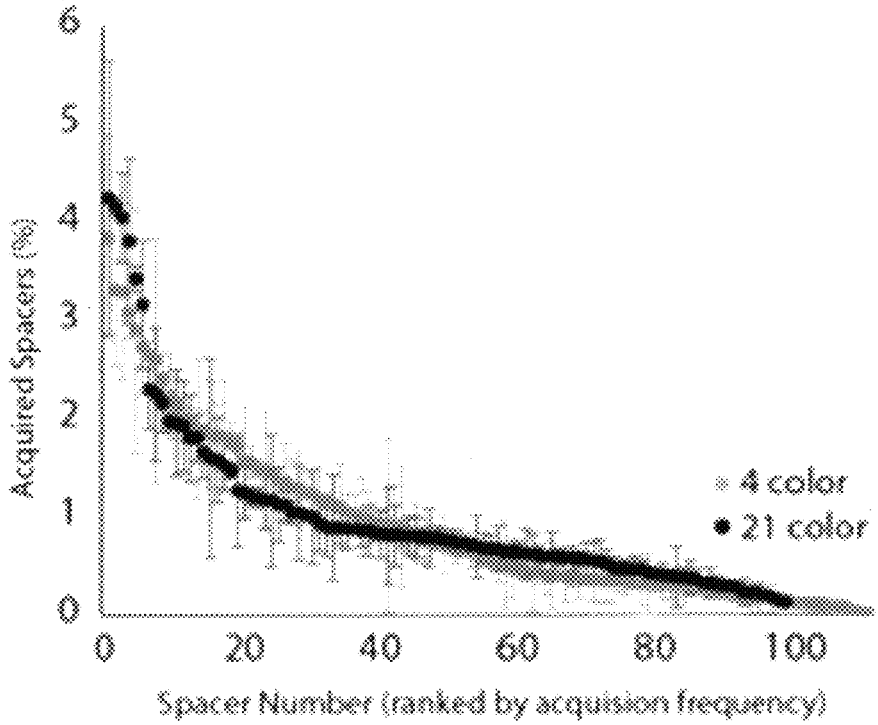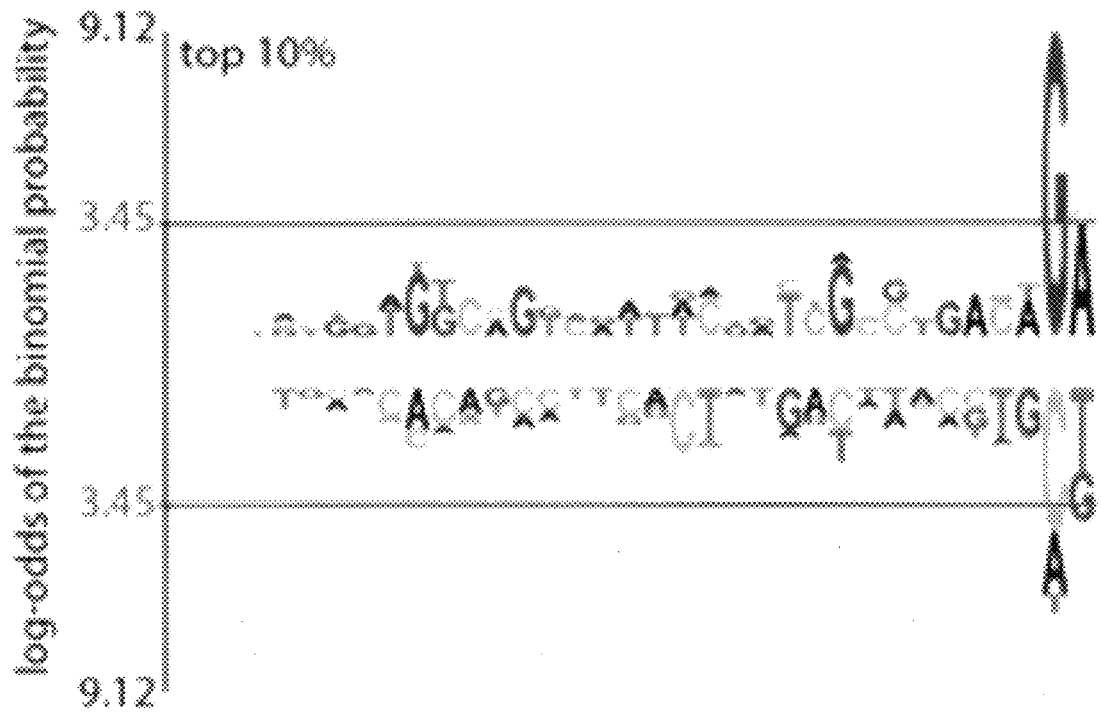

FIG. 14K seq<sup>target</sup>
AAGTATTGTGTCAGCCGTGTACCGTTATCGCTGTGA
TTCATAACACAGTCGCACATGGCAATAGCGACACT seq<sup>target</sup>-CCT
AAGTATTGTGTCAGCCGTGTACCGTTATCGCTGCCT
TTCATAACACAGTCGCACATGGCAATAGCGACGGA seq<sup>under</sup>
AAGCCGAAATATCAATTCCTAAACCCCATATCCCT
TTCGGCTTTATAGTTAAGGATTTGGGGTATAGGGA seq<sup>under</sup>-TGA
AAGCCGAAATATCAATTCCTAAACCCCATATCTGA
TTCGGCTTTATAGTTAAGGATTTGGGGTATAGACT

FIG. 15A seq^over:
AAGTATTGTGTCAGCGTGTACCGTTATCGCTGTGA
TTCATAACACAGTCGCACATGGCAATAGCGACACT seq^over (CCT):
AAGTATTGTGTCAGCGTGTACCGTTATCGCTGCCT
TTCATAACACAGTCGCACATGGCAATAGCGACGGA seq^under:
AAGCCGAAATATCAATTCCTAAACCCCATATCCCT
TTCGGCTTTATAGTTAAGGATTTGGGGTATAGGGA seq^under (TGA):
AAGCCGAAATATCAATTCCTAAACCCCATATCTGA
TTCGGCTTTATAGTTAAGGATTTGGGGTATAGACT

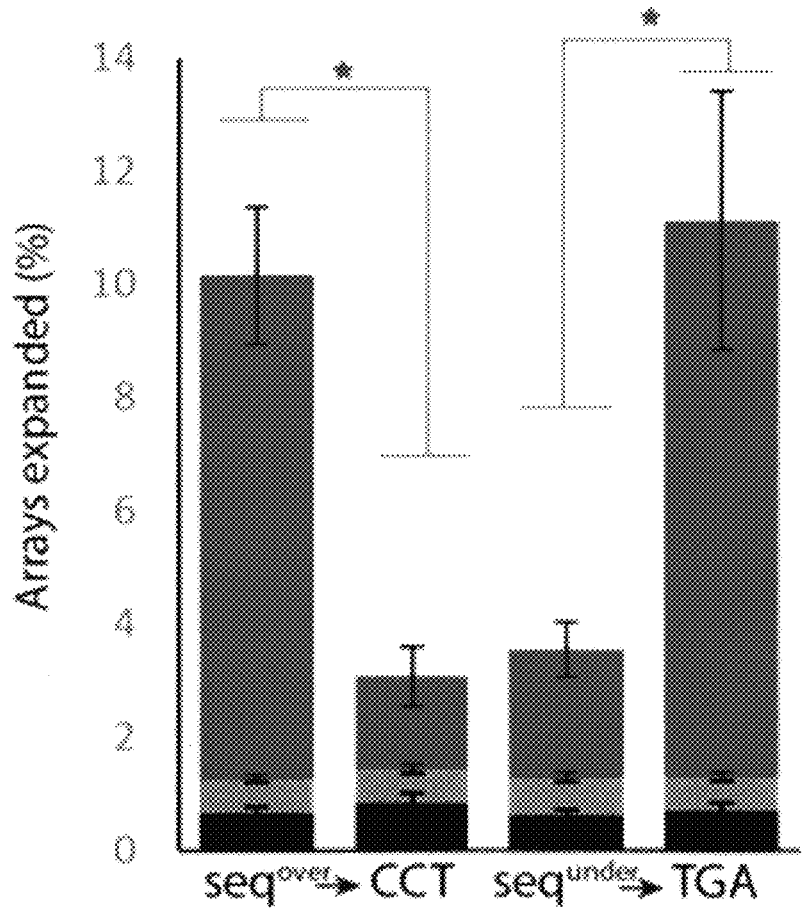

FIG. 15B

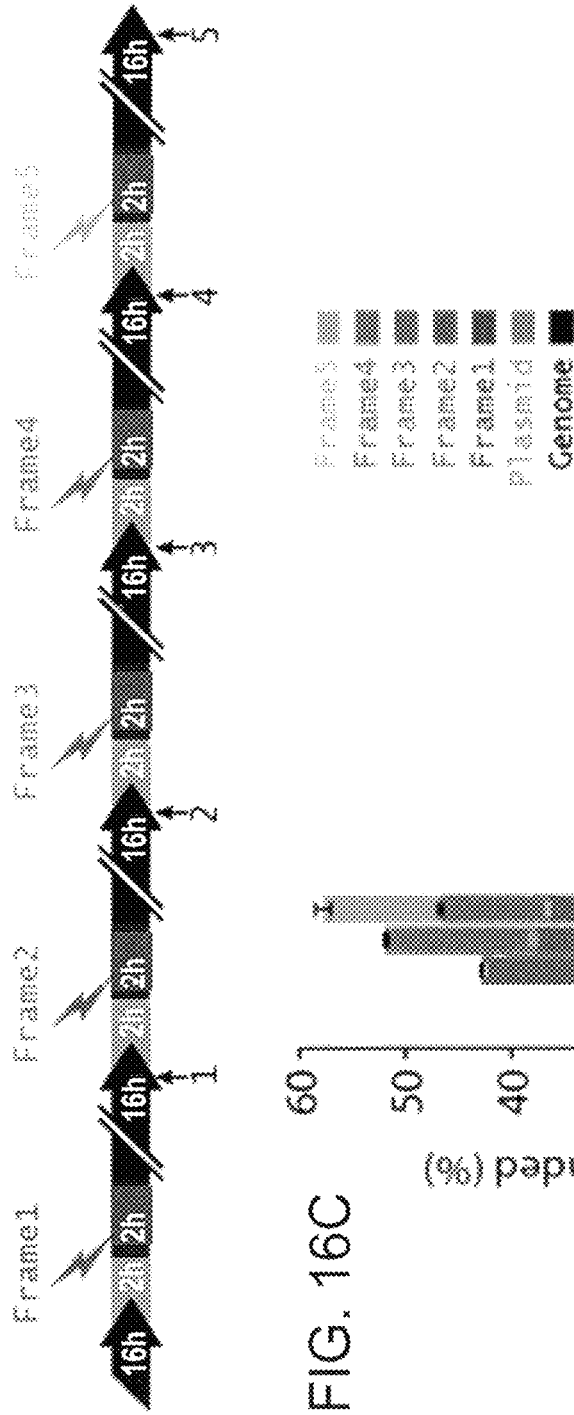
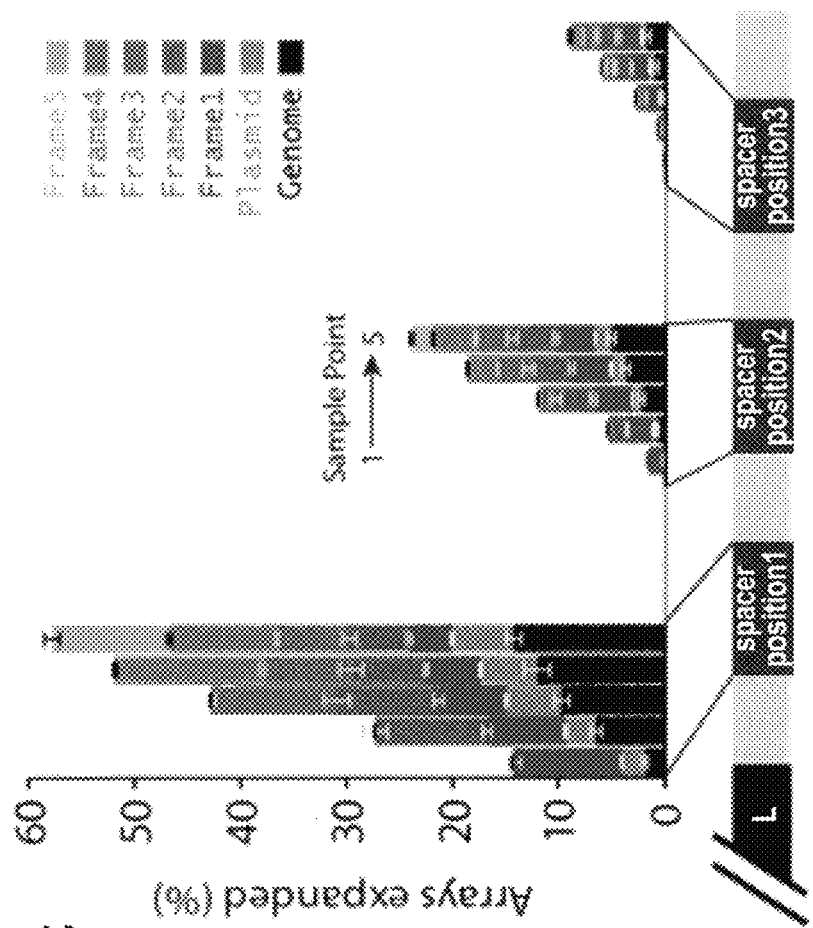
FIG. 16B
FIG. 16C

Reads Sampled

| 1st Base | 2nd Base | | | | 3rd Base |
| --- | --- | --- | --- | --- | --- |
| | T | C | A | G | |
| T | 1 | 2 | 3 | 4 | T |
| | 5 | 6 | 7 | 8 | C |
| | 9 | 10 | 11 | 12 | A |
| | 13 | 14 | 15 | 16 | G |
| C | 17 | 18 | 19 | 20 | T |
| | 21 | 1 | 2 | 3 | C |
| | 4 | 5 | 6 | 7 | A |
| | 8 | 9 | 10 | 11 | G |
| A | 12 | 13 | 14 | 15 | T |
| | 16 | 17 | 18 | 19 | C |
| | 20 | 21 | 1 | 2 | A |
| | 3 | 4 | | 5 | G |
| G | 6 | 7 | 8 | 9 | T |
| | 10 | 11 | 12 | 13 | C |
| | 14 | 15 | 16 | 17 | A |
| | 18 | 19 | 20 | 21 | G |

Pixel

GC ~ 50%, mononucleotide repeats, PAMs

AAGCGCG  7  7  12  15  8  9  8  7  13
51        1  2  3   4   5  6  7  8  9

Rules (when adding new triplet):
For every new triplet, rank by GC%, according to the current GC% of the growing protospacer:
   if overall spacer is <35%, rank [high GC%, mid GC%, low GC%]
   if overall spacer is 35-50%, rank [mid GC%, high GC%, low GC%]
   if overall spacer is 51-65%, rank [mid GC%, low GC%, high GC%]
   if overall spacer is >65%, rank [low GC%, mid GC%, high GC%]

Chose the first spacer from the list that does not violate the following rules (after appending new triplet):
   consider last 6 bases, choose next triplet if AAG or CTT occurs
   consider last 6 bases, choose next triplet if repeat of 4 of more occurs For final extra base, add least numerous base in the spacer

FIG. 18D

```
  Pixel
 ┌────┐         TAC(low)      GCGTAC acceptable
AAGCGCG  7      CGA(mid)           ‾
        ‾1‾     GCT(high)
```
current GC: ~71%, rank possible triplets [low GC,% mid GC%, high GC%]

```
    Pixel
  ┌──────┐       CGA(mid)     TACCGA acceptable
AAGCGCGTAC  7    TAC(low)       ‾
         ‾1‾ ‾2‾ GCT(high)
```
current GC: ~60%, rank possible triplets [mid GC,% low GC%, high GC%]

```
      Pixel
   ┌─────────┐     TGA(mid)    CGATGA acceptable
AAGCGCGTACCGA  12  ATT(low)      ‾
         ‾1‾ ‾2‾   GAC(high)
```
current GC: ~61%, rank possible triplets [mid GC,% low GC%, high GC%]

```
       Pixel
    ┌────────────┐    AGT(mid)    TGAAGT unacceptable
AAGCGCGTACCGATGA  15  TAG(low)    TGATAG acceptable
         ‾1‾ ‾2‾ ‾4‾  GCA(high)         ‾4‾
```
current GC: ~56%, rank possible triplets [mid GC,% low GC%, high GC%]

```
         Pixel
      ┌──────────────┐   CTG(mid)    TAGCTG acceptable
AAGCGCGTACCGATGATAG  8   GAT(low)      ‾4 ‾5
         ‾1‾ ‾2‾ ‾4‾ ‾5‾ TGC(high)
```
current GC: ~53%, rank possible triplets [mid GC,% low GC%, high GC%]

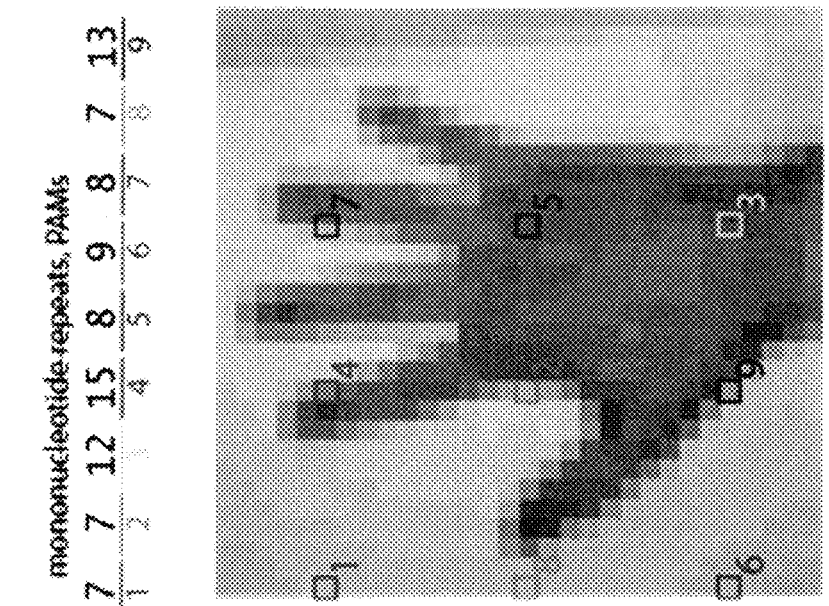

FIG. 18G

Rules (when adding new triplet):

X substitutions based on:
    consider last 6 bases, choose X if AAG or CTT occurs
    consider last 6 bases, choose X if repeat of 4 of more occurs
For final extra base, add least numerous base in the spacer

FIG. 18H

AAGCGCG 7  A: TAC   GCGTAC acceptable
           X: GCT

AAGCGCGTAC 7  B: CGA   TACCGA acceptable
             X: GCT

AAGCGCGTACCGA 12  A: TGA   CGATGA acceptable
                X: GAC

AAGCGCGTACCGATGA 15  B: AGT   TGAAGT unacceptable
                     X: GCA   TGAGCA acceptable AAGCGCGTACCGATGAGCA 8  A: TGC   GCATGC acceptable
                         X: GAT

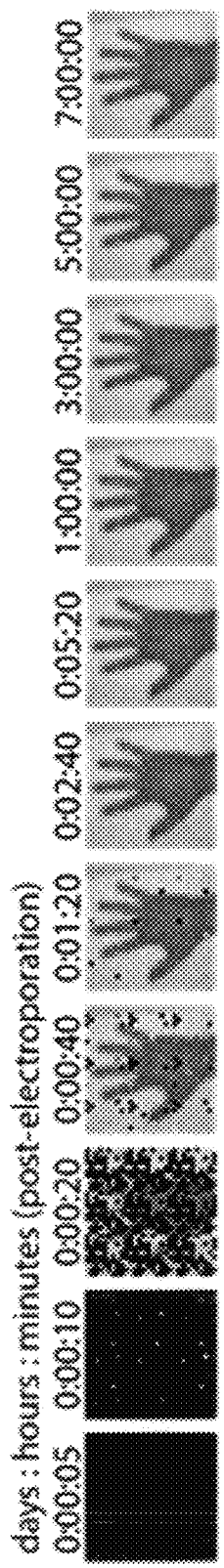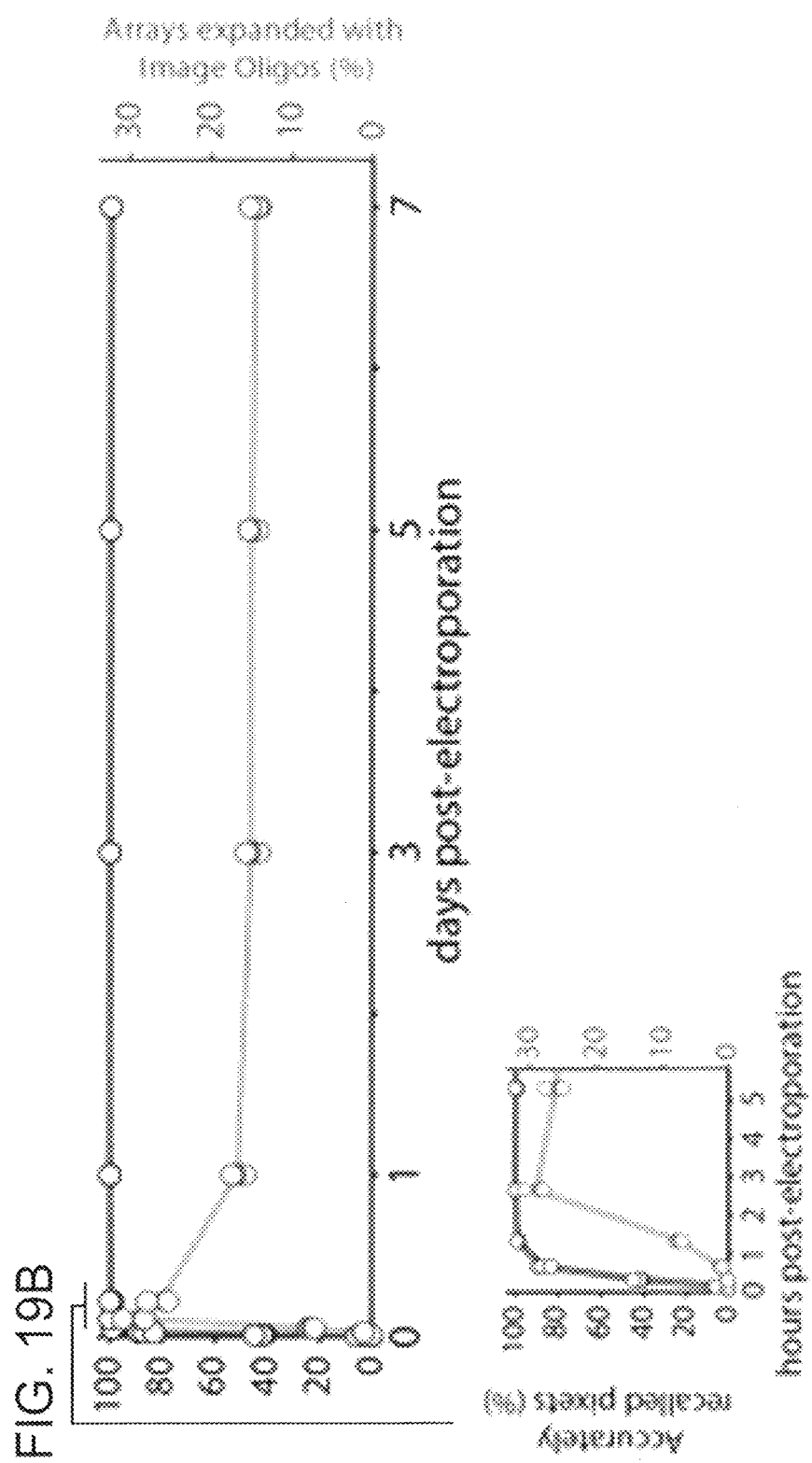
FIG. 19A
FIG. 19B

FIG. 21

Statistical Details

| Figure | Panel | Biological Replicates | Sequences Analyzed | Comparison | Test | P Value |
|---|---|---|---|---|---|---|
| 1 | a | >3 | | | | |
| | b | 4 | 15 / 11 / 10 / 8 | genome versus plasmid | Wilcoxon matched-pairs signed rank | 0.5 |
| | d | 3 | | | | |
| | e | 3 | | | | |
| | f | 3 | 393,792 / 1,121,529 / 1,657,772 | A two-way ANOVA revealed a significant effect of spacer source by concentration (F(2, 60) = 5.134; p = 0.0087). A follow-up Dunnett's test found that the only significant difference from the control (0 uM) condition was that of the oligo-derived spacers at 3.125 uM (corrected for multiple comparisons, p < 0.05). No significant differences were found in the plasmid- or genome-derived spacers as compared to the control condition (0 uM). | ANOVA; Dunnett's | 0.0087; < 0.005 |
| | g | 3 | 59,610 / 158,140 / 191,918 | No significant effect of oligo-derived spacer incorporation was found for plasmids containing an additional array versus a plasmid with no additional array at a concentration of 12.5 uM. | Wilcoxon matched-pairs signed rank | 0.25 |

Fig. 21 (continued)

| | | | | |
|---|---|---|---|---|
| h | 3 | 393,792 / 1,121,529 / 1,657,772 | | |
| i | 3 | 393,792 / 1,121,529 / 1,657,772 | | |
| a | 3 | 79,861 | | |
| b | 3 | 7,597 / 5,229 / 7,330 | direction, forward versus reverse | Wilcoxon matched-pairs signed rank | 0.0954 |
| c | >3 | 896 (unique) | | | |
| d | 3 | 11,955 / 13,679 / 17,771 | red bar indicates p < 0.05, Bonferroni corrected, at +/- 3.75 | | |
| e | 3 | 584,256 / 1,089,922 / 1,049,881 | After the discovery of a significant difference in the percentage of oligo-derived spacers between group means as determined by a one-way ANOVA (P < 0.0001), follow-up Dunnett's tests found significant differences between the 33 group and the no oligo group, the AA33 group, and the 1AA33 group (corrected for multiple comparisons, p < 0.05). No significant difference was found between the 33 and 10TC33 groups. | ANOVA; Dunnett's | < 0.0001; range |

| | | | | ANOVA; Dunnett's | <0.0001; range |
|---|---|---|---|---|---|
| f | 3 | 8,666 / 35,180 / 15,483 | After the discovery of a significant difference in the ratio of forward to reverse oligo-derived spacers between group means as determined by a one-way ANOVA (P < 0.0001), follow-up Dunnett's tests found significant differences between the 33 group and the AA33 group as well as between the 33 group and the 10AA33 group (corrected for multiple comparisons, p < 0.05). No significant difference was found between the 33 and 10TC33 groups. | | |
| g | 3 | 8,666 / 35,180 / 15,483 | | | |
| h | 3 | 8,666 / 35,180 / 15,483 | | | |
| i | 3 | 8,666 / 35,180 / 15,483 | | | |
| j | 3 | 8,666 / 35,180 / 15,483 | | | |
| c | 3 | 2,770,316 / 3,050,523 / 3,444,262 | | | |
| d | 3 | 2,770,316 / 3,050,523 / 3,444,262 | | | |
| e | 3 | 1,856,479 / 1,978,711 / 2,405,733 | | | |
| f | 3 | 577,587 / 617,580 / 826,392 | | | |

FIG. 21 (continued)

| Figure | Panel | Biological Replicates | Sequences Analyzed | Comparison | Test | $p$ Value |
|---|---|---|---|---|---|---|
| 8 | b | 1 | 16,935,280 | | | |
|  | c | 1 | 58,103 | | | |
|  | d | 3 | 616,936 | | | |
|  | c | 3 | 537,036 / 546,779 / 619,472 | After the discovery of a significant difference among the percentage of oligo-derived spacers as determined by a one-way ANOVA ($p < 0.05$), follow-up Dunnett's tests found that the only significant difference between condition one and condition two was in the percentage of Rd3 spacers (corrected for multiple comparisons, $p < 0.05$). | ANOVA; Dunnett's | $< 0.05; < 0.05$ |
|  | d | 3 | 79,094 / 81,994 / 79,182 | A two-tailed, unpaired t-test found no significant difference between the two conditions ($p < 0.05$). | t-test | $> 0.05$ |
| 10 | e | 3 | 79,094 / 81,994 / 79,182 | A two-tailed, unpaired t-test found a significant difference between the two conditions ($p < 0.01$). | t-test | $< 0.01$ |
|  | f | 3 | 79,094 / 81,994 / 79,182 | A two-tailed, unpaired t-test found a significant difference between the two conditions ($p < 0.05$). | t-test | $< 0.05$ |
|  | g | 3 | 79,094 / 81,994 / 79,182 | After the discovery of a significant difference between the conditions as determined by a one-way ANOVA ($p < 0.05$), follow up Holm-Sidak's multiple comparisons tests found significant differences between the conditions at each round (corrected for multiple comparisons, $p < 0.05$). | ANOVA; Holm-Sidak's | $< 0.05; < 0.05$ |
| Figure | Panel | Biological Replicates | Sequences Analyzed | Comparison | Test | $p$ Value |
| 2A-E | a | 4 | 15 / 11 / 10 / 8 | | | |
|  | b | 4 | 15 / 11 / 10 / 8 | | | |
|  | c | 3 | | | | |
|  | d | 3 | | | | |
|  | e | 3 | | | | |

FIG. 21 (continued)

| | | | | |
|---|---|---|---|---|
| 4A-F | a-c | 3 | 18,166 | ranking based on 18,166 protospacers from 3 biological replicates |
| | d | 3 | | |
| | f | 3 | 572,177 / 3,071,638 / 3,063,756 | After discovering significant effects of condition, spacer source, and interaction as determined by a two-way ANOVA (p < 0.0001), follow-up Turkey's multiple comparisons testing found significant differences between the percentage of spacers derived from oligos between the condition fed A and those fed C (corrected for multiple comparisons, p < 0.05) or A/C (corrected for multiple comparisons, p < 0.05), but no significant difference between the condition fed A and those fed B or C/A. | ANOVA; Turkey's | <0.0001; range |
| 5A-C | a | 3 | | |
| | b | 3 | | |
| | c | 3 | | |
| | d | 3 | | |
| 6A-I | c | 1 | 94,952 | |
| | d | 1 | 1,863,211 | |
| | e | 1 | 1,863,211 | |
| | f | 1 | 94,952 | |
| | g | 1 | 94,952 | |
| | h | 1 | 94,952 | |
| | i | 1 | 94,952 | |
| 9A-E | b | 1-3 | 744881 | A Mann Whitney test found no significant difference between the selected and the selected+refined mutants (p>0.05). | Mann Whitney | 0.7613 |
| | c | 1-3 | 16,935,280 | | | |

FIG. 22

Plasmids Used

| Plasmid | Gene(s) | CRISPR | Promoter(s) | Origin | Resistance | Source | Used in: |
|---|---|---|---|---|---|---|---|
| pWUR 1+2 | Cas1 (K12), Cas2 (K12) | Array | T7/lac | CloDF13 (CDF) | spectinomycin | Yosef, Goren, Qimron, NAR, 2012 | Fig. 1a-e.g. 3c-f; Extended Fig. 1a-d; 3b-c; 4c-i |
| pWUKI 1+2 | Cas1 (K12), Cas2 (K12) | K12 Array | T7/lac | CloDF13 (CDF) | spectinomycin | this study | Fig. 1f-l; 2a-j; 4b-d; Extended Fig. 1e; 2a-c; 3a; 5c |
| pRSF-DUET 1/2 | Cas1 (K12), Cas2 (K12) | | T7/lac | RSF | kanamycin | this study | Extended Fig. d, f |
| pWURA Cas1 | Cas1 (K12) | | T7/lac | CloDF13 (CDF) | ampicillin | this study | Extended Fig. 3c |
| pWUR Cas2 | Cas2 (K12) | | T7/lac | CloDF13 (CDF) | spectinomycin | this study | Extended Fig. 3c |
| pWUKI Cas1 Cas2 E9Q | Cas1 (K12), Cas2 E9Q (K12) | | T7/lac | CloDF13 (CDF) | spectinomycin | this study | Extended Fig. 3b |
| pWUKI Cas Mutant Library | mutCas1 (K12), mutCas2 (K12) (see Table 4) | K12 Array | T7/lac | CloDF13 (CDF) | spectinomycin | this study | Fig. 4b-d; Extended Fig. 5b-d |
| pWUKI Cas1 V134L Cas2 | Cas1 (K12) V134L, Cas2 (K12) | K12 Array | T7/lac | CloDF13 (CDF) | spectinomycin | this study | Fig. 4d |
| pWUKI Cas1 V33A Cas2 | Cas1 (K12) V33A, Cas2 (K12) | K12 Array | T7/lac | CloDF13 (CDF) | spectinomycin | this study | Fig. 4d |
| pWUKI Cas1 V190I Cas2 | Cas1 (K12) V190I, Cas2 (K12) | K12 Array | T7/lac | CloDF13 (CDF) | spectinomycin | this study | Fig. 4d |
| pWUKI Cas1 V279L Cas2 | Cas1 (K12) P279L, Cas2 (K12) | K12 Array | T7/lac | CloDF13 (CDF) | spectinomycin | this study | Fig. 4d |
| pWUKI Cas1 P202Q Cas2 | Cas1 (K12) P202Q, Cas2 (K12) | K12 Array | T7/lac | CloDF13 (CDF) | spectinomycin | this study | Fig. 4c |
| pWUKI Cas1 P212L Cas2 | Cas1 (K12) P212L, Cas2 (K12) | K12 Array | T7/lac | CloDF13 (CDF) | spectinomycin | this study | Fig. 4c |
| pWUKI Cas1 P282L Cas2 | Cas1 (K12) P282L, Cas2 (K12) | K12 Array | T7/lac | CloDF13 (CDF) | spectinomycin | this study | Fig. 4c |

FIG. 22 (continued)

| | | | | | | |
|---|---|---|---|---|---|---|
| pWUK1 Cas1 P294H Cas2 | Cas1 (K12) P294H, Cas2 (K12) | K12 Array | T7lac | CloDF13 (CDF) | spectinomycin | this study | Fig. 4d |
| pWUK1 Cas1 Cas2 T72I | Cas1 (K12), Cas2 T72I (K12) | K12 Array | T7lac | CloDF13 (CDF) | spectinomycin | this study | Fig. 4d |
| pWUK1 Cas1 Cas2 G74A | Cas1 (K12), Cas2 G74A (K12) | K12 Array | T7lac | CloDF13 (CDF) | spectinomycin | this study | Fig. 4d |
| pWUR 1+2 tetO mut89 | wt: Cas1 (K12), Cas2 (K12), mut: Cas1 Q24H, P202Q, G241D, E276D, L297Q (K12), Cas2 (K12) | | T7lac/putetO | CloDF13 (CDF) | spectinomycin | this study | Fig. 5c-g |

FIG. 23

| Cas Mutants | Random or Targeted Mutagenesis | Mutations Cas1 | Mutations Cas2 | Initial Screen Activity (% expanded) | Initial Screen Specificity (% AAG) | Follow-up (triplicate) Activity (% expanded) | Follow-up (triplicate) Specificity (% AAG) |
|---|---|---|---|---|---|---|---|
| wt | | | | 1.43 | 41.8 | 20.02 | 51.5 |
| s05 | Random | T42I | | | | | |
| | | V134L | | | | | |
| | | V190I | | | | | |
| | | A286T | | 1.17 | 11.9 | | |
| | | P294H | | | | | |
| | | | I47L | | | | |
| | | | T72I | | | | |
| s06 | Random | V145M | | | | | |
| | | A262V | | 0.49 | 8.3 | | |
| | | | P80L | | | | |
| s07 | Random | A262S | | 1.38 | 28.5 | | |
| | | | G74A | | | | |
| s08 | Random | I277K | | 1.6 | 17.7 | | |
| | | | V56A | | | | |
| s09 | Random | P202Q | | 3.1 | 41 | | |
| s10 | Random | | | 4.9 | 24.6 | | |
| s11 | Random | | T72I | 7.96 | 29.6 | | |
| s12 | Random | A94S | T72I | 11.3 | 27.6 | 5.54 | |

FIG. 23 (continued)

| | | | | | | |
|---|---|---|---|---|---|---|
| s13 | Random | Q21K | | | | |
| | | I277V | | 6.6 | 30.9 | |
| | | P279R | | | | |
| s14 | Random | E109G | | 3.3 | 45.5 | |
| | | I176V | | | | |
| | | D13N | | | | |
| s16 | Random | G301N | | 0.21 | 14.4 | |
| | | | V6M | | | |
| | | A94S | | | | |
| s17 | Random | I277T | | 3.72 | 19.3 | |
| | | S304N | | | | |
| | | A94S | | | | |
| s18 | Random | P202R | | | | |
| | | I277T | | 0.12 | 0.06 | |
| | | S304N | | | | |
| | | A286T | | | | |
| s19 | Random | P294H | | 0.11 | 24 | |
| | | | I47L | | | |
| | | | T72I | | | |
| s20 | Random | I277K | | 4.38 | 40.3 | |
| | | | V56A | | | |

FIG. 23 (continued)

| Sample | Type | Mut1 | Mut2 | Mut3 | Mut4 | Mut5 | | | | |
|---|---|---|---|---|---|---|---|---|---|---|
| s23 | Random | A286T | P294H | | | | | | | |
| s24 | Random | | | I47L | A59V | T72I | 1.03 | 23.2 | | |
| s25 | Random | D108H | P288S | G74A | | | 18.46 | 43.6 | 13.61 | 36.6 |
| s26 | Random | A286T | P294H | | | | 3.49 | 43.6 | | |
| s27 | Random | D108H | | I47L | T72I | | 1.43 | 23.5 | | |
| s28 | Random | A286T | P294H | I47L | T72I | | 4.14 | 68.5 | 15.05 | 52.1 |
| | | | | | | | 1 | 24.6 | | |
| s31 | Random | V83I | Q278Y | A300T | I4F | A20T | 0.57 | 17.5 | | |
| s33 | Random | P91R | | | | | 1.39 | 18 | | |

FIG. 23 (continued)

| | | | | | |
|---|---|---|---|---|---|
| s35 | Random | A94S<br>P202R<br>I277T<br>S304N | | | |
| s36 | Random | A286T<br>P294H | I47L<br>T72I | 0.15 | 26.2 |
| s37 | Random | A286T<br>P294H | I47L<br>T72I | 1.16 | 19.8 |
| s38 | Random | G189S<br>A197V | | 0.96 | 21.1 |
| s40 | Random | E109G<br>I176V | | 2.05 | 13 |
| s41 | Random | P202Q | | 1.55 | 45.1 |
| s43 | Random | M171 | | 1.26 | 15.6 |
| s44 | Random | P167L | T72I | 2.05 | 26.3 |
| s45 | Random | P243S | | 5.43 | 26.1 | 13.5 |
| s46 | Random | | | 1.17 | 47.5 | 12.9 |
| | | | | 3.18 | 15.7 | |

FIG. 23 (continued)

| | | | | | | |
|---|---|---|---|---|---|---|
| s47 | Random | P202Q | | | | |
| | | K172R | | | | |
| | | P202Q | G67R | 2.8 | 19.5 | |
| s48 | Random | I223V | M58V | 0.86 | 52.2 | |
| s49 | Random | D108H | | 2.35 | 58.9 | |
| s50 | Random | V33A | | 2.61 | 18.1 | |
| | | Q287E | | | | |
| s51 | Random | P202Q | | | | |
| s53 | Random | I223V | M58V | 1.28 | 51.1 | |

FIG. 23 (continued)

| ID | Random or Targeted Mutagenesis | Mutations Cas1 | Mutations Cas2 | Initial Screen Activity (% expanded) | Initial Screen Specificity (% AAG) | Follow-up (triplicate) Activity (% expanded) | Follow-up (triplicate) Specificity (% AAG) |
|---|---|---|---|---|---|---|---|
| s60 | Random | | | 3.02 | 43.9 | | |
| s61 | Random | G210R | R78H | 0.51 | 24.3 | | |
| s64 | Random | P279L | | 5.25 | 41.8 | | |
| s67 | Random | P212L | | 1.23 | 12.2 | | |
| s69 | Random | S143N P280L | L23M T66M F70L | 0.37 | 12.4 | | |
| s70 | Random | A262P A286T P294H | I47L T72I | 0.91 | 17.7 | | |
| s71 | Random | L261S | A59S S90T | 1.49 | 43.7 | | |

FIG. 23 (continued)

| ID | Type | Mutations | | | | |
|---|---|---|---|---|---|---|
| s73 | Random | V46I, A194V, P279S, A300V | | | | |
| s74 | Random | K172R, K211E, T72I | 0.11 | 32.9 | | |
| s75 | Random | | 1.25 | 8.8 | 0.39 | 6.1 |
| s77 | Random | | 3.23 | 42.5 | | |
| s80 | Random | V33A, T42I, V134L, Q178R, G199C | 2.43 | 37.2 | | |
| s82 | Random | M17T, V60I | 0.87 | 6.5 | 1.13 | 13 |
| s83 | Random | A273T, A286T, P294H, I47L, T72I | 8.21 | 18.6 | 24.37 | 23.1 |
| s85 | Random | V190L, P279A, G74R | 1.56 | 20.9 | | |
| | | | 1.79 | 15.2 | | |

FIG. 23 (continued)

| ID | Type | Mutations | | Val1 | Val2 | Val3 | Val4 |
|---|---|---|---|---|---|---|---|
| s86 | Random | K114E, V190I, A198T | A48D, T79A | 1.28 | 11.3 | | |
| s88 | Random | A273T, A286T, P294H | I47L, I72I | 0.71 | 17.4 | | |
| s89 | Random | Q24H, P202Q, G241D, E276D, L297Q | | 0.93 | 9.7 | 13.74 | 16 |
| s90 | Random | | | 2.51 | 40.7 | | |
| s91 | Random | | E9K | 1.58 | 18.5 | | |
| s94 | Random | | | 9.66 | 44.4 | | |
| s96 | Random | A273T, A286T, P294H | | 5.1 | 17.5 | 5.38 | 18.8 |
| p01 | Targeted | D13N | | 1.37 | 41.4 | | |
| p02 | Targeted | M17T | | 2.65 | 39.5 | | |
| p03 | Targeted | Q24H | | 0.9 | 38.8 | | |

FIG. 23 (continued)

| | | | | | | |
|---|---|---|---|---|---|---|
| p04 | Targeted | V33A | | 11.8 | 22.2 | 18.59 | 25.7 |
| p05 | Targeted | T42I | | 4.1 | 32.6 | | |
| p06 | Targeted | V46A | | 1.32 | 43 | | |
| p07 | Targeted | V60I | | 1.65 | 45.6 | | |
| p08 | Targeted | V64S | | 1.6 | 40.9 | | |
| p09 | Targeted | A94S | | 1.32 | 59.9 | | |
| p10 | Targeted | D108H | | 1.37 | 54.8 | | |
| p11 | Targeted | R112G | | 0.46 | 48 | | |
| p12 | Targeted | R112L | | 0.16 | 43.9 | | |
| p13 | Targeted | R112M | | 0.2 | 49.4 | | |
| p14 | Targeted | K114E | | 2.32 | 31.9 | | |
| p15 | Targeted | V134L | | 7.07 | 24 | 11.33 | 32.1 |
| p16 | Targeted | R138L | | 0.54 | 39.9 | | |
| p17 | Targeted | R138S | | 0.26 | 18.4 | | |
| p18 | Targeted | V145M | | 2.79 | 29.4 | | |
| p19 | Targeted | Q178R | | 5.38 | 44.5 | | |
| p20 | Targeted | V190I | | 25.2 | 40.8 | 20.23 | 39.7 |
| p21 | Targeted | G199C | | 0.74 | 33.8 | | |
| p22 | Targeted | P202Q | | 3.06 | 18.1 | 9.47 | 20.5 |
| p23 | Targeted | K211E | | 0.17 | 14.3 | | |
| p24 | Targeted | P212L | | 1.73 | 18.2 | 7.4 | 16.5 |
| p25 | Targeted | G241D | | 2.82 | 42.2 | | |
| p26 | Targeted | P279L | | 7.71 | 48 | 20.24 | 46.6 |
| p27 | Targeted | P282L | | 1.17 | 11.9 | 16.93 | 39 |

FIG. 23 (continued)

| | | | | | | |
|---|---|---|---|---|---|---|
| p28 | Targeted | A286T | | 0.49 | 8.3 | | |
| p29 | Targeted | P294H | | 1.38 | 18.2 | 25.27 | 44.6 |
| p30 | Targeted | | I47L | 1.6 | 28.5 | | |
| p31 | Targeted | | T72I | 3.1 | 17.7 | 19.07 | 32.6 |
| p32 | Targeted | | G74A | 6.25 | 43.6 | 18.99 | 44.7 |

FIG. 24

Protospacer Oligos

| Oligos | Sequence (5'→3'), Top Strand Only | Used In: |
|---|---|---|
| ps33 | GCCCAATTTACTACTCGTTCTGGTGTTTCTCGT | Fig. 1d-i; 2b,e-g; Extended Fig. 1d-e; 3a,c |
| psAA33 | AACCCCAATTTACTACTCGTTCTGGTGTTTCTCGT | Fig. 2e-f,h; Extended Fig. 3a |
| ps10AA33 | CACTAGCCATAAAGCCCAATTTACTACTCGTTCTGGTGTTTCTCGT | Fig. 2e-f,j; Extended Fig. 3a |
| ps10TC33 | CACTAGCCATATCGCCCAATTTACTACTCGTTCTGGTGTTTCTCGT | Fig. 2e-f,j; Extended Fig. 3a |
| psH | CTCCCGCCTGTAGAAGTCACCATTGTGTGCACCACGACCATTCCGTGGGTTATCCAGCT | Extended Fig. 2d,f |
| psM | CCACACTTCCCGTAAGGGAGAAGCGGAACAGGTATCCGTAAACCGCAGGTCGGAACAGG | Extended Fig. 2d,f |
| psL | AAATGGACTCCTTAAGATTCTTGTACGACGGTATTAGACGGTAAGCTGATCAGCCCCTGAAG | Extended Fig. 2d,f |
| psL/H | CTCCCGCCTGTAGAAGTCACCATTGTGTGCACCACGACCATTCCGTGGGTTATCCAGCT | Extended Fig. 2d,f |
| psH/L | AAATGGACTCCTTAAGTCACCATTGTGTGCACCACGACATTCCGTGGGTTATCCAGCCCCTGAAG | Extended Fig. 2d,f |
| ps58 | CACTAGCCATAAAGCCCAATTTACTACTCGTTCTGGTGTTTCTCGTCAGGGCAAAGGAA (psAA3) | Extended Fig. 3b,c |
| 1 X 3 Rd1 | AAGCTCGATTTTCGTCGCCCTTGACCTTATTGA | Extended Fig. 4c-i |
| 1 X 3 Rd2 | AAGCATTTTACTGGTGTCTTTATGTCTCCGCCA | Extended Fig. 4c-i |
| 1 X 3 Rd3 | AAGGCATAGTTCAGCCGTTAGAGGGTAGTCCTACG | Extended Fig. 4c-i |
| 3 X 5 Rd1, Set1 | AAGGCATAGTTCAGCCGTTAGAGGGTAGTCCTACG | Fig. 3 c-e |
| 3 X 5 Rd2, Set1 | AAGGCATATTTACCCGCTGAATCCGAGGTCTGAGGC | Fig. 3 c-e |

FIG. 24 (continued)

| | | |
|---|---|---|
| 3 X 5 Rd3, Set1 | AAGGCATAACATTGAACAACTGAGGACTGACGAA | Fig. 3 c-e |
| 3 X 5 Rd4, Set1 | AAGGCATACGGCCACTCGGACCGTCCGATTACCCA | Fig. 3 c-e |
| 3 X 5 Rd5, Set1 | AAGGCATATGATGATTATTCAGGACCTCCTACTAT | Fig. 3 c-e |
| 3 X 5 Rd1, Set2 | AAGAGTACTCTATAGAGTATCAAATGTATCCCTAC | Fig. 3 c-e |
| 3 X 5 Rd2, Set2 | AAGAGTACTATAGTCCTAGACTGAAACGACTACAT | Fig. 3 c-e |
| 3 X 5 Rd3, Set2 | AAGAGTACGGCCGTTGTAGGCACGGATTAGTG | Fig. 3 c-e |
| 3 X 5 Rd4, Set2 | AAGAGTACTCCACTATAACTCGAGTACGCGGACC | Fig. 3 c-e |
| 3 X 5 Rd5, Set2 | AAGAGTACGCTCTGATACATATCCATTGATTACTCC | Fig. 3 c-e |
| 3 X 5 Rd1, Set3 | AAGTACGTACTCTGTGTAGGTAGGCACTAATACG | Fig. 3 c-e |
| 3 X 5 Rd2, Set3 | AAGTACGTCGTGGATGACGGAATCATACAACGCA | Fig. 3 c-e |
| 3 X 5 Rd3, Set3 | AAGTACGTTGGATATAACCAATAACACTCGTTGAT | Fig. 3 c-e |
| 3 X 5 Rd4, Set3 | AAGTACGTGACTCCGCCGATATAGTGACTGGATG | Fig. 3 c-e |
| 3 X 5 Rd5, Set3 | AAGTACGTCTCCGCCGGTCGTACGTCCATACGACG | Fig. 3 c-e |

FIG. 24 (continued)

| | | |
|---|---|---|
| DirEvol Rd1 | TCGCCCAATTTACTACTCGTTCTGGTGTTTCTGTCTT | Fig. 4a; Extended Fig. 5a |
| DirEvol Rd2 | TCGCTCTGATTTTCGTCGCCCTTGACCTTATTGACTT | Fig. 4a; Extended Fig. 5a |
| MultiMod Rd1 | AAGGCATAACATTGAACAACTGGAGCACTGACGAACGA | Fig. 5c-g |
| MultiMod Rd2 | AAGAGTACGTCTGATAGATATCCATTGATTACTCCCGA | Fig. 5c-g |
| MultiMod Rd3 | AAGTACGTTGCATATAACCAATAACACTCGTTGATCGA | Fig. 5c-g |

SEQUENCE LISTING

```
<160> NUMBER OF SEQ ID NOS: 87

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcccaattta ctactcgttc tggtgtttct cgt                                    33

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagcccaatt tactactcgt tctggtgttt ctcgt                                  35

<210> SEQ ID NO 3
<211> LENGTH: 45
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cactagcata aagcccaatt tactactcgt tctggtgttt ctcgt            45

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cactagcata tcgcccaatt tactactcgt tctggtgttt ctcgt            45

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctccgcgctg tagaagtcac cattgttgtg cacgacgaca tcattccgtg gcgttatcca    60
gct                                                                 63

<210> SEQ ID NO 6
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccacacttcc cgtaagggag aaaggcggaa caggtatccg gtaaacggca gggtcggaac    60
agg                                                                 63

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaatggactc cttaagattc ttgtacgacg gtattagaat tcaagctgat caggcccctg    60
aag                                                                 63

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
```

```
ctccgcgctg tagaagattc ttgtacgacg gtattagaat tcaagctgtg gcgttatcca    60
gct                                                                  63
```

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
aaatggactc cttaagtcac cattgttgtg cacgacgaca tcattccgat caggcccctg    60
aag                                                                  63
```

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
tcgcccaatt tactactcgt tctggtgttt ctcgtctt                            38
```

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
tcgctctgat ttttcgtcgc ccttgacctt attgactt                            38
```

<210> SEQ ID NO 12
<211> LENGTH: 305
<212> TYPE: PRT
<213> ORGANISM: Unknown
<220> FEATURE:
<223> OTHER INFORMATION: Description of Unknown:
      wild type Cas1 sequence

<400> SEQUENCE: 12

```
Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125
```

Pro Ala Arg Arg Ser Val Glu Gln Leu Arg Gly Ile Glu Gly Ser Arg
            130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
            195                 200                 205

Thr Gly Lys Pro Leu Ser Phe Val Tyr Asp Ile Ala Asp Ile Ile Lys
        210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Ala Gln Pro
            275                 280                 285

Val Ala Ile Pro Leu Pro Val Ser Leu Gly Asp Ala Gly His Arg Ser
        290                 295                 300

Ser
305

<210> SEQ ID NO 13
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Ile His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Leu Glu Gln Leu Arg Gly Ile Glu Gly Ser Arg
            130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile

```
            165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
            195                 200                 205

Thr Gly Lys Pro Leu Ser Phe Val Tyr Asp Ile Ala Asp Ile Ile Lys
            210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Thr Gln Pro
            275                 280                 285

Val Ile Ile Pro Leu His Val Ser Leu Gly Asp Ala Gly His Arg Ser
290                 295                 300

Ser
305

<210> SEQ ID NO 14
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Thr Trp Leu Pro Leu Asn Pro Ile Pro Leu Lys Asp Arg Val Ser
1               5                  10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
            35                  40                  45

Val Ala Cys Ile Met Leu Glu Pro Gly Thr Arg Val Ser His Ala Ala
        50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
            115                 120                 125

Pro Ala Arg Arg Ser Val Glu Gln Leu Arg Gly Ile Glu Gly Ser Arg
        130                 135                 140

Met Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
            195                 200                 205
```

```
Thr Gly Lys Pro Leu Ser Phe Val Tyr Asp Ile Ala Asp Ile Ile Lys
            210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
            245                 250                 255

Ser Ser Lys Thr Leu Val Lys Leu Ile Pro Leu Ile Glu Asp Val Leu
            260                 265                 270

Ala Ala Gly Glu Ile Gln Pro Ala Pro Glu Asp Ala Gln Pro
            275                 280                 285

Val Ala Ile Pro Leu Pro Val Ser Leu Gly Asp Ala Gly His Arg Ser
290                 295                 300

Ser
305

<210> SEQ ID NO 15
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Thr Trp Leu Pro Leu Asn Pro Ile Pro Leu Lys Asn Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ile Gly Phe Val His
        195                 200                 205

Thr Gly Lys Pro Leu Ser Phe Val Tyr Asp Ile Ala Asp Ile Ile Lys
    210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255
```

```
Ser Ser Lys Thr Leu Ala Lys Leu Ile Pro Leu Ile Glu Asp Val Leu
            260                 265                 270

Ala Ala Gly Glu Ile Gln Pro Pro Ala Pro Pro Glu Asp Ala Gln Pro
            275                 280                 285

Val Ala Ile Pro Leu Pro Val Ser Leu Gly Asp Ala Asn His Arg Ser
            290                 295                 300

Ser
305

<210> SEQ ID NO 16
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
            35                  40                  45

Val Ala Cys Ile Met Leu Glu Pro Gly Thr Arg Val Ser His Ala Ala
            50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ser Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
            115                 120                 125

Pro Ala Arg Arg Ser Val Glu Gln Leu Arg Gly Ile Glu Gly Ser Arg
            130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Arg Ala Ile Gly Phe Val His
            195                 200                 205

Thr Gly Lys Pro Leu Ser Phe Val Tyr Asp Ile Ala Asp Ile Ile Lys
            210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Thr Gln Pro Pro Ala Pro Pro Glu Asp Ala Gln Pro
            275                 280                 285

Val Ala Ile Pro Leu Pro Val Ser Leu Gly Asp Ala Gly His Arg Asn
```

Ser
305

<210> SEQ ID NO 17
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Ser Val Thr Glu
            180                 185                 190

Ala Ala Ile Leu Val Ala Gly Tyr Ala Pro Ala Ile Gly Phe Val His
        195                 200                 205

Thr Gly Lys Pro Leu Ser Phe Val Tyr Asp Ile Ala Asp Ile Ile Lys
    210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Ala Gln Pro
        275                 280                 285

Val Ala Ile Pro Leu Pro Val Ser Leu Gly Asp Ala Gly His Arg Ser
    290                 295                 300

Ser
305

<210> SEQ ID NO 18
<211> LENGTH: 305

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
        195                 200                 205

Thr Gly Lys Leu Leu Ser Phe Val Tyr Asp Ile Ala Asp Ile Ile Lys
    210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Ala Gln Pro
        275                 280                 285

Val Ala Ile Pro Leu Pro Val Ser Leu Gly Asp Ala Gly His Arg Ser
    290                 295                 300

Ser
305
```

<210> SEQ ID NO 19
<211> LENGTH: 305
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Asn Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
        195                 200                 205

Thr Gly Lys Pro Leu Ser Phe Val Tyr Asp Ile Ala Asp Ile Ile Lys
    210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Leu Ala Pro Glu Asp Ala Gln Pro
        275                 280                 285

Val Ala Ile Pro Leu Pro Val Ser Leu Gly Asp Ala Gly His Arg Ser
    290                 295                 300

Ser
305

<210> SEQ ID NO 20
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Val Leu Ile Asp Lys Thr Gly Ile Arg Thr His Ile Pro Val Gly Ser
        35                  40                  45
```

Val Ala Cys Ile Met Leu Glu Pro Gly Thr Arg Val Ser His Ala Ala
 50                  55                  60

Val Arg Leu Ala Ala Gln Val Gly Thr Leu Leu Val Trp Val Gly Glu
 65                  70                  75                  80

Ala Gly Val Arg Val Tyr Ala Ser Gly Gln Pro Gly Gly Ala Arg Ser
                 85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
        115                 120                 125

Pro Ala Arg Arg Ser Val Glu Gln Leu Arg Gly Ile Glu Gly Ser Arg
130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Arg Gly Asp Thr Ile
                165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Pro Ala Ile Gly Phe Val His
        195                 200                 205

Thr Gly Glu Pro Leu Ser Phe Val Tyr Asp Ile Ala Asp Ile Ile Lys
210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Ala Gln Pro
        275                 280                 285

Val Ala Ile Pro Leu Pro Val Ser Leu Gly Asp Ala Gly His Arg Ser
    290                 295                 300

Ser
305

<210> SEQ ID NO 21
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
            20                  25                  30

Ala Leu Ile Asp Lys Thr Gly Ile Arg Ile His Ile Pro Val Gly Ser
        35                  40                  45

Val Ala Cys Ile Met Leu Glu Pro Gly Thr Arg Val Ser His Ala Ala
 50                  55                  60

Val Arg Leu Ala Ala Gln Val Gly Thr Leu Leu Val Trp Val Gly Glu
 65                  70                  75                  80

Ala Gly Val Arg Val Tyr Ala Ser Gly Gln Pro Gly Gly Ala Arg Ser

```
                    85                  90                  95
Asp Lys Leu Leu Tyr Gln Ala Lys Leu Ala Leu Asp Glu Asp Leu Arg
                100                 105                 110
Leu Lys Val Val Arg Lys Met Phe Glu Leu Arg Phe Gly Glu Pro Ala
                115                 120                 125
Pro Ala Arg Arg Ser Leu Glu Gln Leu Arg Gly Ile Glu Gly Ser Arg
            130                 135                 140
Val Arg Ala Thr Tyr Ala Leu Leu Ala Lys Gln Tyr Gly Val Thr Trp
145                 150                 155                 160
Asn Gly Arg Arg Tyr Asp Pro Lys Asp Trp Glu Lys Gly Asp Thr Ile
                165                 170                 175
Asn Arg Cys Ile Ser Ala Ala Thr Ser Cys Leu Tyr Gly Val Thr Glu
            180                 185                 190
Ala Ala Ile Leu Ala Ala Cys Tyr Ala Pro Ala Ile Gly Phe Val His
                195                 200                 205
Thr Gly Lys Pro Leu Ser Phe Val Tyr Asp Ile Ala Asp Ile Ile Lys
            210                 215                 220
Phe Asp Thr Val Val Pro Lys Ala Phe Glu Ile Ala Arg Arg Asn Pro
225                 230                 235                 240
Gly Glu Pro Asp Arg Glu Val Arg Leu Ala Cys Arg Asp Ile Phe Arg
                245                 250                 255
Ser Ser Lys Thr Leu Ala Lys Leu Ile Pro Leu Ile Glu Asp Val Leu
            260                 265                 270
Ala Ala Gly Glu Ile Gln Pro Pro Ala Pro Pro Glu Asp Ala Gln Pro
            275                 280                 285
Val Ala Ile Pro Leu Pro Val Ser Leu Gly Asp Ala Gly His Arg Ser
        290                 295                 300
Ser
305

<210> SEQ ID NO 22
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Thr Trp Leu Pro Leu Asn Pro Ile Pro Leu Lys Asp Arg Val Ser
1               5                   10                  15
Met Ile Phe Leu Gln Tyr Gly Gln Ile Asp Val Ile Asp Gly Ala Phe
                20                  25                  30
Val Leu Ile Asp Lys Thr Gly Ile Arg Thr His Ile Pro Val Gly Ser
            35                  40                  45
Val Ala Cys Ile Met Leu Glu Pro Gly Thr Arg Val Ser His Ala Ala
        50                  55                  60
Val Arg Leu Ala Ala Gln Val Gly Thr Leu Leu Val Trp Val Gly Glu
65                  70                  75                  80
Ala Gly Val Arg Val Tyr Ala Ser Gly Gln Pro Gly Gly Ala Arg Ser
                85                  90                  95
Asp Lys Leu Leu Tyr Gln Ala Lys Leu Ala Leu Asp Glu Asp Leu Arg
                100                 105                 110
Leu Lys Val Val Arg Lys Met Phe Glu Leu Arg Phe Gly Glu Pro Ala
            115                 120                 125
```

Pro Ala Arg Arg Ser Val Glu Gln Leu Arg Gly Ile Glu Gly Ser Arg
    130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

Asn Gln Cys Ile Ser Ala Ala Thr Ser Cys Leu Tyr Gly Leu Thr Glu
                180                 185                 190

Ala Ala Ile Leu Ala Ala Gly Tyr Ala Pro Ala Ile Gly Phe Val His
                195                 200                 205

Thr Gly Lys Pro Leu Ser Phe Val Tyr Asp Ile Ala Asp Ile Ile Lys
    210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
                260                 265                 270

Ala Ala Gly Glu Ile Gln Ala Pro Ala Pro Glu Asp Ala Gln Pro
    275                 280                 285

Val Ala Ile Pro Leu Pro Val Ser Leu Gly Asp Ala Gly His Arg Ser
    290                 295                 300

Ser
305

<210> SEQ ID NO 23
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Thr Trp Leu Pro Leu Asn Pro Ile Pro Leu Lys Asp Arg Val Ser
1               5                   10                  15

Met Ile Phe Leu Gln Tyr Gly Gln Ile Asp Val Ile Asp Gly Ala Phe
                20                  25                  30

Val Leu Ile Asp Lys Thr Gly Ile Arg Thr His Ile Pro Val Gly Ser
                35                  40                  45

Val Ala Cys Ile Met Leu Glu Pro Gly Thr Arg Val Ser His Ala Ala
    50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
                85                  90                  95

Asp Lys Leu Leu Tyr Gln Ala Lys Leu Ala Leu Asp Glu Asp Leu Arg
                100                 105                 110

Leu Glu Val Val Arg Lys Met Phe Glu Leu Arg Phe Gly Glu Pro Ala
    115                 120                 125

Pro Ala Arg Arg Ser Val Glu Gln Leu Arg Gly Ile Glu Gly Ser Arg
                130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
                165                 170                 175

```
Asn Gln Cys Ile Ser Ala Ala Thr Ser Cys Leu Tyr Gly Ile Thr Glu
            180                 185                 190

Ala Ala Ile Leu Ala Thr Gly Tyr Ala Pro Ala Ile Gly Phe Val His
            195                 200                 205

Thr Gly Lys Pro Leu Ser Phe Val Tyr Asp Ile Ala Asp Ile Ile Lys
            210                 215                 220

Phe Asp Thr Val Val Pro Lys Ala Phe Glu Ile Ala Arg Arg Asn Pro
225                 230                 235                 240

Gly Glu Pro Asp Arg Glu Val Arg Leu Ala Cys Arg Asp Ile Phe Arg
            245                 250                 255

Ser Ser Lys Thr Leu Ala Lys Leu Ile Pro Leu Ile Glu Asp Val Leu
            260                 265                 270

Ala Ala Gly Glu Ile Gln Pro Pro Ala Pro Glu Asp Ala Gln Pro
            275                 280                 285

Val Ala Ile Pro Leu Pro Val Ser Leu Gly Asp Ala Gly His Arg Ser
            290                 295                 300

Ser
305

<210> SEQ ID NO 24
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Thr Trp Leu Pro Leu Asn Pro Ile Pro Leu Lys Asp Arg Val Ser
1               5                   10                  15

Met Ile Phe Leu Gln Tyr Gly His Ile Asp Val Ile Asp Gly Ala Phe
            20                  25                  30

Val Leu Ile Asp Lys Thr Gly Ile Arg Thr His Ile Pro Val Gly Ser
            35                  40                  45

Val Ala Cys Ile Met Leu Glu Pro Gly Thr Arg Val Ser His Ala Ala
            50                  55                  60

Val Arg Leu Ala Ala Gln Val Gly Thr Leu Leu Val Trp Val Gly Glu
65                  70                  75                  80

Ala Gly Val Arg Val Tyr Ala Ser Gly Gln Pro Gly Gly Ala Arg Ser
            85                  90                  95

Asp Lys Leu Leu Tyr Gln Ala Lys Leu Ala Leu Asp Glu Asp Leu Arg
            100                 105                 110

Leu Lys Val Val Arg Lys Met Phe Glu Leu Arg Phe Gly Glu Pro Ala
            115                 120                 125

Pro Ala Arg Arg Ser Val Glu Gln Leu Arg Gly Ile Glu Gly Ser Arg
            130                 135                 140

Val Arg Ala Thr Tyr Ala Leu Leu Ala Lys Gln Tyr Gly Val Thr Trp
145                 150                 155                 160

Asn Gly Arg Arg Tyr Asp Pro Lys Asp Trp Glu Lys Gly Asp Thr Ile
            165                 170                 175

Asn Gln Cys Ile Ser Ala Ala Thr Ser Cys Leu Tyr Gly Val Thr Glu
            180                 185                 190

Ala Ala Ile Leu Ala Ala Gly Tyr Ala Gln Ala Ile Gly Phe Val His
            195                 200                 205

Thr Gly Lys Pro Leu Ser Phe Val Tyr Asp Ile Ala Asp Ile Ile Lys
```

```
                210                 215                 220
Phe Asp Thr Val Val Pro Lys Ala Phe Glu Ile Ala Arg Arg Asn Pro
225                 230                 235                 240

Asp Glu Pro Asp Arg Glu Val Arg Leu Ala Cys Arg Asp Ile Phe Arg
                245                 250                 255

Ser Ser Lys Thr Leu Ala Lys Leu Ile Pro Leu Ile Glu Asp Val Leu
            260                 265                 270

Ala Ala Gly Asp Ile Gln Pro Pro Ala Pro Glu Asp Ala Gln Pro
        275                 280                 285

Val Ala Ile Pro Leu Pro Val Ser Gln Gly Asp Ala Gly His Arg Ser
    290                 295                 300
```

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaggcataac attgaacaac tggaggactg acgaacga                                38

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aagagtacgt ctgatagata tccattgatt actcccga                                38

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aagtacgttg gatataacca ataacactcg ttgatcga                                38

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aagccctaat gtctgactct caaacgcttt agcgc                                   35

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aagcgcgaat ctctgtccct aaactccgtt aacct                           35

<210> SEQ ID NO 30
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatgtctgac tctcaaacgc tttagccgaa agcgtttgag agtcagacat tagggctt    58

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aatctctgtc cctaaactcc gttaacctaa cggagtttag ggacagagat tcgcgctt    58

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
acgagaaaca ccagaacgag tagtaaattg ggc                             33

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acgagaaaca ccagaacgag tagtaaattg ggctt                           35

<210> SEQ ID NO 34
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgtcattta ctactcgttc tggtgtttct cgtaggctct gcaaacacca gaacgagtag  60
taaattgggc tt                                                     72

<210> SEQ ID NO 35
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atgtcattta ctactcgttc tggtgtttct cgtggctctg caaacaccag aacgagtagt    60
aaattgggct t    71

<210> SEQ ID NO 36
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atgtcattta ctactcgttc tggtgtttct cgtgctctgc aaacaccaga acgagtagta    60
aattgggctt    70

<210> SEQ ID NO 37
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atgtcattta ctactcgttc tggtgtttct cgtctctgca acaccagaa cgagtagtaa    60 attgggctt    69

<210> SEQ ID NO 38
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atgtcattta ctactcgttc tggtgtttct cgttctgcaa acaccagaac gagtagtaaa    60
ttgggctt    68

<210> SEQ ID NO 39
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atgtcattta ctactcgttc tggtgtttct cgtctgcaaa caccagaacg agtagtaaat    60
tgggctt    67

<210> SEQ ID NO 40
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atgtcattta ctactcgttc tggtgtttct cgttgcaaac accagaacga gtagtaaatt    60

<210> SEQ ID NO 41
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
atgtcattta ctactcgttc tggtgtttct cgtgcaaaca ccagaacgag tagtaaattg    60
ggctt    65

<210> SEQ ID NO 42
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
atgtcattta ctactcgttc tggtgtttct cgtcaaacac cagaacgagt agtaaattgg    60
gctt    64

<210> SEQ ID NO 43
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
atgtcattta ctactcgttc tggtgtttct cgtaaacacc agaacgagta gtaaattggg    60
ctt    63

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
atttactact cgttctggtg tttctcgtaa acaccagaac gagtagtaaa ttgggctt    58

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
aagccctggt cagctgagat aggctgttcg acagt    35

<210> SEQ ID NO 46
<211> LENGTH: 35
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 46
aagcgcgtac cgatgatagc tgggttgccg aactc                               35

<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggtcagctga gataggctgt tcgacagtcg aacagcctat ctcagctgac cagggctt     58

<210> SEQ ID NO 48
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
taccgatgat agctgggttg ccgaactccg gcaacccagc tatcatcggt acgcgctt     58

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aagtattgtg tcagcgtgta ccgttatcgc tgtga                              35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aagtattgtg tcagcgtgta ccgttatcgc tgcct                              35

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aagccgaaat atcaattcct aaaccccata tccct                              35

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 52
aagccgaaat atcaattcct aaaccccata tctga                     35

<210> SEQ ID NO 53
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(28)
<223> OTHER INFORMATION: a, c, t, g, unknown or other

<400> SEQUENCE: 53
gtgtcagcgt gtaccgttat cgctgnnngc gataacggta cacgctgaca caatactt    58

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aagcacaaat ccagatctgt cagatgatct actga                     35

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(10)
<223> OTHER INFORMATION: This region may encompass "tac" or "cga" or
      "gct"
<220> FEATURE:
<221> NAME/KEY: modified_base
<222> LOCATION: (11)..(13)
<223> OTHER INFORMATION: This region may encompass "tac" or "cga" or
      "gct"
<220> FEATURE:
<221> NAME/KEY: modified_base
<222> LOCATION: (14)..(16)
<223> OTHER INFORMATION: This region may encompass "tga" or "att" or
      "gac"
<220> FEATURE:
<221> NAME/KEY: modified_base
<222> LOCATION: (17)..(19)
<223> OTHER INFORMATION: This region may encompass "tag" or "agt" or
      "gca"
<220> FEATURE:
<221> NAME/KEY: modified_base
<222> LOCATION: (20)..(22)
<223> OTHER INFORMATION: This region may encompass "tgc" or "ctg" or
      "gat"
<220> FEATURE:
<221> NAME/KEY: modified_base
<222> LOCATION: (23)..(25)
<223> OTHER INFORMATION: This region may encompass "tta" or "ccg" or
      "ggt"
<220> FEATURE:
<221> NAME/KEY: modified_base
<222> LOCATION: (26)..(28)
<223> OTHER INFORMATION: This region may encompass "tgc" or "ctg" or
      "gat"

```
<220> FEATURE:
<221> NAME/KEY: modified_base
<222> LOCATION: (29)..(31)
<223> OTHER INFORMATION: This region may encompass "tac" or "cga" or
      "gct"
<220> FEATURE:
<221> NAME/KEY: modified_base
<222> LOCATION: (32)..(34)
<223> OTHER INFORMATION: This region may encompass "ttg" or "act" or
      "ggc"

<400> SEQUENCE: 55
aagcgcgnnn nnnnnnnnnn nnnnnnnnnn nnnn                              34

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(10)
<223> OTHER INFORMATION: This region may encompass "tac" or "cga" or
      "gct"

<400> SEQUENCE: 56 aagcgcgnnn                                                         10

<210> SEQ ID NO 57
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(13)
<223> OTHER INFORMATION: This region may encompass "cga" or "tac" or
      "gct"

<400> SEQUENCE: 57
aagcgcgtac nnn                                                     13

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(16)
<223> OTHER INFORMATION: This region may encompass "tga" or "att" or
      "gac"

<400> SEQUENCE: 58
aagcgcgtac cgannn                                                  16

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (17)..(19)
<223> OTHER INFORMATION: This region may encompass "agt" or "tag" or
      "gca"

<400> SEQUENCE: 59
aagcgcgtac cgatgannn                                                    19

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(22)
<223> OTHER INFORMATION: This region may encompass "ctg" or "gat" or
      "tgc"

<400> SEQUENCE: 60
aagcgcgtac cgatgatagn nn                                                22

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(10)
<223> OTHER INFORMATION: This region may encompass "tac" or "gct"

<400> SEQUENCE: 61 aagcgcgnnn                                                              10

<210> SEQ ID NO 62
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(13)
<223> OTHER INFORMATION: This region may encompass "cga" or "gct"

<400> SEQUENCE: 62
aagcgcgtac nnn                                                          13

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(16)
<223> OTHER INFORMATION: This region may encompass "tga" or "gac"

<400> SEQUENCE: 63
aagcgcgtac cgannn                                                       16

<210> SEQ ID NO 64
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(19)
<223> OTHER INFORMATION: This region may encompass "agt" or "gca"

<400> SEQUENCE: 64
aagcgcgtac cgatgannn                                                  19

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(22)
<223> OTHER INFORMATION: This region may encompass "tgc" or "gat"

<400> SEQUENCE: 65
aagcgcgtac cgatgagcan nn                                              22

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(34)
<223> OTHER INFORMATION: a, c, t, g, unknown or other

<400> SEQUENCE: 66
aagcgcgtac cgatgatagc tgggttgcnn nnnnc                                35

<210> SEQ ID NO 67
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aagcgcgtac cgatgatagc tgggttgccg tatgc                                35

<210> SEQ ID NO 68
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cactagcata agcccaatt tactactcgt tctggtgttt ctcgtcaggg caaaggaa        58

<210> SEQ ID NO 69
<211> LENGTH: 35
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 69
aagctctgat ttttcgtcgc ccttgacctt attga                              35

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aagcatttta ctggtgtctt ttatgtctcc cgcca                              35

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aaggcatagt tcagccgtta gagggtagtc ctacg                              35

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
aaggcatatt tacccgctga atcgaggtct gaggc                              35

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aaggcataac attgaacaac tggaggactg acgaa                              35

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaggcatacg cgcactcgga ccgtccgatt accca                              35

<210> SEQ ID NO 75
<211> LENGTH: 35
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 75
aaggcatatg atgattattc aggacctcct actat                                35

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aagagtactc tatagagtat caaatgtatc cctac                                35

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aagagtacta tagtcctaga ctgaaacgac tacat                                35

<210> SEQ ID NO 78
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aagagtacgg ccgtttgtag gcacgggatt tagtg                                35

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aagagtactc cactataact cgagtacgcg ggacc                                35

<210> SEQ ID NO 80
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aagagtacgt ctgatagata tccattgatt actcc                                35

<210> SEQ ID NO 81
<211> LENGTH: 35
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 81
aagtacgtac tctgtctagg gtaggcacta atacg                                35

<210> SEQ ID NO 82
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aagtacgtcg tgggatgacg gaatcataca acgca                                35

<210> SEQ ID NO 83
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aagtacgttg gatataacca ataacactcg ttgat                                35

<210> SEQ ID NO 84
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aagtacgtga ctccggcgga tatagtgact ggatg                                35

<210> SEQ ID NO 85
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aagtacgtct cgcggcgtcg tacgtccata cgacg                                35

<210> SEQ ID NO 86
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaggcataac attgaacaac tggaggactg acgaacga                             38

<210> SEQ ID NO 87
<211> LENGTH: 38
<212> TYPE: DNA
<213> ORGANISM: Artificial Sequence
<220> FEATURE:
<223> OTHER INFORMATION: Description of Artificial Sequence: Synthetic

```
            oligonucleotide

<400> SEQUENCE: 87
aagagtacgt ctgatagata tccattgatt actcccga                                              38
```

METHODS AND SYSTEMS OF MOLECULAR RECORDING BY CRISPR-CAS SYSTEM

RELATED APPLICATION DATA

This application is a National Stage Application under 35 U.S.C. 371 of PCT application PCT/US17/18071 designating the United States and filed Feb. 16, 2017; which claims priority to U.S. Provisional Application No. 62/296,812 filed on Feb. 18, 2016 and to U.S. Provisional Application No. 62/395,738 filed on Sep. 16, 2016 which are hereby incorporated herein by reference in their entirety for all purposes.

STATEMENT OF GOVERNMENT INTERESTS

This invention was made with government support under Grant Nos. AG000222, MH103910, and NS045523 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 27, 2017, is named 010498_00909-WO_SL.txt and is 56,790 bytes in size.

BACKGROUND

DNA is unmatched in its potential to encode, preserve, and propagate information (G. M. Church, Y. Gao, S. Kosuri, Next-generation digital information storage in DNA. Science 337, 1628 (2012); published online Epub-September 28 (10.1126/science.1226355)). The precipitous drop in DNA sequencing cost has now made it practical to read out this information at scale (J. Shendure, H. Ji, Next-generation DNA sequencing. Nat Biotechnol 26, 1135-1145 (2008); published online EpubOctober (10.1038/nbt1486)). However, the ability to write arbitrary information into DNA, in particular within the genomes of living cells, has been restrained by a lack of biologically compatible recording systems that can exploit anything close to the full encoding capacity of nucleic acid space.

A number of approaches aimed at recording information within cells have been explored (D. R. Burrill, P. A. Silver, Making cellular memories. Cell 140, 13-18 (2010); published online EpubJanuary 8 (10.1016/j.cell.2009.12.034)). Some systems encode events at the transcriptional level using feedback loops and toggles. See N. T. Ingolia, A. W. Murray, Positive-feedback loops as a flexible biological module. Current biology: CB 17, 668-677 (2007); published online EpubApril 17 (10.1016/j.cub.2007.03.016), C. M. Ajo-Franklin, D. A. Drubin, J. A. Eskin, E. P. Gee, D. Landgraf, I. Phillips, P. A. Silver, Rational design of memory in eukaryotic cells. Genes & development 21, 2271-2276 (2007); published online EpubSeptember 15 (10.1101/gad.1586107), D. R. Burrill, M. C. Inniss, P. M. Boyle, P. A. Silver, Synthetic memory circuits for tracking human cell fate. Genes & development 26, 1486-1497 (2012); published online EpubJuly 1 (10.1101/gad.189035.112), T. S. Gardner, C. R. Cantor, J. J. Collins, Construction of a genetic toggle switch in *Escherichia coli*. Nature 403, 339-342 (2000); published online EpubJanuary 20 (10.1038/35002131), D. Greber, M. D. El-Baba, M. Fussenegger, Intronically encoded siRNAs improve dynamic range of mammalian gene regulation systems and toggle switch. Nucleic acids research 36, e101 (2008); published online EpubSeptember (10.1093/nar/gkn443), M. R. Atkinson, M. A. Savageau, J. T. Myers, A. J. Ninfa, Development of genetic circuitry exhibiting toggle switch or oscillatory behavior in *Escherichia coli*. Cell 113, 597-607 (2003); published online EpubMay 30, H. Kobayashi, M. Kaern, M. Araki, K. Chung, T. S. Gardner, C. R. Cantor, J. J. Collins, Programmable cells: interfacing natural and engineered gene networks. Proc Natl Acad Sci USA 101, 8414-8419 (2004); published online EpubJune 1 (10.1073/pnas.0402940101), N. Vilaboa, M. Fenna, J. Munson, S. M. Roberts, R. Voellmy, Novel gene switches for targeted and timed expression of proteins of interest. Molecular therapy: the journal of the American Society of Gene Therapy 12, 290-298 (2005); published online EpubAugust (10.1016/j.ymlhe.2005.03.029), B. P. Kramer, M. Fussenegger, Hysteresis in a synthetic mammalian gene network. Proc Natl Acad Sci USA 102, 9517-9522 (2005); published online EpubJuly 5 (10.1073/pnas.0500345102), D. R. Burrill, P. A. Silver, Synthetic circuit identifies subpopulations with sustained memory of DNA damage. Genes & development 25, 434-439 (2011); published online EpubMarch 1 (10.1101/gad.1994911), M. Wu, R. Q. Su, X. Li, T. Ellis, Y. C. Lai, X. Wang, Engineering of regulated stochastic cell fate determination. Proc Natl Acad Sci USA 110, 10610-10615 (2013); published online EpubJune 25 (10.1073/pnas.1305423110). Some systems encode information permanently into the genome, most often employing recombinases to store information via the orientation of DNA segments. See T. S. Ham, S. K. Lee, J. D. Keasling, A. P. Arkin, Design and construction of a double inversion recombination switch for heritable sequential genetic memory. PLoS One 3, e2815 (2008)10.1371/journal.pone.0002815), T. S. Moon, E. J. Clarke, E. S. Groban, A. Tamsir, R. M. Clark, M. Eames, T. Kortemme, C. A. Voigt, Construction of a genetic multiplexer to toggle between chemosensory pathways in *Escherichia coli*. Journal of molecular biology 406, 215-227 (2011); published online EpubFebruary 18 (10.1016/j.jmb.2010.12.019), J. Bonnet, P. Subsoontorn, D. Endy, Rewritable digital data storage in live cells via engineered control of recombination directionality. Proc Natl Acad Sci USA 109, 8884-8889 (2012); published online EpubJune 5 (10.1073/pnas.1202344109), L. Yang, A. A. Nielsen, J. Fernandez-Rodriguez, C. J. McClune, M. T. Laub, T. K. Lu, C. A. Voigt, Permanent genetic memory with >1-byte capacity. Nat Methods 11, 1261-1266 (2014); published online EpubDecember (10.1038/nmeth.3147), P. Siuti, J. Yazbek, T. K. Lu, Synthetic circuits integrating logic and memory in living cells. Nat Biotechnol 31, 448-452 (2013); published online EpubMay (10.1038/nbt.2510). While the majority of these systems are effectively binary, more recent efforts have also been made toward analogue recording systems (see F. Farzadfard, T. K. Lu, Synthetic biology. Genomically encoded analog memory with precise in vivo DNA writing in living cell populations. Science 346, 1256272 (2014); published online EpubNovember 14 (10.1126/science.1256272)) and digital counters (see A. E. Friedland, T. K. Lu, X. Wang, D. Shi, G. Church, J. J. Collins, Synthetic gene networks that count. Science 324, 1199-1202 (2009); published online EpubMay 29 (10.1126/science.1172005)). Despite these efforts, the recording and genetic storage of little more than a single byte of information has remained out of reach (see L. Yang, A. A. Nielsen, J. Fernandez-Rodriguez, C. J. McClune, M. T. Laub, T. K. Lu, C. A. Voigt, Permanent genetic memory with >1-byte capacity. Nat Methods 11, 1261-1266 (2014); published online EpubDecember (10.1038/nmeth.3147)).

Immunological memory is essential to an organism's adaptive immune response, and hence must be an efficient and robust form of recording molecular events into living cells. The CRISPR-Cas system is a recently understood form of adaptive immunity used by prokaryotes and archaea (see R. Barrangou, C. Fremaux, H. Deveau, M. Richards, P. Boyaval, S. Moineau, D. A. Romero, P. Horvath, CRISPR provides acquired resistance against viruses in prokaryotes. Science 315, 1709-1712 (2007); published online Epub-March 23 (10.1126/science.1138140)). This system remembers past infections by storing short sequences of viral DNA within a genomic array. These acquired sequences are referred to as protospacers in their native viral context, and spacers once they are inserted into the CRISPR array. Importantly, new spacers are integrated into the CRISPR array ahead of older spacers (I. Yosef, M. G. Goren, U. Qimron, Proteins and DNA elements essential for the CRISPR adaptation process in *Escherichia coli*. Nucleic acids research 40, 5569-5576 (2012); published online EpubJuly (10.1093/nar/gks216)). Over time, a long record of spacer sequences can be stored in the genomic array, arranged in the order in which they were acquired. Thus, the CRISPR array functions as a high capacity temporal memory bank of invading nucleic acids. However, there is a need for a CRISPR-Cas system that can direct recording of specific and arbitrary DNA sequences into the genome of prokaryotic and eukaryotic cells.

SUMMARY

The present disclosure addresses this need and is based on the discovery that specific and arbitrary DNA sequences can be introduced and recorded into the genome of cells. According to one aspect, a method of altering a cell is provided. The method includes providing the cell with a nucleic acid sequence encoding a Cas1 protein and/or a Cas2 protein of a CRISPR adaptation system, providing the cell with a CRISPR array nucleic acid sequence including a leader sequence and at least one repeat sequence, wherein the cell expresses the Cas1 protein and/or the Cas2 protein and wherein the CRISPR array nucleic acid sequence is within genomic DNA of the cell or on a plasmid. In one embodiment, the method further comprises providing the cell with an oligo nucleotide sequence comprising a protospacer. In another embodiment, the protospacer is a defined synthetic DNA. In one embodiment, the oligo nucleotide sequence includes a modified "AAG" protospacer adjacent motif (PAM). In another embodiment, the nucleic acid sequence encoding the Cas1 protein and/or a Cas2 protein is provided to the cell within a vector. In certain embodiments, the cell is a prokaryotic or a eukaryotic cell. In one embodiment, the prokaryotic cell is *E. coli*. In another embodiment, the *E. coli* is BL21-AI. In one embodiment, the eukaryotic cell is a yeast cell, plant cell or a mammalian cell. In certain embodiments, the cell lacks endogenous Cas1 and Cas2 proteins. In one embodiment, the nucleic acid sequence encoding the Cas1 protein and/or a Cas2 protein comprises inducible promoters for induction of expression of the Cas1 and/or Cas2 protein. In another embodiment, the nucleic acid sequence encoding the Cas1 protein and/or a Cas2 protein includes a first regulatory element operable in a eukaryotic cell. In one embodiment, the nucleic acid sequence encoding the Cas1 protein and/or a Cas2 protein is codon optimized for expression of Cas1 and/or Cas2 in a eukaryotic cell. In another embodiment, the cell is altered by inserting the oligo nucleotide sequence into the CRISPR array nucleic acid sequence.

According to another aspect, an engineered, non-naturally occurring cell is provided. In one embodiment, the cell includes a nucleic acid sequence encoding a Cas1 protein and/or a Cas2 protein of a CRISPR adaptation system wherein the cell expresses the Cas1 protein and/or the Cas 2 protein. In another embodiment, the cell includes a CRISPR array nucleic acid sequence including a leader sequence and at least one repeat sequence, wherein the CRISPR array nucleic acid sequence is inserted within genomic DNA of the cell or on a plasmid. In yet another embodiment, the cell further includes at least one oligo nucleotide sequence including a protospacer inserted into the CRISPR array nucleic acid sequence.

According to one aspect, an engineered, non-naturally occurring cell is provided. In one embodiment, the cell includes a nucleic acid sequence encoding a Cas1 protein and/or a Cas2 protein of a CRISPR adaptation system and a CRISPR array nucleic acid sequence including a leader sequence and at least one repeat sequence, wherein the cell expresses the Cas1 protein and/or the Cas 2 protein, and wherein the CRISPR array nucleic acid sequence is inserted within genomic DNA of the cell or on a plasmid.

According to another aspect, a method of inserting a target DNA sequence within genomic DNA of a cell is provided. In one embodiment, the method includes administering the target DNA sequence to the cell including a nucleic acid sequence encoding a Cas1 protein and/or a Cas2 protein of a CRISPR adaptation system and a CRISPR array nucleic acid sequence including a leader sequence and at least one repeat sequence, wherein the cell expresses the Cas 1 protein and/or the Cas2 protein and wherein the CRISPR array nucleic acid sequence is within genomic DNA of the cell or on a plasmid, and wherein the target DNA sequence is administered under conditions within the cell wherein the Cas1 protein and/or the Cas2 protein processes the target DNA and the target DNA is inserted into the CRISPR array nucleic acid sequence adjacent a corresponding repeat sequence. In one embodiment, the target DNA sequence is a protospacer. In another embodiment, the target DNA protospacer is a defined synthetic DNA. In yet another embodiment, the target DNA sequence includes a modified "AAG" protospacer adjacent motif (PAM). In certain embodiments, the step of administering is repeated such that a plurality of target DNA sequences is inserted into the CRISPR array nucleic acid sequence at corresponding repeat sequences. In one embodiment, the nucleic acid sequence encoding the Cas1 protein and/or a Cas2 protein is provided to the cell within a vector.

According to one aspect, a nucleic acid storage system is provided. In one embodiment, the nucleic acid storage system includes an engineered, non-naturally occurring cell including a nucleic acid sequence encoding a Cas1 protein and/or a Cas2 protein of a CRISPR adaptation system and a CRISPR array nucleic acid sequence including a leader sequence and at least one repeat sequence, wherein the cell expresses the Cas1 protein and/or the Cas2 protein and wherein the CRISPR array nucleic acid sequence is within genomic DNA of the cell or on a plasmid. In one embodiment, at least one oligo nucleotide sequence comprises a protospacer inserted into the CRISPR array nucleic acid sequence.

According to another aspect, a method of recording molecular events into a cell is provided. In one embodiment, the method includes administering a DNA sequence or sequences containing information about the molecular events in the cell including a nucleic acid sequence encoding a Cas1 protein and/or a Cas2 protein of a CRISPR adaptation system and a CRISPR array nucleic acid sequence including a leader sequence and at least one repeat sequence, wherein the cell expresses the Cas1 protein and/or the Cas2 protein and wherein the CRISPR array nucleic acid sequence is within genomic DNA of the cell or on a plasmid, and wherein the DNA sequence is administered under conditions within the cell wherein the Cas1 protein and/or the Cas2 protein processes the DNA and the DNA is inserted into the CRISPR array nucleic acid sequence adjacent a corresponding repeat sequence. In certain embodiments, the step of administering is repeated such that a plurality of DNA sequences is inserted into the CRISPR array nucleic acid sequence at corresponding repeat sequences. In one embodiment, a plurality of DNA sequences is administered. In another embodiment, the DNA sequence includes a protospacer. In yet another embodiment, the protospacer is a defined synthetic DNA. In one embodiment, the DNA sequence includes a modified "AAG" protospacer adjacent motif (PAM). In certain embodiments, the molecular events comprise transcriptional dynamics, molecular interactions, signaling pathways, receptor modulation, calcium concentration, and electrical activity. In one embodiment, the recorded molecular events are decoded. In another embodiment, the decoding is by sequencing. In yet another embodiment, the decoding by sequencing comprises using the order information from pairs of acquired spacers in single cells to extrapolate and infer the order information of all recorded sequences within the entire population of cells. In one embodiment, the plurality of DNA sequences is recorded into a specific genomic locus of the cell in a temporal manner. In another embodiment, the DNA sequence is recorded into the genome of the cell in a sequence and/or orientation specific manner. In one embodiment, the DNA sequence includes a modified "AAG" protospacer adjacent motif (PAM). In another embodiment, the modified PAM is recognized by specific cas1 and/or cas2 mutants. In one embodiment, the protospacer is barcoded.

According to another aspect, a system for in vivo molecular recording is provided. In one embodiment, the system includes an engineered, non-naturally occurring cell including a nucleic acid sequence encoding a cas1 protein and/or a cas2 protein of a CRISPR adaptation system and a CRISPR array nucleic acid sequence including a leader sequence and at least one repeat sequence, wherein the cell expresses the cas1 protein and/or the cas 2 protein and wherein the CRISPR array nucleic acid sequence is within genomic DNA of the cell or on a plasmid. In certain embodiments, the system records in single or multiple modalities. In one embodiment, the multiple modality recordation comprises altering Cas1 PAM recognition through directed evolution by specific cas1 or cas2 mutants.

According to one aspect, the disclosure provides a kit of directed recording of molecular events into a cell comprising an engineered, non-naturally occurring cell including a nucleic acid sequence encoding a cas1 protein and/or a cas2 protein of a CRISPR adaptation system and a CRISPR array nucleic acid sequence including a leader sequence and at least one repeat sequence, wherein the cell expresses the cas1 protein and/or the cas 2 protein and wherein the CRISPR array nucleic acid sequence is within genomic DNA of the cell or on a plasmid.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A shows schematic of the minimal elements of the type I-E CRISPR acquisition system, used including Cas1, Cas2, and array with leader (L), repeat (R), and spacer (S) along with PCR detection of an expanded array following the overnight induction of Cas1-Cas2. FIG. 1B shows origin of new spacers (plasmid or genome) mean±SEM. FIG. 1C shows genome- and plasmid-derived spacers following overnight induction are mapped back to the approximate location of their protospacer (marked in red). FIG. 1D shows array expansion (top) and specific acquisition of synthetic oligo protospacer (bottom) following electroporation. Top schematic shows the experimental outline. Schematics under each gel show specific PCR strategy. FIG. 1E shows sequence-specific acquisition in either the forward (top) (SEQ ID NO: 1) or reverse (bottom) orientation following electroporation with various single- and double-stranded oligos. 5'PT indicates phosphorothioate modifications to the oligos at the 5' ends. FIG. 1F shows time course of expansion following electroporation, mean±SEM. FIG. 1G shows percent of arrays expanded by spacer source as a function of electroporated oligo concentration, mean±SEM. FIG. 1H shows position of new spacers relative to the leader, mean±SEM. FIG. 1I shows size of new spacers in base-pairs, mean±SEM. All gels are representative of ≥3 biological replicates, * indicates p<0.05, additional statistical details in FIG. 21.

FIG. 2A depicts initial experiments (FIGS. 1A-1C, utilizing overnight induction and Sanger sequencing analysis) showing position of new spacers acquired from the genome and plasmid relative to the leader, mean±SEM. FIG. 2B depicts initial experiments showing size of new spacers acquired from the genome and plasmid in base-pairs, mean±SEM. FIG. 2C depicts array expansion with or without electroporation. Top schematic shows the experimental outline. Schematic under the gel shows PCR strategy. FIG. 2D depicts PCR assay checking for sequence-specific acquisition of DNA, RNA, or DNA-RNA hybrid oligo protospacers. FIG. 2E depicts gel electrophoresis analysis of one sequence-specific spacer replicate from FIG. 1G. Numbers above the gel indicate oligo concentration (µM). All gels are representative of ≥3 biological replicates, additional statistical details in FIG. 21.

FIGS. 3A-3J depicts PAMs modifying the efficiency and orientation of spacer acquisition. FIG. 3A shows genome- (count/10 kb) and plasmid- (coverage/base) derived spacers mapped to their protospacer location on the forward (purple)

or reverse (green) strands. FIG. 3B shows direction of oligo-derived spacers in the forward (purple) or reverse (green) orientation, mean±SEM. FIG. 3C shows representative sequence pLOGO (J. P. O'Shea, M. F. Chou, S. A. Quader, J. K. Ryan, G. M. Church, D. Schwartz, pLogo: a probabilistic approach to visualizing sequence motifs. Nat Methods 10, 1211-1212 (2013); published online EpubDecember (10.1038/nmeth.2646)) generated based on 896 unique genome- and plasmid-derived protospacers. Five bases of the protospacer are included at each end of the spacer. FIG. 3D shows plot of the summed spacer coverage mapped to the plasmid among three replicates at each nucleotide for a 553 nucleotide stretch. Carrots demarcate canonical PAMs on the forward (purple) or reverse (green) strand. Scale bar is 33 bases. Individual replicates are shown below. FIG. 3E shows percent of arrays expanded by spacer source for different oligo protospacers, mean±SEM. FIG. 3F shows ratio of oligo-derived spacers acquired in the forward vs. reverse orientation for different oligo protospacers, mean±SEM. FIGS. 3G-3J show normalized representation of oligo-derived spacers (SEQ ID NOS 1-4, respectively, in order of appearance) by base acquired in the forward and reverse direction for each oligo. Bars in FIG. 3I and FIG. 3J are 33 bases long to show dominant and minority spacers drawn from the oligo protospacers. For all panels, * indicates $p<0.05$, additional statistical details in FIG. 21.

FIGS. 4A-4F are related to FIGS. 3A-3J. FIG. 4A shows frequency of protospacer acquisition as normalized count for all potential plasmid protospacers containing a 5' AAG PAM ranked by count, highest to lowest, mean±SEM. Also highlighted are selected protospacers psH, psM, and psL. FIG. 4B shows GC percentage of plasmid protospacers, shown in the same ranked order as A. FIG. 4C shows free energy (delta G) of plasmid protospacers, shown in the same ranked order as A. FIG. 4D shows sequence-specific acquisition of oligo-derived spacers, testing the three selected protospacers (psH, psM, and psL). Cas1-Cas2 were expressed from an alternate plasmid not containing any of the tested protospacer sequences. Additionally, tests of psL with 15 base flanking regions from psH (psL/H) and psH with 15 base flanking regions from psL (psH/L) are also shown. FIG. 4E shows nucleotide sequences (SEQ ID NOS 5-9, respectively, in order of appearance) of the oligos used in FIG. 4 D and FIG. 4F. FIG. 4F shows percent of expanded arrays with each of the indicated oligo-derived spacers, mean±SEM. All gels are representative of ≥3 biological replicates, for F, * indicates $p<0.05$, additional statistical details in FIG. 21.

FIGS. 5A-5C are related to FIGS. 3A-3J. FIG. 5A shows gel electrophoresis analysis of the experiment presented in FIGS. 3E-3J showing sequence-specific spacer acquisition in both orientations (SEQ ID NOS 3 and 4, respectively, in order of appearance). Schematics below each gel show PCR strategy. FIG. 5B shows sequence-specific acquisition of spacers from a 58-mer oligo protospacer independent of Cas2 nuclease activity (mutant E9Q). FIG. 5C shows gel electrophoresis analysis of all spacer acquisitions and sequence-specific acquisitions when electroporated with a 33-mer or 58-mer oligo protospacer. Both overall expansion and sequence-specific acquisition depend on the combined expression of both Cas1 and Cas2. All gels are representative of ≥3 biological replicates, additional statistical details in FIG. 21.

FIG. 6A shows experimental outline of the 1×3 recording. Three synthetic protospacers were electroporated into a culture expressing Cas1-Cas2 over three days (one protospacer each day). Time points at which cells were sampled for sequencing are labeled 1-3. FIG. 6B shows schematic illustrating the analysis, which considers all pairwise ordering of new spacers. G/P denotes a spacer derived from the genome or plasmid. Ordering rules are shown below. In the case of i=j, * indicates a tolerance within ±20% of the mean of both values. FIG. 6C shows results of the tested rule are shown for each permutation. Green indicates pass, red indicates fail. Only one permutation passed all rules and that permutation matched the actual order in which the oligos were electroporated. FIG. 6D shows single, double, and triple expansions as at each sample point. FIG. 6E shows expanded arrays with spacers from each of the indicated rounds during each sample points. FIGS. 6F-6I show observed counts for the ordering of pairwise comparisons (a-l) that were used to decipher the correct sequence of protospacer electroporation in C. Additional statistical details are in FIG. 21.

FIGS. 7A-7F depict a molecular recording over time. FIG. 7A shows experimental outline of the 3×5 recording. Over five days, three sets of five oligo protospacers (fifteen elements) were electroporated (one protospacer from each of the three sets each day) into cells expressing Cas1-Cas2. Time points at which cells were sampled for sequencing are numbered 1-6. FIG. 7B shows schematic illustrating all possible pairwise ordering of new spacers. G/P denotes a spacer derived from the genome or plasmid. Ordering rules are shown below. In the case of y=z, * indicates a tolerance within ±20% of the mean of both values. FIG. 7C shows at each of the six sample points (marked in A), percent of all arrays expanded with synthetic spacers from each of the indicated rounds, mean±SEM. FIG. 7D shows single, double, and triple expansions for each round, mean±SEM. FIG. 7E shows percent of all expansions at sample point six, broken down by electroporation round and set. Open circles are individual replicates, filled bars are mean±SEM. FIG. 7F shows results of ordering rule analysis for one replicate across each set. For all 120 permutations, results of the tested rule are shown (green indicates pass, red indicates fail). For all sets, only one permutation passed all rules and in every case that permutation matched the actual order in which the oligos were electroporated (as indicated by check mark). Additional statistical details are in FIG. 21.

FIGS. 8A-8E depict directed evolution of PAM recognition. FIG. 8A shows schematic of the directed evolution approach. FIG. 8A discloses SEQ ID NOS 10 and 11, respectively, in order of appearance. FIG. 8B shows testing of selected mutants, plotting 5' AAG versus non-AAG PAM protospacers normalized to count per 100,000 sequences. Scatter plot shows 65 induced mutants (open black circles), three induced wild-type replicates (open green circles), an uninduced wild-type (open red circle), the average of the induced mutants (filled black circle), and the average of the induced wild-types (filled green circle) ±SEM. Scatter plot to the right is an inset of the larger plot. FIG. 8C shows heatmap of protospacer PAM frequency over the entire sequence space for wild type Cas1-Cas2 (wt), mutants that increase or maintain AAG PAM specificity (m-27 and m-24), and mutants that lose AAG PAM specificity (m-74, m-80, m-89). Numbers in the upper right correlate to numbers in B. FIG. 8D shows a subset of selected mutants re-assayed in triplicate as well as a subset of single point mutants chosen from the original selection. All points are the average of three replicates ±SEM. FIG. 8E shows crystal structure of Cas1-Cas2 complex bound to a protospacer (see J. Wang, J. Li, H. Zhao, G. Sheng, M. Wang, M. Yin, Y. Wang, Structural and Mechanistic Basis of PAM-Dependent Spacer Acquisition in CRISPR-Cas Systems. Cell 163, 840-

853 (2015); published online EpubNovember 5 (10.1016/j.cell.2015.10.008)). Inset highlights, in magenta, residues in the Cas1 active site that (when mutated) decrease PAM specificity. The protospacer PAM complementary sequence (T30 T29 C28, numbering as in PDB ID 5DQZ) is also noted. Additional statistical details are in FIG. 21.

Figure 7A:
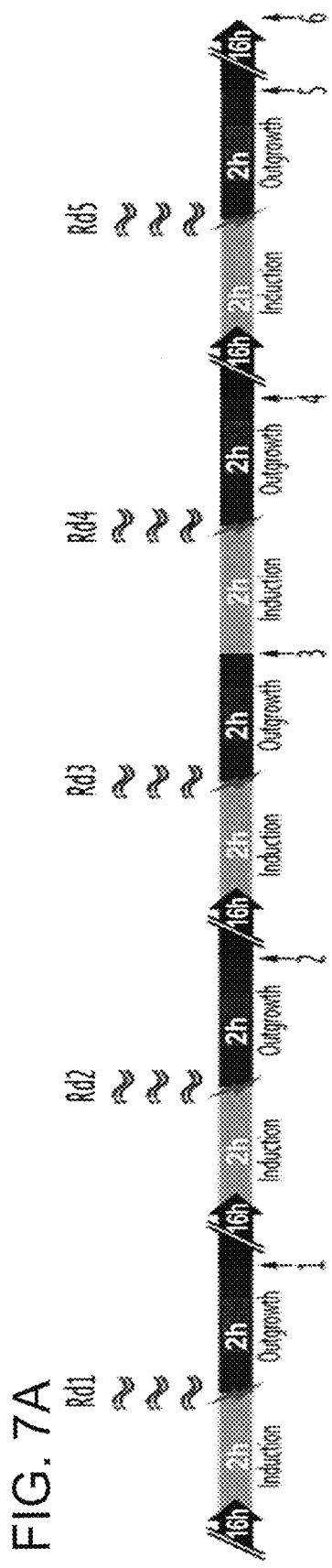
Figure 8A:
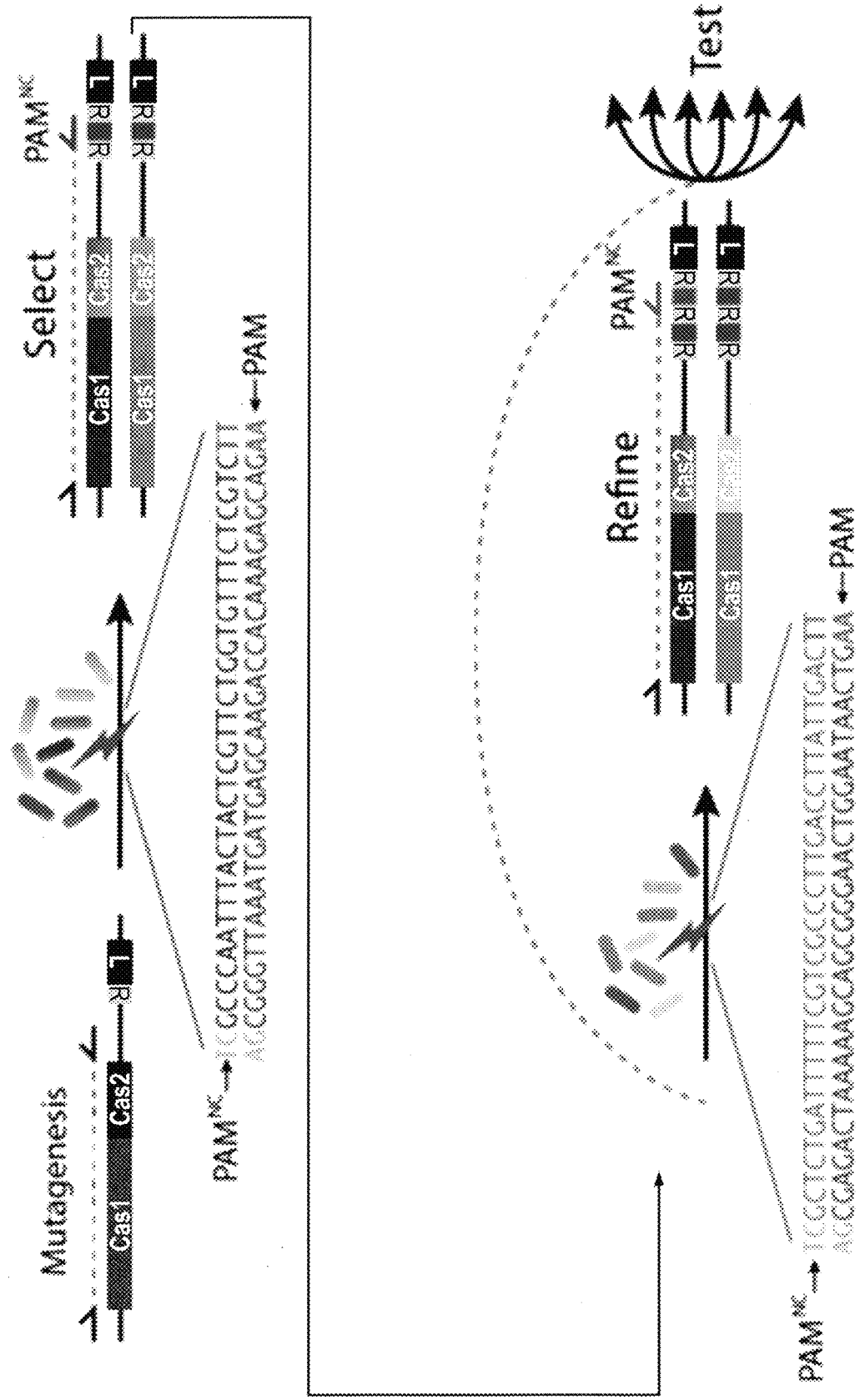
Figure 8C:
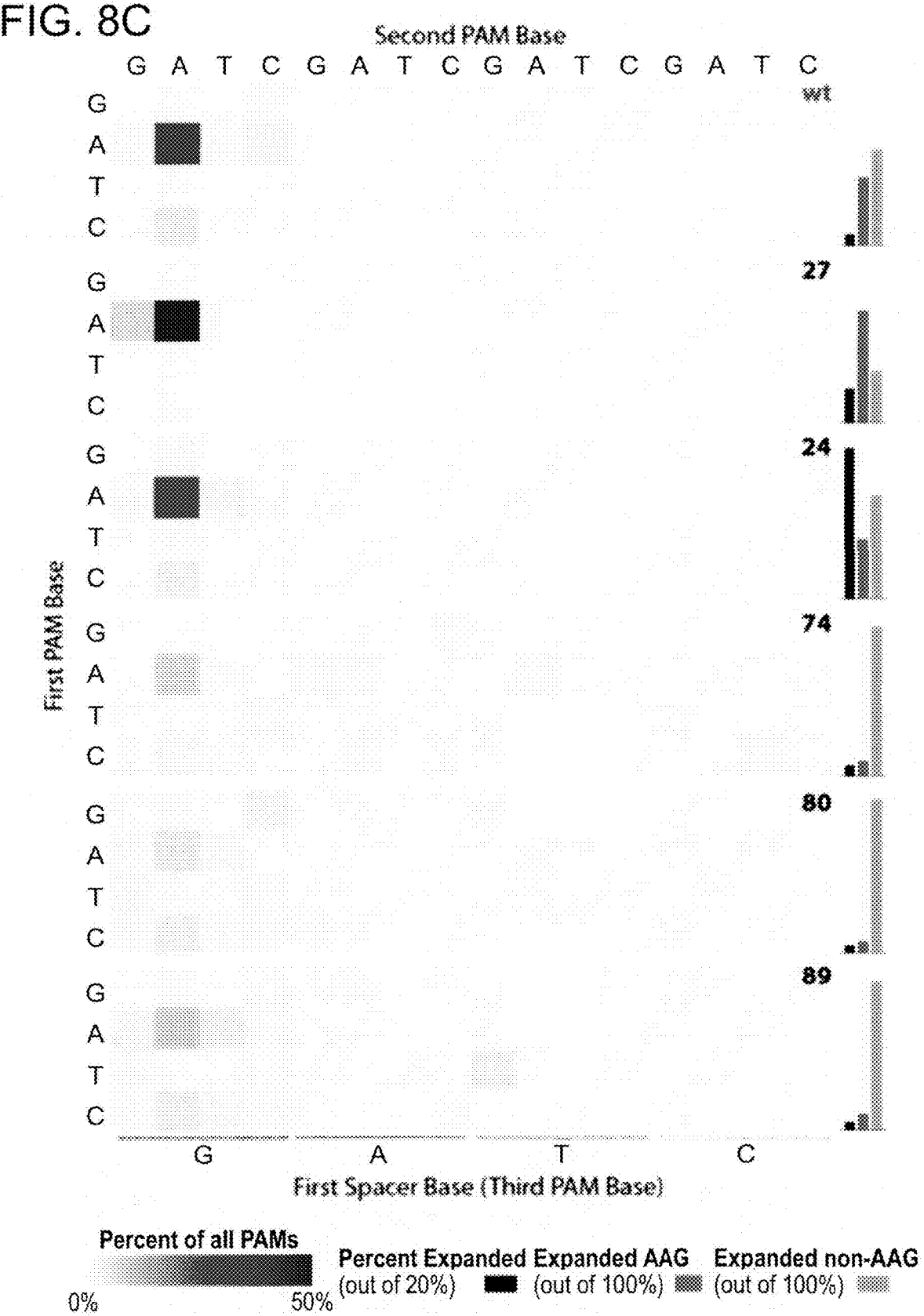
Figure 8D:
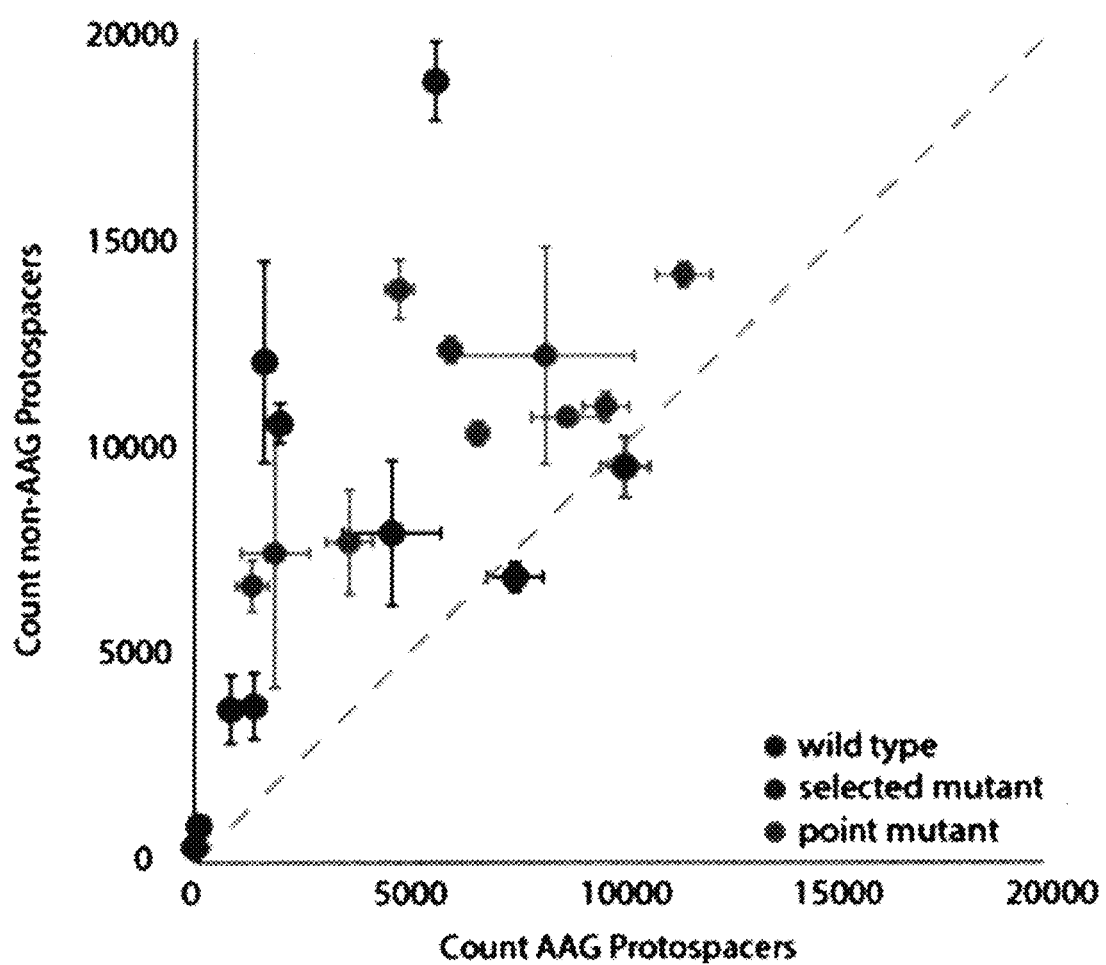
Figure 9A:
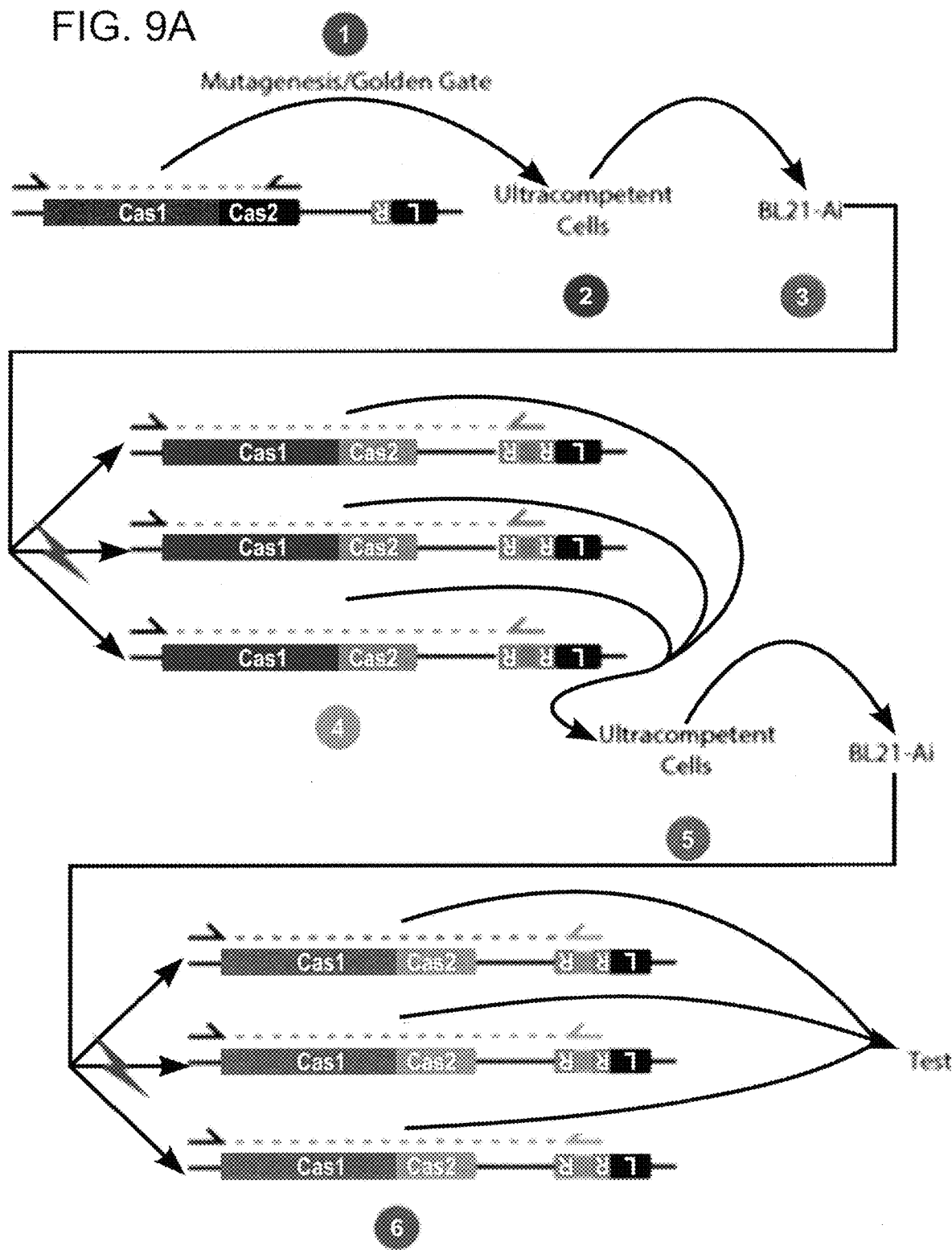
Figure 9C:
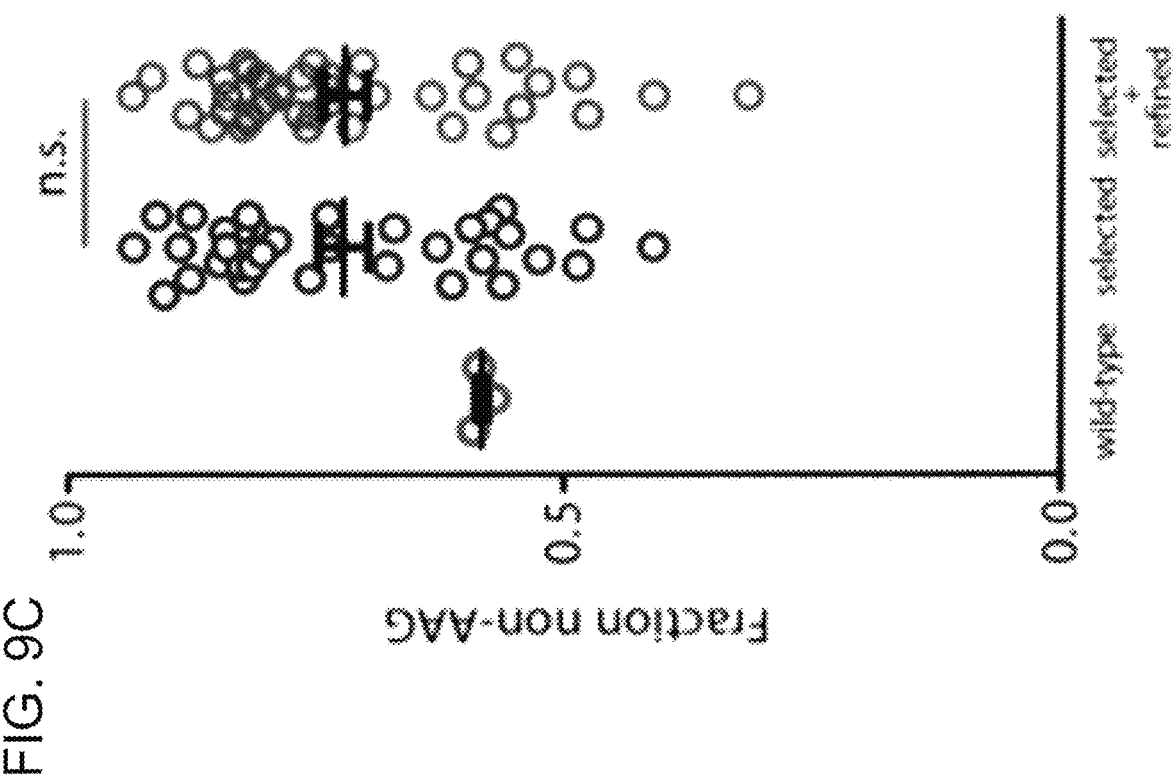
Figure 9B:
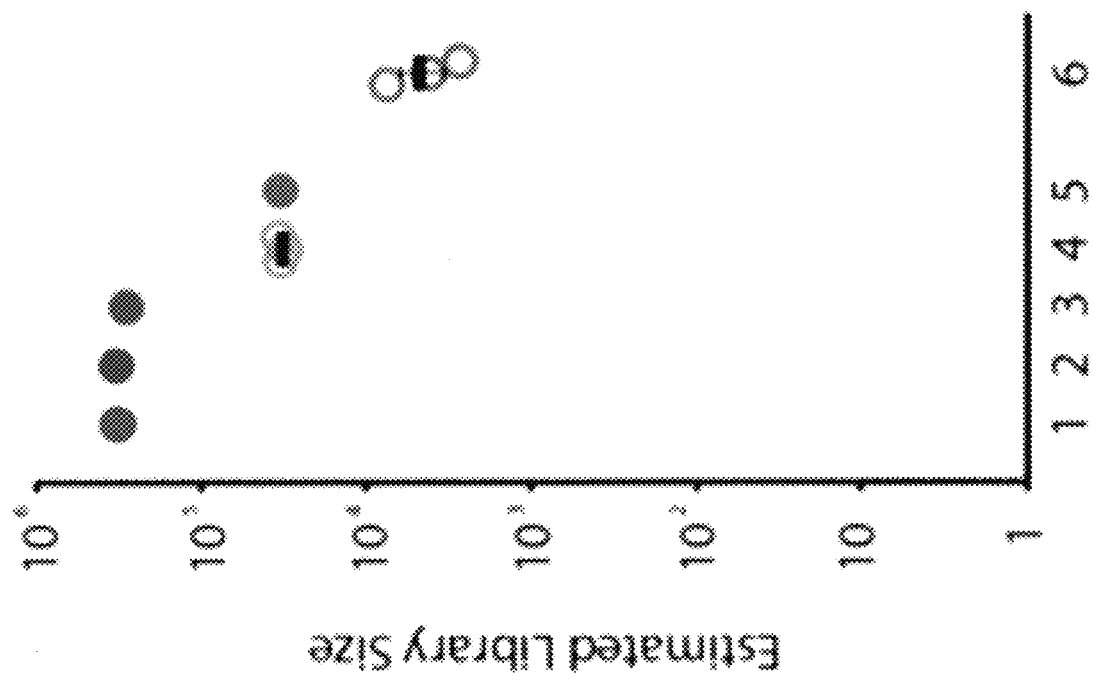
Figure 9D:
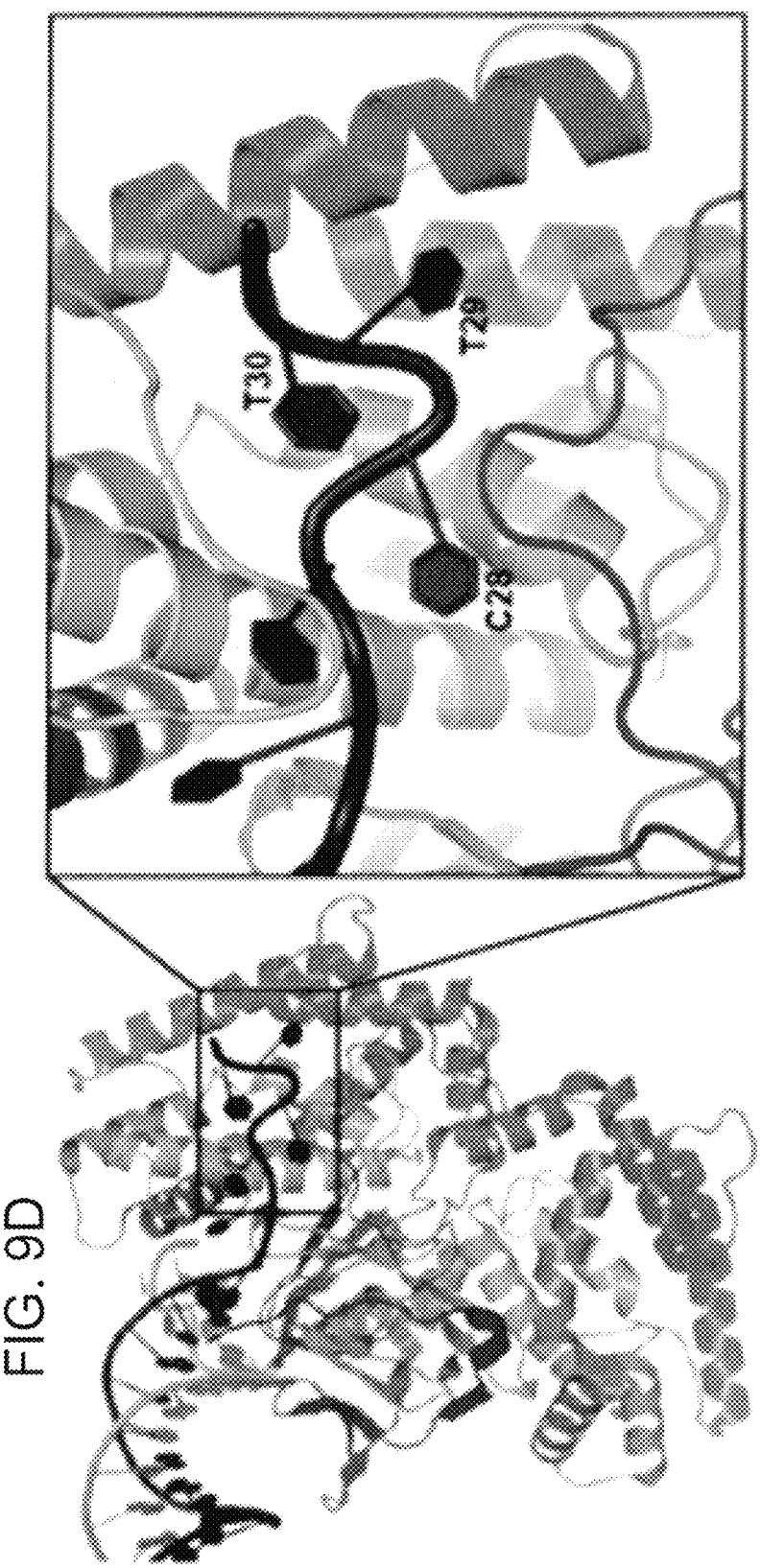
Figures 1, 9E:
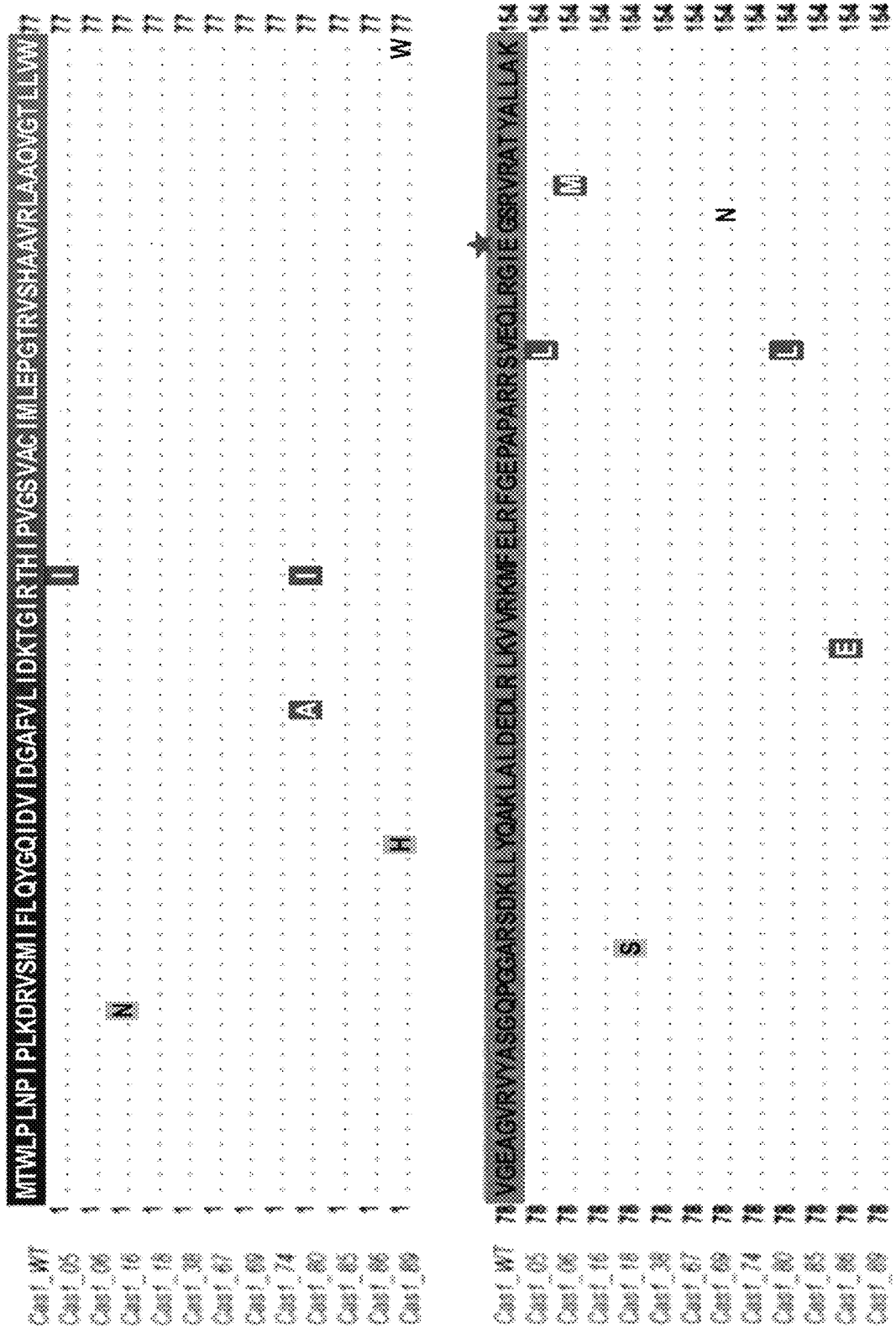
Figures 2, 9E:
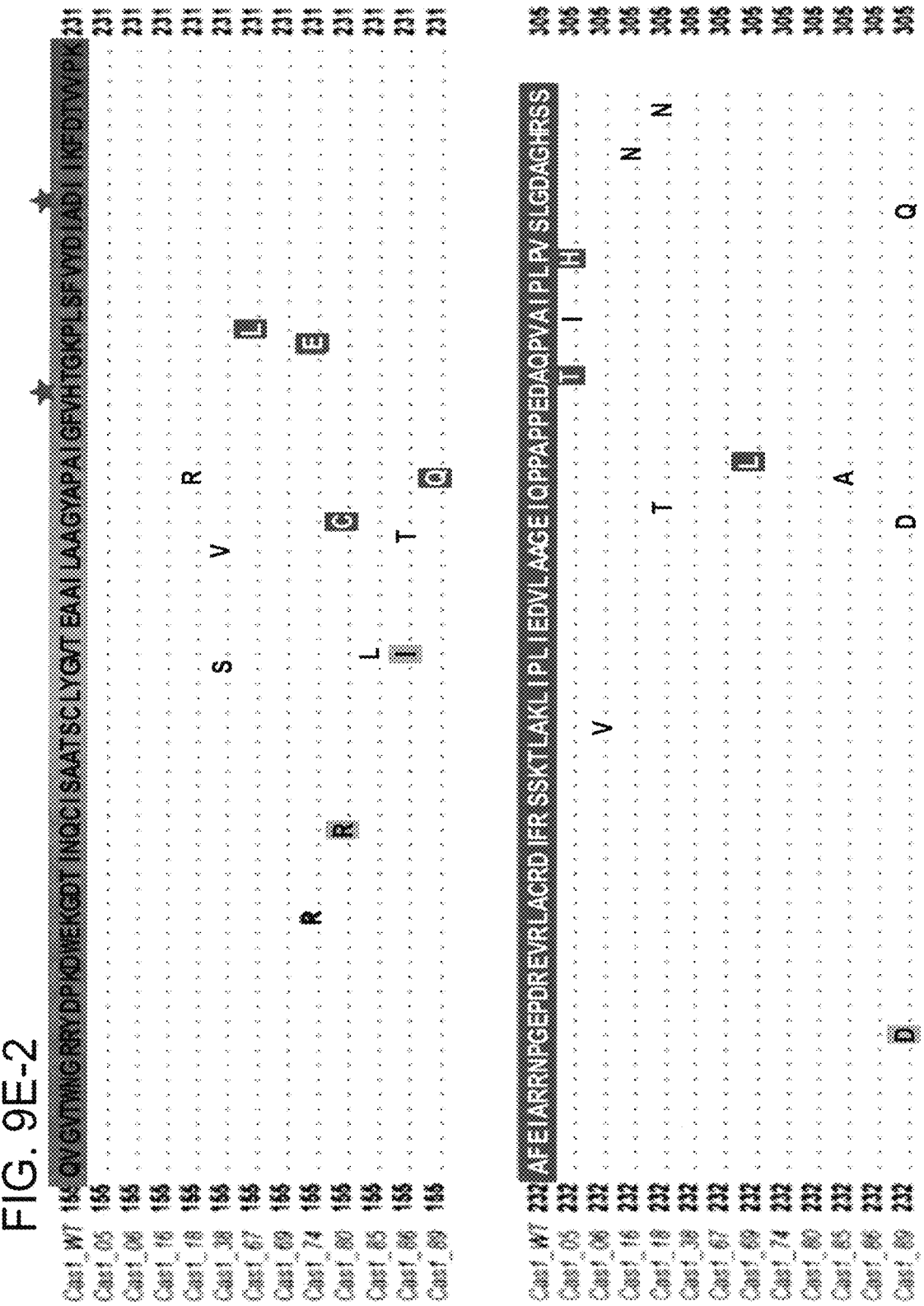
FIGS. 2A-2E are related to FIGS. 1A-1I.

FIGS. 9A-9E-2 are related to FIGS. 8A-8E. FIG. 9A shows expanded schematic of the directed evolution approach, showing cloning steps and parallelized protospacer electroporations. FIG. 9B shows estimated library sizes based on non-parametric species estimation of sequence diversity of fragmented amplicons (see R. K. Colwell, J. A. Coddington, Estimating terrestrial biodiversity through extrapolation. Philosophical transactions of the Royal Society of London. Series B, Biological sciences 345, 101-118 (1994); published online EpubJuly 29 (10.1098/rstb.1994.0091)). Numbers along the x-axis correlate to points marked in FIG. 9A. For points 4 and 6, open circles are individual parallel libraries and filled bar is mean±SEM. FIG. 9C shows fraction of all protospacers with a non-AAG PAM for the mutants presented in FIG. 3B. Open circles are individual replicates/mutants, filled bars are mean±SEM. No significant difference was found between those mutants that were tested immediately after the first selection and those mutants that underwent an additional round of refinement (see FIG. 7A). FIG. 9D shows crystal structure of Cas1 dimer bound to protospacer colored in chainbow from N-terminus (blue) to C-terminus (red). Inset shows local structure around the 5' TTC PAM complementary nucleotides of the protospacer (PDB ID 5DQZ). FIGS. 9E-1 and 9E-2 show multiple sequence alignment of selected Cas1 mutants (SEQ ID NOS 13-24, respectively, in order of appearance) that acquired protospacers with non-AAG PAMs at >85% frequency. The wild type sequence (SEQ ID NO: 12) is colored as in E. Red stars denote catalytic residues. Mutations highlighted in magenta and grey were also assayed independently as single point mutants and produced a greater or less than 10% increase in acquiring non-AAG PAM protospacers (relative to wild type), respectively. Non-highlighted residues were not independently assayed. Additional statistical details are in FIG. 21.

Figure 10A:
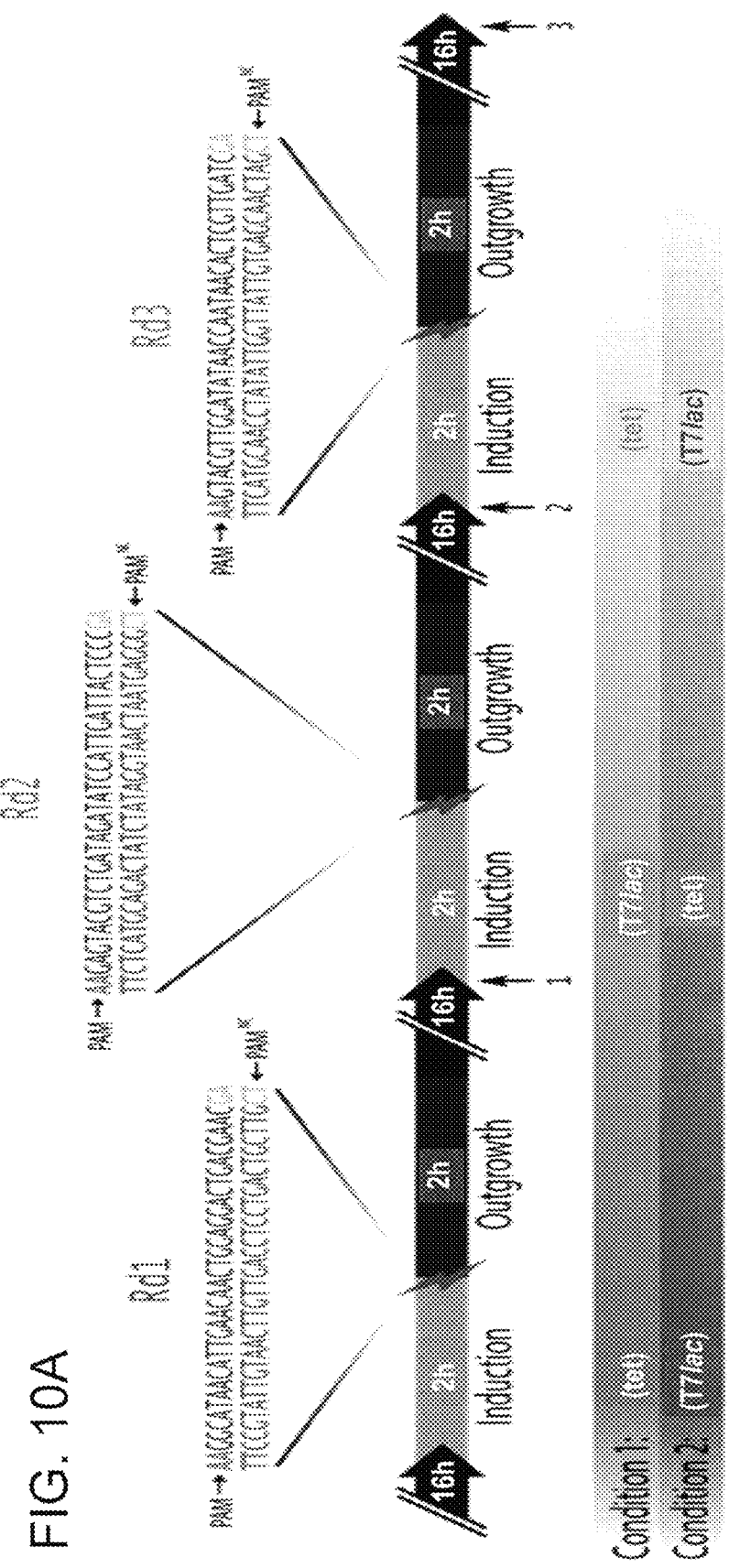
Figure 10B:
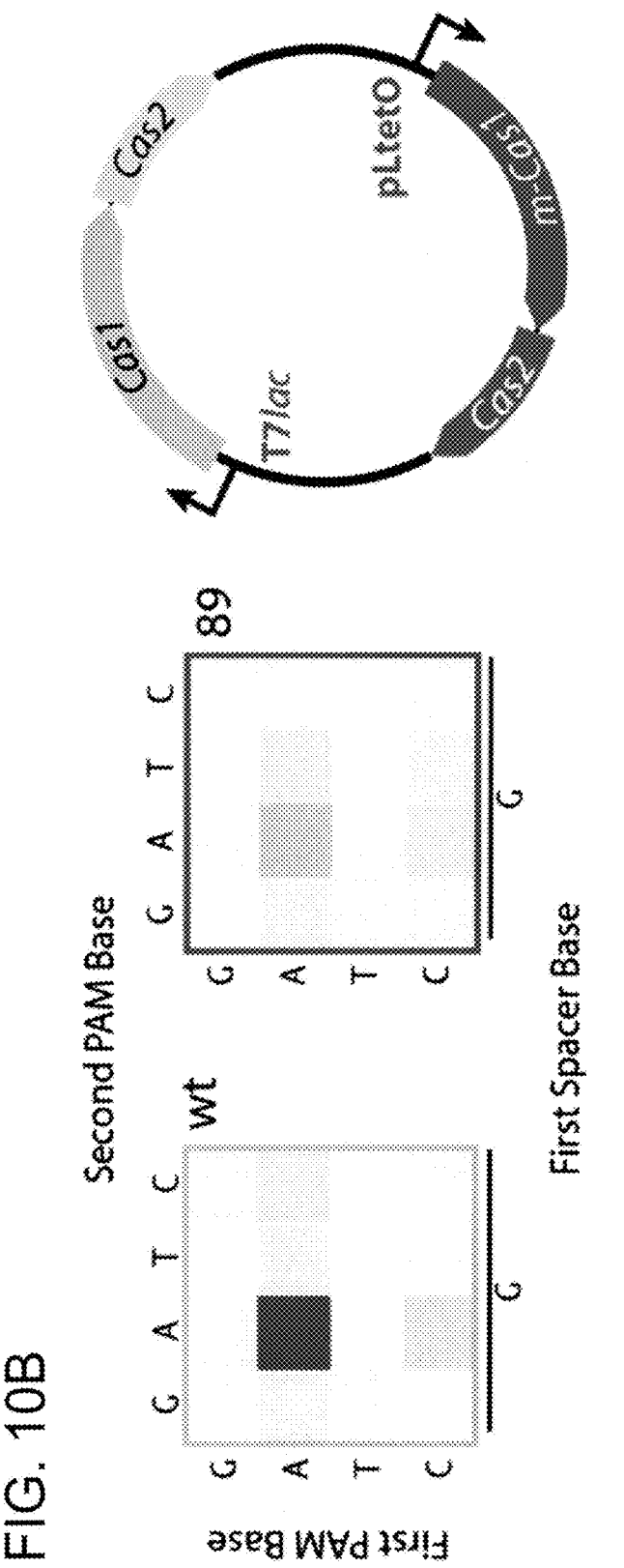
Figure 10D:
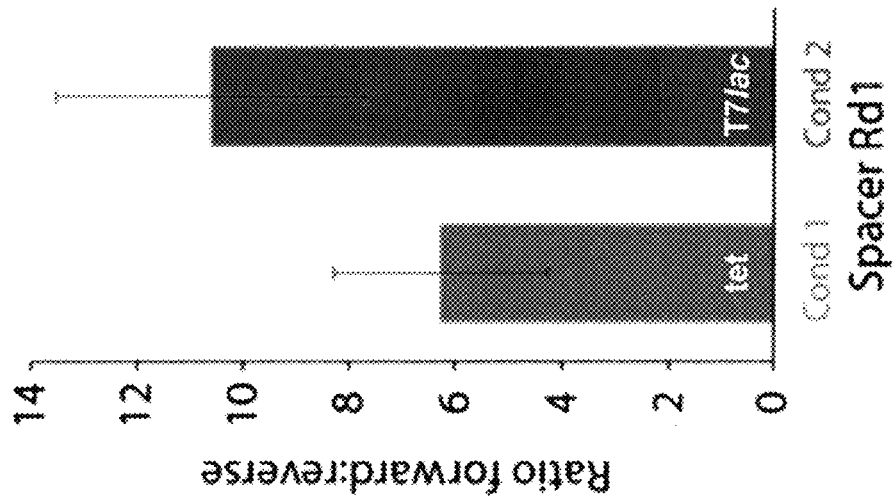
Figure 10C:
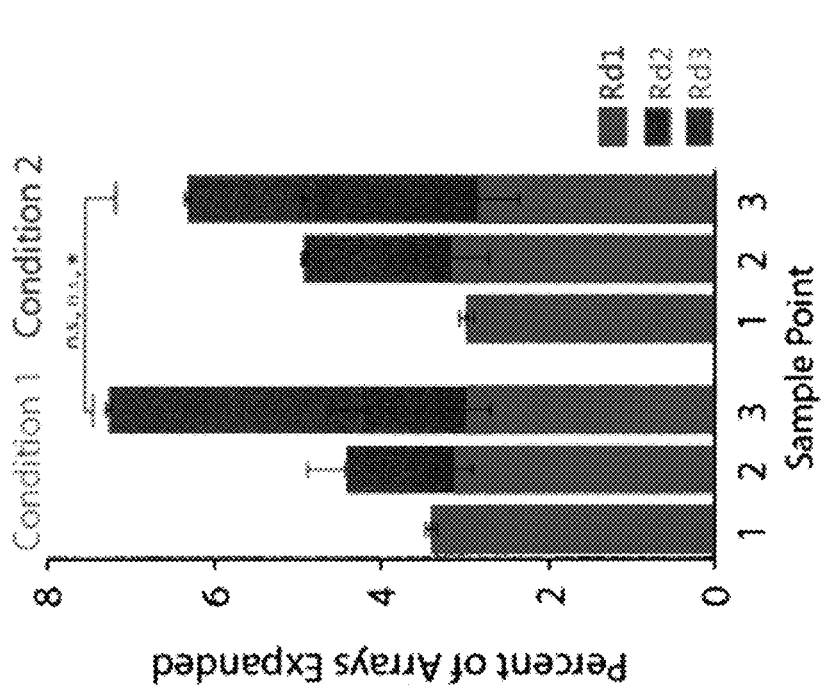
Figure 10E:
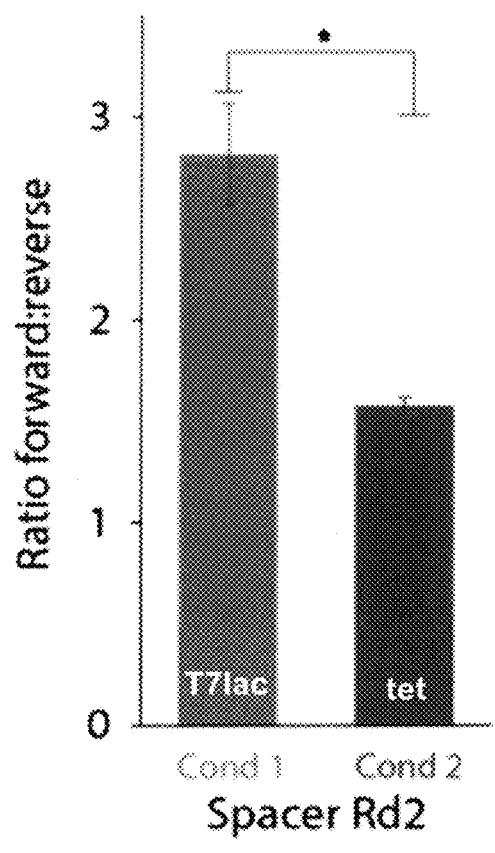
Figure 10F:
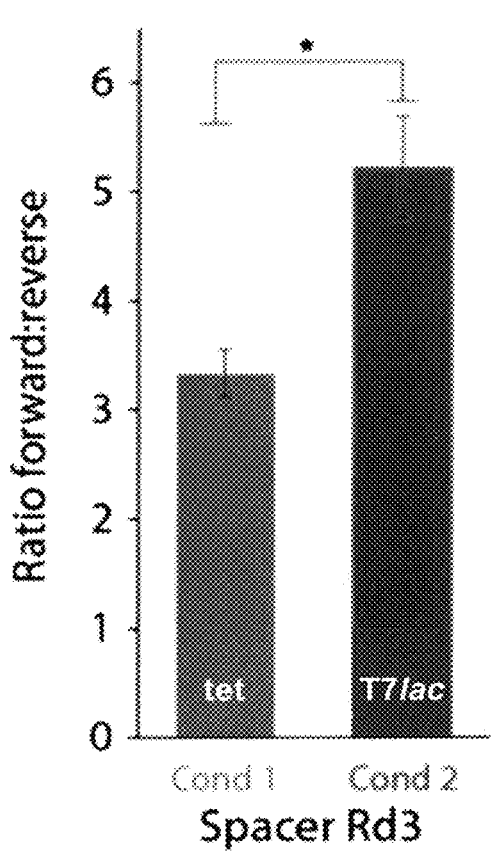

FIGS. 10A-10G depict recording with an additional modality. FIG. 10A shows outline of the recording process. Three different synthetic protospacers (SEQ ID NOS 25-27, respectively, in order of appearance) (each containing a 5' AAG PAM on the forward strand, and a 5' TCG PAM on the reverse) were electroporated over three days (one protospacer each day) into two bacterial cultures under different induction conditions (shown below timeline). Sampling time points are numbered 1-3. FIG. 10B shows schematic of the plasmid construct used, showing wild-type and PAMNC mutant (m-89) Cas1-Cas2 driven by independently inducible promoters (T7lac and pLtetO, respectively). The heatmap shows 5' PAM specificity for wild-type (boxed in yellow) and mutant m-89 (boxed in red). FIG. 10C shows at each of the three sample points (marked in B), percent of expanded arrays with spacers from each of the indicated rounds for the two conditions, mean±SEM. FIGS. 10D-10F show ratio of synthetic spacers acquired in the forward versus reverse orientation for each round under each condition, mean±SEM. FIG. 10G shows ratio of forward to reverse integrations normalized to the sum of both possible orientations for each of the two conditions, mean±SEM. For all panels, * indicates p<0.05, additional statistical details are in FIG. 21.

Figure 11:
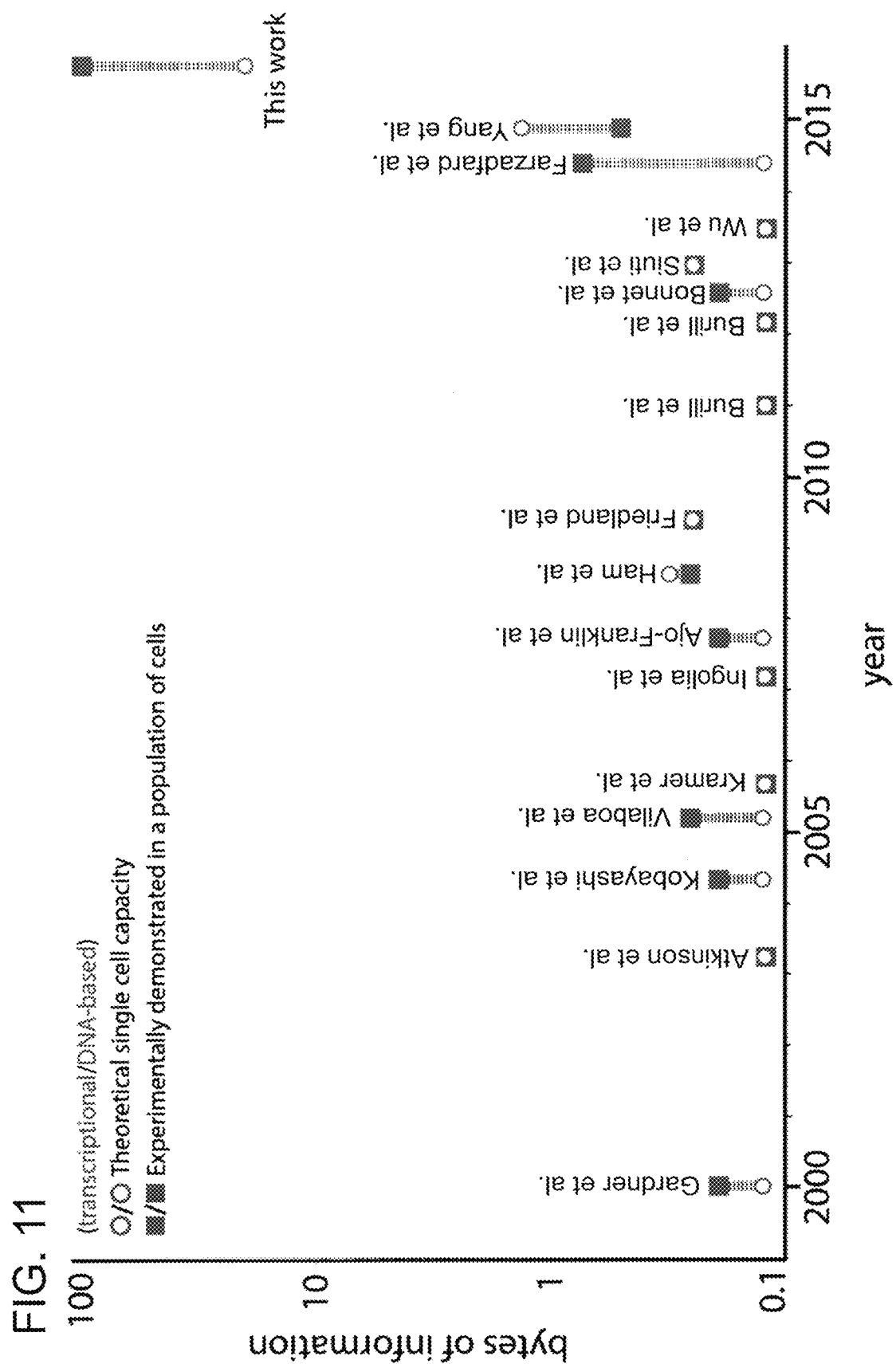

FIG. 11 depicts comparison of cellular recording strategies. For a selection of previous publications, the amount of information that was encoded (in bytes) is plotted against the publication date. Each publication has two points, the theoretical maximum number of bytes that could have been encoded in a single cell given the specific synthetic tools and analyses employed (circles), and the maximum number of bytes encoded in a population of cells in a single reported experiment (squares). Color differentiates approaches that utilize transcriptional encoding (magenta) from approaches that encode information in DNA (green).

Figure 12A:
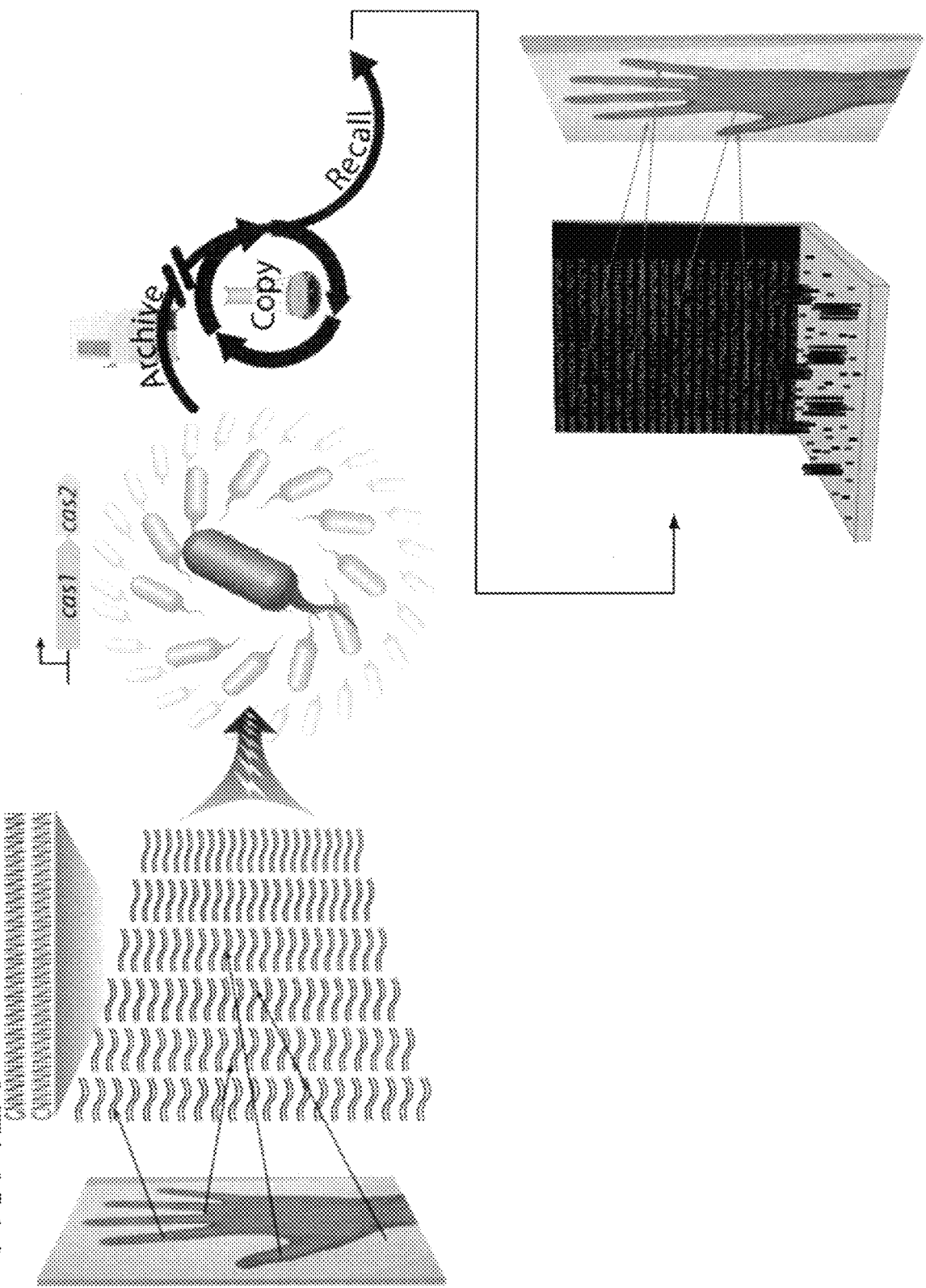
Figure 12E:
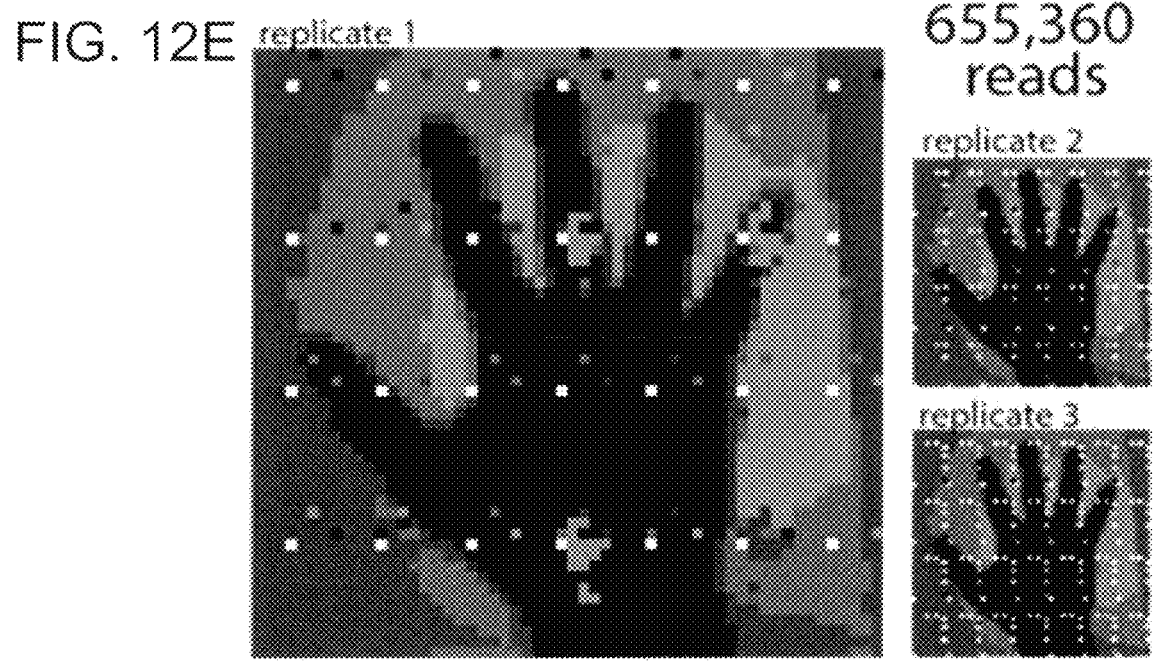
Figure 12F:
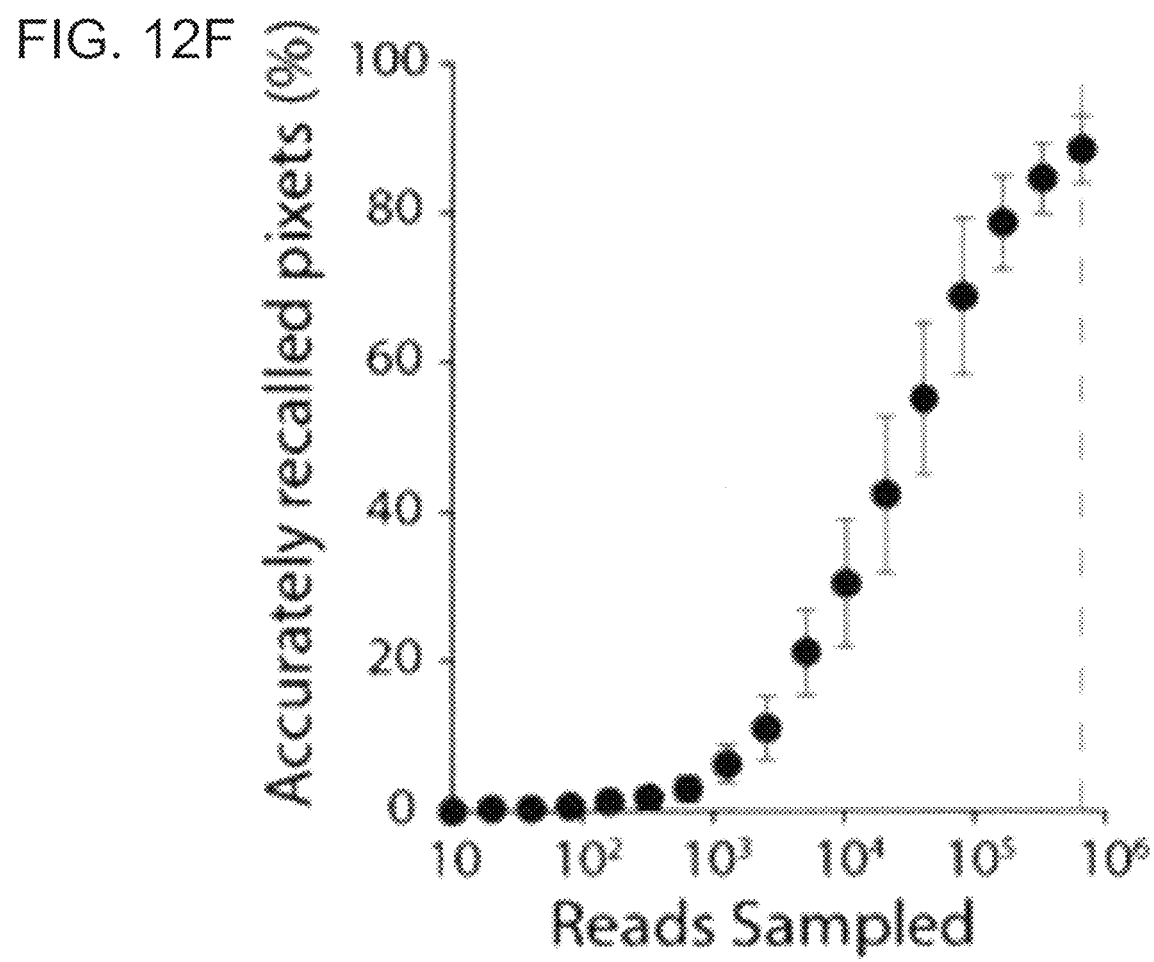

FIGS. 12A-12H are directed to recording an image into the genome. FIG. 12A shows that pixel values are encoded across many protospacers, which are electroporated into a population of bacteria that overexpress Cas1 and Cas2 to store the image data. These bacteria can be archived, propagated, and eventually sequenced to recall the image. FIG. 12B shows an initial image to be encoded. FIG. 12C shows a nucleotide-to-color encoding scheme. FIG. 12D shows two examples of the encoding scheme. Sequence at top shows the protospacer linear view with pixet code followed by pixel values, which are distributed across the image. Bottom right shows the same protospacer in minimal hairpin format for electroporation. FIG. 12D discloses SEQ ID NOS 28-31, respectively, in order of appearance. FIG. 12E shows results of the experiment. Three replicates shown at a depth of 655,360 reads. FIG. 12F shows percentage of accurately recalled pixets as a function of read depth. FIG. 12G shows examples of the images that result from down-sampling the sequencing reads. FIG. 12H shows effect of supplying fewer oligos on recall accuracy.

Figure 13A:
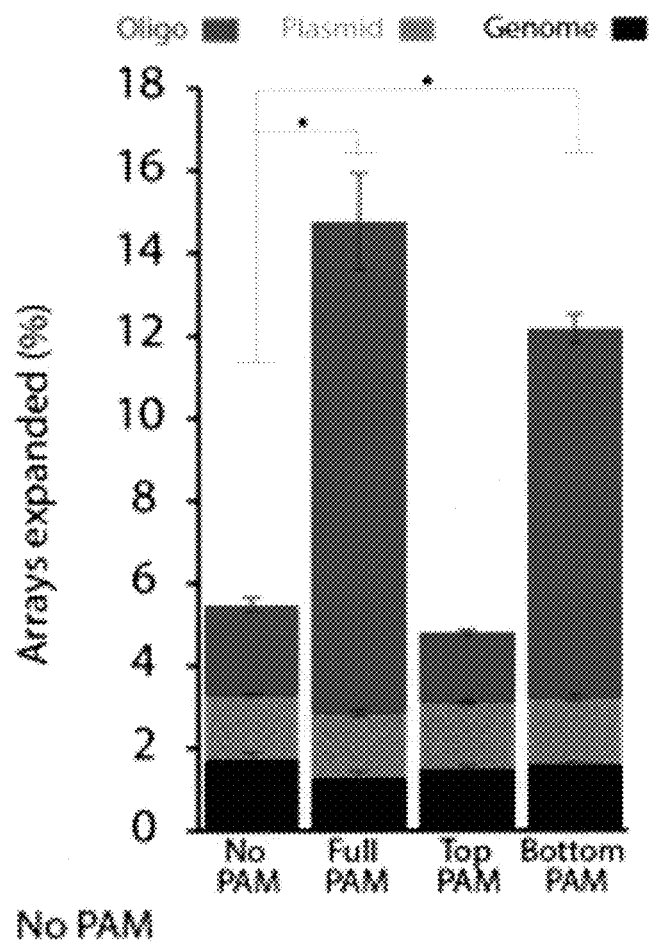
Figure 13B:
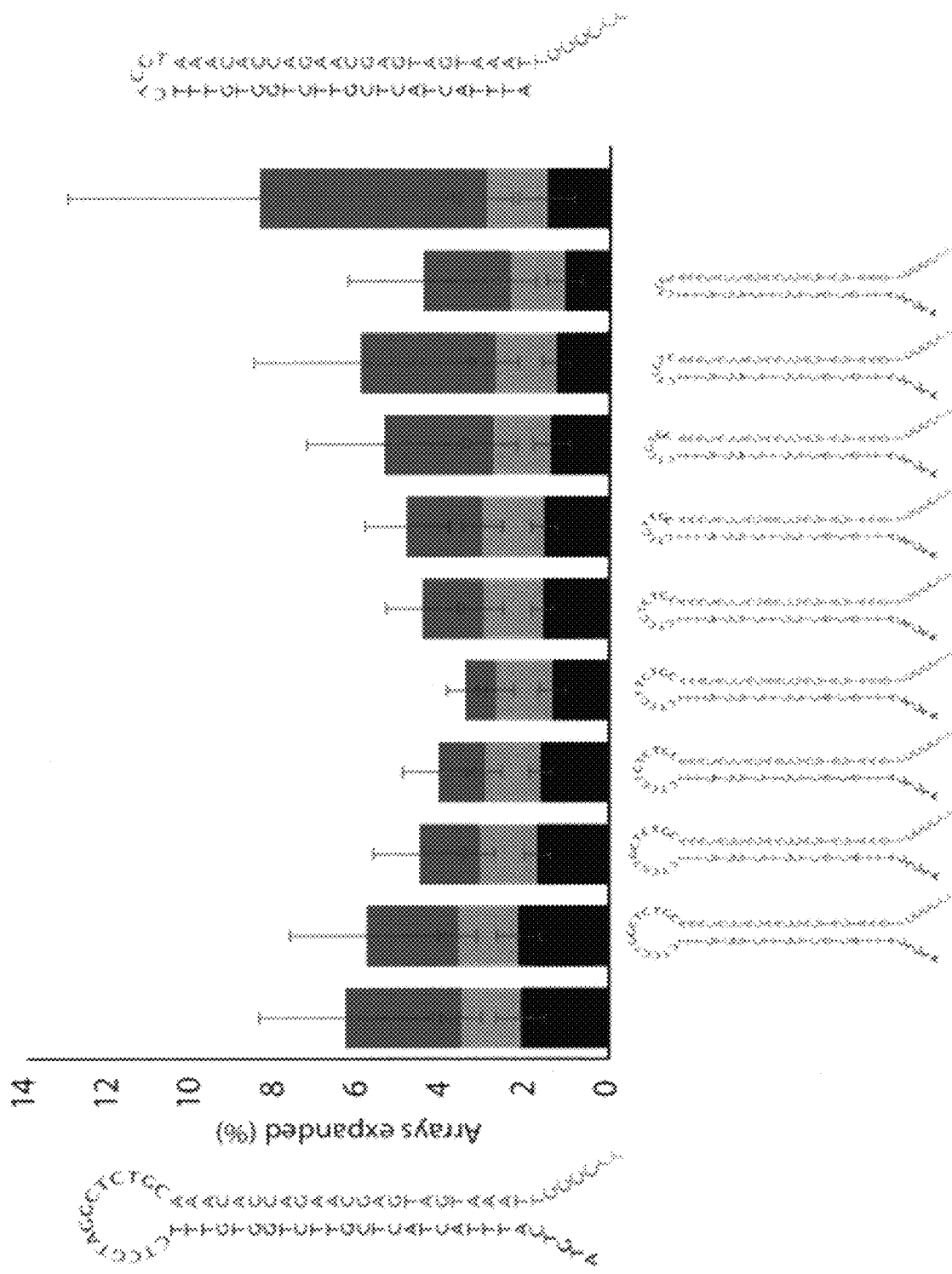
Figure 13C:
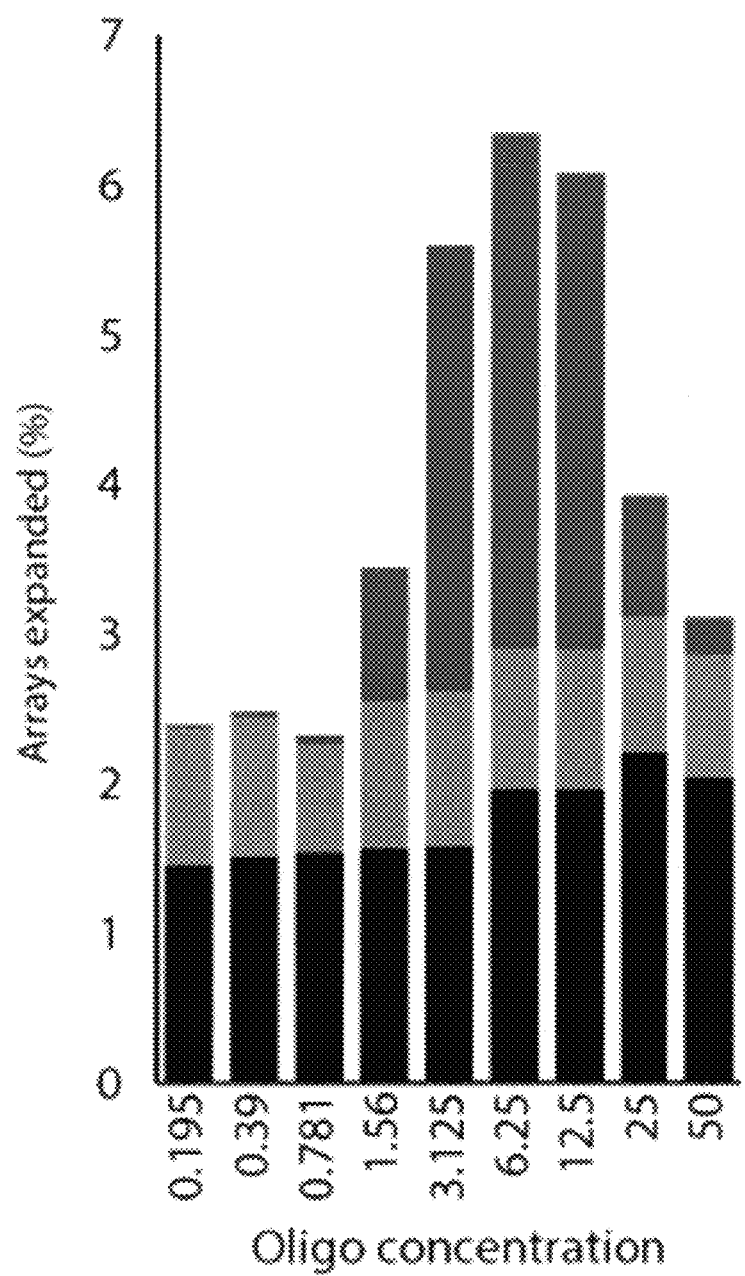

FIGS. 13A-13C are related to FIG. 12A-12H. FIG. 13A shows percent of arrays expanded following electroporation of the sequences indicated below (SEQ ID NOS 1, 2, 2, 32, 1, and 33, respectively, in order of appearance) aimed at testing PAM inclusion on both the top and bottom strands, broken down by protospacer origin. * indicates p<0.05. FIG. 13B shows percent of arrays expanded following electroporation of the sequences indicated to the left (SEQ ID NO: 34), right (SEQ ID NO: 44), and below (SEQ ID NOS 35-43, respectively, in order of appearance) aimed at finding a minimal functional hairpin protospacer, broken down by protospacer origin. FIG. 13C shows percent of arrays expanded following electroporation of different concentrations of the minimal hairpin oligo protospacer, broken down by protospacer origin.

Figures 14A, 14B:
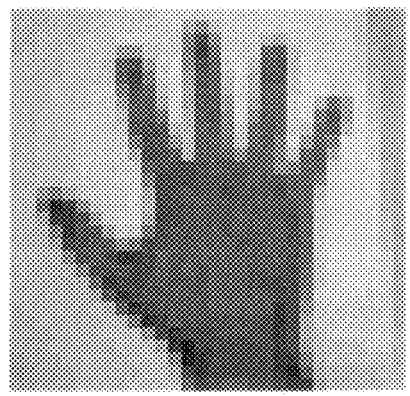
Figures 1, 14C:
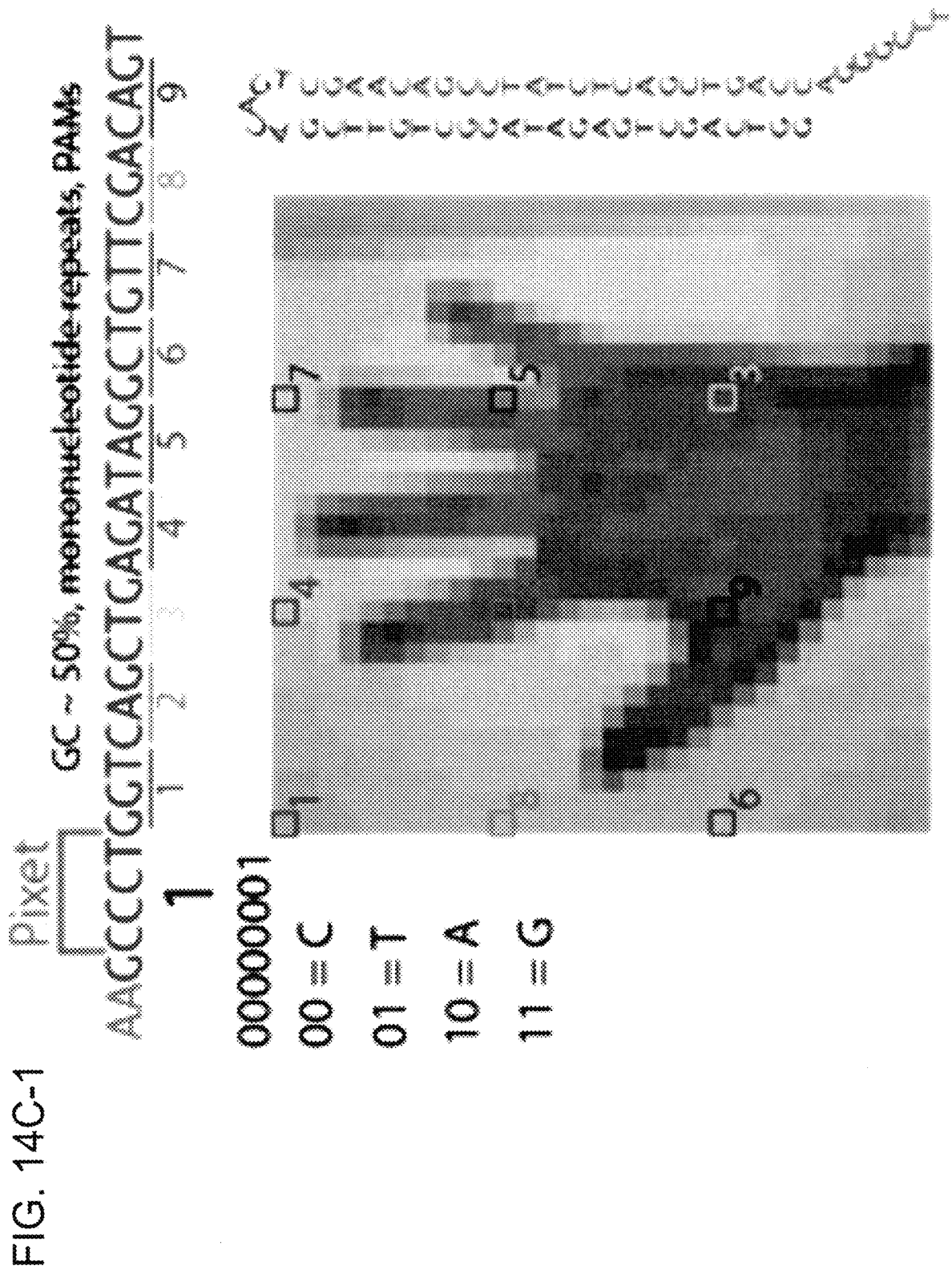
Figures 2, 14C:
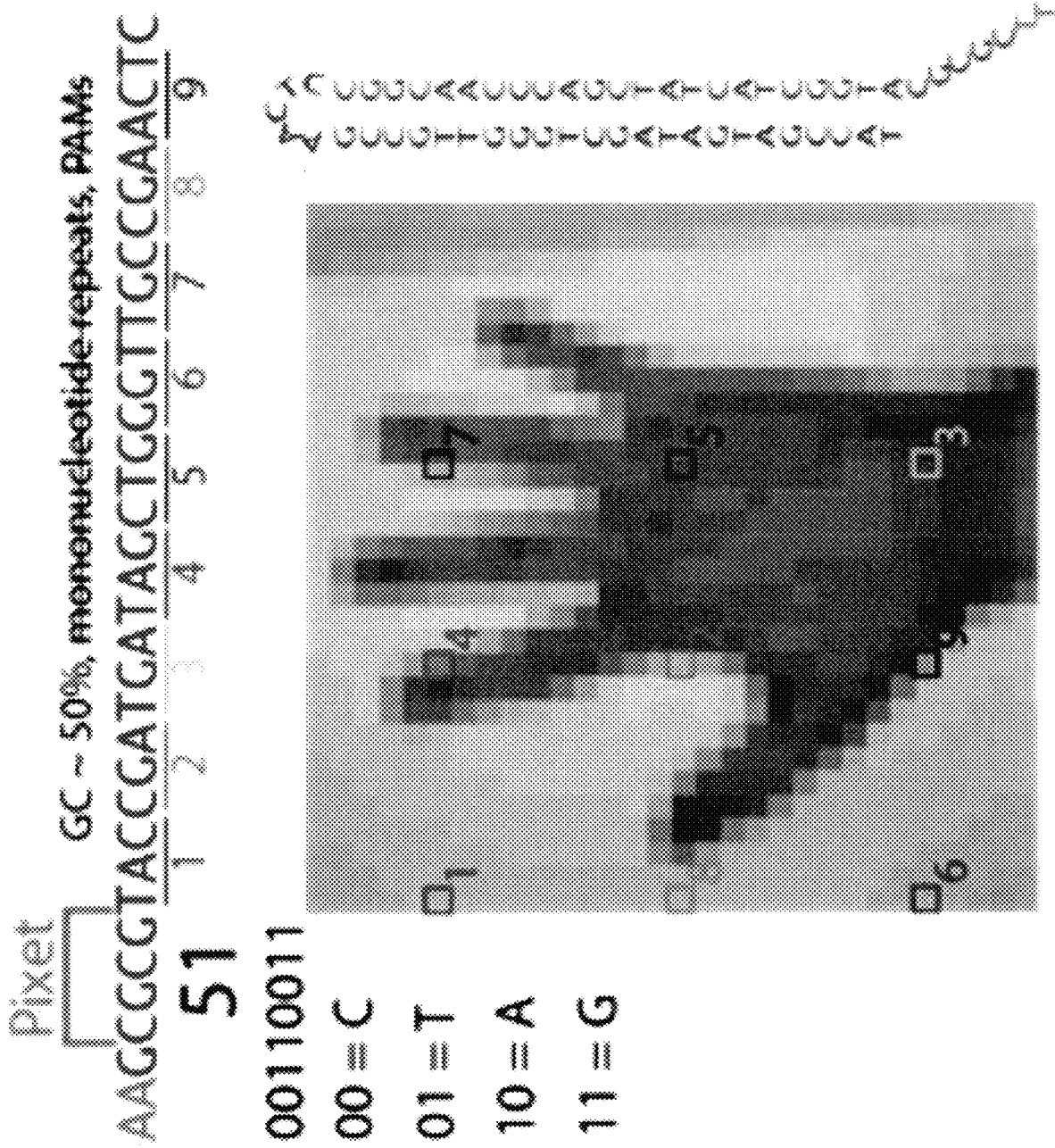
Figure 14D:
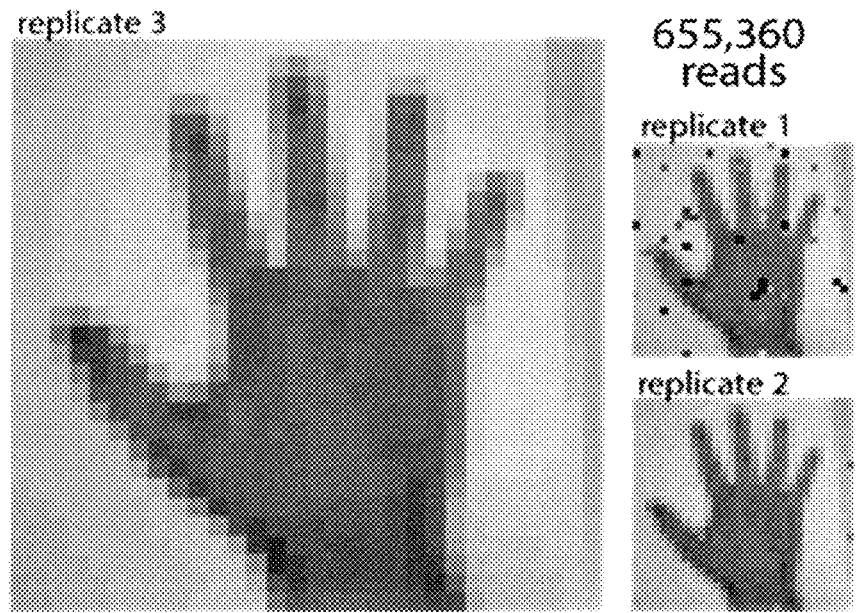
Figure 14E:
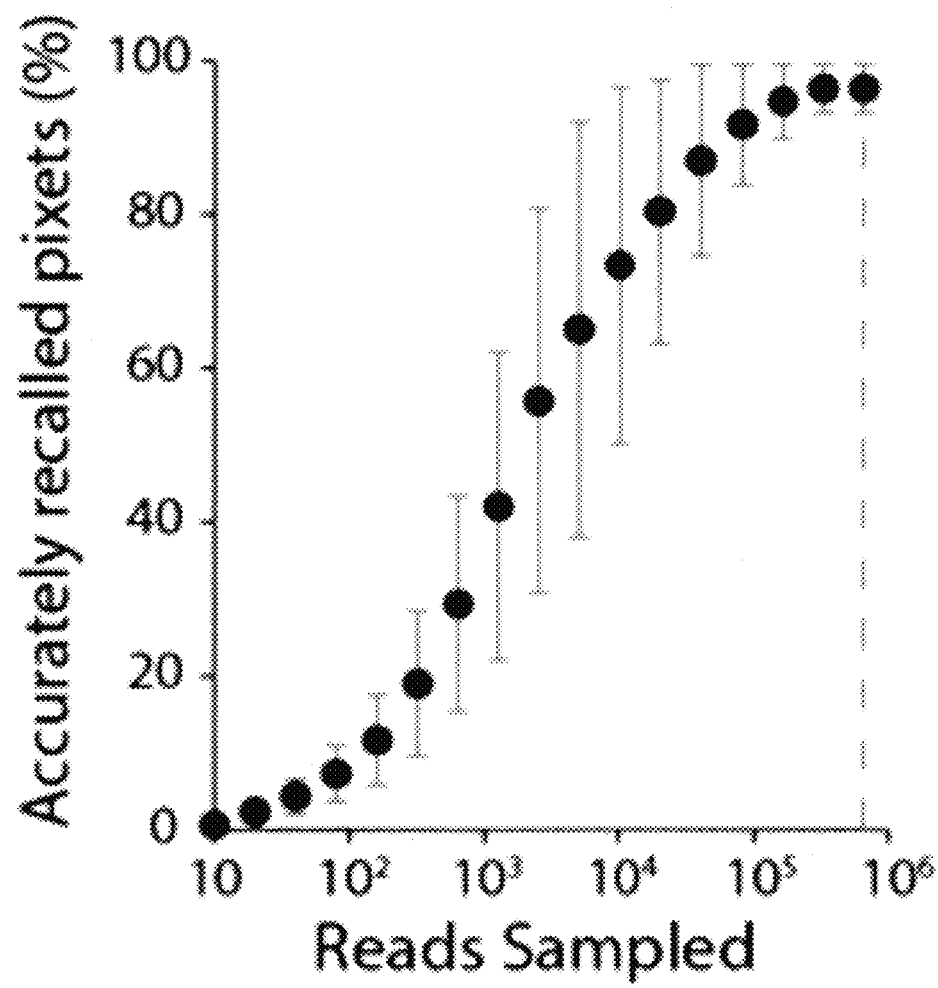
Figure 14F:
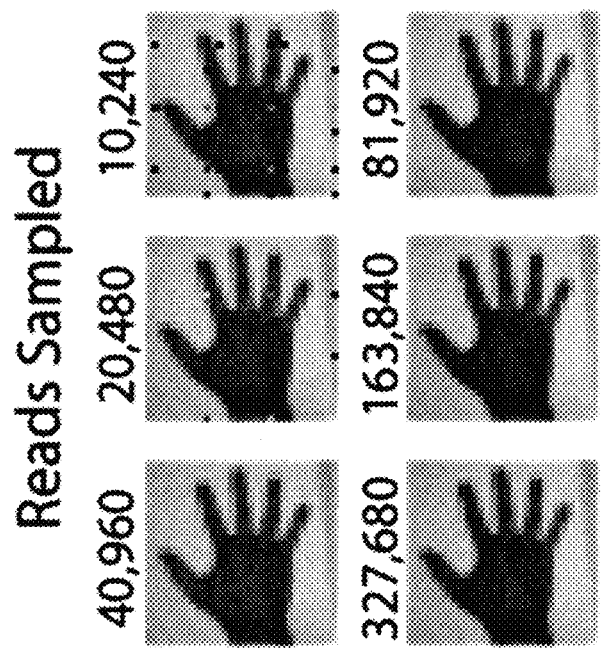
Figure 14G:
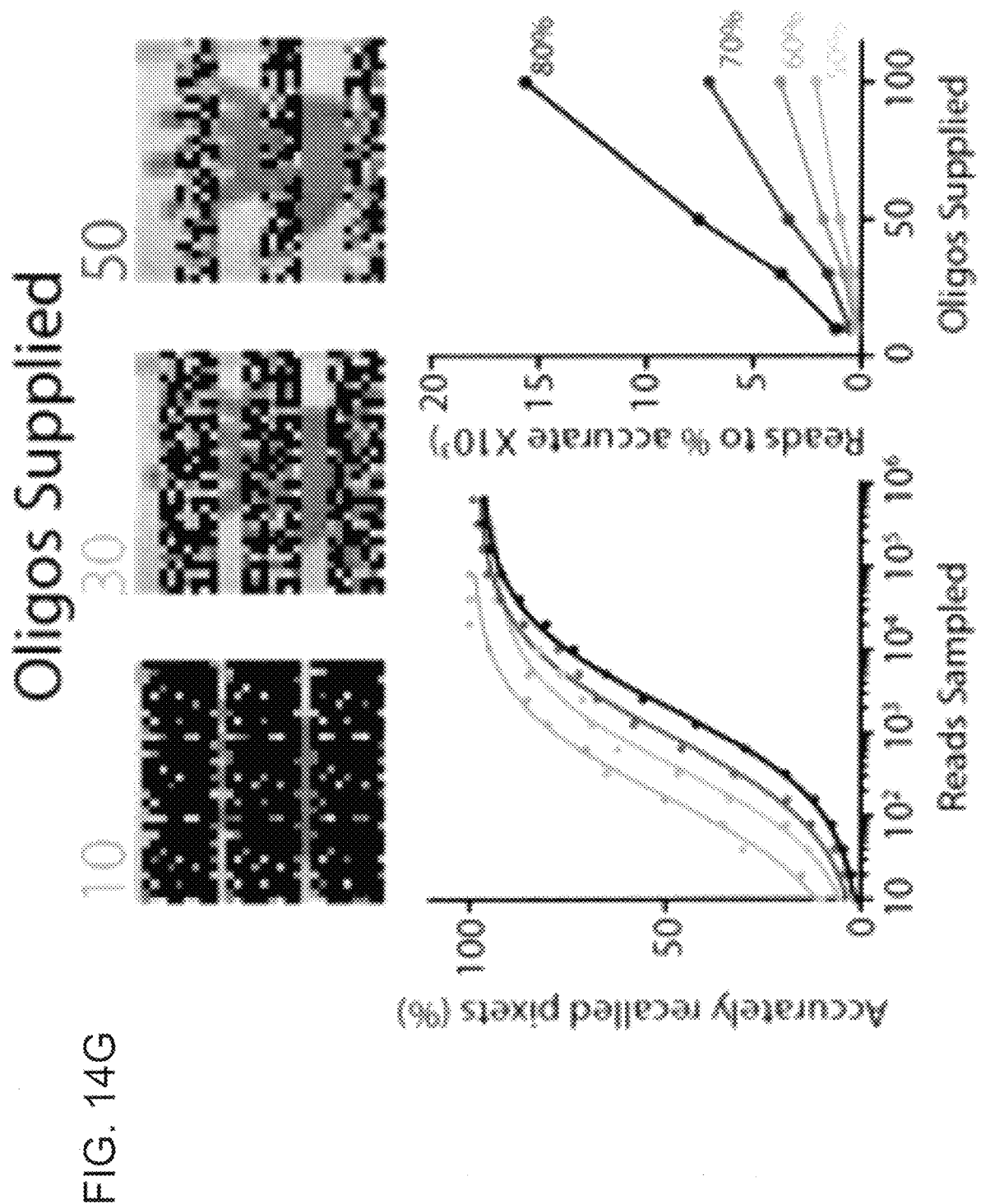
Figure 14M:
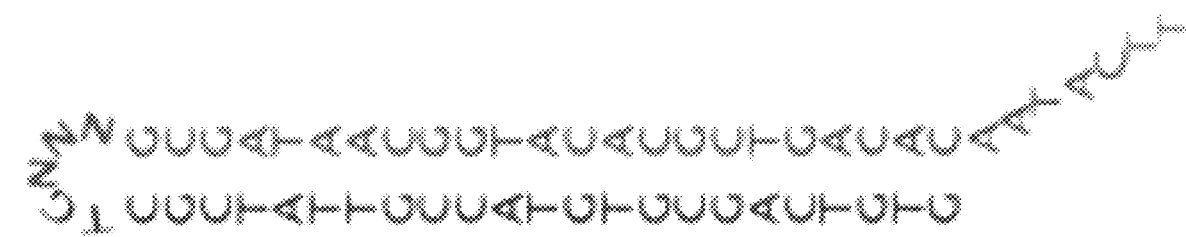
Figure 14L:
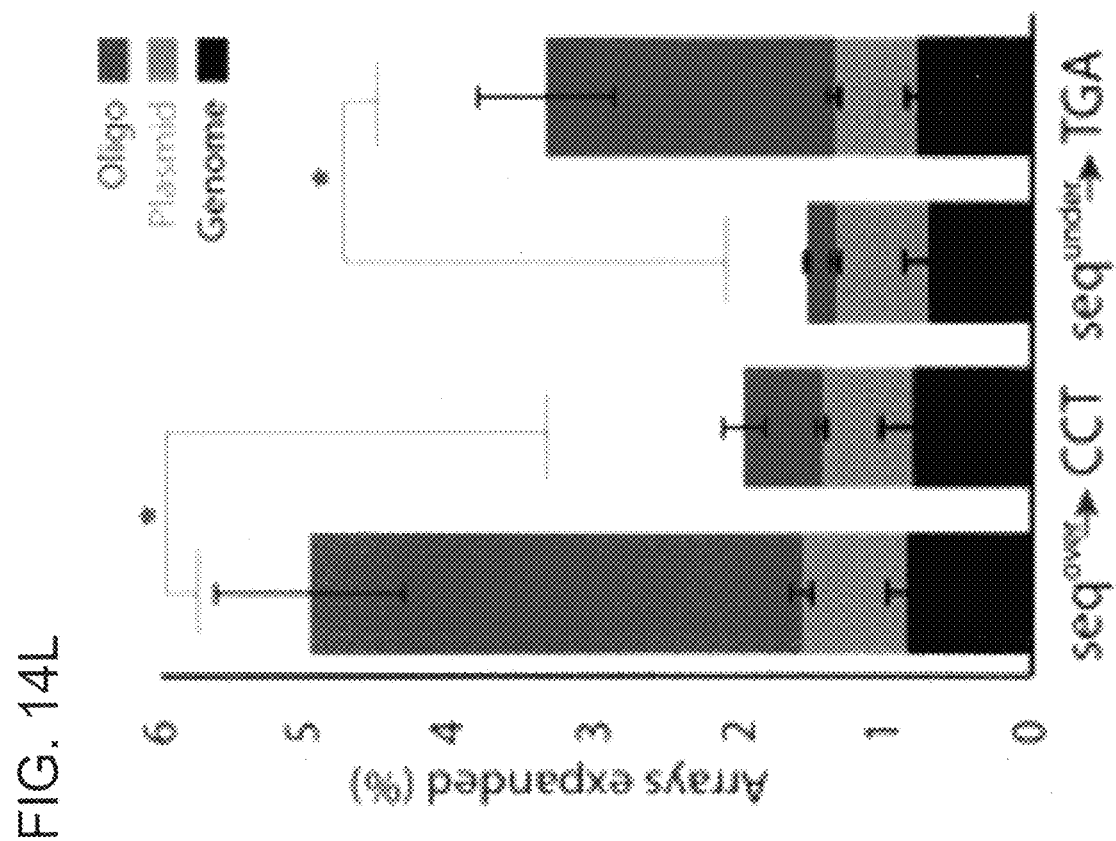
Figure 14N:
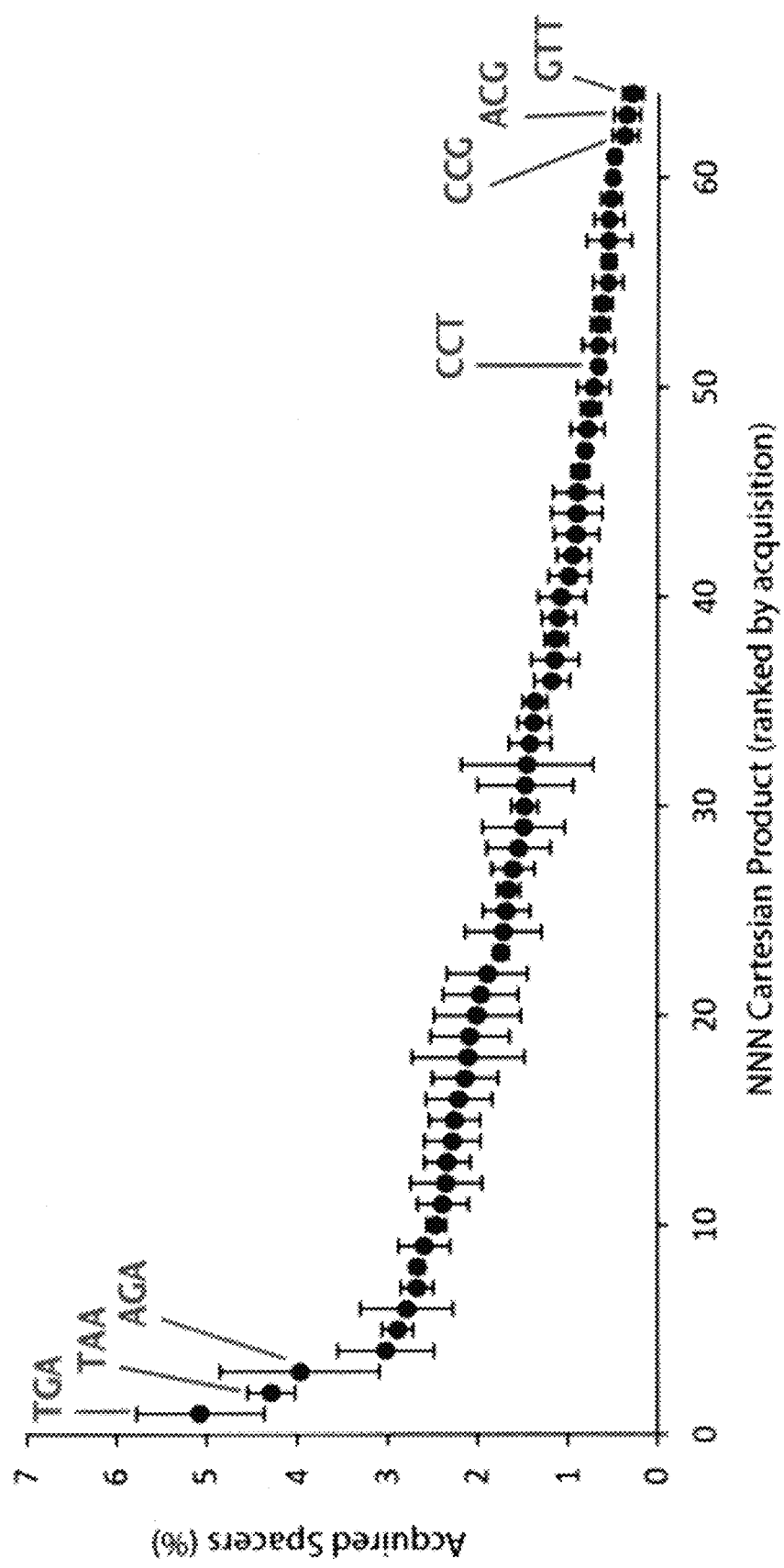
Figure 14O:
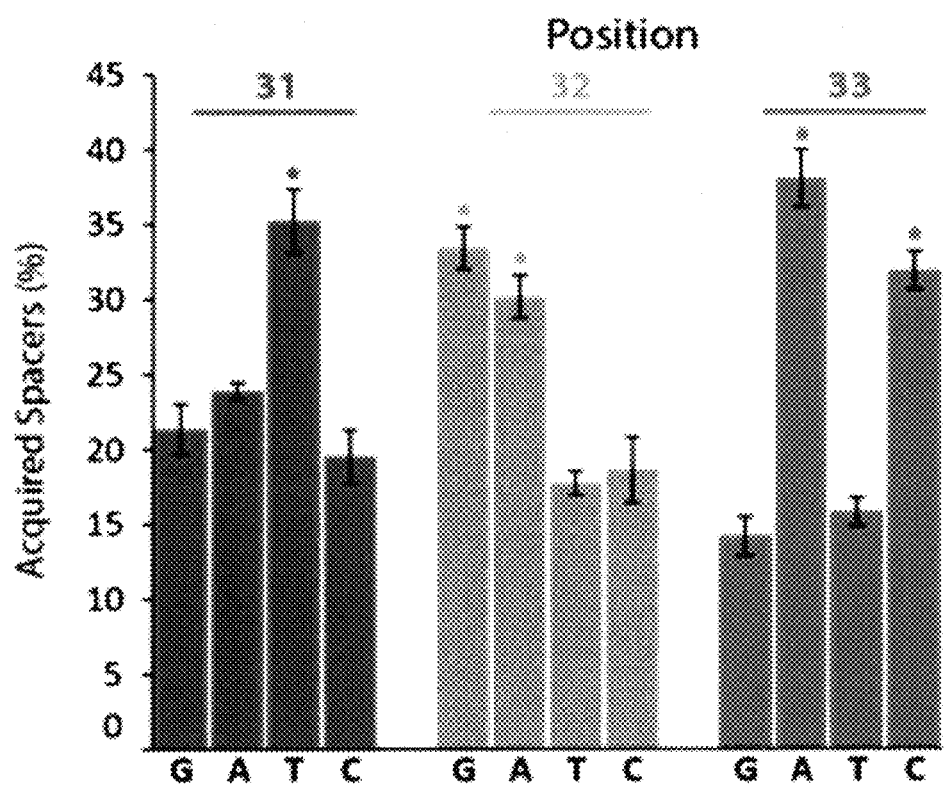

FIGS. 14A-14O are directed to recording a second image with a flexible code. FIG. 14A shows a second image to be encoded. FIG. 14B shows a triplet encoding scheme for 21 colors. FIGS. 14C-1 and 14C-2 show two examples of the encoding scheme. FIGS. 14C-1 and 14C-2 disclose SEQ ID NOS 45-48, respectively, in order of appearance. Similar to FIG. 12D. FIG. 14D shows results of the second experiment. Three replicates shown at a depth of 655,360 reads. FIG. 14E shows percentage of accurately recalled pixels as a function of read depth. FIG. 14F shows examples of the images that result from down-sampling the sequencing reads. FIG. 14G shows effect of supplying fewer oligos on recall accuracy. FIG. 14H shows comparison of the percentage of arrays that were expanded after encoding the first (4 color) and second (21 color) images. FIG. 14I shows distribution of protospacer acquisition frequency for individual protospacers (expressed as percentage of oligo-derived acquisitions) for both the 4 color and 21 color images. Protospacers ranked by acquisition frequency for clarity. FIG. 14J shows pLOGO of the most frequently acquired 10% of protospacers, with all protospacers serving as background. Red line at 13.45 indicates p<0.05. Nucleotides in the positive direction are over-represented, while those in the negative direction are under-represented. FIG. 14K shows individual sequences (SEQ ID NOS 49-52, respectively, in order of appearance) designed to directly test the motif identified in FIG. 14J. FIG. 14L shows percent of arrays expanded following electroporation of the sequences indicated in FIG. 14K, broken down by protospacer origin. * indicates p<0.05. FIG. 14M shows design of NNN-containing oligo (SEQ ID NO: 53). FIG. 14N shows distribution of acquisition frequency of protospacers containing each NNN Cartesian product as a percentage of oligo-derived acquisitions, ranked by frequency. FIG. 14O shows relative representation of each nucleotide at positions 31, 32, and 33 in acquired spacers derived from the NNN-containing oligo.

FIGS. 15A-15B is related to FIG. 14A-14O. FIG. 15A (SEQ ID NOS 49-52, respectively, in order of appearance) shows individual sequences designed to directly test the motif identified in FIG. 14J. FIG. 15B shows percent of arrays expanded following electroporation of the sequences indicated in a as two complementary oligos, rather than a minimal oligo hairpin, broken down by protospacer origin. * indicates p<0.05.

Figure 16A:
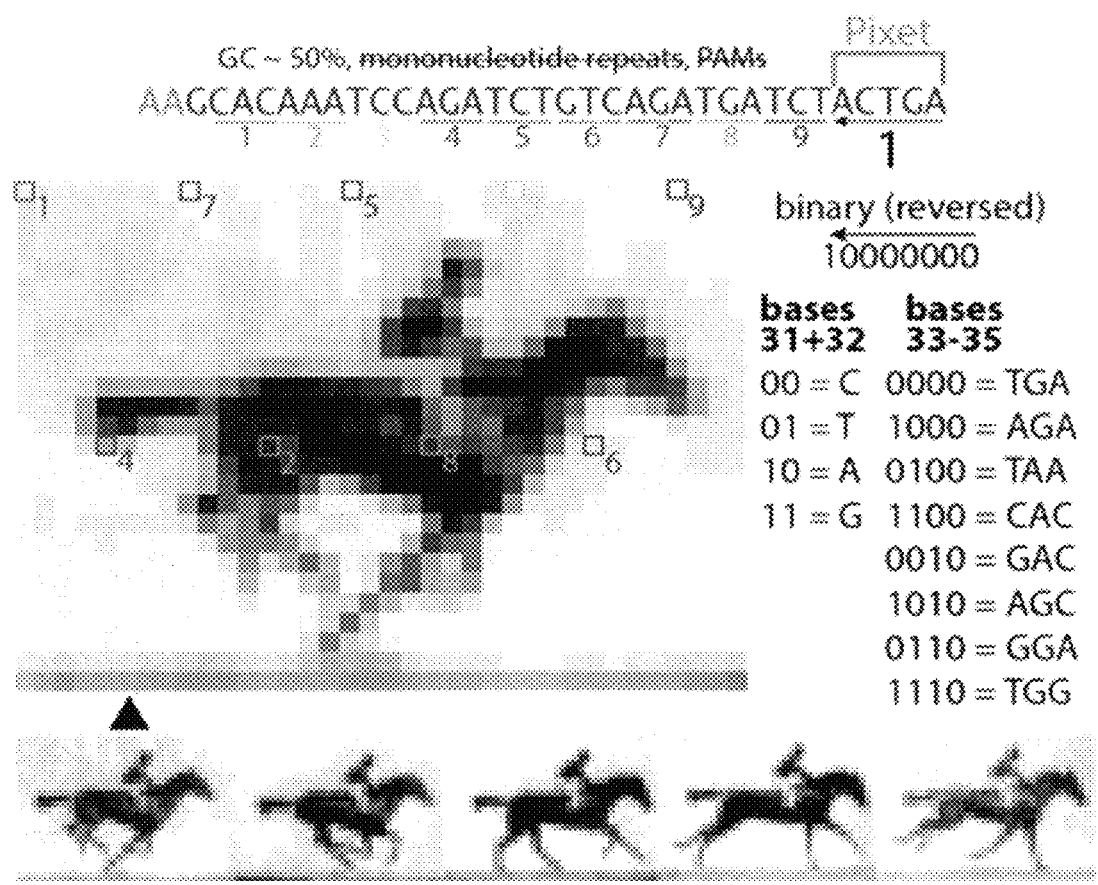
Figure 16D:
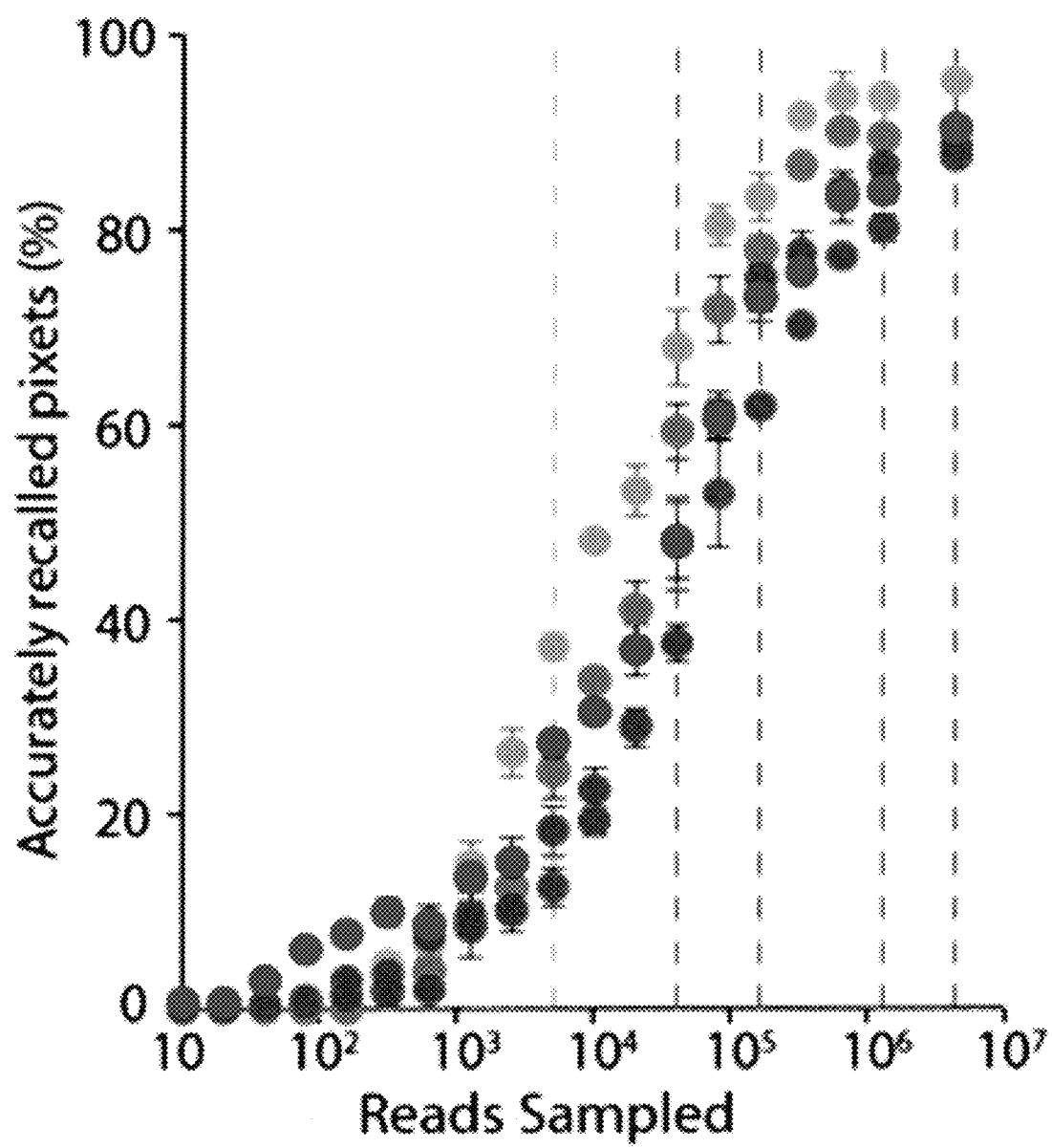
Figure 16E:
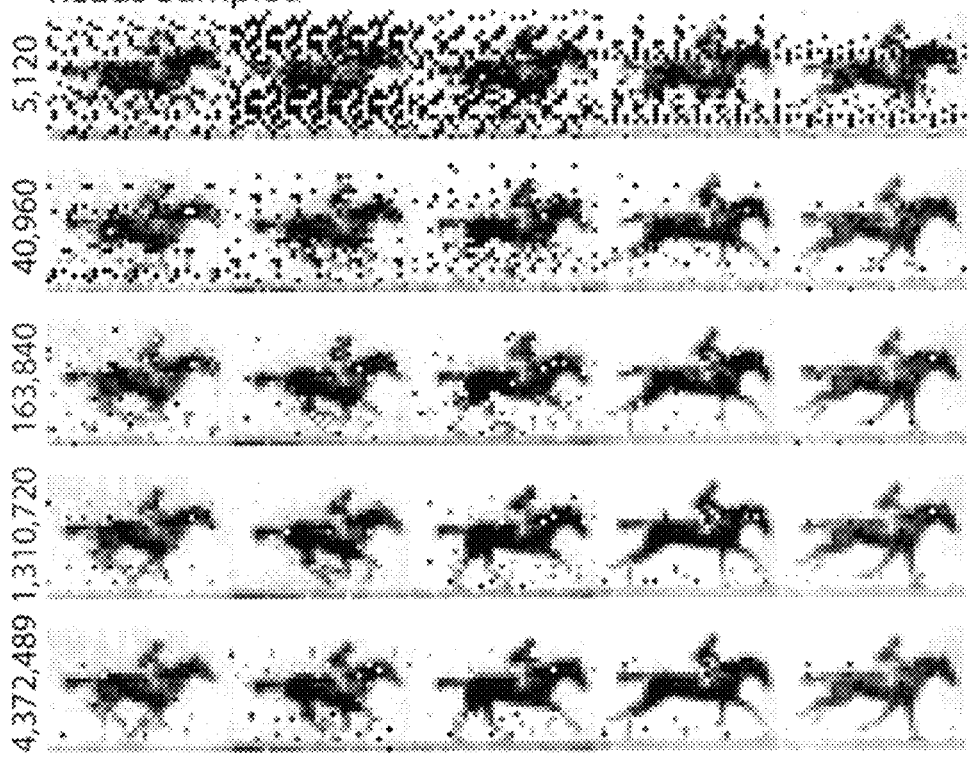
Figure 16F:
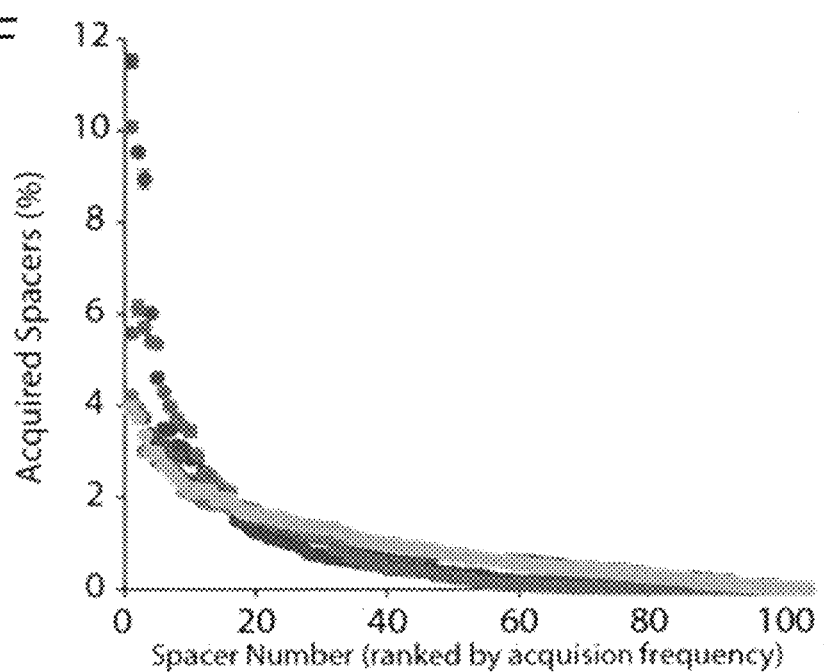
Figure 16G:
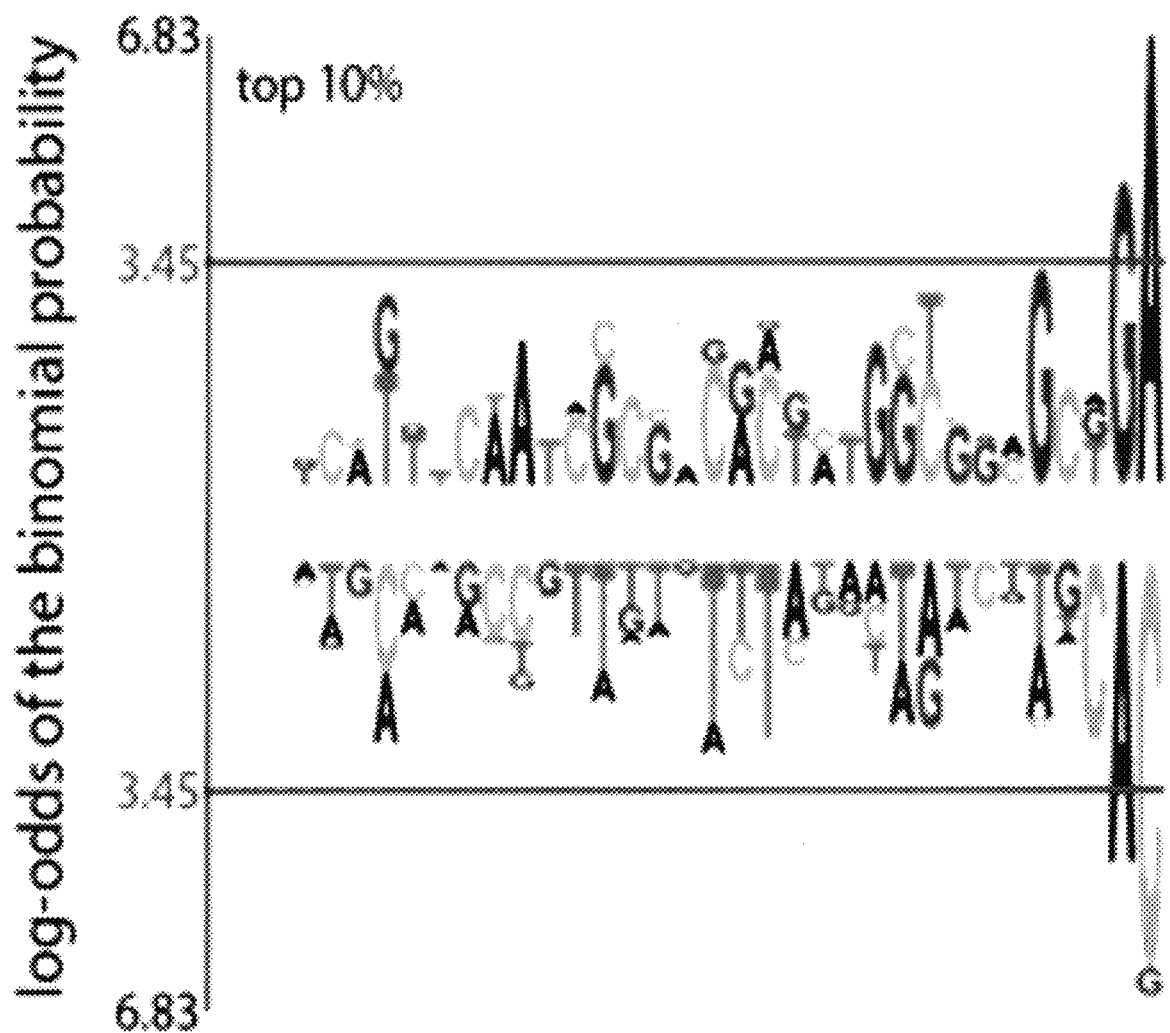
Figure 16H:
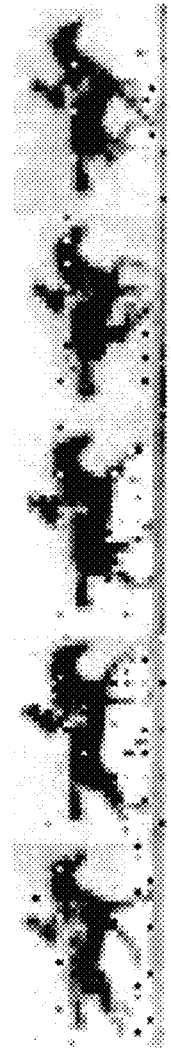

FIGS. 16A-16H are directed to encoding a GIF in bacteria. FIG. 16A shows a GIF to be encoded, along with an example of one pixet protospacer (SEQ ID NO: 54) from the first frame. FIG. 16B shows a schematic of the recording design. Pooled oligo frames are electroporated successively into the same population of bacteria over the course of five days. FIG. 16C shows percentage of arrays with an expansion in the first three spacer positions, broken down by protospacer origin at each of the sample points. FIG. 16D shows percentage of accurately recalled pixets as a function of read depth and frame. FIG. 16E shows examples of the images that result at a range of sequence depths. FIG. 16F shows distribution of protospacer acquisition frequency for individual protospacers (expressed as percentage of oligo-derived acquisitions) by frame. Protospacers ranked by acquisition frequency for clarity. FIG. 16G shows pLOGO of the most frequently acquired 10% of protospacers, with all protospacers serving as background. Red line at ±3.45 indicates p<0.05. Nucleotides in the positive direction are over-represented, while those in the negative direction are under-represented. FIG. 16H shows result of electroporating the same oligos in the reverse order.

Figure 17A:
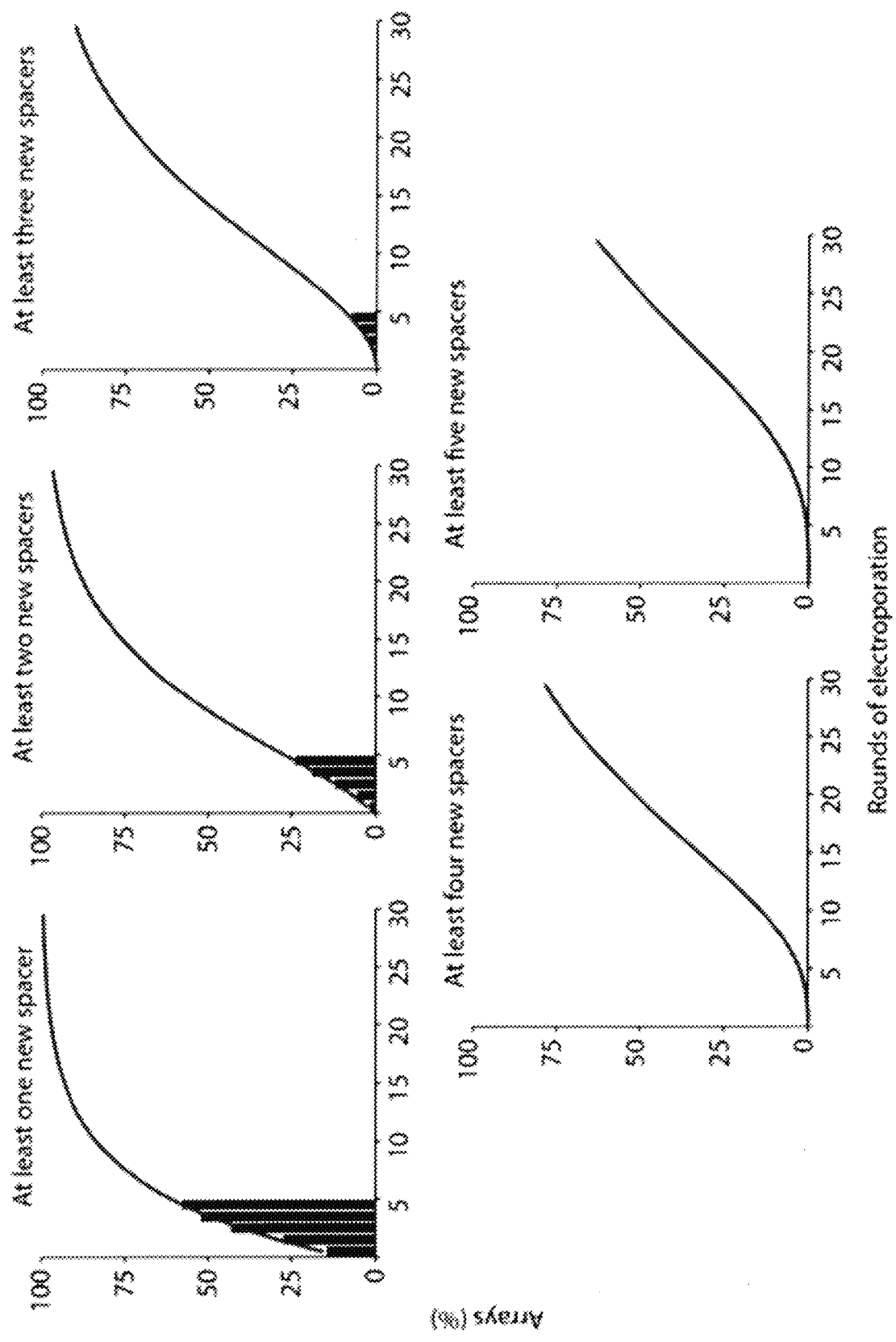
Figures 1, 17B:
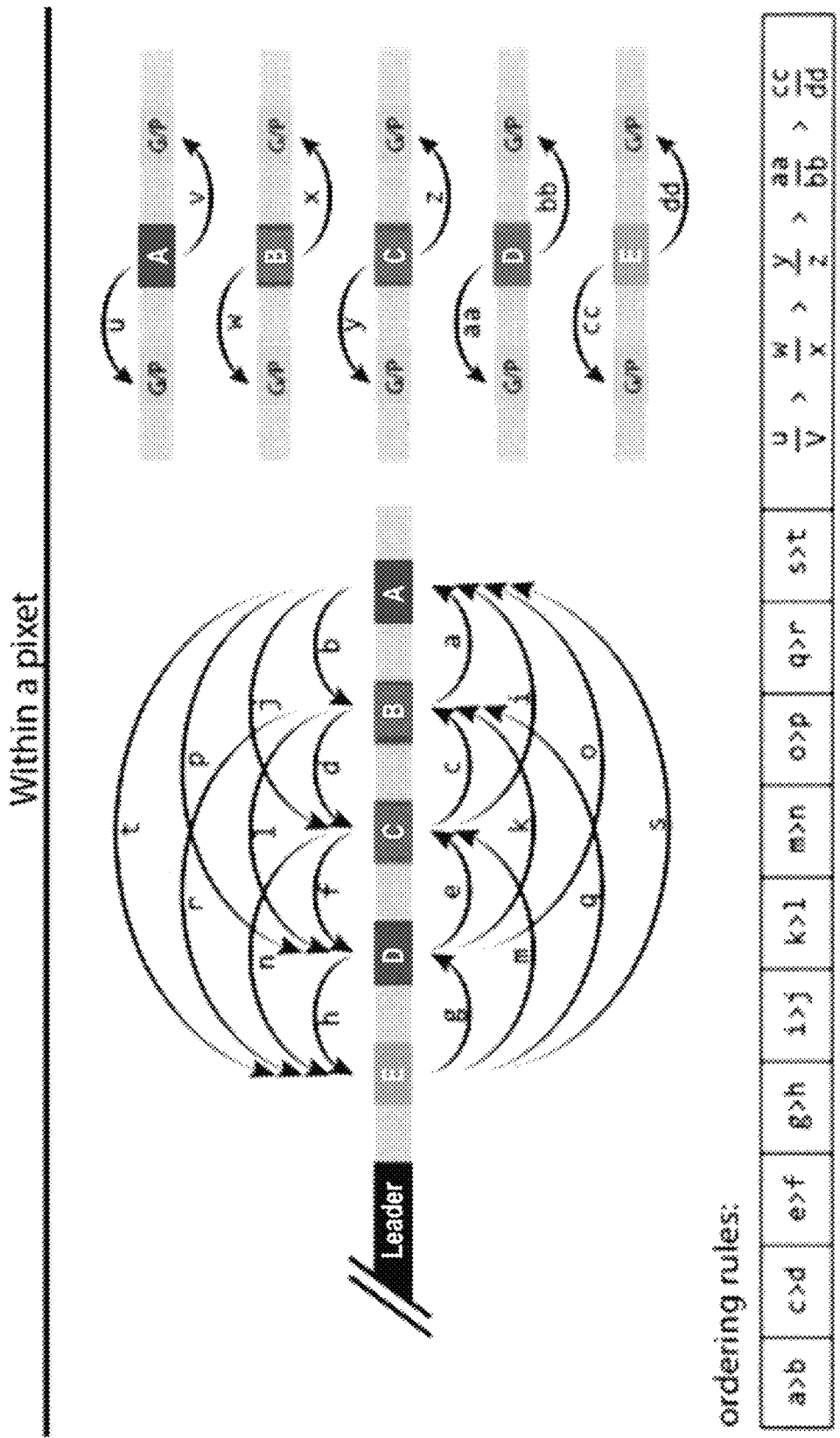
Figures 2, 17B:
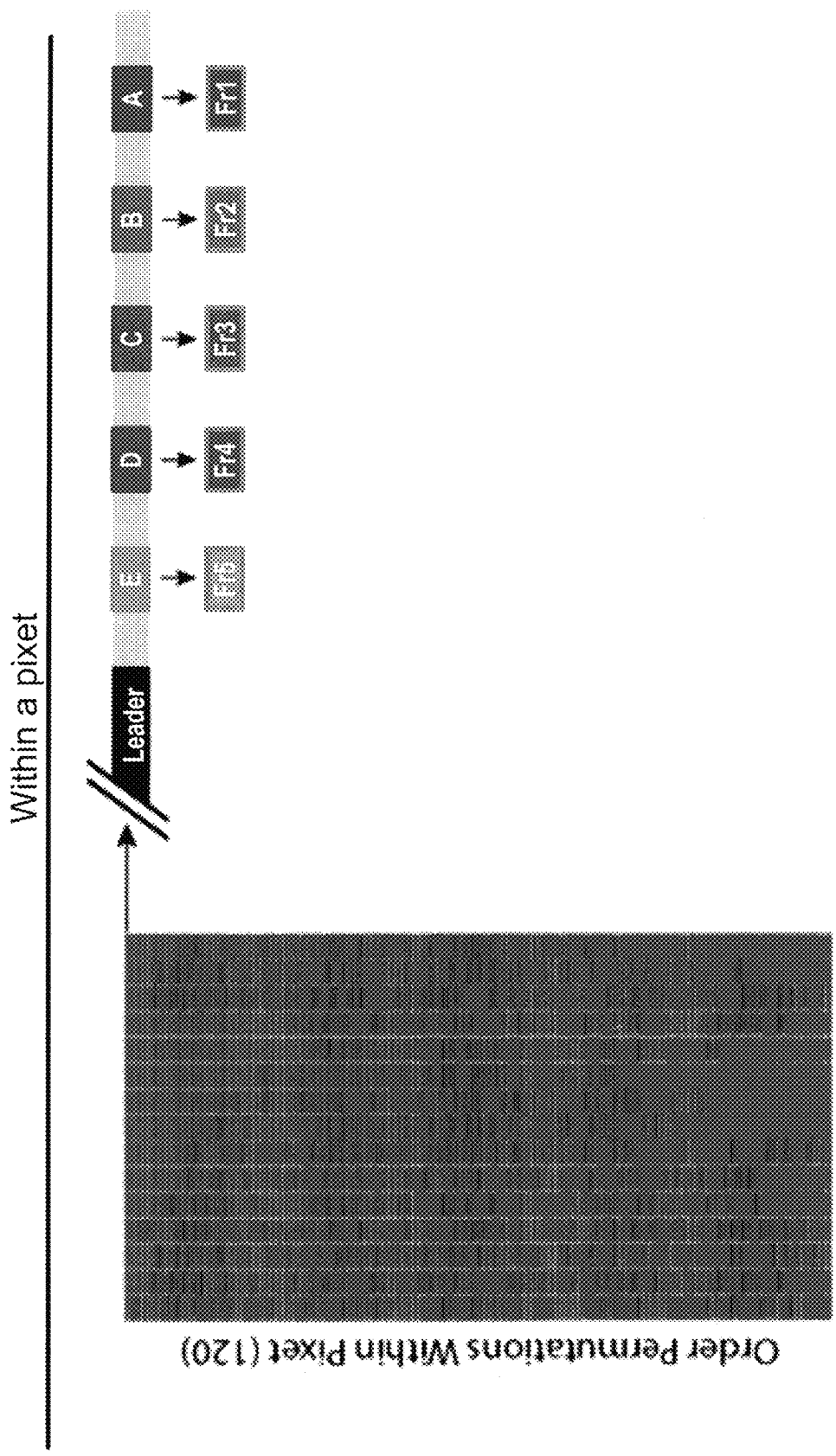
Figure 17C:
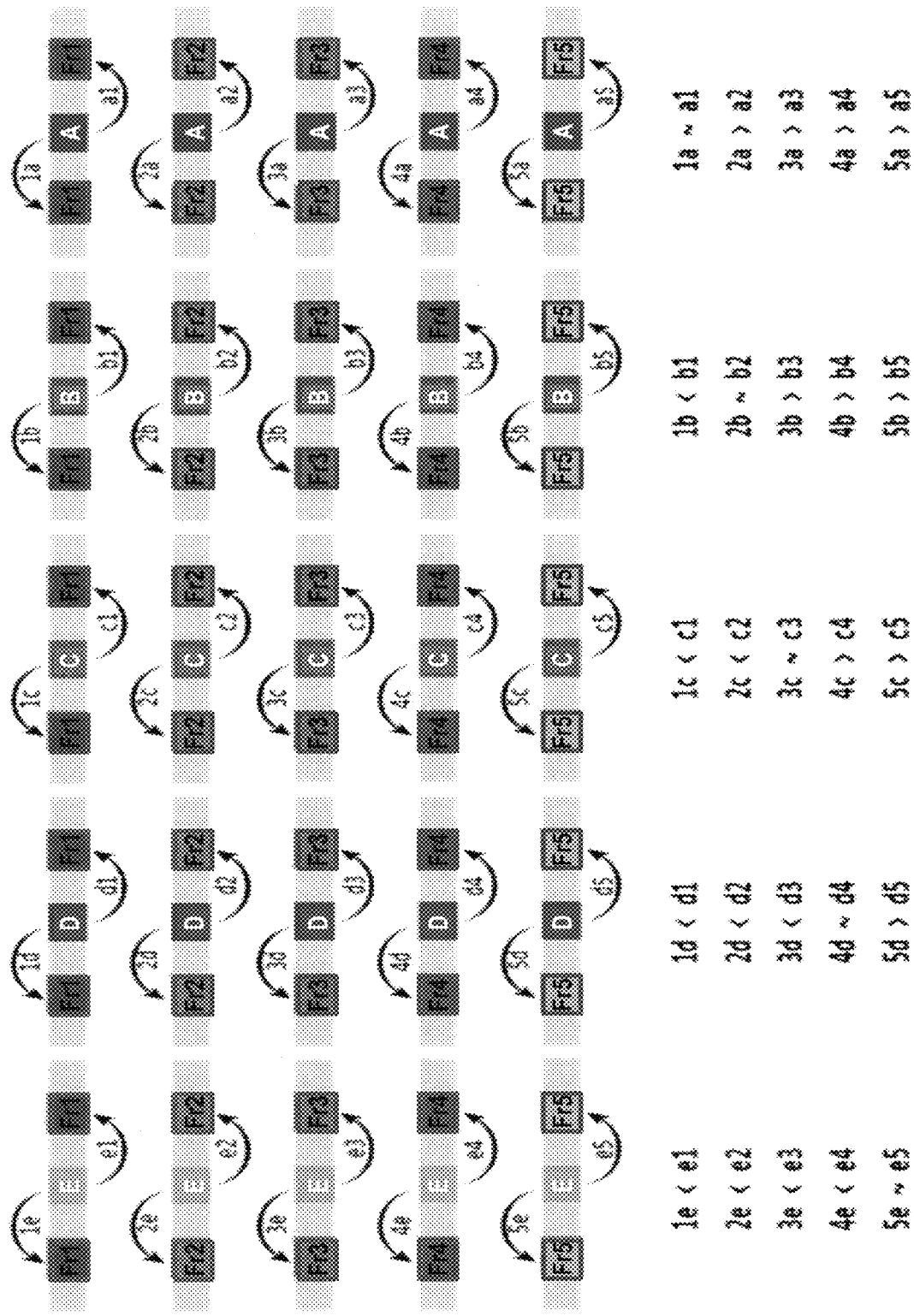
Figures 1, 17C:
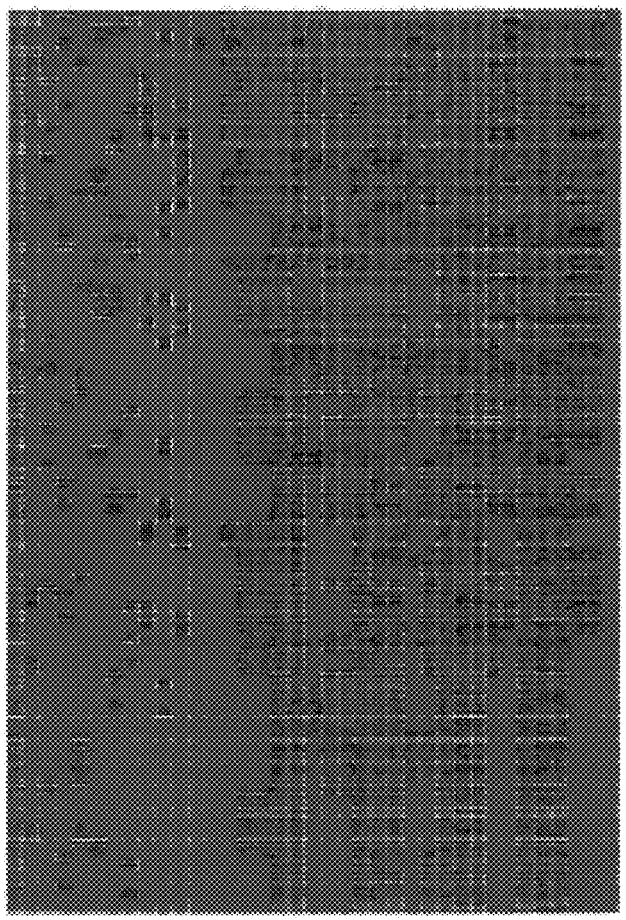

FIGS. 17A-17C-1 are related to FIG. 16A-16H. FIG. 17A shows a percent of arrays expanded with varying numbers of spacers, as a function of rounds of electroporation. Black bars are real data from the GIF experiment. Purple lines are an extrapolation (see additional details in Materials and Methods. FIGS. 17B-1 and 17B-2 shows initial set of rules to test the order of spacers within a pixet. For a given pixet, all permutations of spacer order are tested against these rules—spacers are compared pairwise when found in the same array or compared with spacers derived from the plasmid and genome. If a permutation passes all rules, the spacers are assigned to frame based on that permutation. FIGS. 17C and 17C-1 show a second set of tests to compare between pixets. If no permutation satisfies all of the tests in FIGS. 17B-1 and 17B-2, spacers are compared to previously assigned spacers from other pixets pairwise when found in the same array. All possible order permutations are tested, and order is assigned based on the score among all tests.

Figures 18A, 18B:
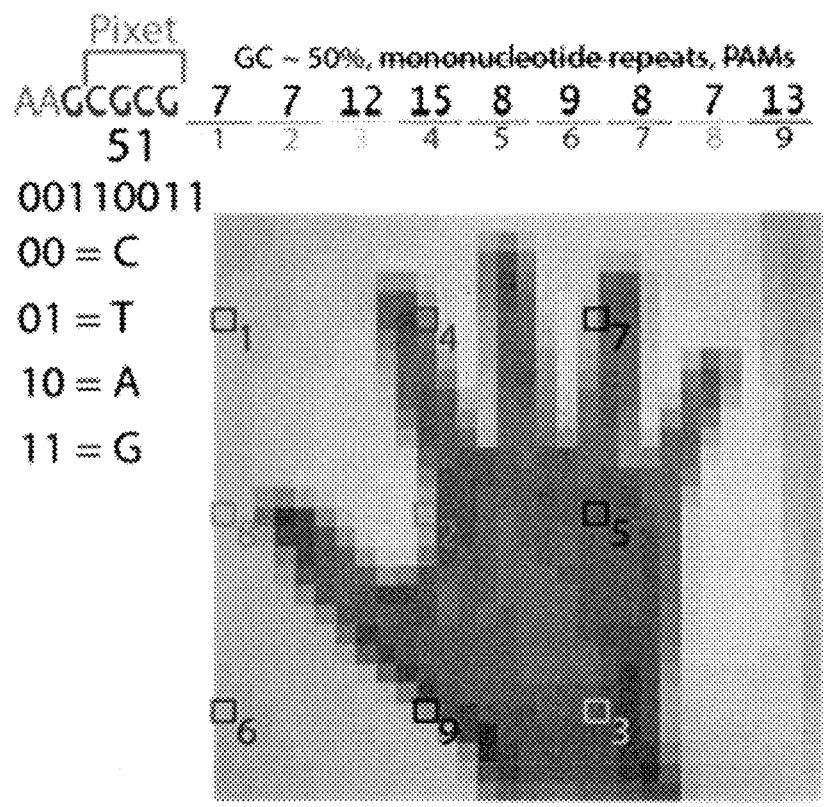
Figure 18I:
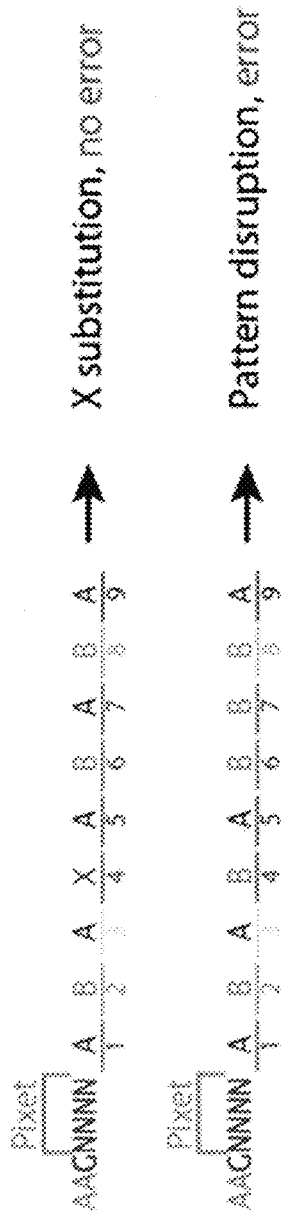
Figure 18J:
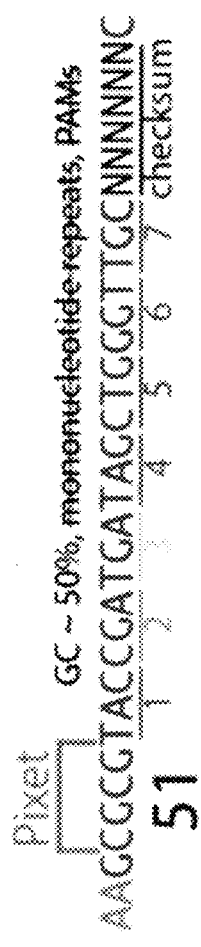
Figure 18K:
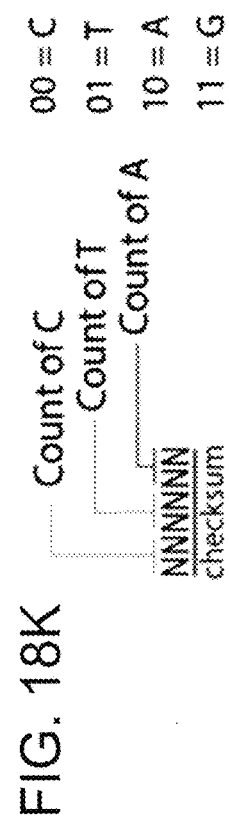
Figure 18L:
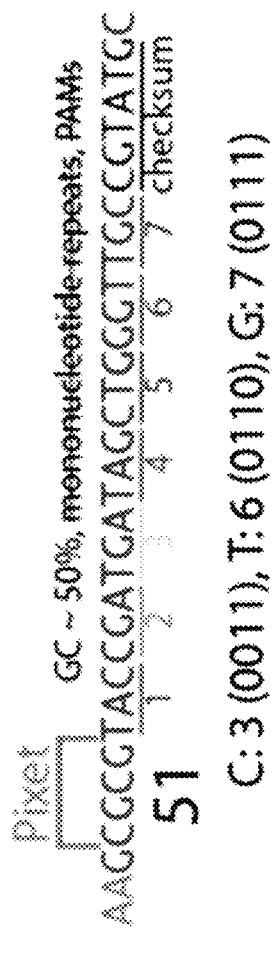

FIGS. 18A-18L are directed to methods of image encoding for error-correction. FIGS. 18A-18D relate to the method used in FIG. 14A-14O. FIG. 18A shows a triplet code to flexibly specify 21 colors. FIG. 18B shows an example of a pixet to be encoded into nucleotide space with pixel values marked. FIG. 18B discloses SEQ ID NO: 55. FIG. 18C shows rules specifying how the protospacer will be built. FIG. 18D shows an example of the build of the protospacer. The AAG introduced by the addition of pixel 4 is unacceptable and invokes the flexible switch to another triplet. FIG. 18D discloses SEQ ID NOS 56-60, respectively, in order of appearance. FIG. 18E-18I relate to a method of alternating clusters for error correction. FIG. 18E shows triplet assignment to clusters A, B, and X. FIG. 18F shows an example of a pixet to be encoded into nucleotide space with pixel values marked. FIG. 18F discloses SEQ ID NO: 55. FIG. 18G shows rules for adding new triplets in this scheme. FIG. 18H shows an example of the build of the protospacer. The AAG introduced by the addition of pixel 4 is unacceptable and invokes the flexible switch to cluster X. FIG. 18H discloses SEQ ID NOS 61-65, respectively, in order of appearance. FIG. 18I shows an example of an error signal. FIGS. 18J-18L are directed to a method of checksum error correction. FIG. 18J shows annotation of protospacer with the addition of a checksum (SEQ ID NO: 66). FIG. 18K shows annotation of the checksum itself. FIG. 18L shows full protospacer with checksum implemented (SEQ ID NO: 67).

FIGS. 19A and 19B are directed to the kinetic of information capture using the methods described herein. FIG. 19A shows results of image recall at a series of time-points after electroporation for one replicate. FIG. 19B shows quantification of the percentage of accurately recalled pixets (in black) and percentage of arrays with oligo-derived spacers (in red) at each time-point. Unfilled circles represent individual biological replicates, lines show the mean. Inset graph to the left expands just the first six hours, a subset of the entire time as indicated on the larger, complete graph to the right.

Figure 20A:
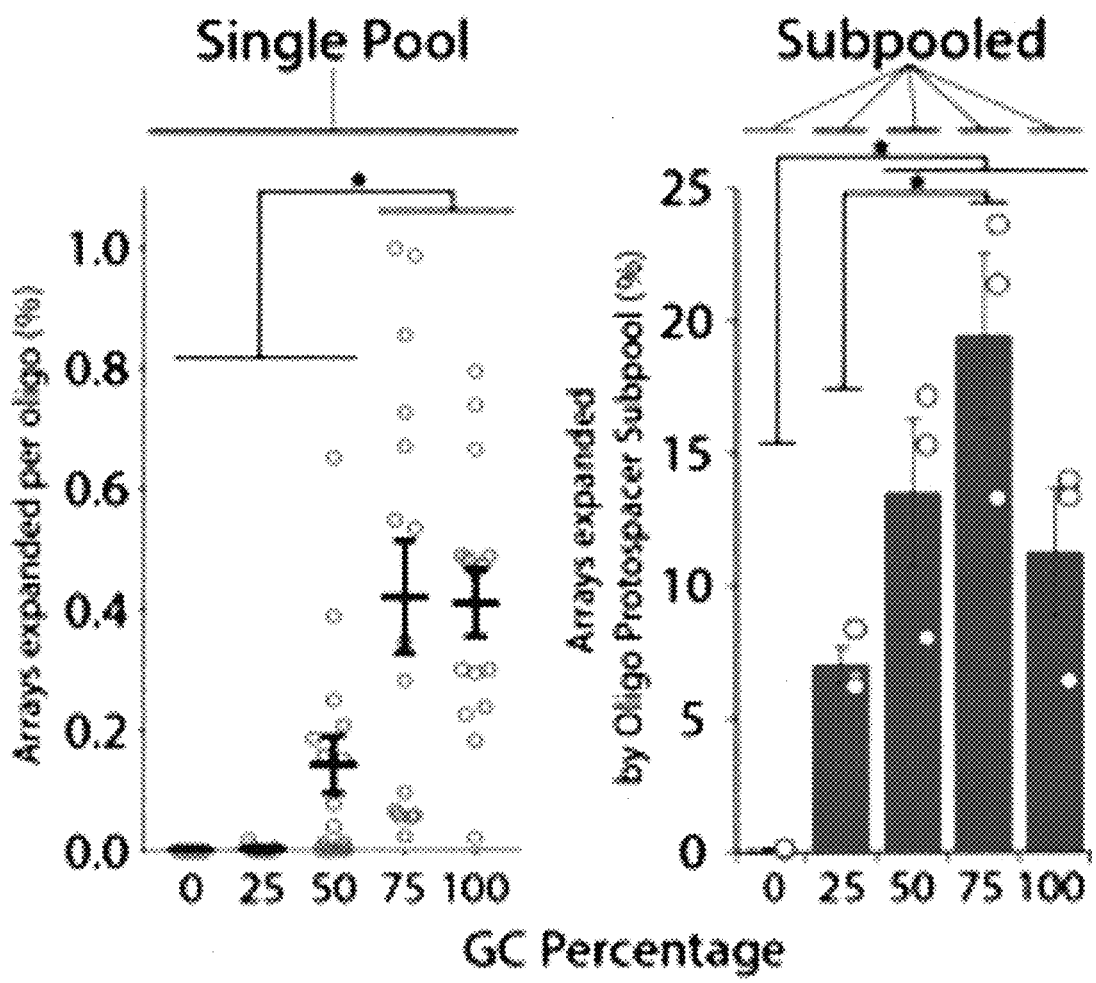
Figure 20B:
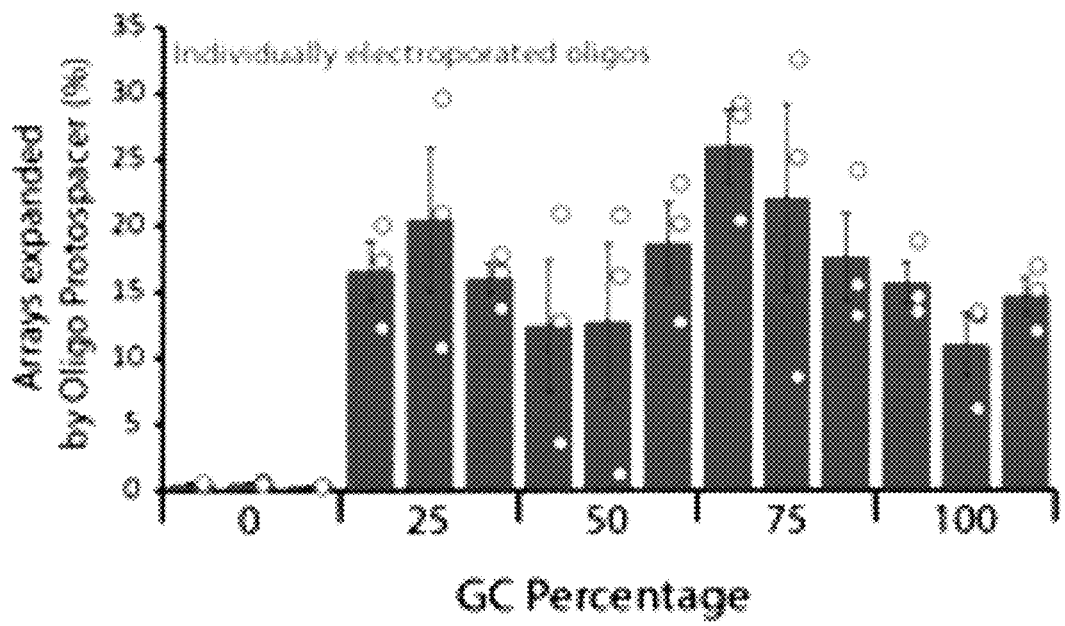
Figure 20C:
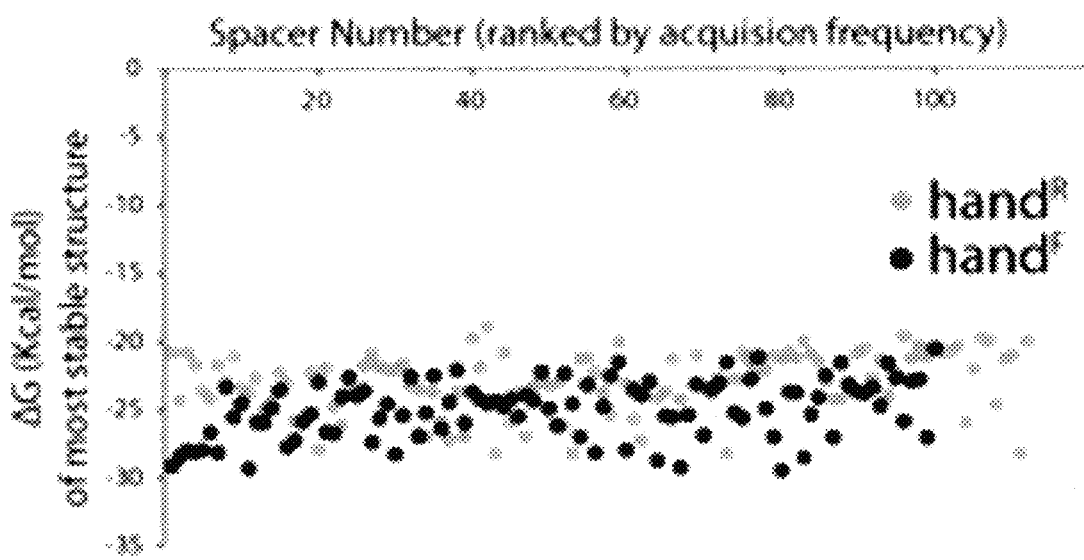
Figure 20D:
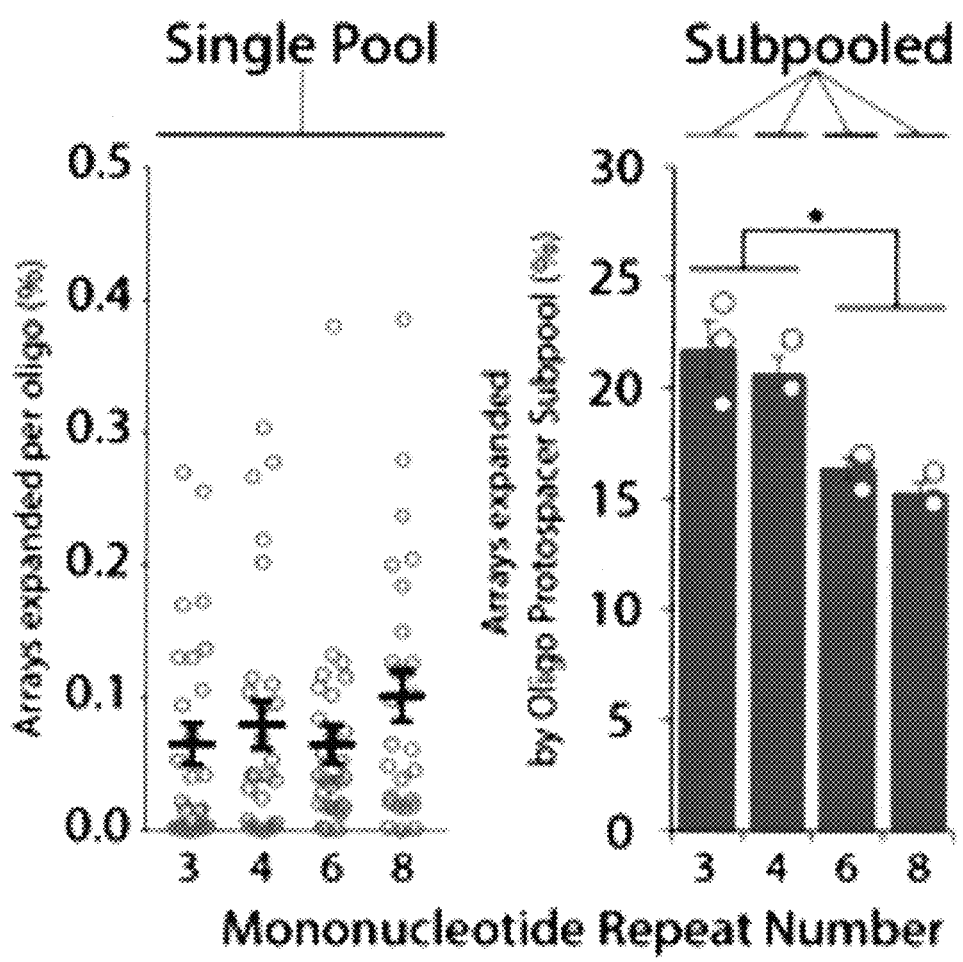
Figure 20E:
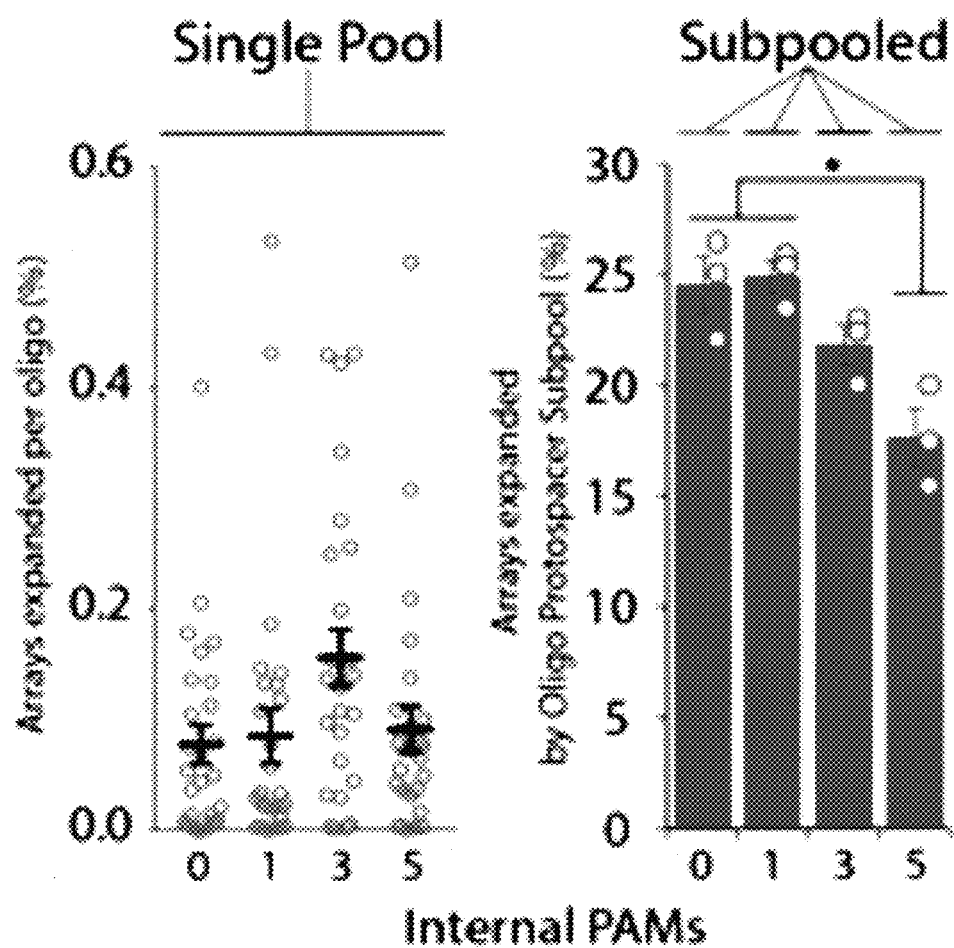

FIGS. 20A-20E are directed to design of the sequences of the information-containing protospacers. FIG. 20A depicts data of the percentage of arrays expanded per oligo (single pool) or per subpool (subpooled) across a range of GC percentages. Unfilled black circles to the left represent individual oligo protospacer sequences (three biological replicates each), while black line shows mean±SEM. Unfilled red circles to the right represent individual biological replicates. Bars are mean±SEM. * indicates p<0.05. FIG. 20B depicts data of the percentage of arrays expanded per oligo electroporated individually across a range of GC percentages. Unfilled red circles are individual biological replicates. Bars show mean±SEM. FIG. 20C depicts data of Gibbs free energy of minimal hairpin protospacers structures for each of the images, with protospacers ranked by overall acquisition frequency. FIG. 20D depicts data of percentage of arrays expanded per oligo (single pool) or per subpool (subpooled) with different numbers of mononucleotide repeats. Panel attributes as in FIG. 20A. FIG. 20E depicts data of the percentage of arrays expanded per oligo (single pool) or per subpool (subpooled) with different numbers of internal PAMs. Panel attributes as in FIG. 20A.

FIG. 21 is a table of statistical details of experiments and data described herein.

FIG. 22 is a table of plasmids used in embodiments described herein. FIG. 22 discloses SEQ ID NOS 1-9, 68-85, 10, 11, 86, 87, and 27, respectively, in order of appearance.

FIG. 23 is a table of Cas mutants used in embodiments described herein.

FIG. 24 is a table of protospacer oligonucleotides used in embodiments described herein.

DETAILED DESCRIPTION

Embodiments of the present disclosure are directed to methods of altering a cell via CRISPR-Cas system. According to certain aspects, the Cas1-Cas2 complex integrates synthetic oligo spacers into the genome of cells in vivo. According to one aspect, integration of synthetic oligo spacers via the Cas1-Cas2 complex can be harnessed as a multi-modal molecular recording system.

The ability to write a stable record of identified molecular events into a specific genomic locus would enable the examination of long cellular histories and have many applications, ranging from developmental biology to synthetic devices. According to one aspect, the disclosure provides that the type I-E CRISPR-Cas system of *E. coli* can acquire defined pieces of synthetic DNA. According to another aspect, the feature of a CRISPR-Cas system of acquiring defined pieces of synthetic DNA is harnessed to generate records of specific DNA sequences with >100 bytes of information into a population of bacterial genomes. According to certain aspects, the disclosure provides applying directed evolution to alter PAM recognition of the Cas1-Cas2 complex. In certain embodiments, the disclosure provides expanded recordings into multiple modalities. In related embodiments, the disclosure provides using this system to reveal previously unknown aspects of spacer acquisition, which are fundamental to the CRISPR-Cas adaptation process. In certain other embodiments, the disclosure provides results that lay the foundations of a multimodal intracellular recording device with information capacity far exceeding any previously published synthetic biological memory system.

In one embodiment, the CRISPR-Cas system is harnessed to record specific and arbitrary DNA sequences into a bacterial genome. In certain embodiments, a record of defined sequences, recorded over many days, and in multiple modalities can be generated. In certain other embodiments, this system is explored to elucidate fundamental aspects of native CRISPR-Cas spacer acquisition and leverage this knowledge to enhance the recording system.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. The term also includes genetic modification or alteration to produce a cell or nucleic acid not found in nature.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In general, "a CRISPR adaptation system" refers collectively to transcripts and other elements involved in the expression of or directing the activity of CRISPR-associated ("Cas") genes, including sequences encoding a Cas gene, and a CRISPR array nucleic acid sequence including a leader sequence and at least one repeat sequence. In some embodiments, one or more elements of a CRISPR adaption system is derived from a type I, type II, or type III CRISPR system. Cas1 and Cas2 are found in all three types of CRISPR-Cas systems, and they are involved in spacer acquisition. In the I-E system of *E. coli*, Cas1 and Cas2 form a complex where a Cas2 dimer bridges two Cas1 dimers. In this complex Cas2 performs a non-enzymatic scaffolding role, binding double-stranded fragments of invading DNA, while Cas1 binds the single-stranded flanks of the DNA and catalyzes their integration into CRISPR arrays.

In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

In certain embodiments, the disclosure provides protospacers that are adjacent to short (3-5 bp) DNA sequences termed protospacer adjacent motifs (PAM). The PAMs are important for type I and type II systems during acquisition. In type I and type II systems, protospacers are excised at positions adjacent to a PAM sequence, with the other end of the spacer is cut using a ruler mechanism, thus maintaining the regularity of the spacer size in the CRISPR array. The conservation of the PAM sequence differs between CRISPR-Cas systems and appears to be evolutionarily linked to Cas1 and the leader sequence.

In some embodiments, the disclosure provides for integration of defined synthetic DNA into a CRISPR array in a directional manner, occurring preferentially, but not exclusively, adjacent to the leader sequence. The term synthetic includes meaning that the DNA is synthesized using synthesis techniques, and in most cases is non-naturally occurring. In the type I-E system from *E. coli*, it was demonstrated that the first direct repeat, adjacent to the leader sequence is copied, with the newly acquired spacer inserted between the first and second direct repeats.

In one embodiment, the protospacer is a defined synthetic DNA. In some embodiments, the defined synthetic DNA is at least 10, 20, 30, 40, or 50 nucleotides, or between 10-100, or between 20-90, or between 30-80, or between 40-70, or between 50-60, nucleotides in length.

In one embodiment, the oligo nucleotide sequence or the defined synthetic DNA includes a modified "AAG" protospacer adjacent motif (PAM).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (see Ishino et al., J. Bacteriol., 169: 5429-5433 [1987]; and Nakata et al., J. Bacteriol., 171: 3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (see Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (see Mojica et al., [2000], supra). Although the repeat sequences are highly conserved between strains, the number of interspersed repeats and the sequences of the spacer regions typically differ from strain to strain (see van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on; among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

Target DNA Sequence

The term "target DNA sequence" includes a nucleic acid sequence which is to be inserted into a CRISPR array nucleic acid sequence within the genomic DNA of the cell or on a plasmid according to methods described herein. The target DNA sequence may be expressed by the cell.

According to one aspect, the target DNA sequence is exogenous to the cell. According to one aspect, the target DNA sequence is foreign to the cell. According to one aspect, the target DNA sequence is non-naturally occurring within the cell. According to another aspect, the target DNA sequence is synthetic. According to one aspect, the target DNA has a defined sequence.

Foreign Nucleic Acids

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. According to one aspect, a foreign nucleic acid is exogenous to the cell. According to one aspect, a foreign nucleic acid is foreign, i.e., non-naturally occurring, within the cell.

Cells

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Further, cells include any in which it would be beneficial or desirable to add a target nucleic acid sequence.

According to one aspect, the cell is a eukaryotic cell or a prokaryotic cell. According to one aspect, the cell is a yeast cell, bacterial cell, fungal cell, a plant cell or an animal cell. According to one aspect, the cell is a mammalian cell. According to one aspect, the cell is a human cell. According to one aspect, the cell is a stem cell whether adult or embryonic. According to one aspect, the cell is a pluripotent stem cell. According to one aspect, the cell is an induced pluripotent stem cell. According to one aspect, the cell is a human induced pluripotent stem cell. According to one aspect, the cell is in vitro, in vivo or ex vivo.

Vectors

Vectors according to the present disclosure include those known in the art as being useful in delivering genetic material into a cell and would include regulators, promoters, nuclear localization signals (NLS), start codons, stop codons, a transgene etc., and any other genetic elements useful for integration and expression, as are known to those of skill in the art. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory Elements and Terminators and Tags

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Materials and Methods

Bacterial Strains and Culturing Conditions

Expression and new spacer acquisition were carried out in BL21-AI cells. Unless otherwise specified, cells were grown in Luria Broth (LB) shaking (240 rpm) at 37° C. Genes expressed from the T7lac promoter were induced using L-arabinose (Sigma-Aldrich) at a final concentration of 0.2% (w/w) from a 20% stock solution in water and isopropyl-beta-D-thiogalactopyranoside (IPTG; Sigma-Aldrich) at a final concentration of 1 mM from a 100 mM stock solution in water. Cas mutants expressed from the pLtetO promoter were induced via anhydrotetracycline (aTc; Clontech) at a final concentration of 214 nM from a 214 μM stock in 50% ethanol. While expressing from the pLtetO promoter, 0.2% glucose was added to reduce unintended background expression from the T7lac promoter. For new spacer acquisition experiments not involving oligo-derived spacers, cells were induced and grown overnight (16 h). All cloning was performed using NEB5α cells.

Cloning and Library Construction

Plasmid containing Cas1 and Cas2 under the expression of a T7lac promoter (pWUR 1+2) was a generous gift of Udi Qimron (see I. Yosef, M. G. Goren, U. Qimron, Proteins and DNA elements essential for the CRISPR adaptation process in *Escherichia coli*. Nucleic acids research 40, 5569-5576 (2012); published online EpubJuly (10.1093/nar/gks216)). A variant of this plasmid was created harboring an additional CRISPR array based on an array found in the K12 strain. This additional array was synthesized and cloned into pWUR 1+2 to generate pWUKI 1+2. Cas1+2 were cloned into pRSF-DUET for a different plasmid context (pRSF-DUET 1/2). Cas1 and Cas2 were extracted from pWUR 1+2 by PCR and re-cloned into the same plasmid separately. In the case of Cas1, the selection was also changed in this step from spectinomycin to ampicillin to create pWURA Cas1 and pWUR Cas2. The point mutation E9Q was introduced into Cas2 by PCR to generate pWUR Cas1+Cas2 E9Q. Similarly, point mutants of Cas1+2 based on mutants from the directed evolution experiment were created by PCR. Mutant 89 from the directed evolution experiment was cloned into pWUR 1+2 along with a terminator, pLtetO, and the tetR repressor from pJKR-H-tetR (see J. K. Rogers, C. D. Guzman, N. D. Taylor, S. Raman, K. Anderson, G. M. Church, Synthetic biosensors for precise gene control and real-time monitoring of metabolites. Nucleic acids research 43, 7648-7660 (2015); published online EpubSeptember 3 (10.1093/nar/gkv616)) to create pWUR 1+2 tetO mut89. Mutant library was created via error-prone PCR using GeneMorph II Random Mutagenesis Kit (Agilent) and cloned into ElectroTen-Blue ultracompetent cells (Agilent) before being transferred to the expression strain (BL21-AI). For additional details on plasmids, see FIG. 22.

Oligo Protospacer Electroporation

For spacer acquisition experiments involving oligo-derived spacers, cells were first grown overnight from individual plated clones. In the morning, 100 μl of the overnight culture was diluted into 3 ml of LB, with induction components as dictated by the experiment. Cells were grown with inducers for 2 h. For an individual experimental condition, 1 ml of this culture was pelleted and re-suspended in water. Cells were further washed by two additional pelleting and re-suspension steps, then pelleted a final time and re-suspended in 50 μl of a 3.125 μM solution of double stranded oligonucleotides (unless otherwise noted). All pelleting steps were via centrifugation at 13,000×g for 1 minute and the entire process from the first pelleting to the final re-suspension was carried out at 4° C. Finally, the cell-oligo mixture was transferred to a 1 mm gap cuvette and electroporated using a Bio-Rad gene pulser set to 1.8 kV and 25 μF with pulse controller at 200Ω. Only those conditions with an electroporation time constant >4.0 ms were carried through to analysis. Immediately after electroporation, cells were transferred into a culture tube containing 3 ml of LB and grown for 2 h (unless otherwise noted). At this time, 50 μl of the culture was lysed by heating to 95° C. for 5 minutes, cooled, then either used directly for analysis or saved for later analysis at −20° C. For multi-day recordings, 50 ul of the culture was used to inoculate an overnight culture (in the absence of inducers) to restart the process the next day.

Analysis of Spacer Acquisition

Qualitative assessment of new spacer acquisition was achieved by PCR across the array (for all expansions) or PCR from either side of the array with the opposite primer matching the oligo that was electroporated (for sequence-specific acquisition). New spacer sequences were assigned to their origin in initial experiments by TOPO cloning (ThermoFisher) the expanded amplicons, followed by Sanger sequencing of the resulting colonies. For the majority of experiments, however, acquisition events were assessed by sequencing a library of all expanded and unexpanded arrays for a given condition using an Illumina MiSeq sequencer. Libraries were created from an initial PCR across the genomic array, then single- or dual-indexed using NEB-Next Multiplex Oligos (NEB). Up to 96 conditions were run per flow cell. A list of oligo protospacers used can be found in FIG. 24.

Processing and Analysis of MiSeq Data

Sequences were analyzed using custom written software (Python). Briefly, spacer sequences were extracted from reads based on their arrangement between identifiable repeat sequences (four mismatches permitted in the repeat to allow for errors in sequencing), then compared against the sequences of spacers that populated the array prior to the experiment (five mismatches allowed against old spacers) to identify new spacers. At this time, metrics were collected as to the number of expanded versus unexpanded arrays, the number of expansions in each array, the position of new expansions, and the length of new spacers. The sequences of new spacers were then blasted (NCBI, blastn) against a database containing the genome, plasmid, and any electroporated oligo sequences. From this, origin and orientation were determined as was the protospacer flanking sequence for PAM analysis. To analyze the recordings over time, all reads containing double and triple expansions were analyzed. Oligo-derived sequences were identified based on their frequency among all new spacers, then, if applicable, set identifiers were extracted based on their known location in the sequences and sets of oligo-derived sequences were assembled. The order of all oligo-derived spacers relative to each other and genome- or plasmid-derived spacers in pairwise comparisons in all double and triple expanded arrays was assessed. Then, those values were used to test all ordered permutations of the oligo-derived across each of the ordering rules. Sets were analyzed independently. An estimate of the time course of spacer acquisition was inferred by relative qPCR Ct values at all time points, referenced to a quantitative analysis of expansions by MiSeq at the two-hour time point. Library sizes for various mutant libraries were estimated by sequencing of fragmented mutant amplicons on a MiSeq sequencer. Sequence diversity was estimated as $S_1=S_{obs}+(F_1^2)/(2F_2)$, where Sobs observed unique sequences in the sample, F1 is the number of sequences with a single occurrence and F2 is the number of sequences with exactly two occurrences (see R. K. Colwell, J. A. Coddington, Estimating terrestrial biodiversity through extrapolation. Philosophical transactions of the Royal Society of London. Series B, Biological sciences 345, 101-118 (1994); published online EpubJuly 29 (10.1098/rstb.1994.0091)). For statistics, see FIG. 21.

EXAMPLE II

A Type I-E CRISPR-Cas System Accepts Synthetic Spacers In Vivo.

Figure 1A:
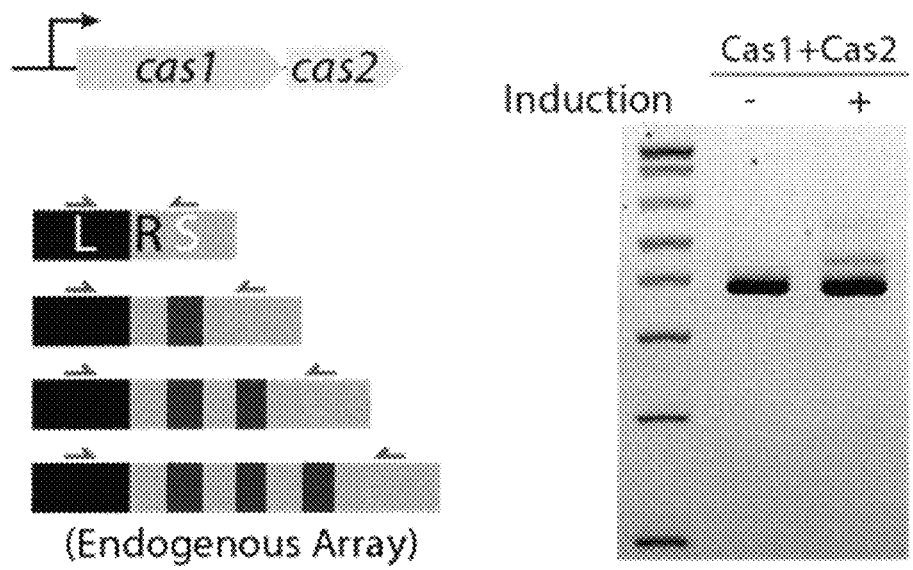
FIGS. 1A-1I depicts the acquisition of synthetic spacers.
Figure 1B:
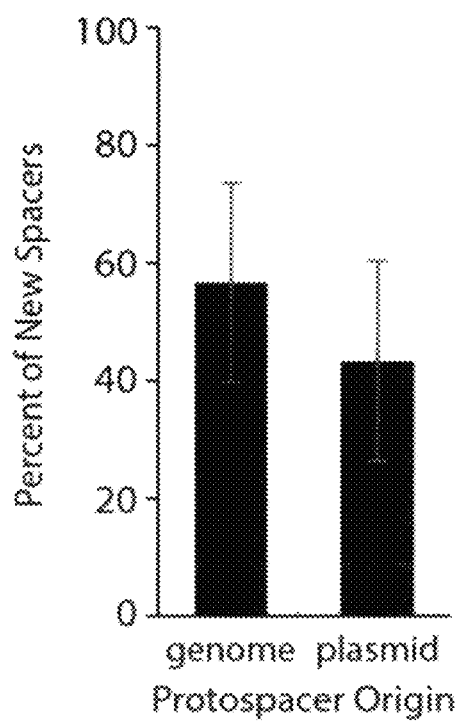
Figure 1C:
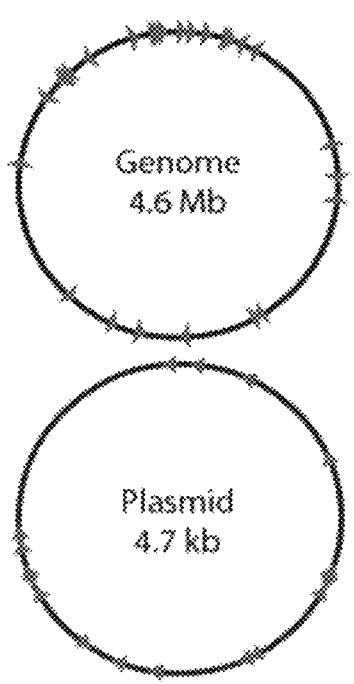

It was recently shown that overexpression of the *E. coli* type I-E CRISPR-Cas proteins Cas1 and Cas2 is sufficient to drive acquisition of new spacers in a strain containing two genomic CRISPR arrays but lacking endogenous Cas proteins (BL21-AI) (see I. Yosef, M. G. Goren, U. Qimron, Proteins and DNA elements essential for the CRISPR adaptation process in *Escherichia coli*. Nucleic acids research 40, 5569-5576 (2012); published online EpubJuly (10.1093/nar/gks216)). This result was replicated (see FIG. 1A), and it was similarly found that new spacers were consistently integrated into the first position of array I directly adjacent to the leader with a consistent size of 33 bases (see FIGS. 2A-B). These spacers were drawn in roughly equal number from the cell's own genome and from the plasmid used to overexpress Cas1 and Cas2 (see FIG. 1B). Considering the overall DNA content of the cell, this ratio of genome-to-plasmid-derived spacers represents a substantial bias toward the plasmid as a protospacer source (see A. Levy, M. G. Goren, I. Yosef, O. Auster, M. Manor, G. Amitai, R. Edgar, U. Qimron, R. Sorek, CRISPR adaptation biases explain preference for acquisition of foreign DNA. Nature 520, 505-510 (2015); published online EpubApril 23 (10.1038/nature14302)). Despite this bias, new spacers were drawn from a diverse range of sites around the genome and plasmid (see FIG. 1C) and, besides the overrepresentation of a 5' AAG protospacer adjacent motif (PAM), there was no way to predict a priori the full sequence of a new spacer without sequencing the expanded array.

To extend the function of the CRISPR acquisition system into a synthetic device for recording molecular events, it is necessary to direct the system to capture spacers of specific, defined sequence rather than drawing spacers randomly from DNA in the cell. In an in vitro reconstruction of Cas1-Cas2-mediated spacer acquisition, Nunez et al. (see J. K. Nunez, A. S. Lee, A. Engelman, J. A. Doudna, Integrase-mediated spacer acquisition during CRISPR-Cas adaptive immunity. Nature 519, 193-198 (2015); published online EpubMarch 12 (10.1038/nature14237)) demonstrated the integration of synthetic 33 bp DNA oligos into plasmid-based arrays. According to the present disclosure, an exogenous source of one or more or a plurality of protospacers are provided to a cell as described herein to direct sequence-specific spacer acquisition in-vivo. To do so, an overnight culture of *E. coli* BL21-AI containing inducible Cas1 and Cas2 genes with or without induction by arabinose and IPTG was passaged for two hours. The cells were then electroporated with a complementary pair of 33 base oligos (protospacer ps33), which matched the sequence of the most abundant M13-derived spacer found after phage challenge of a native type I-E system (see K. A. Datsenko, K. Pougach, A. Tikhonov, B. L. Wanner, K. Severinov, E. Semenova, Molecular memory of prior infections activates the CRISPR/Cas adaptive bacterial immunity system. Nature communications 3, 945 (2012)10.1038/ncomms1937)). After the cells were incubated for another two hours post-transformation, the genomic array was checked for expansion and specific integration of the synthetic protospacer into the array by PCR (see FIG. 1D). Sequence-specific bands were observed when Cas1 and Cas2 were induced or (more weakly) uninduced, but never for the case in which the oligos were not supplied. It was additionally confirmed that the specific ps33 nucleotide sequence was present within a fraction of the expanded arrays by Sanger sequencing. These results demonstrate that the CRISPR-Cas system can be successfully directed to acquire a sequence-specific spacer.

To better understand both the properties of this synthetic system, as well as the fundamental properties of Cas1-Cas2-mediated spacer acquisition, additional experiments were performed in which the oligos that were provided via electroporation were altered. It was found that the system required both complementary strands for acquisition, and that the double-stranded protospacer was capable of insertion in either direction (see FIG. 1E). The 5' ends of the oligos were also modified with phosphorothioate bonds to help resist degradation by cellular nucleases, but found no significant differences in acquisition efficiency (see FIG. 1E). Finally, it was tested whether RNA could serve as a protospacer by supplying either one or both of the oligo strands as RNA, but no sequence-specific integration of RNA oligos was detected (see FIG. 2D).

To investigate these results more quantitatively, a PCR was performed across the array (as in FIG. 1D) and the resulting amplicon was subjected to high-throughput sequencing on an Illumina MiSeq platform. Using this methodology, the percentage of all arrays that were expanded at the completion of an experiment could be quantified, as well as the protospacer source. Coupled with qPCR, a time course of spacer acquisition was generated (see FIG. 1F). Sequence-specific acquisitions were first detected as early as 20 minutes after electroporation, reaching ~4% of all arrays by two hours. It was found that the system was sensitive to the concentration of oligo supplied, dropping off at both low and high oligo concentrations (see FIG. 1G, FIG. 2E). Interestingly, whether oligos were delivered or acquired as spacers had no detectable effect on the genome- or plasmid-derived spacers. This suggests that protospacer availability in the cell may be a limiting factor in spacer acquisition. On the other hand, the addition of an array on the expression plasmid had little to no effect on the acquisition frequency of new spacers into the endogenous genomic array (see FIG. 1G). Finally, like genome- and plasmid-derived spacers, the synthetic spacers were inserted into the first (or occasionally first and second) positions of the array, and were almost invariably of 33 bases (see FIGS. 1H and 1I).

EXAMPLE III

PAMs Modify the Efficiency and Directionality of Spacer Acquisition.

Figure 3C:
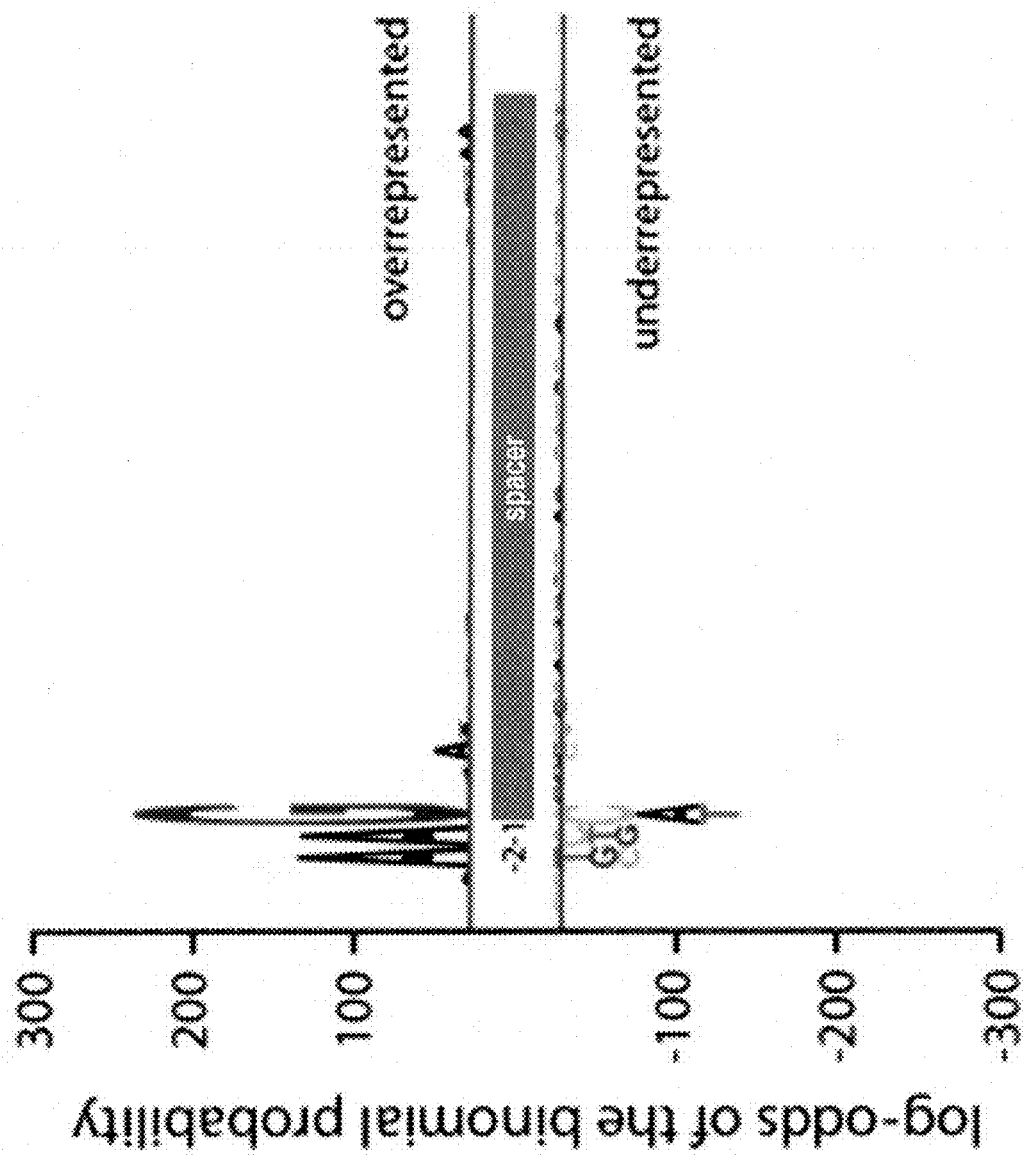
Figure 3B:
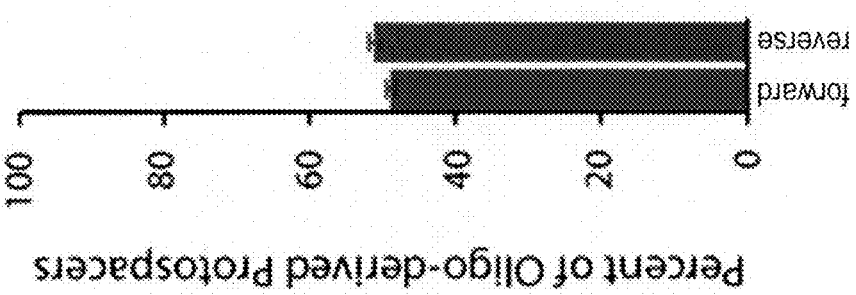

Using the data we collected from sequencing millions of arrays following expansion, it was found that genome- and plasmid-derived protospacers were drawn in equivalent numbers from the forward and reverse strands overall, with the only apparent gross bias being toward the genomic origin of replication (see FIG. 3A). Similarly, oligo-derived protospacers were also found in equal proportions in the forward and reverse orientation in the array (see FIG. 3B). When further examining the context of the genomic- and plasmid-derived protospacers, strong evidence was found for a PAM on the 5' end of the protospacer consisting of two adenines at positions −2 and −1 from the spacer and a strong bias for a guanine as the first spacer base (see FIG. 3C). This is largely consistent with previous characterizations of the *E. coli* type I-E system (see I. Yosef, D. Shitrit, M. G. Goren, D. Burstein, T. Pupko, U. Qimron, DNA motifs determining the efficiency of adaptation into the *Escherichia coli* CRISPR array. Proc Natl Acad Sci USA 110, 14396-14401 (2013); published online EpubAugust 27 (10.1073/pnas.1300108110), E. Savitskaya, E. Semenova, V. Dedkov, A. Metlitskaya, K. Severinov, High-throughput analysis of type I-E CRISPR/Cas spacer acquisition in *E. coli*. RNA biology 10, 716-725 (2013); published online EpubMay (10.4161/rna.24325)).

Figure 3D:
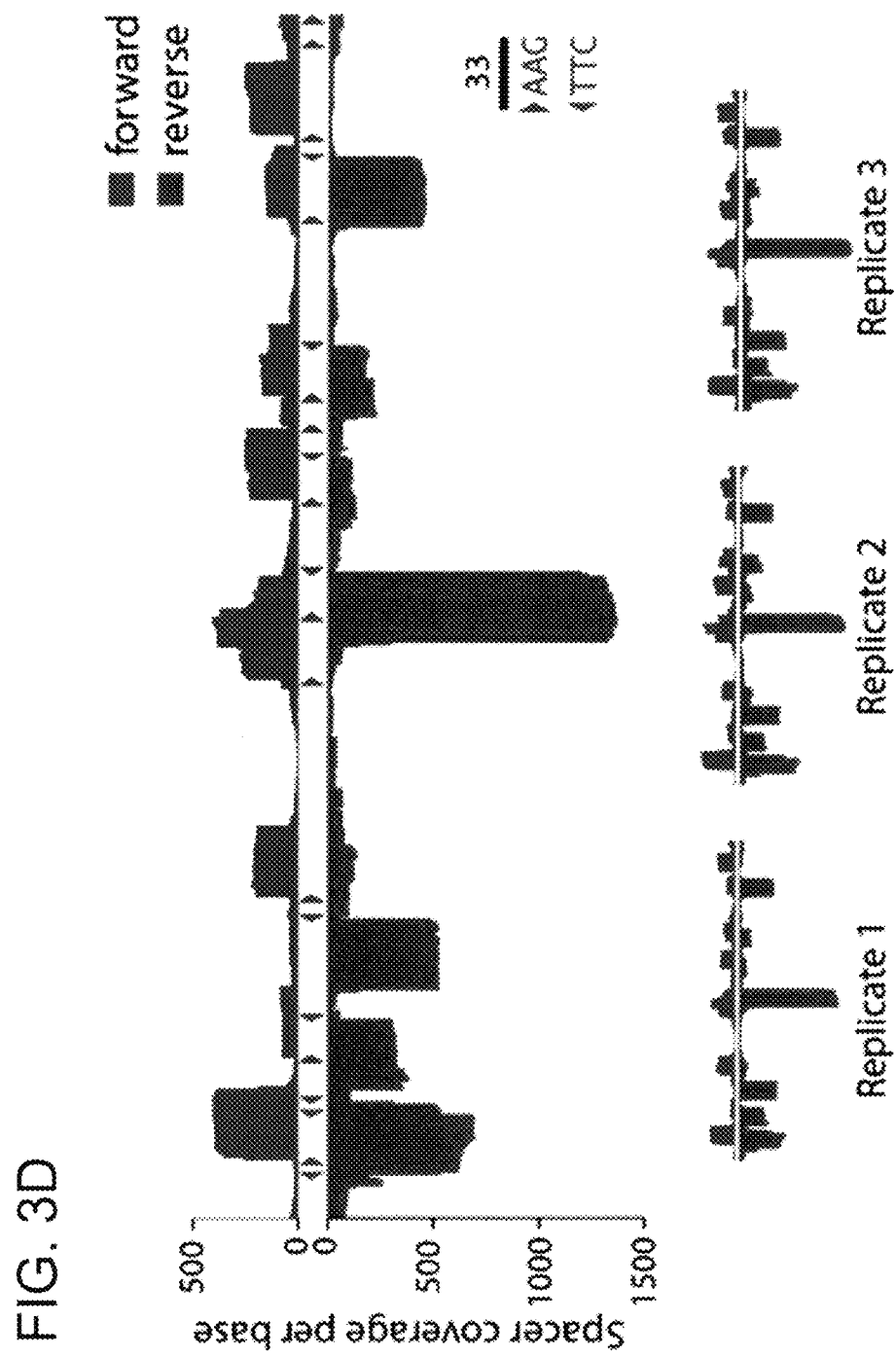
Figure 3F:
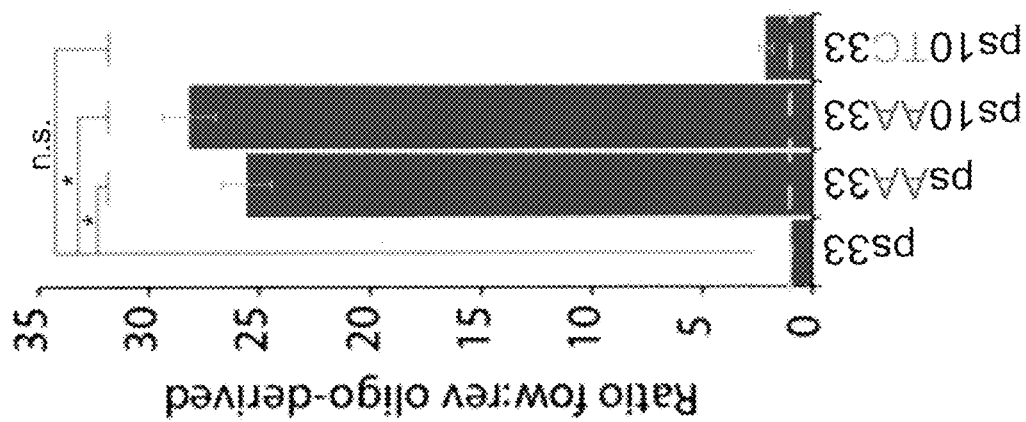

Although there is no bias in forward- or reverse-strand-derived protospacers from the genome or plasmid on the whole, a sharper picture emerges at the level of individual nucleotides. For example, examining one small stretch of the plasmid (~550 bases), asymmetric peaks emerge (see FIG. 3D). Plotting the forward and reverse PAMs along the same stretch of plasmid reveals that, in addition to biasing toward specific sequences for acquisition, the PAM also specifies the orientation of integration into the array. Interestingly, although nearly every protospacer that contains a PAM is acquired as a spacer, not all are acquired at the same frequency (see FIG. 3D).

Figure 4A:
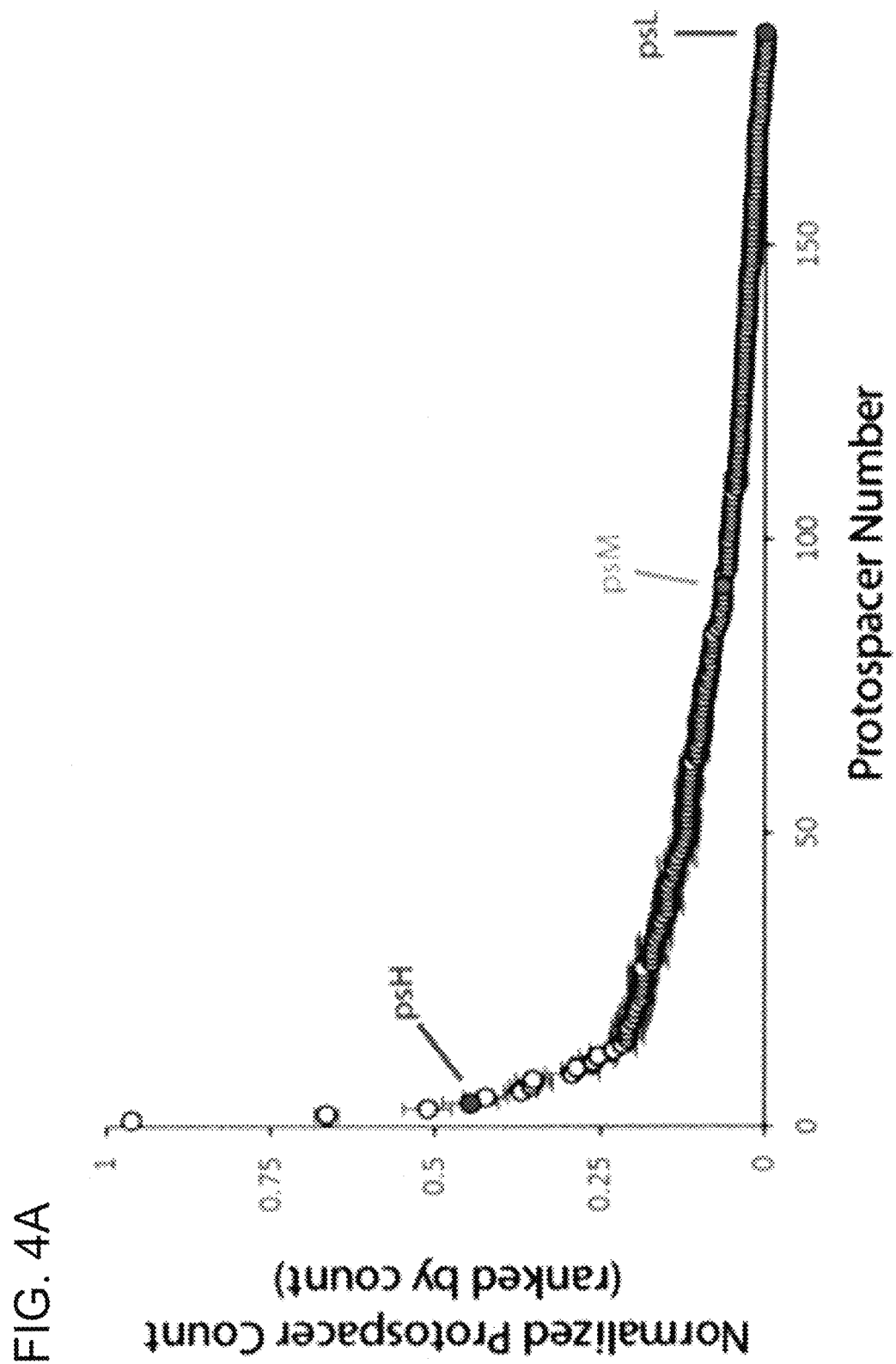
Figure 4B:
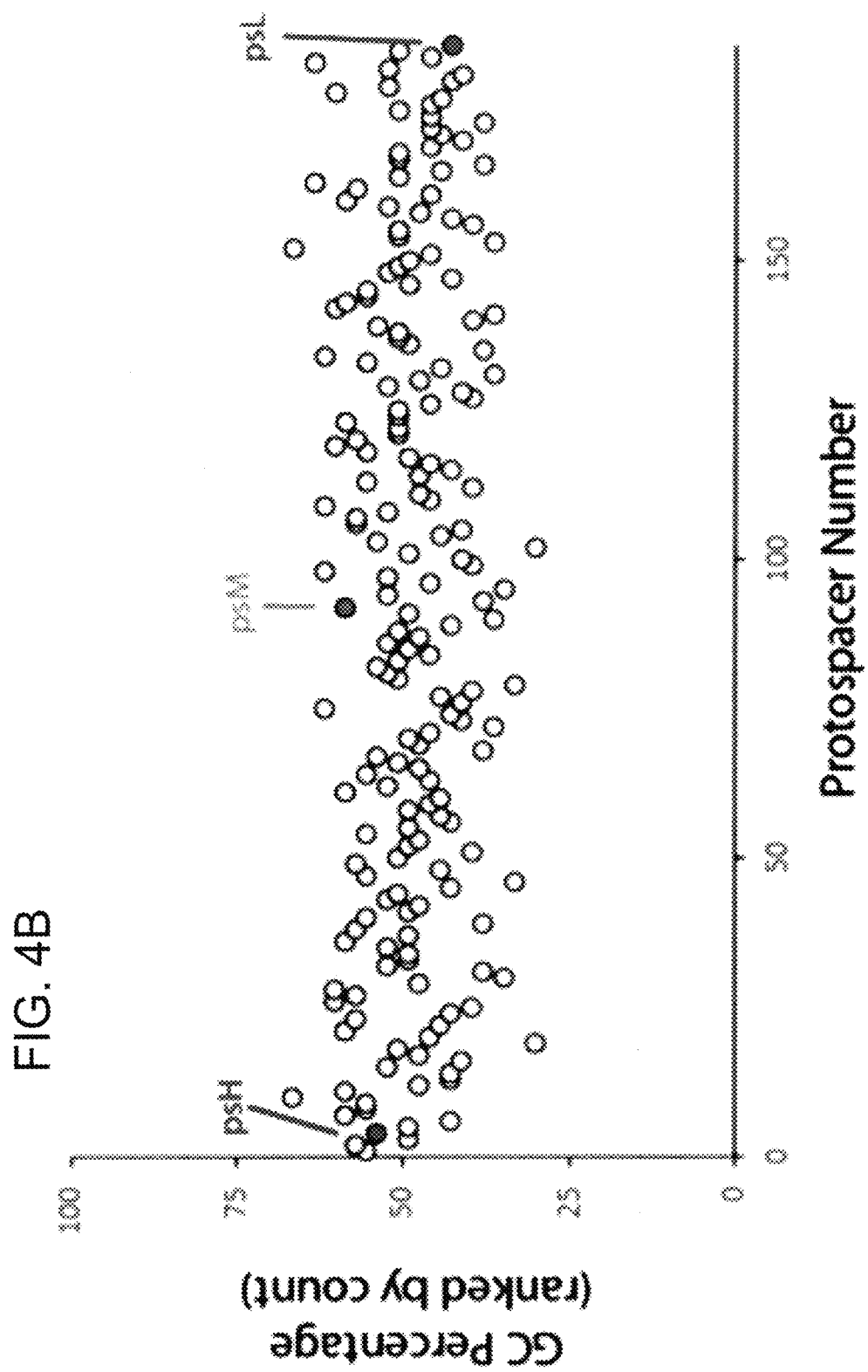
Figure 4C:
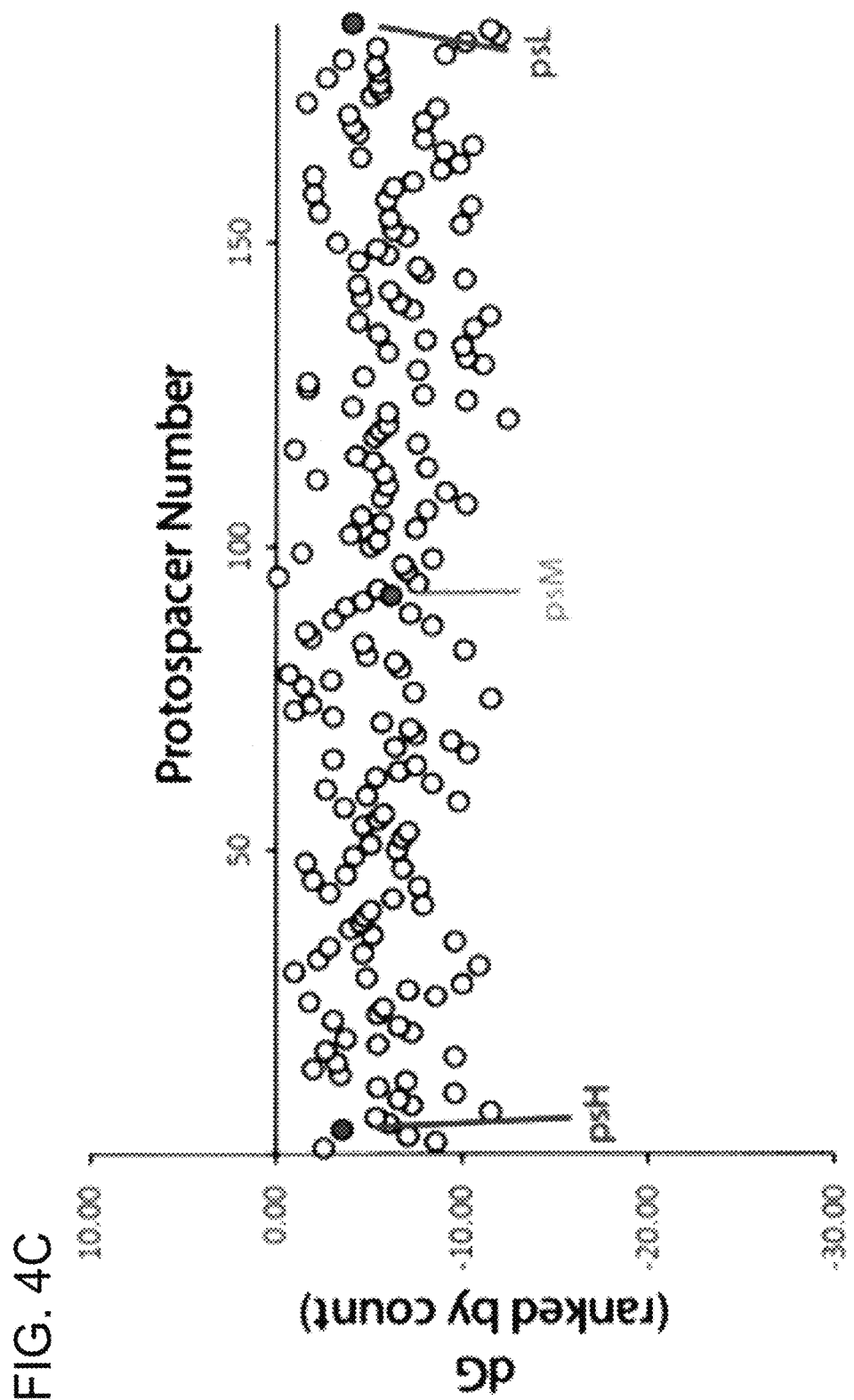
Figure 4D:
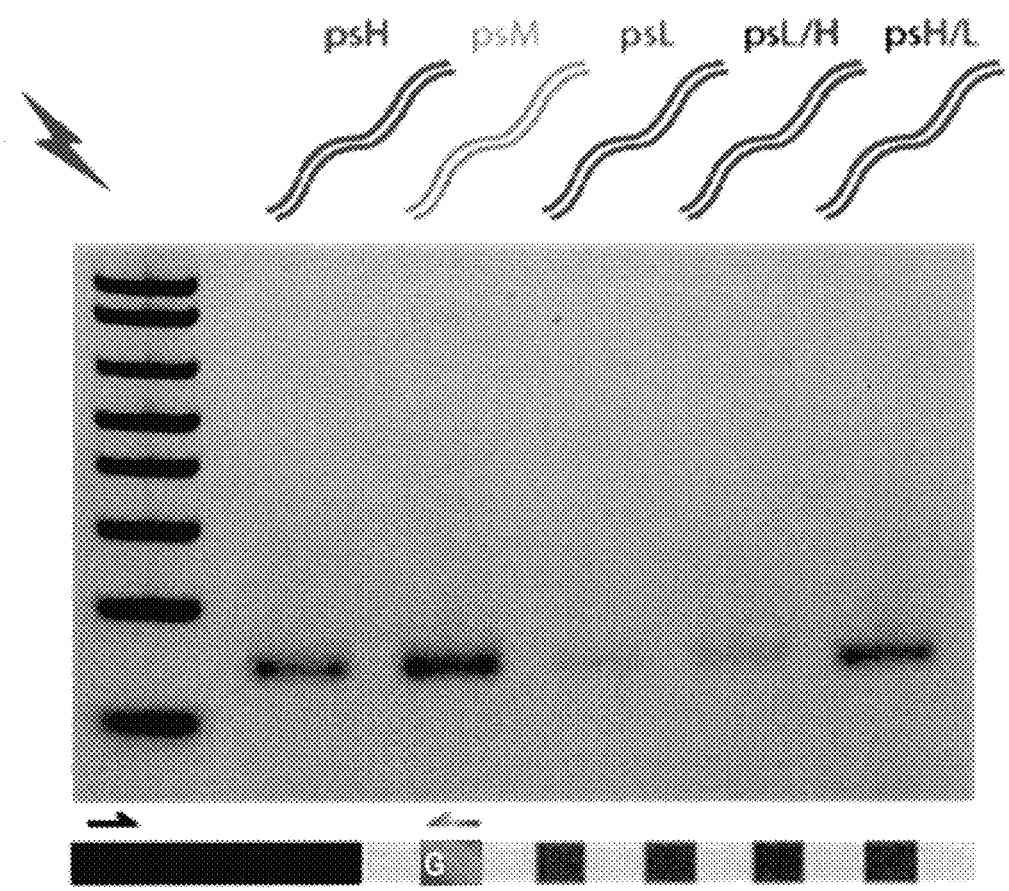
Figure 4F:
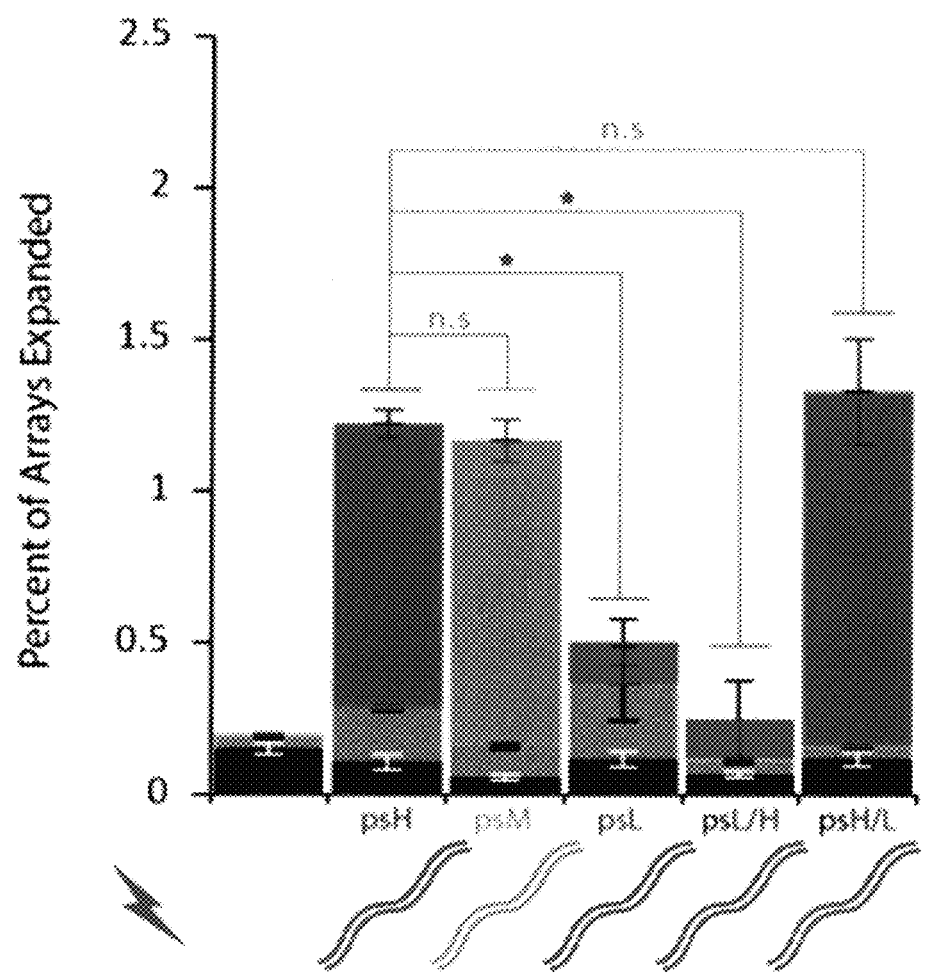
Figure 5A:
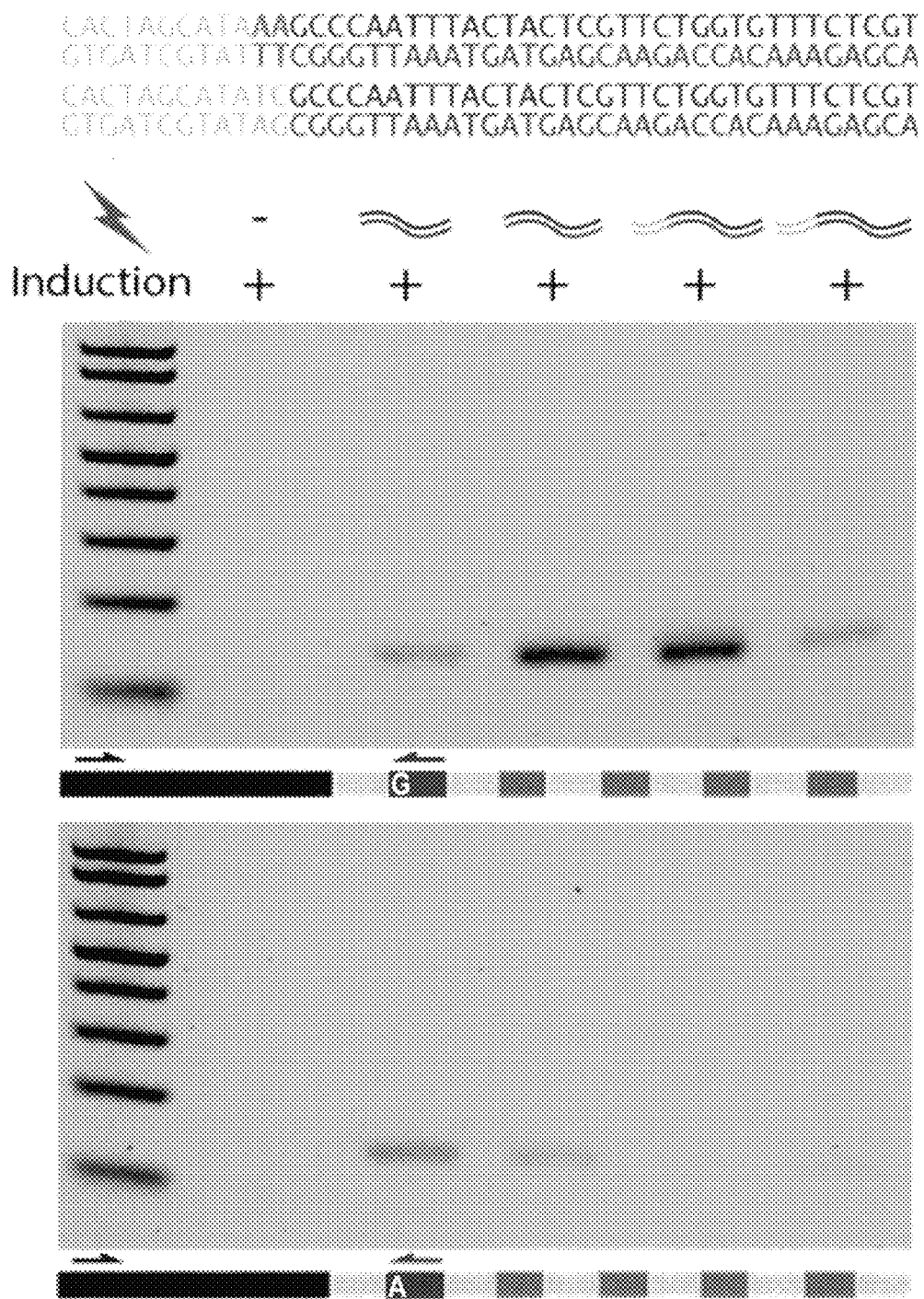
Figure 5C:
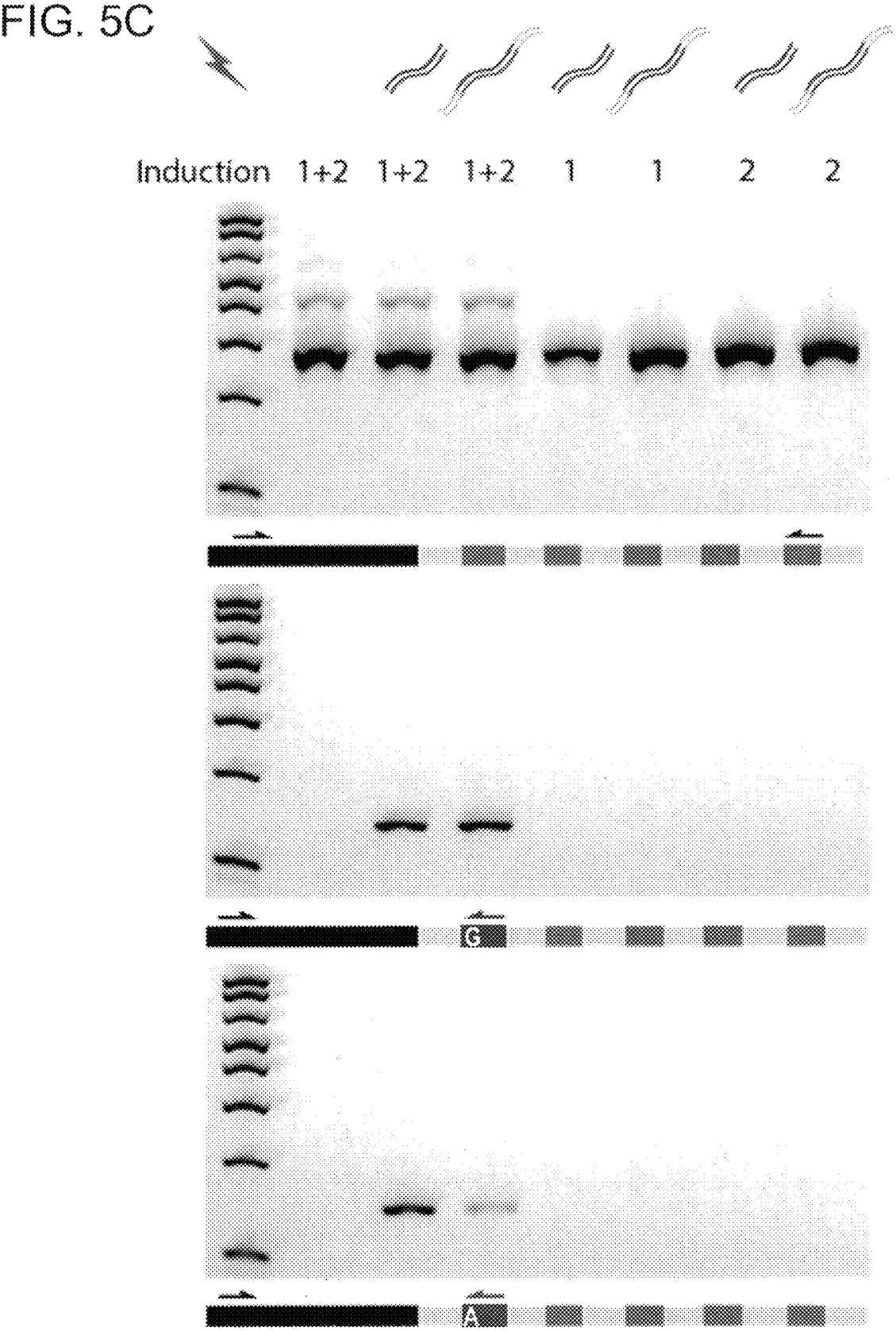

Recently, it was found that the presence of Chi sites within a genome or plasmid bias the frequency of protospacer acquisitions (see A. Levy, M. G. Goren, I. Yosef, O. Auster, M. Manor, G. Amitai, R. Edgar, U. Qimron, R. Sorek, CRISPR adaptation biases explain preference for acquisition of foreign DNA. Nature 520, 505-510 (2015); published online EpubApril 23 (10.1038/nature14302)). According to the present disclosure, methods are provided of using a sequence of the protospacer to bias acquisition frequency. Every PAM (AAG)-containing potential protospacer in the plasmid was ranked according to the frequency that it was acquired into the genomic array (see FIG. 4A). Characteristics for among protospacers including GC percentage and free energy that might explain the difference in acquisition frequency were searched, but it was failed to identify a correlation (see FIGS. 4B and 4C). For a direct test, three protospacer sequences were selected and synthesized (including their 15 bp flanking regions): one each from the high (psH), middle (psM), and low (psL) end of the frequency spectrum. Each of these oligo protospacers was then electroporated into cells expressing Cas1-Cas2 from an alternate plasmid that did not include these particular sequences. Surprisingly, psL was acquired much less frequently than both psH and psM (see FIG. 4F). To determine whether this was due to the sequence of the spacer itself, or a flanking region, the 15 bp flanking regions of psH were swapped with those of psL, and vice versa (psH/L and psL/H, respectively). Again, the psL/H spacer was acquired at a lower frequency than psH/L, independent of the flanking regions. These results indicate the sequence of the protospacer itself is capable of influencing the efficiency of acquisition.

Figure 3E:
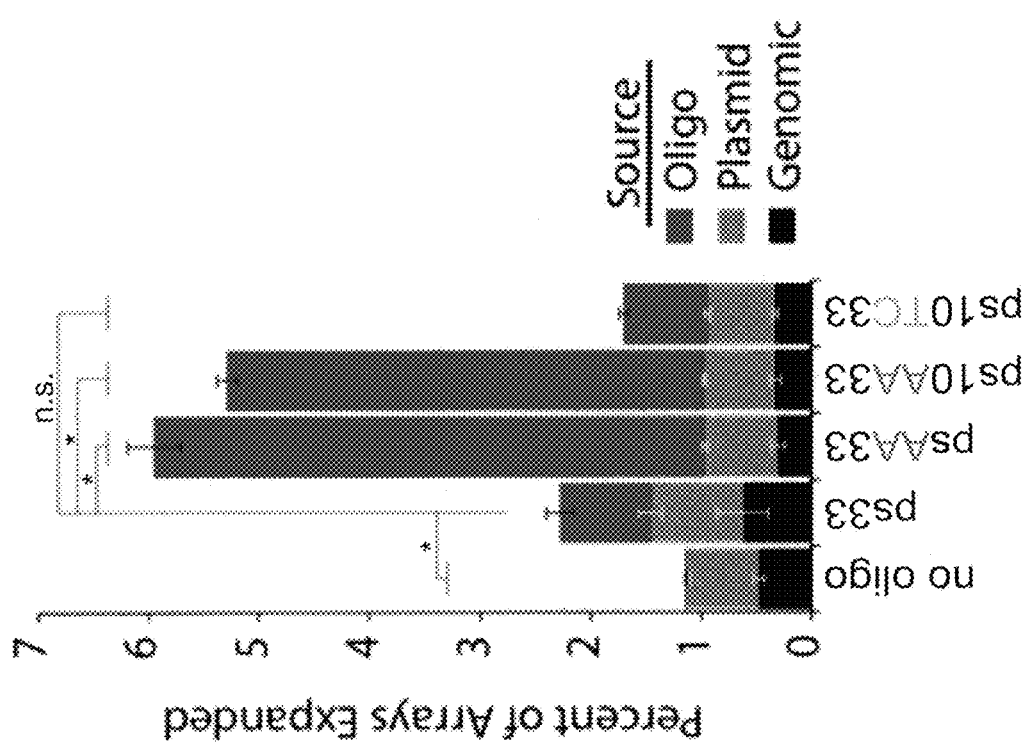
Figure 3G:
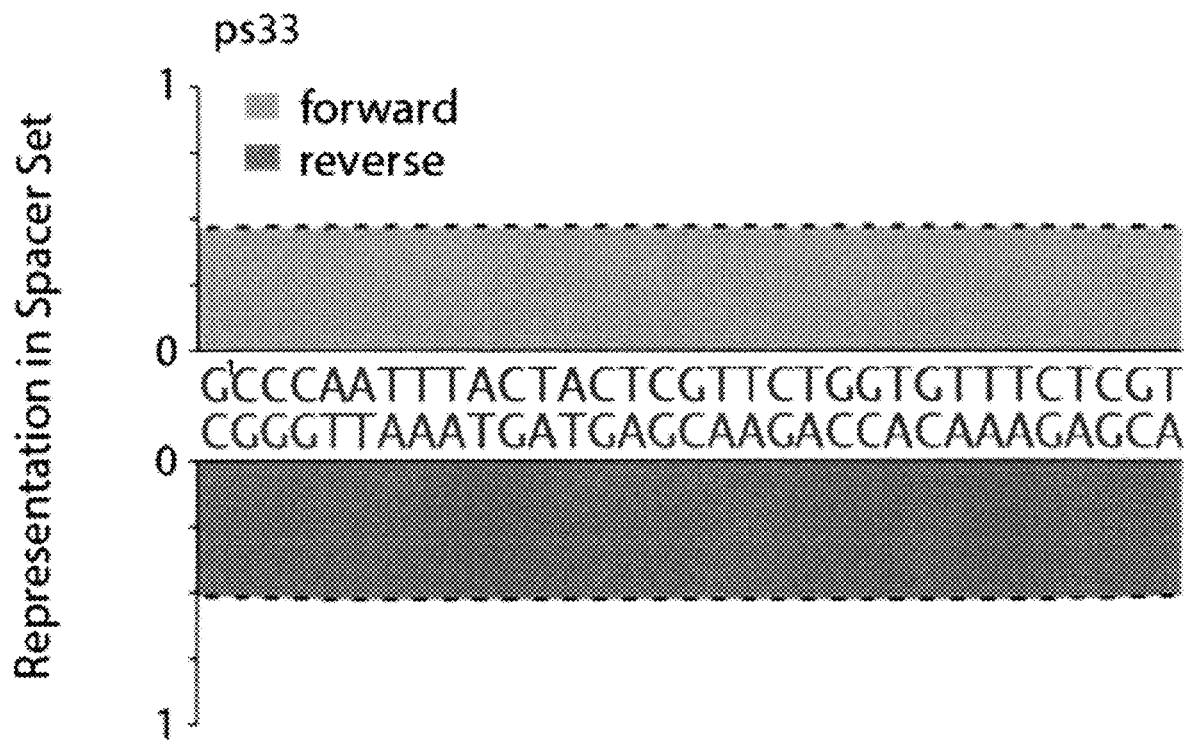

Given that spacers are selected from the genome and plasmid according to an adjacent sequence, methods are provided for use of a PAM in a synthetic protospacer ps33 to alter acquisition frequency. Three additional oligo protospacers were designed: psAA33, in which two adenines were included at the 5' end of ps33 to create the entire canonical AAG PAM; ps10AA33, which includes an additional ten 5' nucleotides; and ps10TC33, in which the AA of the PAM has been mutated to TC to create a non-canonical PAM (PAMNC). Using these oligos, it was found that the inclusion of a PAM greatly increased the efficiency of sequence-specific acquisition (see FIG. 3E). Whether preceded by ten extra nucleotides or not, oligos with the AAG PAM (psAA33 and ps10AA33) were acquired at greater than 5 times the frequency of those that did not include a PAM (ps33). Conversely, including the TCG PAMNC did not change acquisition frequency relative to ps33 (see FIG. 3E).

Figure 3H:
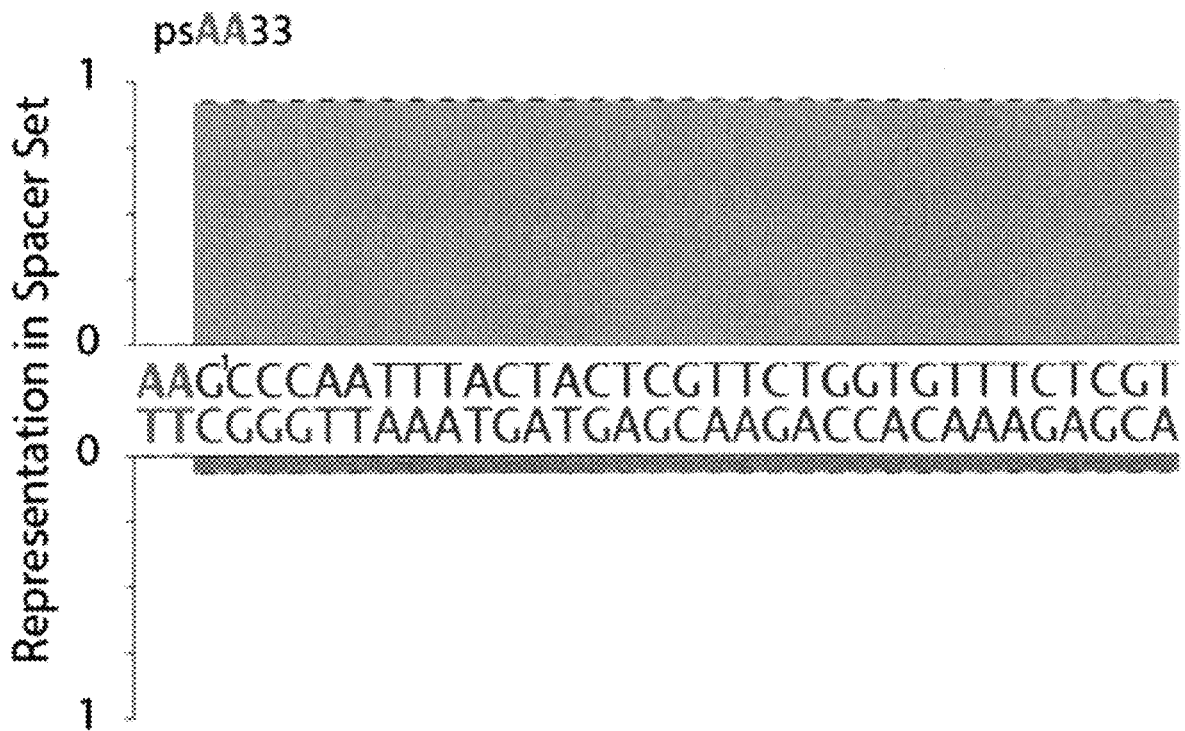
Figure 3I:
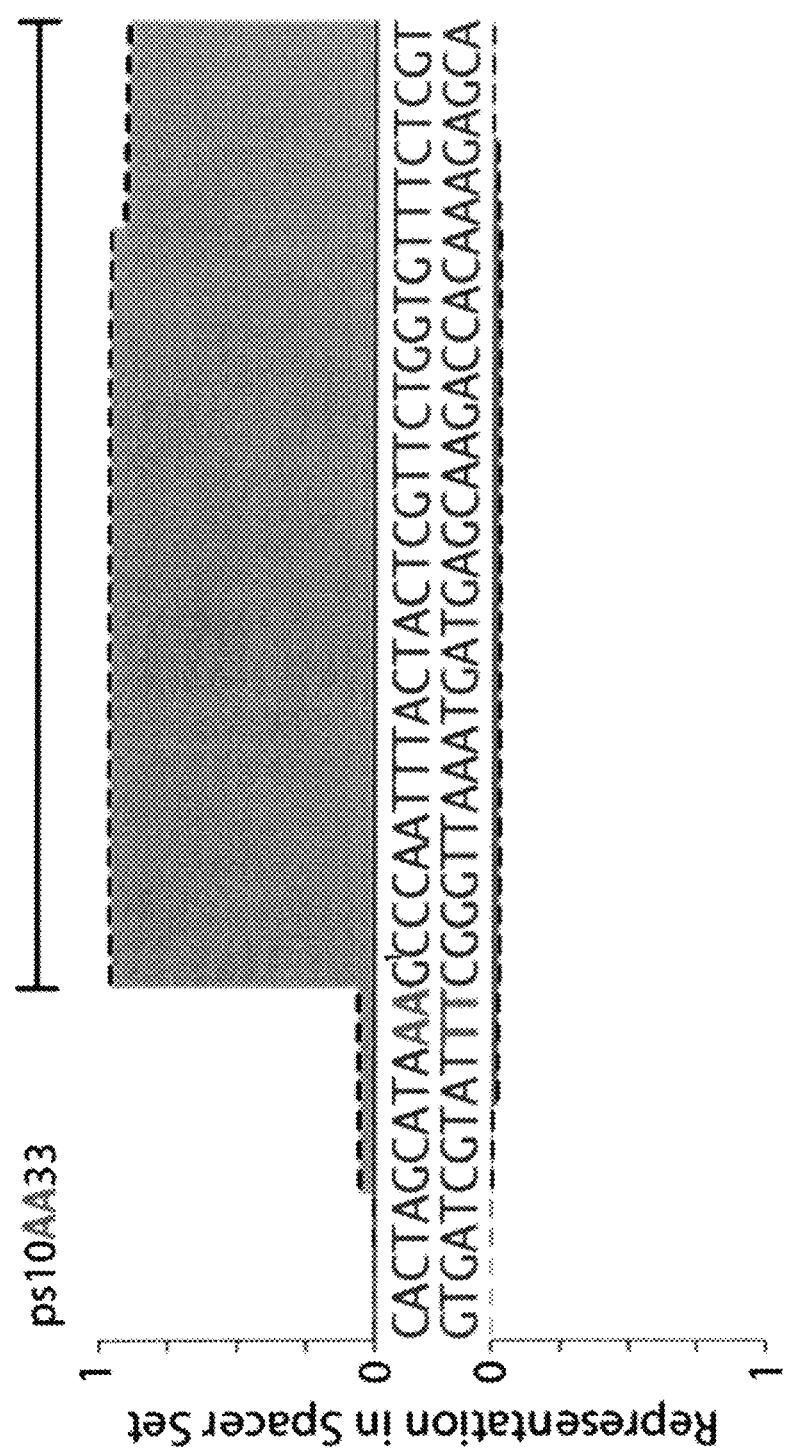
Figure 3J:
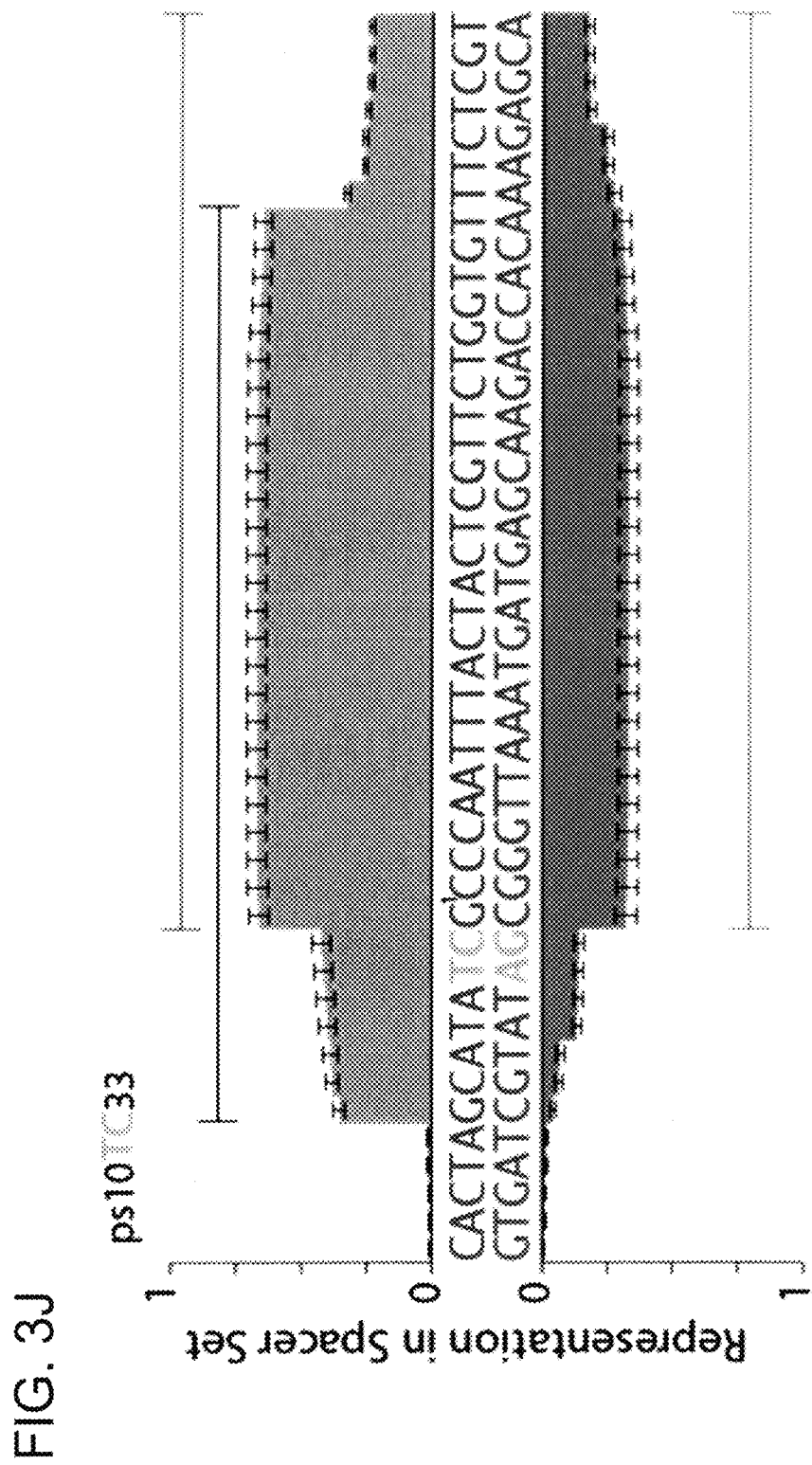

The inclusion of a PAM also dramatically altered the orientation of spacer acquisition. Whereas ps33 and ps10TC33 were acquired equally in both orientations, psAA33 and ps10AA33 were acquired almost exclusively in the forward orientation (see FIGS. 3F-3J and FIG. 5A). Consistent with the type I-E preference for an AAG PAM, psAA33 and ps10AA33 were consistently inserted with nucleotide G1 as the first base of the spacer (see FIGS. 3H and 3I). In contrast, ps10TC33 lacked a single dominant spacer product, and was inserted at several different PAMsNC (see FIG. 3J). Finally, it was verified that both Cas1 and Cas2 are necessary for synthetic spacer integration, whereas Cas2 nuclease activity is not required (see J. K. Nunez, A. S. Lee, A. Engelman, J. A. Doudna, Integrase-mediated spacer acquisition during CRISPR-Cas adaptive immunity. Nature 519, 193-198 (2015); published online EpubMarch 12 (10.1038/nature14237)). Therefore, the inclusion of a PAM in synthetic protospacers dictates both the efficiency and orientation of the spacer that is acquired by the Cas1-Cas2 complex.

EXAMPLE IV

A Molecular Recording Over Time.

Figure 6A:
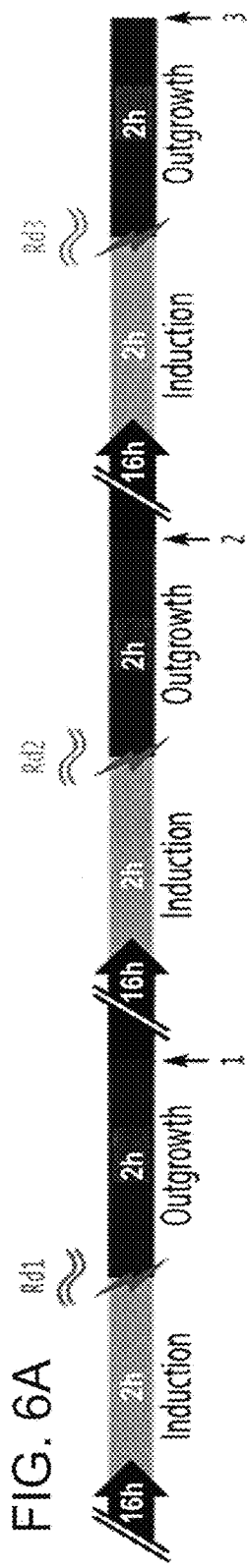
FIGS. 6A-6I are related to FIGS. 7A-7F.
Figure 6B:
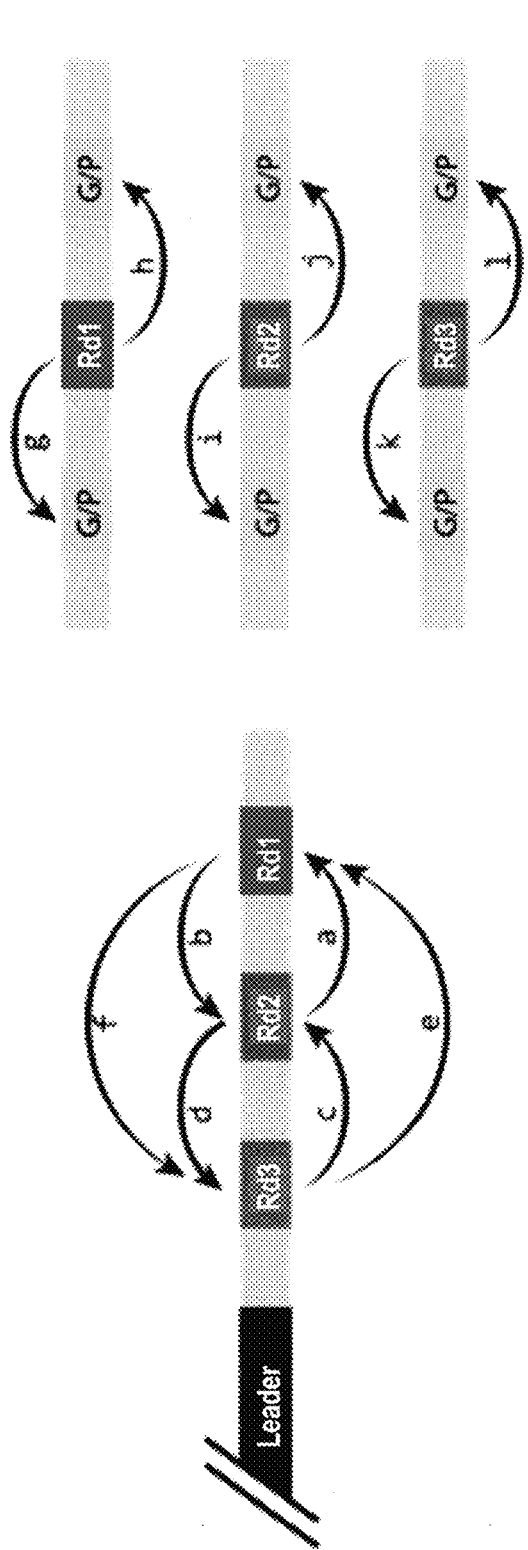
Figure 6C:
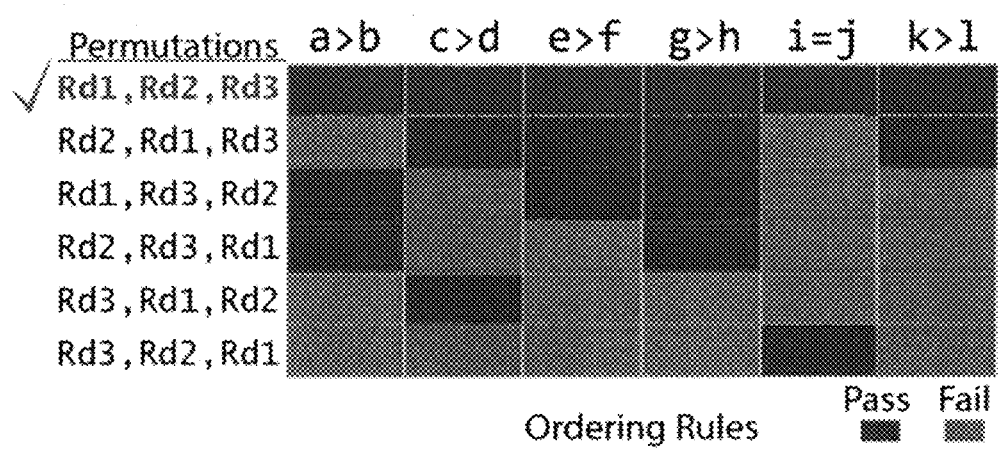
Figure 6D:
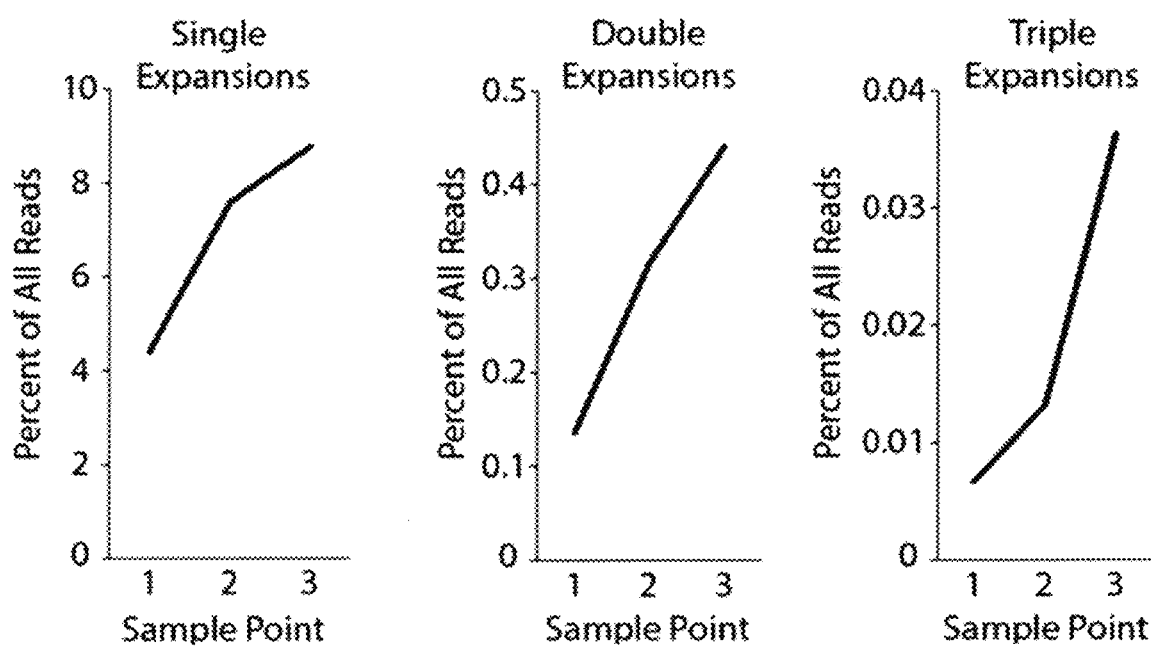
Figure 7B:
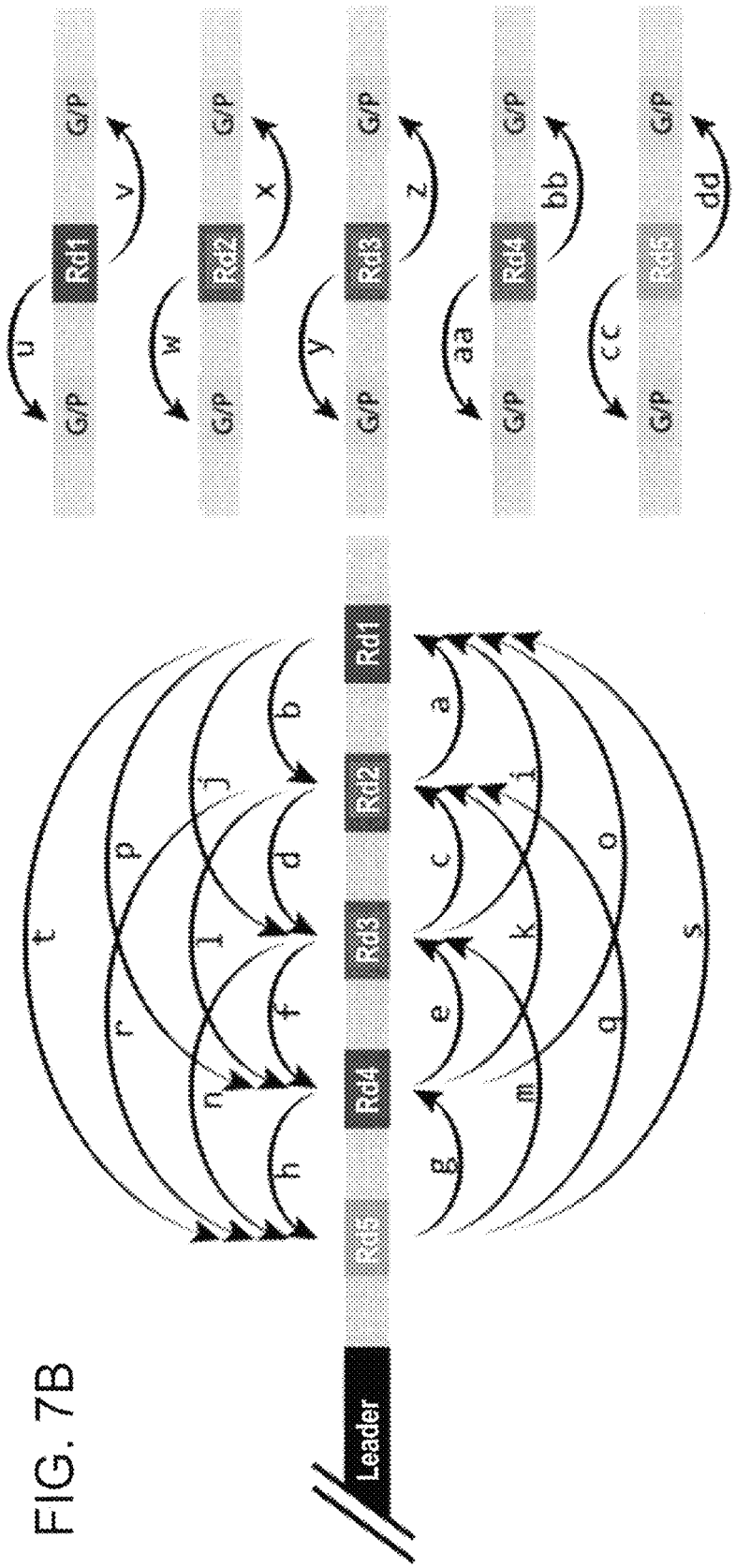

It was next tested if the acquisition of specific spacer sequences could be harnessed to record a series of synthetic spacers into a population of cells over time. As an initial test, three unique elements were recorded (1×3) into a single culture of E. coli by sequentially electroporating a series of three different oligo protospacer sequences into the culture, over a period of three days (one protospacer each day) (see FIG. 6A). After sequencing a population of the arrays on day three, the order in which the spacers were delivered could be faithfully reconstructed (see FIGS. 6B, C, and discussed in detail below). To further probe the limits of this system, fifteen unique elements were next recorded (3×5): three sets of five protospacers, electroporated three-at-a-time over five days (see FIG. 7A). The analysis of both the 1×3 and 3×5 recordings are conceptually similar so the latter is discussed in detail (see FIG. 6B and FIG. 7B, respectively).

Figure 7E:
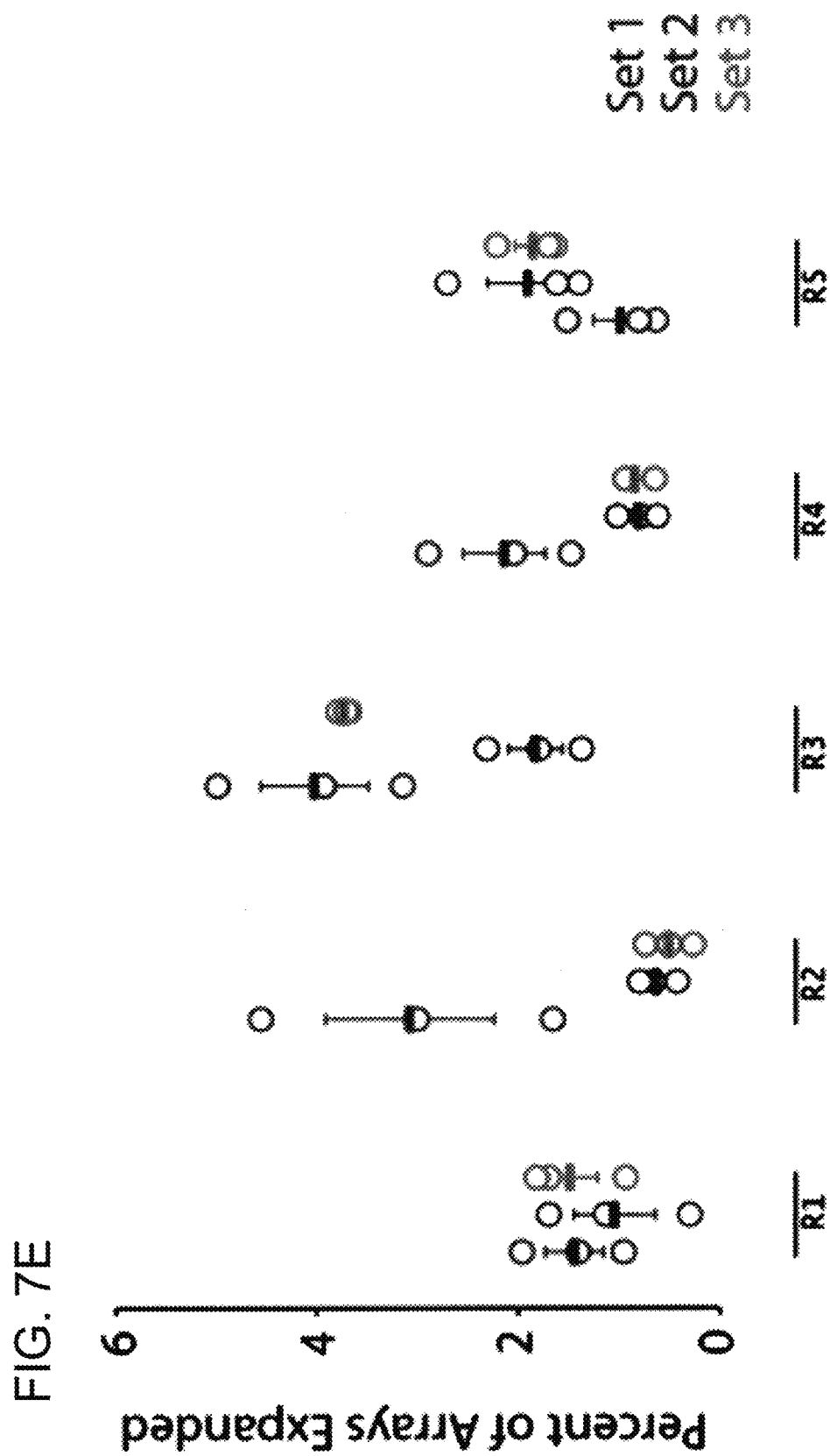

For the 3×5 recording, all oligo protospacers were 35 nucleotides, beginning with a 5' AAG PAM followed by a 5-base-barcode (unique to each of the 3 sets) and 27 more bases (unique to each of the 15 protospacers). At the end of the 3×5 recording, nearly a quarter of all arrays in the cell population contained at least one oligo-derived spacer, with spacers from each round of electroporation represented in roughly equivalent proportions (see FIGS. 7C, D). Individual variations among the spacer acquisition frequency were more heavily driven by spacer nucleotide sequence than by round (see FIG. 7E).

Figure 7F:
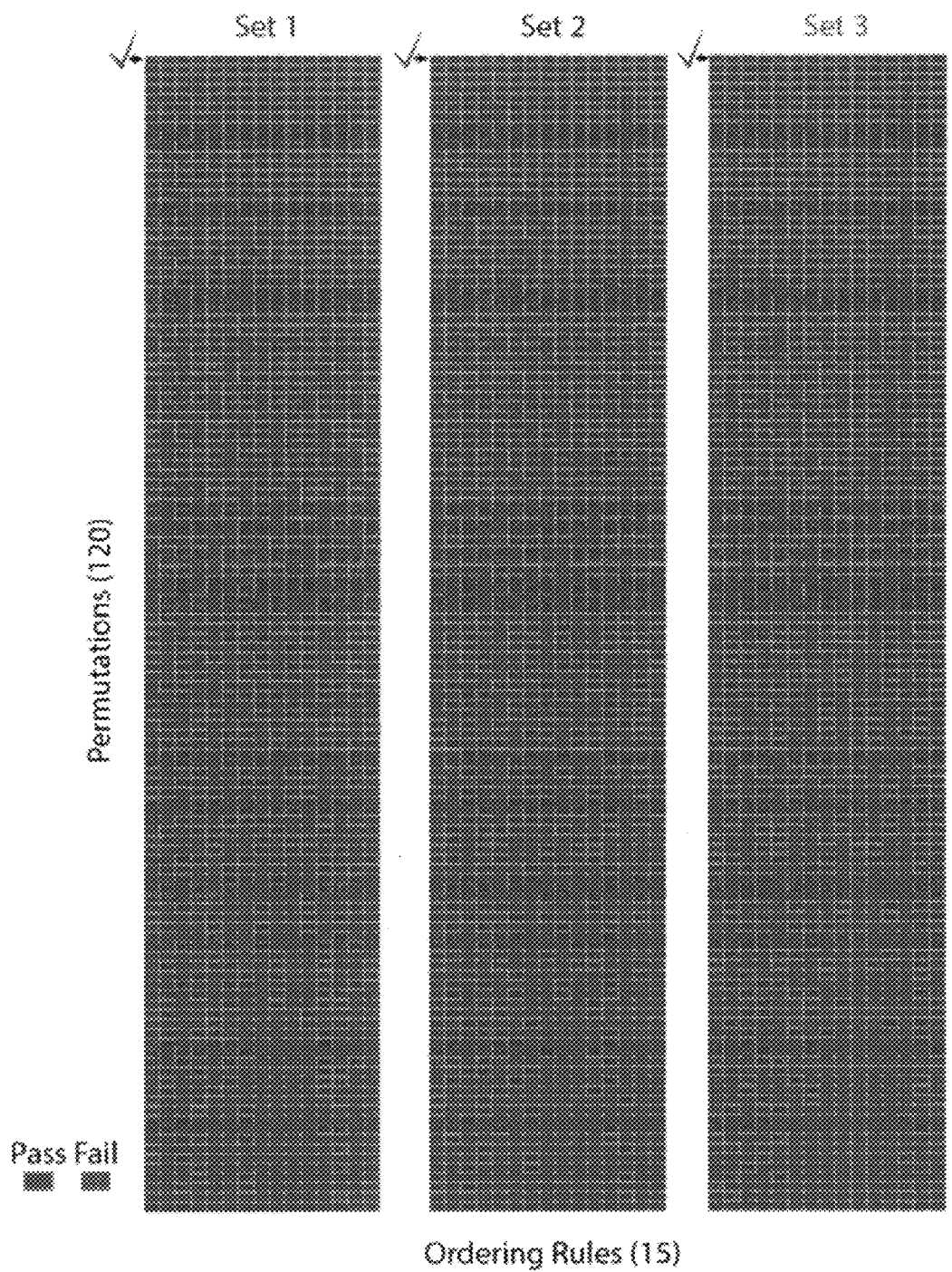

Due to the low probability of acquiring spacers from every round in any single array (see FIG. 7D), successful readout of the recording required analyzing a population of arrays. Therefore, the first three spacers of each array were sequenced (moving in from the leader), and considered only the order of pairs of newly acquired spacers (see FIG. 7B). For any given synthetic spacer pair within the same set, the order should follow a predictable rule: among all arrays that contain any two new spacers, a spacer electroporated in an earlier round will always be found further from the leader than a spacer introduced at a later round. Information can also be gained by considering the arrangement of oligo-derived spacers in relation to newly acquired genome- and plasmid-derived spacers. Because the endogenous spacers will accumulate over time, synthetic spacers from an earlier round will be paired more often with a new genome/plasmid spacer in one direction (toward the leader) than in the other (relative to the synthetic spacer), and vice versa for oligo-derived spacers from a later round. With five possible spacers (in each set), all possible pairwise comparisons can be considered and 15 ordering rules were generated from which the order of the entire set can be reconstructed (see FIG. 7B). The sequences of arrays after the completion of the 3×5 recording were taken and they were passed through an algorithm that, with the only sequence-based input being the sequence of the CRISPR repeat, all oligo-derived spacer sequences would be predicted, they were assigned to a set based on the barcodes, and then all possible permutations of the sequence against the 15 ordering rules were tested. For each set, only one permutation satisfied all 15 ordering rules, and in every case that permutation matched the actual order of electroporated oligos (see FIG. 7F). Although ~2 million reads for each replicate were analyzed, it was found that order could be correctly reconstructed in most cases using 20,000 reads or fewer. Thus, the fifteen element recording could be reliably recorded and read out.

EXAMPLE V

Cas1-Cas2 PAM Recognition Can be Modified.

The ability to control not only the sequence of new spacers, but also the orientation of new spacer integration would enable one to record information in multiple modalities simultaneously. Because the addition of a 5' AAG PAM on our synthetic spacers controlled the orientation of new acquisitions (see FIG. 2E), it was sought to modify integration orientation by altering PAM recognition of Cas1-Cas2. To do this, the directed evolution approach shown in FIG. 8A was performed. First, a large library of random Cas1-Cas2 mutants were generated by error-prone PCR (see FIGS. 9A and 9B), and this library was inserted into a plasmid upstream of a minimal CRISPR array. After cloning the plasmid library into BL21-AI, mutants were induced and transformed with a protospacer bearing the canonical 5' AAG PAM on the forward strand, and a non-canonical 5' TCG PAMNC on the reverse strand. After outgrowth, mutants were selected using a forward primer ahead of the Cas1-Cas2 mutant genes, and a reverse primer matching the PAMNC spacer sequence to yield specific amplification of only those mutants that had acquired the spacer in the (reverse) PAMNC orientation. A subset of these selected mutants were then tested for PAM specificity, while a separate subset were subjected to another round of selection for refinement prior to testing. For testing, individually selected mutant clones were induced overnight, and their expanded arrays were analyzed by sequencing. Specifically, the PAMs of the all genome- and plasmid-derived spacers were analyzed to determine what, if any, PAM specificity remained. Wild-type Cas1-Cas2 acquires spacers from AAG PAM protospacers at nearly the same frequency as from all other (non-AAG) PAM protospacers combined (see FIG. 8B). In contrast, the majority of mutants that were selected acquired non-AAG protospacers at a greater frequency than AAG protospacers (see FIG. 8B). There was no gain in non-AAG acquisition frequency from the extra step of refinement (see FIG. 9C), so mutants from both subsets are shown together (see FIG. 8B and FIG. 9D).

To visualize shifts in PAM specificity, a heat map was plotted that showed the normalized frequency of observed PAMs among all potential PAMs for wild type Cas1-Cas2 and several selected mutants (see FIG. 8C). Wild type Cas1-Cas2 displays strong selectivity for the canonical AAG PAM. A minority of mutants also retained (m-24) or even increased (m-27) this preference. However, many more mutants showed reduced or, in the case of the three mutants shown (m-74, m-80, m-89), nearly no specificity for the canonical PAM. From the sequence of these selected mutants, a subset of single-point mutations were chosen for follow-up analysis based on repeated observations in the data set or location in the crystal structure of the Cas1-Cas2 complex (see J. K. Nunez, P. J. Kranzusch, J. Noeske, A. V. Wright, C. W. Davies, J. A. Doudna, Cas1-Cas2 complex formation mediates spacer acquisition during CRISPR-Cas adaptive immunity. Nature structural & molecular biology 21, 528-534 (2014); published online EpubJune (10.1038/nsmb.2820), J. Wang, J. Li, H. Zhao, G. Sheng, M. Wang, M. Yin, Y. Wang, Structural and Mechanistic Basis of PAM-Dependent Spacer Acquisition in CRISPR-Cas Systems. Cell 163, 840-853 (2015); published online EpubNovember 5 (10.1016/j.cell.2015.10.008), J. K. Nunez, L. B. Harrington, P. J. Kranzusch, A. N. Engelman, J. A. Doudna, Foreign DNA capture during CRISPR-Cas adaptive immunity. Nature 527, 535-538 (2015); published online EpubNovember 26 (10.1038/nature15760)) (see FIG. 23; FIG. 8E). Most of the single-point mutants tested in isolation also reduced the PAM specificity as compared to wild-type (see FIG. 8D and FIG. 9D). These results demonstrate that PAM recognition by the Cas1-Cas2 complex can be modified by many different mutations without drastically reducing spacer acquisition efficiency.

EXAMPLE VI

Recording in a Second Modality.

As a proof-of-concept, a PAMNC Cas1-Cas2 mutant was selected (m-89, FIG. 8C and FIG. 9D) to add an extra modality to the 1×3 recording (see FIGS. 6A-6I). Bacteria were subjected to three sequential rounds of electroporation, with each oligo protospacer containing a 5' AAG PAM on the forward strand, and a 5' TCG PAMNC on the reverse (see FIG. 10A), while controlling expression of wild type Cas1-Cas2 and m-89 using different inducible promoters (pLTetO and pT7lac, respectively) on the same plasmid (see FIG. 10B). The bacteria were split between two conditions, each alternating between T7lac and tet induction from round-to-round. It was found that cells of both conditions acquired spacers from each round at similar frequencies, indicating that induction levels and integration activity of the wild type and m-89 Cas1-Cas2 were both adequate (see FIG. 10C). At the completion of the recording, the orientation of each spacer between the two conditions was compared. A difference in the ratio of forward to reverse oriented spacers was found as expected between the conditions—that is, shifted toward PAMNC (reverse) during tet induction (see FIGS. 10D and 10F). After normalization for the total spacer orientation ratio for each spacer, it could be clearly discriminated which condition received which inducer at each time point based only on the direction of integration (see FIG. 10G). Thus, this system can simultaneously record in two modalities.

The disclosure provides for the fundamentals of a CRISPR-Cas-based system to record molecular events into a genome in the form of essentially arbitrary synthetic DNA sequences. While the information is only partially encoded within any given cell, the complete record remains distributed across a population of cells. To read out the recordings, high-throughput sequencing was used, and only the pairwise order of any two new spacer sequences within single CRISPR arrays were considered. Using many of these binary comparisons, a complete record of events could then be assembled, faithfully decoding the distributed memory fully preserved within the cell population.

The disclosure also provides for uncovered details of the native CRISPR-Cas adaptation system. The ability of the Cas1-Cas2 protein complex to integrate synthetic oligo sequences in vivo enabled direct assessment of the detailed aspects of protospacer acquisition. For instance, because the frequency of spacers acquired from the genome and plasmid is largely unaltered in the presence of oligo-derived acquisition (see FIGS. 1G, 3E), it is concluded that the availability of adequate protospacers is likely one limiting aspect of the adaptation system. Further, these experiments show that the presence of a 5' AAG PAM modulates both the frequency and orientation of spacer acquisition, and that the interior sequence of the protospacer can influence acquisition efficiency. As a method, delivering synthetic protospacers to an in vivo CRISPR-Cas system should be a valuable technique to probe the system going forward.

The disclosure further provides a directed evolution approach that allowed experimentally modifying PAM recognition of the Cas1-Cas2 complex, which enabled generation of a record in multiple modalities simultaneously. This directed evolution method requires no structural information and should also be generally applicable to evolving other activities of CRISPR-Cas proteins by coupling them to the spacer acquisition process (e.g. modifying target site specificity).

To date, the highest storage capacity of a synthetic in vivo recording device was achieved using 11 orthogonal recombinases, capable of 2$^{11}$ (2,048) unique states, capturing 1.375 bytes of information (L. Yang, A. A. Nielsen, J. Fernandez-Rodriguez, C. J. McClune, M. T. Laub, T. K. Lu, C. A. Voigt, Permanent genetic memory with >1-byte capacity. Nat Methods 11, 1261-1266 (2014); published online EpubDecember (10.1038/nmeth.3147)). Comparatively, as shown in FIG. 11, in the 3×5 recording disclosed herein, 15 individual elements were encoded. However, because this system can record arbitrary defined sequences, the number of possible states is expanded dramatically. Using the constraints that were imposed—an invariable G at the beginning of the spacer and a 5 base set identifier—that leaves 27 bases to encode information, yielding 4$^{27}$ possible unique sequences per spacer. Furthermore, it was showed that it is possible to encode the order within each set to at least five elements, resulting in a unique state capacity for each set based on the permutation P(4$^{27}$,5)=1.9×10$^{81}$, or 5.7×10$^{81}$ combining the three sets and assuming set independence. If interdependence between each set was included, total unique states would rise to (4$^{27}$)$^{15}$ or ~7×10$^{243}$. As a point of comparison, the number of atoms in the observable universe is estimated at 1×10$^{80}$. In more practical terms, it is entirely within the range of this system to uniquely encode information among, for example, every possible transcript within a human cell.

Those calculations define the theoretical capacity for unique states of the system as have been tested herein. Regarding the amount of information captured in an individual recording, with 15-recorded spacers, each with 27 bases of recording potential (and four bases per byte), the amount of recorded information could reach 101.25 bytes in the 3×5 recording. By also considering the ability to control spacer orientation (an extra modality), it could potentially be encoding an additional 1.875 bytes for a total of 103.125 bytes. Of course, this only reflects the information of the current recordings, which was arbitrarily limited to 15 spacers. Native species have been found with as many as 458 spacers in a single cell (S. tokodaii) (C. Rousseau, M. Gonnet, M. Le Romancer, J. Nicolas, CRISPI: a CRISPR interactive database. Bioinformatics (Oxford, England) 25, 3317-3318 (2009); published online EpubDecember 15 (10.1093/bioinformatics/btp586)), illustrating the potential space to encode complex biological phenomena.

EXAMPLE VII

Time Dependent Recording of Protospacer Sequences Encoding Information

Aspects of the present disclosure are directed to including a plurality of protospacer sequences into a CRISPR array using Cas 1 and Cas2 enzymes to produce a corresponding plurality of spacer sequences in the CRISPR array. Each protospacer sequence encodes for a portion of information, such as text, an image or images, a video format, an audio format or other information formats known to those of skill in the art and which may be in electronic form such as html, pdf, jpeg, and the like. Each protospacer sequence may include a barcode sequence or pixel which identifies the order or location in which the protospacer sequences are to be placed so as to be decoded into the format of information. In this manner, the set of protospacers representative of the format of information as a whole, such as text, an image or images, or a video format or an audio format or other information format, may be supplied to a cell in whole or in part and inserted into the CRISPR array without regard to the timing of insertion of protospacers. The spacer sequences are then identified and the barcode sequences are used to order the information encoded by the protospacer to arrive at the format of information originally encoded. The protospacer sequences in total represent information that has been encoded into a nucleic acid sequence. Methods for storing information using nucleic acids are described in U.S. Pat. No. 9,384,320 hereby incorporated by reference in its entirety.

Aspects of the present disclosure are directed to including a plurality of protospacer sequences in a time dependent manner into a CRISPR array using Cas1 and Cas2 enzymes to produce a corresponding plurality of spacer sequences in the CRISPR array. Protospacer sequences may be inserted into a CRISPR array one by one or set of protospacers by set of protospacers. Such a method is advantageous when the format of information is an ordered sequence of images, such as with an ordered sequence of images making a moving picture, where the sequence of images is part of the information to be conveyed. Each protospacer sequence encodes for a portion of information, such as text, an image or images, a video format, an audio format or other information formats known to those of skill in the art and which may be in electronic form such as html, pdf, jpeg, and the like. Because new spacers are nearly always acquired adjacent to the leader sequence in the CRISPR array (see Yosef, I., Goren, M. G. & Qimron, U. Proteins and DNA elements essential for the CRISPR adaptation process in *Escherichia coli. Nucleic acids research* 40, 5569-5576, doi:10.1093/nar/gks216 (2012) hereby incorporated by reference in its entirety), pushing previously acquired spacers away from the leader, the order of protospacers electroporated (and thus frames of the GIF) can be reconstructed based on the order of the spacers in the array. Accordingly, while a first image in a sequence of N images, for example, may be recorded without regard to the timing of insertion of the set of protospacers making up the first image, the set of protospacers representing the second image may be inserted at a time point after the set of protospacers representing the first image have been inserted into the CRISPR array. Likewise, the set of protospacers representing the third image may be inserted at a time point after the set of protospacers representing the second image have been inserted into the CRISPR array. Likewise, the set of protospacers representing the Nth third image may be inserted at a time point after the set of protospacers representing the N-1 image have been inserted into the CRISPR array. However, a barcode sequence or pixel can be used to identify the set of protospacers making up a particular image so that the protospacers may be inserted into the CRISPR array without regard to timing, as the barcode can be used to identify the set of protospacers corresponding to particular image and an additional barcode can be used to identify how to order the spacer sequences for decoding to arrive at the format of information.

According to one aspect, information, such as text, or sound, or an image or series of images or a video is encoded by a series of nucleotides. It is to be understood that information may be encoded by nucleotides using methods known to those of skill in the art and as describe herein. For example, a format of information may be electronically represented by binary code or a series of bits which may then be represented by a series of nucleotides. Formats of information are digitized into a series of zeros and ones using computer implemented algorithms. Each bit may represent a nucleotide, or two more bits may represent a particular nucleotide, or fewer than one bit may represent a particular nucleotide depending upon the algorithm. One or more nucleotides may represent information within a pixel of an image, such as color or shading. A color within an image can be represented by one or more or two or more or three or more nucleotides depending upon the number of colors and the need to provide flexibility of the coding system.

According to one exemplary aspect, a format of information represented by binary code, text and/or images and/or sound and/or video is converted to a bit stream or portions of a bit stream which together comprise the bit stream. The bit stream may be encoded as a nucleic acid and then separated into oligomers such as oligonucleotides. The portions of the bit stream may be encoded as oligomers such as oligonucleotides. It is to be understood that formats of information may be encoded using nucleotides based on methods known to those of skill in the art. The present disclosure is not intended to be limited to a binary code format of information, as the binary code format of information is merely exemplary and illustrative. All that is required is that an encoding method be used such that the format of information is represented by a series of nucleotides which are protospacers to be inserted into a CRISPR array within a cell.

The nucleic acid sequence or oligomer sequences such as oligonucleotide sequences are designed and then synthesized using enzymatic nucleic acid synthesis reactions. As an example, the oligonucleotide sequences are designed and then synthesized using enzymatic oligonucleotide synthesis reactions where an enzyme and a nucleotide are placed at a desired site on a substrate under appropriate reaction conditions and the nucleotide is covalently bound to an existing nucleotide attached to a support. The oligonucleotide sequences may be synthesized using polymerases, such as template independent polymerases, such as error-prone polymerases, under conditions where the reagents are localized at a location on a substrate for a period of time and under such conditions to maximize probability of adding a single nucleotide. According to one aspect, the oligomer, such as an oligonucleotide includes a data block sequence. According to one aspect, the oligomer, such as an oligonucleotide includes an address sequence (such as a barcode sequence) specifying the location of the data block in the bit stream or differentiating between different individual formats of information within a format of information as a whole. According to one aspect, the oligonucleotide includes flanking common sequences at each end of the oligonucleotide for amplification and sequencing. According to one aspect, the oligonucleotide includes one or more or all of a data block sequence, an address sequence (such as a barcode sequence) specifying the location of the data block in the bit stream or differentiating between different individual formats of information within a format of information as a whole, and flanking common sequences at each end of the oligonucleotide for amplification and sequencing.

According to one aspect of the present disclosure, a one bit per base encoding system is used or a two bits per base encoding system is used or a one or more bit per base encoding system is used or a two or more bit per base encoding system is used. As used herein, the term "bit" is to be understood according to its common meaning to one of skill in the art. The term "bit" may be a contraction of "binary digit" and may refer to a basic capacity of information in computing and telecommunications. A "bit" represents either a first state or a second state, such as 1 or 0 (one or zero) only. The representation may be implemented, in a variety of systems, by means of a two state device.

According to this aspect, a single message may be encoded in a plurality of ways using nucleotides as known to those of skill in the art. In an exemplary binary code system, i.e., A or C may represent zero, G or T may represent the number 1. Other combination are envisioned such as A or G for zero, C or T for the number 1 or A or T for zero, G or C for the number 1. Other combinations are envisioned such as 00 for a first nucleotide, 01 for a second nucleotide, 10 for a third nucleotide and 11 for a fourth nucleotide. Other combinations are contemplated as discussed herein. According to one exemplary aspect, the bit stream is divided into data blocks which may be addressed within an individual format of information or between different formats of information such as different images making up a plurality of images. According to this aspect, a library of data blocks is created which represents the recorded information. In this manner, a single long nucleic acid sequence representing the recorded information in its entirety or comparatively long nucleic acid sequences are not required. Colors of images may be encoded by using one or more nucleotides with each nucleotide, for example, being represented by one bit or two bits.

According to one aspect, a method of storing information using nucleotides as representative of bits is provided comprising converting a format of information into a plurality of bit sequences of a bit stream using a computer implemented method such as digitization, (if not already present as a plurality of bit sequences of a bit stream), wherein a series of bit sequences comprise the bit stream, converting the plurality of bit sequences to a plurality of corresponding oligonucleotide sequences, such as by using one bit per base encoding or two bit per base encoding or fewer than one bit per base encoding (if not already converted to a plurality of corresponding oligonucleotide sequences) or other encoding method, synthesizing the plurality of corresponding oligonucleotide sequences, and storing the synthesized plurality of corresponding oligonucleotide sequences as protospacer sequences entered into a CRISPR array simultaneously or in pluralities or in sequence or in series over time within a cell using a Cas1 enzyme and a Cas2 enzyme. The cell may then be proliferated creating many cells with the stored information. It is to be understood that many methods or systems of encoding the format of information as a series of nucleotides can be used, so long as a protospacers encoding the format of information are created and which can be decoded into the format of information.

According to one aspect, a method of retrieving a format of information stored within a cell as a plurality of spacer sequences encoding the format of information, which may be represented by bit sequences, is provided comprising identifying the spacer sequences, amplifying the spacer sequences, sequencing the amplified spacer sequences, converting the spacer sequences to bit sequences (if the format of information was in the form of bit sequences), such as by using a one bit per base system or two bit per base system or other bit based encoding system, and converting the bit sequences to the format of information. The spacer sequences may include barcode address information to facilitate assembly into the format of information, or the ordering of the spacer sequences may provide address information to facilitate assembly into the format of information. The method may further include the step of visualizing the format of information or rendering the format of information into audio.

In an exemplary aspect, embodiments of the present disclosure relate to the use of molecules, such as nucleotides, to represent information. The information may be in a digitized state of zeros and ones where the zeros and ones may be encoded or represented by nucleotides according to a desired encoding system. For example, each nucleotide may be represented by either a zero or a one or the nucleotide may be represented by a combination of a zero and a one, and as such the sequences of zeros and ones may be representative of a series of nucleotides and may be converted or encoded into a series of nucleotides and therefor the series of nucleotides may be representative of text, an image, a video or an audio format or other format of information. In this manner, a written material, a picture, a video with an audio component or an audio recording or any other medium of expression, may be stored using nucleic acids as representative of bits, if the format of information is represented by bits. According to certain exemplary aspects, information to be stored is converted into binary bits, such as according to ASCII code or other desired code as determined by algorithm, using a computer and appropriate software for example, which is a series of zeros and ones representative of the information. It is to be understood that the information to be stored may be converted to other coded bits of information, as is known in the art. A series of nucleotides is then determined, such as by using a computer and appropriate software, which is representative of the series of coded bits of information, such as zeros and ones. The series of nucleotides are then synthesized and stored within a cell within a CRISPR array using a Cas1 enzyme and a Cas2 enzyme as described herein. The protospacer sequences may be synthesized using methods known to those of skill in the art including the use of template-independent polymerases such as terminal deoxynucleotidyl transferase (TdT), also known as DNA nucleotidylexotransferase (DNTT) or terminal transferase to create nucleic acid strands by catalyzing the addition of nucleotides to the 3' terminus of a DNA molecule without a template.

When the information is to be accessed from within the cell, the series of nucleotides are determined and then translated, such as by using a computer and appropriate software into the representative format, such as a series, of zeros and ones, which is then translated into the information, for example using a computer and appropriate software. In this manner, aspects of the present disclosure are directed to the use of nucleic acids, whether fully- or partially single stranded, double-stranded, or multi-stranded, as storage media for information within a CRISPR array within a cell as described herein, insofar as the format of information is encoded into the nucleic acids using methods known to those of skill in the art. The nucleic acid polymers which encode the format of information can be sequenced using methods known to those of ordinary skill in the art. Once the nucleic acid sequence is determined from the spacer sequences within the CRISPR array, the nucleic acid sequence can be translated or decoded into the format of information such as being decoded into a series of binary bits, i.e. zeros and ones, which can then be translated into the information represented by the series of binary bits. Other formats of information that can be converted to bits are known to those of skill in the art. Other encoding systems for formats of information are known to those of skill in the art.

According to one aspect, the portion of an html format of information or other format of information to be converted into bits may be referred to as a byte portion. The bit sequence is then converted (encoded), such as by a computer and appropriate software, to a designed sequence of nucleotides, i.e., an oligonucleotide or DNA or RNA, for example, using a 1 bit per base encoding (A or C=0; T/U or G=1) or two bit per base encoding (00=a first nucleotide, 01=a second nucleotide, 10=a third nucleotide and 11=a fourth nucleotide, i.e. 00=C, 01=T, 10=A and 11=G) to form a corresponding encoded oligonucleotide sequence, i.e. the oligonucleotide sequence corresponds to or encodes for the bit sequence. Useful methods of making nucleic acid sequences are disclosed in "Large-scale de novo DNA synthesis: technologies and applications," by Sriram Kosuri and George M. Church, Nature Methods, May, 2014, Vol. 11, No. 5, pp. 499-507 hereby incorporated by reference in its entirety. According to certain aspects, the commercially available CustomArray system from CustomArray, Inc. is an exemplary system that can be used to make the nucleic acid sequences encoding the information, i.e. protospacer, to be stored within a CRISPR array within a cell using a Cas1 enzyme and a Cas2 enzyme as described herein.

When obtained from the CRISPR array, the spacer sequences are amplified using methods known to those of skill in the art to form a library of oligonucleotides. In general, "amplifying" includes the production of copies of a nucleic acid molecule via repeated rounds of primed enzymatic synthesis. Amplification methods useful in the present disclosure may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) Cold Spring Harb. Symp. Quant. Biol. 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) Science 241:1077-1080; and Nakazawa et al. (1994) Proc. Natl. Acad. Sci. U.S.A. 91:360-364), self sustained sequence replication (Guatelli et al. (1990) Proc. Natl. Acad. Sci. U.S.A. 87:1874), transcriptional amplification system (Kwoh et al. (1989) Proc. Natl. Acad. Sci. U.S.A. 86:1173), Q-Beta Replicase (Lizardi et al. (1988) BioTechnology 6:1197), recursive PCR (Jaffe et al. (2000) J. Biol. Chem. 275:2619; and Williams et al. (2002) J. Biol. Chem. 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

The library of oligonucleotides is then sequenced using methods known to those of skill in the art, such as next-generation sequencing methods. Sequencing methods useful in the present disclosure include Shendure et al., Accurate multiplex polony sequencing of an evolved bacterial genome, Science, vol. 309, p. 1728-32. 2005; Drmanac et al., Human genome sequencing using unchained base reads on self-assembling DNA nanoarrays, Science, vol. 327, p. 78-81. 2009; McKernan et al., Sequence and structural variation in a human genome uncovered by short-read, massively parallel ligation sequencing using two-base encoding, Genome Res., vol. 19, p. 1527-41. 2009; Rodrigue et al., Unlocking short read sequencing for metagenomics, PLoS One, vol. 28, e11840. 2010; Rothberg et al., An integrated semiconductor device enabling non-optical genome sequencing, Nature, vol. 475, p. 348-352. 2011; Margulies et al., Genome sequencing in microfabricated high-density picolitre reactors, Nature, vol. 437, p. 376-380. 2005; Rasko et al. Origins of the E. coli strain causing an outbreak of hemolytic-uremic syndrome in Germany, N. Engl. J. Med., Epub. 2011; Hutter et al., Labeled nucleoside triphosphates with reversibly terminating aminoalkoxyl groups, Nucleos. Nucleot. Nucl., vol. 92, p. 879-895. 2010; Seo et al., Four-color DNA sequencing by synthesis on a chip using photocleavable fluorescent nucleotides, Proc. Natl. Acad. Sci. USA., Vol. 102, P. 5926-5931 (2005); Olejnik et al.; Photocleavable biotin derivatives: a versatile approach for the isolation of biomolecules, Proc. Natl. Acad. Sci. U.S.A., vol. 92, p. 7590-7594. 1995; U.S. Pat. No. 5,750,34; US 2009/0062129 and US 2009/0191553.

The sequenced oligonucleotides may then be converted or decoded into the format of information using the coding system employed. For example, the sequenced oligonucleotides may then be converted or decoded into bit sequences. The bit sequences can be converted to the format of information using methods known to those of skill in the art. The format of information can be visualized or displayed or played, if an audio format, using methods and devices known to those of skill in the art.

Terms and symbols of nucleic acid chemistry, biochemistry, genetics, and molecular biology used herein follow those of standard treatises and texts in the field, e.g., Komberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof.

In general, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs thereof. A oligonucleotide is typically composed of a specific sequence of four nucleotide bases: adenine (A); cytosine (C); guanine (G); and thymine (T) (uracil (U) for thymine (T) when the polynucleotide is RNA). According to certain aspects, deoxynucleotides (dNTPs, such as dATP, dCTP, dGTP, dTTP) may be used. According to certain aspects, ribonucleotide triphosphates (rNTPs) may be used. According to certain aspects, ribonucleotide diphosphates (rNDPs) may be used.

The term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. The present disclosure contemplates any deoxyribonucleotide or ribonucleotide and chemical variants thereof, such as methylated, hydroxymethylated or glucosylated forms of the bases, and the like. According to certain aspects, natural nucleotides are used in the methods of making the nucleic acids. Natural nucleotides lack chain terminating moieties. According to another aspect, the methods of making the nucleic acids described herein do not use terminating nucleic acids or otherwise lack terminating nucleic acids, such as reversible terminators known to those of skill in the art. The methods are performed in the absence of chain terminating nucleic acids or wherein the nucleic acids are other than chain terminating nucleic acids.

Examples of modified nucleotides include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012) KlenTaq polymerase replicates unnatural base pairs by inducing a Watson-Crick geometry, Nature Chem. Biol. 8:612-614; See Y J, Malyshev D A, Lavergne T, Ordoukhanian P, Romesberg F E. J Am Chem Soc. 2011 Dec. 14; 133(49):19878-88, Site-specific labeling of DNA and RNA using an efficiently replicated and transcribed class of unnatural base pairs; Switzer C Y, Moroney S E, Benner S A. (1993) Biochemistry. 32(39):10489-96. Enzymatic recognition of the base pair between isocytidine and isoguanosine; Yamashige R, Kimoto M, Takezawa Y, Sato A, Mitsui T, Yokoyama S, Hirao I. Nucleic Acids Res. 2012 March; 40(6):2793-806. Highly specific unnatural base pair systems as a third base pair for PCR amplification; and Yang Z, Chen F, Alvarado J B, Benner S A. J Am Chem Soc. 2011 Sep. 28; 133(38):15105-12, Amplification, mutation, and sequencing of a six-letter synthetic genetic system. Other non-standard nucleotides may be used such as described in Malyshev, D. A., et al., Nature, vol. 509, pp. 385-388 (15 May 2014) hereby incorporated by reference in its entirety.

The practice of the methods disclosed herein may employ conventional biology methods, software, computers and computer systems. Accordingly, the methods described herein may be computer implemented methods in whole or in part. Computer software utilized in the methods of the present disclosure include computer readable medium having computer-executable instructions for performing logic steps of the method of the invention. Suitable computer readable medium include, but are not limited to, a floppy disk, CD-ROM/DVD/DVD-ROM, hard-disk drive, flash memory, ROM/RAM, magnetic tapes, and others that may be developed. The computer executable instructions may be written in a suitable computer language or combination of several computer languages. The methods described herein may also make use of various commercially available computers and computer program products and software for a variety of purposes including translating text or images into binary code, designing nucleic acids sequences representative of the binary code, analyzing sequencing data from the nucleic acid sequences, translating the nucleic acid sequence data into binary code, and translating the binary code into text or images.

EXAMPLE VIII

Use of a CRISPR-Cas System for Time Dependent Recording of Protospacer Sequences Encoding Images and a Short Movie into Bacterial Genomes Aspects of the present disclosure are directed to the use of a CRISPR array within a cell, such as a bacterial cell, to encode images and a short movie, for example, by using the time-dependent nature of protospacer acquisition, i.e. saving each protospacer making up a format of information in series one at a time within a CRISPR array within a cell, and then obtaining the stored information by identifying the series relationship of the spacer sequences which indicates how to assemble the spacer sequences into the format of information and sequencing of the spacer sequences. Aspects of the present disclosure includes a method of including different protospacer sequences in real time into a living cell by the series addition of oligonucleotides, i.e. protospacer sequences, to a CRISPR array within the cell. Aspects described herein are directed to the delivery of the protospacers sequences which encode real information such as text, an image or images, video or audio formats of information. Aspects described herein are directed to the nucleotide content of the protospacers sequences. Aspects described herein are directed to methods of reconstructing the protospacer sequences.

Materials and Methods
Bacterial Strains and Culturing Conditions

All experiments were carried out in BL21-AI *E. coli* (Thermo Fisher), containing an integrated, arabinose-inducible T7 polymerase, an endogenous CRISPR array, but no endogenous Cas1+2 (i.e., the Cas1 enzyme and the Cas2 enzyme). A plasmid encoding inducible (T7/lac) Cas1+2

(K-strain origin, pWUR1+2 a.k.a. pCas1+2) was transformed into cells prior to each experiment. Cells containing the plasmid were maintained in colonies on a plate at 4° C. for up to three weeks.

Oligo Protospacer Electroporation

Protospacer electroporations were performed as previously described in Shipman, S. L., Nivala, J., Macklis, J. D. & Church, G. M. Molecular recordings by directed CRISPR spacer acquisition. *Science*, doi:10.1126/science.aaf1175 (2016) hereby incorporated by reference in its entirety. Briefly, after overnight outgrowth from a single colony, Cas1+2 were induced in a 3 ml dilution of the culture (containing 80 ul of the overnight), and grown at 37 C for 2 hours (L-arabinose 0.2% w/w, Sigma-Aldrich; isopropyl-beta-D-thiogalactopyranoside 1 mM, Sigma-Aldrich). For a given condition, 1 ml of the induced culture was spun down and washed with water three times at 4° C., then resuspended in 50 ul of a 6.25 µM solution of either a single protospacer or set of multiple protospacers and electroporated in a 1 mm gap cuvette using a Bio-Rad gene pulser set to 1.8 kV and 25 µF. Only those conditions with an electroporation time constant >4.0 ms were carried through to analysis. After electroporation, cells were recovered in 3 ml LB at 37 C for 2-3 hours, then diluted (50 ul) into a fresh 3 ml culture and grown overnight. Cells were collected for analysis the following morning.

Analysis of Spacer Acquisition

To analyze spacer acquisition, bacteria were lysed by heating to 95° C. for 5 minutes, then subjected to PCR of their genomic arrays using primers that flank the leader-repeat junction and additionally contain Illumina-compatible adapters. Libraries of up to 96 dual-indexed samples were sequenced on a MiSeq sequencer (Illumina) to read up to three spacer positions in from the leader on each array. Spacer sequences were extracted bioinformatically based on the presence of flanking repeat sequences, and compared against pre-existing spacer sequences to determine the percentage of expanded arrays and the position and sequence of newly acquired spacers. New spacers were blasted (NCBI) against the genome and plasmid sequences to determine the origin of the protospacer, with those sequences not derived from the genome or plasmid assumed to be oligo-derived. This and all subsequent image analysis was performed using custom written scripts in Python.

Image Coding and Decoding

Figure 1D:
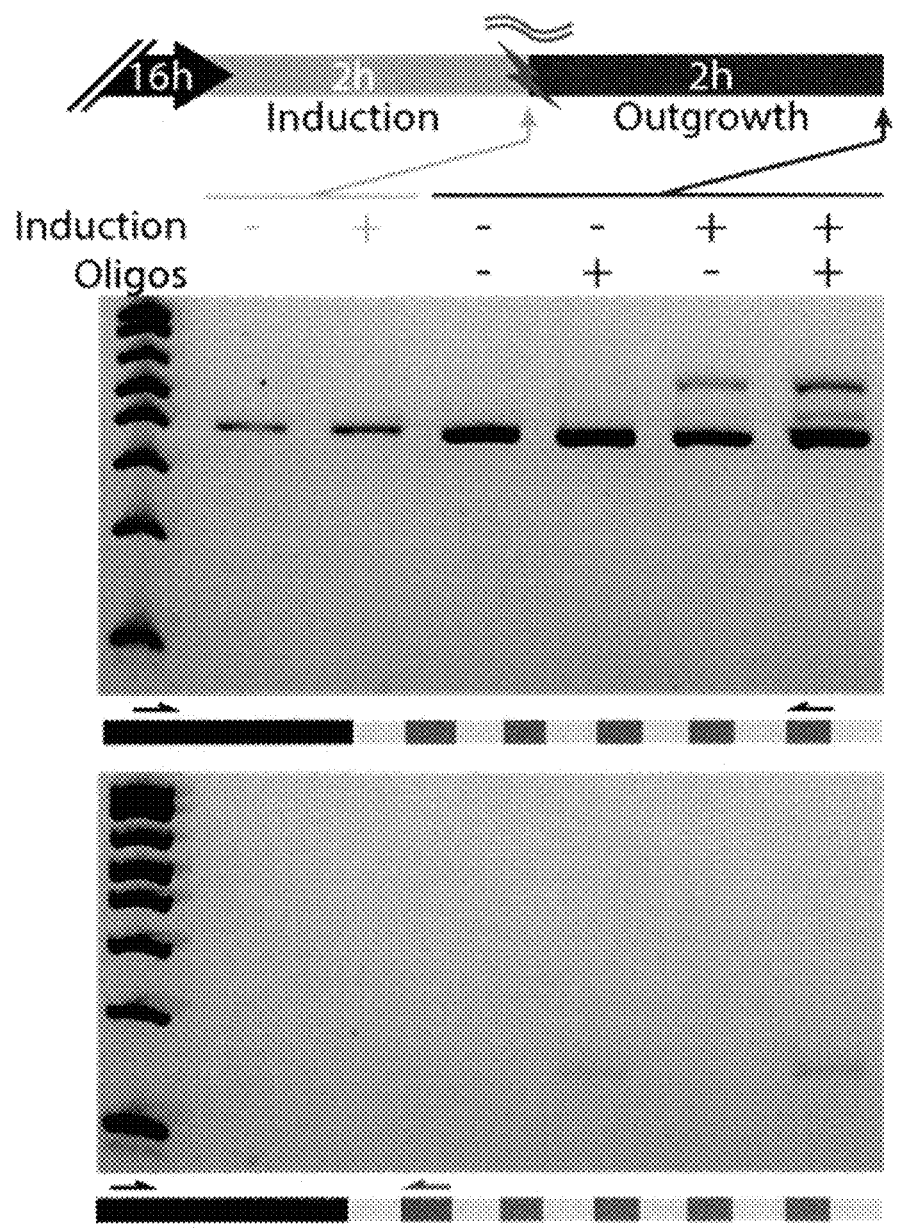
Figure 1E:
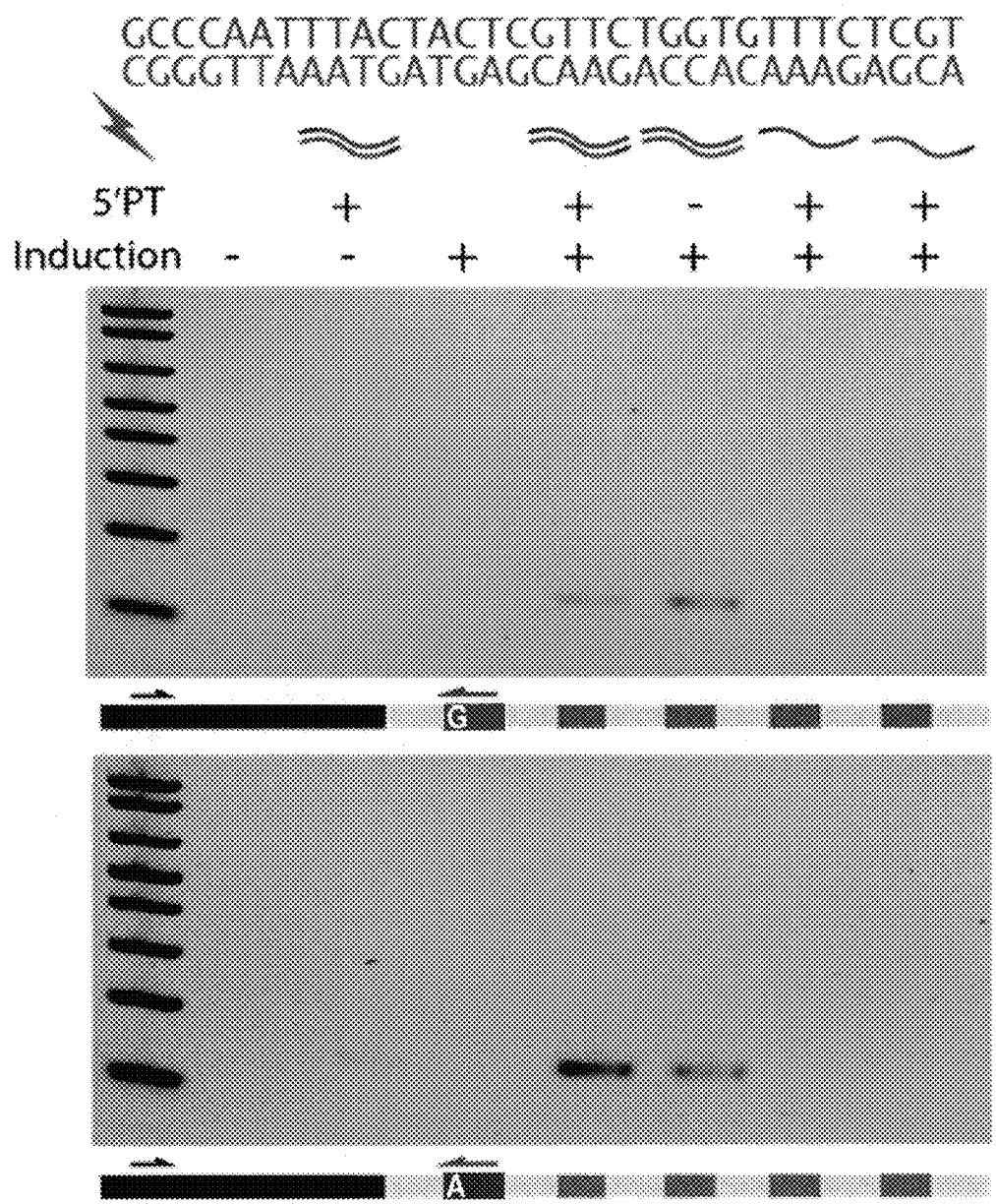
Figure 1F:
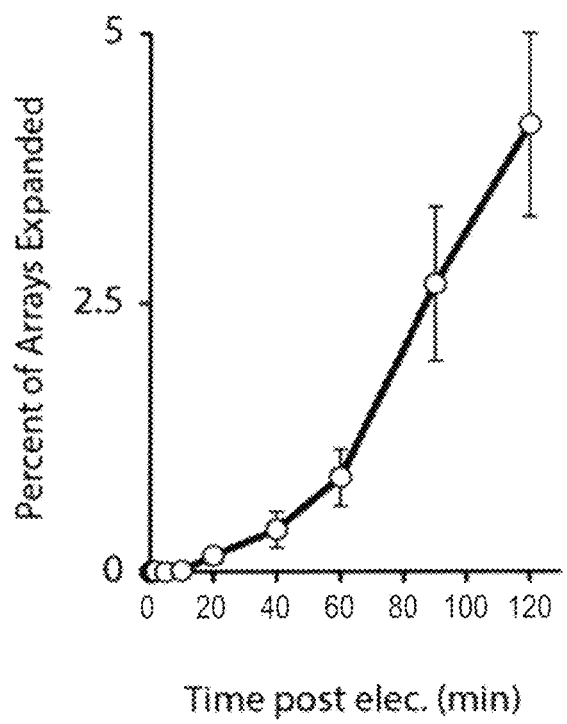
Figure 1H:
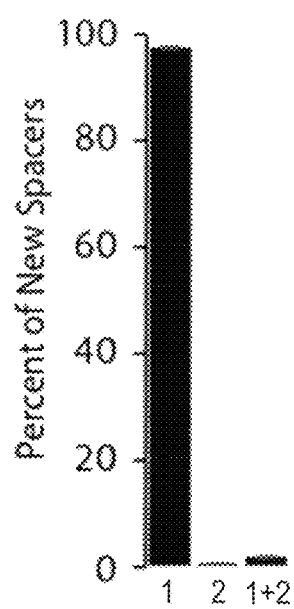
Figure 1G:
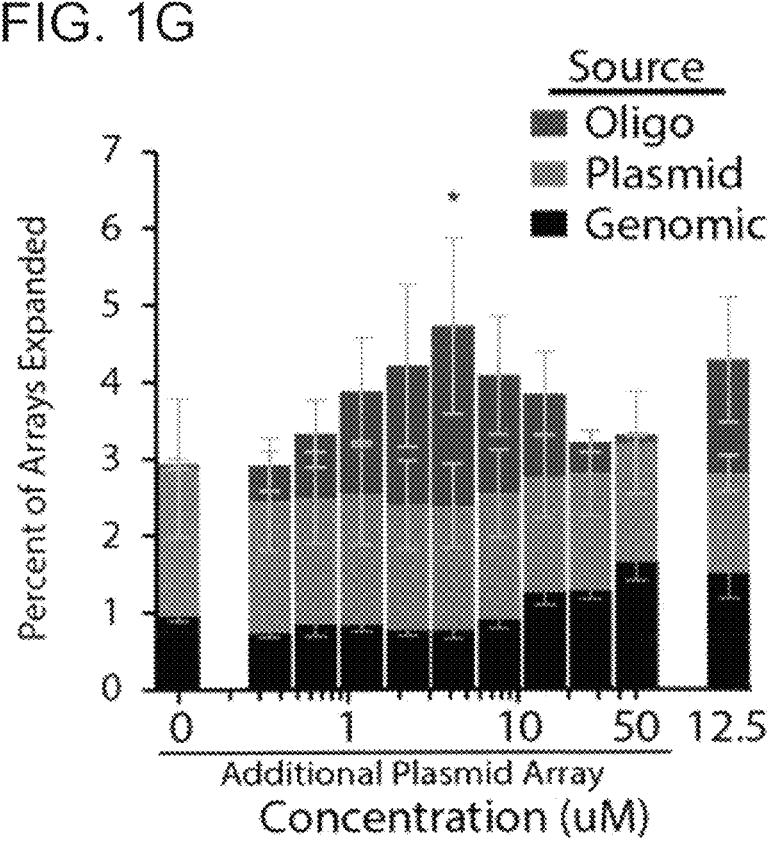
Figure 1I:
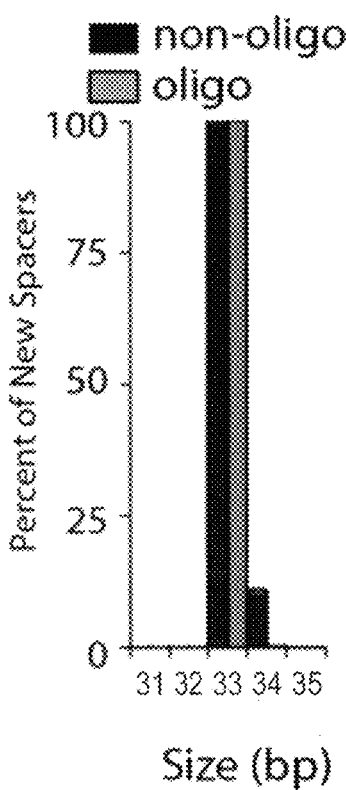

Image protospacer sets were created using a custom Python script to first open and read the pixel values of a previously created image. Each of the four colors was assigned a nucleotide and each nucleotide was assigned a two digit binary number, i.e. 00=C, 01=T, 10=A and 11=G. As shown in FIG. 1D, each protospacer was given a pixet code by a binary-to-nucleotide conversion and populated by nucleotides encoding the pixel values. For the single images, the pixet code was interleaved between ascending and descending numbers to introduce more sequence diversity in neighboring pixet protospacers. In the case of the flexible code employed in FIG. 14B and FIG. 16A, the protospacer was built sequentially. For each new pixel value the three possible nucleotide sequences were ranked according to which triplet would best push GC % of the resulting sequence toward 50%, then tested for whether the addition of the triplet would create either an internal PAM or a mononucleotide repeat >3. If such a situation were created, the next triplet in the list was tested until an acceptable triplet was identified (FIG. 18A). For the image in FIG. 14A, the final base was assigned to the least numerous base in the rest of the spacer. Finally, the sequences were re-formatted to match the minimal hairpin structure and written to a spreadsheet for synthesis by Integrated DNA Technologies. For the GIF, this process was repeated for each frame.

To reconstruct the single images, newly acquired oligo-derived spacers were ranked according to frequency of acquisition, then the most frequent spacer sequences for each pixet (by the reversed nucleotide to binary conversion) were assigned to that pixet. Pixel values were extracted from the remaining spacer sequence and used to populate an image.

Shannon information for the initial image was calculated with each protospacer containing ~6.807 bits in the four pixet nucleotides (112 possible pixets: $\log_2(112)$) and 2 bits per base for the remaining 28 pixel-value-encoding nucleotides, yielding ~62.807 bits per protospacer. The image set included 112 protospacers for ~7,034.424 bits (~879.303 bytes). Likewise, protospacers from the second image contained ~6.644 bits ($\log_2(100)$) in the four pixet nucleotides and ~39.53 bits ($9*\log_2(21)$) in the 27 pixel-value-containing nucleotides for a total of ~46.175 bits per protospacer or ~4,617.5 bits (~577.2 bytes) in the image set. Finally, each GIF protospacer contained ~6.7 bits in the five pixet bases ($\log_2(104)$) and ~39.53 bits ($9*\log_2(21)$) in the 27 pixel-value-containing nucleotides for a total of ~46.23 bits per protospacer or ~4,808.1 bits per frame for ~24,040.3 bits (~3,005 bytes) total.

The expansion of arrays with further rounds of electroporation and beyond those positions that were sequenced (FIG. 16A) was estimated starting with the average rates of new single (~15.8%), double (~2.4%), and triple (~0.1%) expansions per array with a given electroporation and assuming no initial quadruple or quintuple expansions with a single electroporation. As rounds of electroporations progressed, it was assume that subsequent electroporations will lead to the same percentage of single, double, and triple expansions, where single expansions convert unexpanded to single expansions, previous single expansions to double expansions, previous triple expansions to quadruple expansions, and so forth.

EXAMPLE IX

Use of a CRISPR-Cas System for Recording of Protospacer Sequences Encoding an Image into Bacterial Genomes The present disclosure provides a method of recording a format of information, such as an image, into a cell by using a Cas1 enzyme and a Cas2 enzyme to insert a plurality of protospacers encoding the image into a CRISPR array within the cell. The plurality of protospacers (PS) when in series in their entirety, i.e. PS1, PS2, PS3, etc. encodes for the entire image. According to the present disclosure, each protospacer is introduced into the cell in the order in which they encode the image (or other format of information) as a whole to create a series of spacer sequences with the correct ordering of the encoded image (or other format of information). In this manner, the correct order of the protospacer sequences encoding the image may be determined from understanding the in series ordering of the spacer sequences. Each protospacer is then incorporated into the CRISPR array in series as determined by the order in which they were introduced into the cell. In this manner the protospacers are ordered in series in the CRISPR array in the manner in which they encode the image as a whole. The timing of the introduction of each protospacer in series facilitates introduction of the protospacer in series into the CRISPR array such that the series of spacer sequences represents the complete binary format of information representing the image. For example, the first protospacer is introduced into the cell and inserted into the CRISPR array followed by the second protospacer which is inserted into the CRISPR array followed by the third protospacer which is inserted into the CRISPR and so on until the Nth protospacer is inserted into the CRISPR array so that the entire encoded image has been inserted into the CRISPR array. The spacers can then be readily assembled into the format of information simply by placing them end to end in the order in which they are present in the CRISPR array. The spacer sequences can then be decoded into the format of information. For example, if the format of information is a page of text including a series of sentences, then the nucleic acid sequence, i.e. the protospacer sequence, encoding the first sentence (or first portion of the text of the page) (PS1) is delivered to the cell first and inserted into the CRISPR array, then the protospacer sequence encoding the second sentence (or second portion of the text of the page) (PS2) is delivered to the cell second and inserted into the CRISPR array and so on until the Nth (PSN) is delivered to the cell and inserted into the CRISPR array. In this manner, the protospacer sequences will be inserted into the CRISPR array in the ordered manner in which they represent the format of information as a whole. When decoding the spacer sequences within the CRISPR array, the first spacer sequence inserted will represent the first sentence or first portion of the text of the page, the second spacer sequence inserted will represent the second sentence or second portion of the text of the page, and so on. Therefore, identifying the series relationship of the spacer sequences is used to order the spacer sequences end to end to correctly recreate the format of information. Alternatively, barcode sequences can be used to indicate the correct order, i.e. end to end ordering, of spacer sequences to recreate the format of information. However, the time-dependent aspect described above may not be necessary if address barcodes are provided for each protospacer which identifies the order or location of the protospacer in the information format so that the spacer sequences may be correctly assembled into the format of information. In this manner, the timing of insertion of protospacer sequences may not be necessary to decoding the spacer sequences into the format of information.

To encode an image into a cell, i.e. into the genomic DNA or other DNA within the cell including a CRISPR array, a graphical image was the source of real data where the fidelity of encoding and decoding is immediately visually apparent. As shown in FIG. 12A, an image is selected. As described previously, in the native CRISPR-Cas adaptation system of *E. coli*, nucleotides from invading viruses are inserted into a genomic CRISPR array in 33-base units termed spacers, which are interspersed between identical repeats (see van der Oost, J., Jore, M. M., Westra, E. R., Lundgren, M. & Brouns, S. J. CRISPR-based adaptive and heritable immunity in prokaryotes. *Trends in biochemical sciences* 34, 401-407, doi:10.1016/j.tibs.2009.05.002 (2009)). The matching sequences that the spacers are derived from in the virus are termed protospacers (see Deveau, H. et al. Phage response to CRISPR-encoded resistance in *Streptococcus thermophilus*. *Journal of bacteriology* 190, 1390-1400, doi:10.1128/jb.01412-07 (2008). According to the present disclosure, pixel values for the image are stored in or represented by a nucleic acid sequence, with the sequence being divided into many individual synthetic protospacer oligonucleotides ("oligos"). The set of protospacer oligonucleotides is representative of the format of information. These oligos are then electroporated into a population of bacteria that harbor a CRISPR array and overexpress the Cas1-Cas2 integrase complex, allowing these cells to acquire the oligos into their genome. The bacteria may then be archived and expanded (copying the encoded information). To recover the information, multiplexed, high-throughput sequencing is performed to recover all new spacer sequences, which are decoded to reconstruct the original image.

As indicated in FIG. 12B, the image of a human hand was selected. Specifically, 56×56 pixel image comprised of four colors was generated. The colors were encoded using nucleotides by assigning each color a unique base (FIG. 12C). Each base was represented by two binary digits as shown in FIG. 12D. Double-stranded protospacers can be provided as two complementary oligos for encoding formats of information. With respect to the image, a hairpin oligo protospacer was designed for the more than 100 protospacers representing the image, as the hairpin design prevented the complementary oligos from segregating into different cells during the electroporation.

A protospacer adjacent motif (PAM) on one end of the protospacer both increases the efficiency of acquisition and determines the orientation that the spacer is inserted. With respect to the hairpin protospacer design, this requirement for a PAM did not apply to both strands of the protospacer: the 'AAG' on the top strand was dispensable for the PAM effect, whereas the 'TTC' on the bottom strand was required (FIG. 13A). Because the crystal structure of Cas1-Cas2 in complex with a protospacer was solved with ~23 bases of duplexed DNA at the core of the protospacer and forked, non-complementary ends on both sides (see Nunez, J. K., Harrington, L. B., Kranzusch, P. J., Engelman, A. N. & Doudna, J. A. Foreign DNA capture during CRISPR-Cas adaptive immunity. *Nature* 527, 535-538, doi:10.1038/nature15760 (2015) and Wang, J. et al. Structural and Mechanistic Basis of PAM-Dependent Spacer Acquisition in CRISPR-Cas Systems. *Cell* 163, 840-853, doi:10.1016/j.cell.2015.10.008 (2015) each of which are hereby incorporated by reference in their entireties), an oligo hairpin structure was designed that mimicked this design (FIG. 13B), joining the non-complementary ends on one side with a looped linker. This initial hairpin oligo protospacer was acquired efficiently. The hairpin oligo protospacer design was modified by removing nucleotides from the linker loop, which modification did not compromise acquisition. Then, the 5' forked end was eliminated (FIG. 13B). This resulted in a 58-base hairpin protospacer that, once optimized for concentration, was acquired efficiently into the array upon electroporation (FIG. 13C).

To distribute the image information (i.e., color to nucleotide code) across multiple protospacers, each protospacer included a barcode that defined which pixel set—or "pixet"—would be encoded by the nucleotides in that spacer. The pixel set is a portion of pixels from among the entire number of pixels making up the image. Each protospacer begins with a PAM motif to enable efficient and directional acquisition. The next four nucleotides define the pixet—yielded by a binary to nucleotide conversion (FIG. 12D)—leaving 28 bases on each spacer to encode pixel values. Mononucleotide runs are reduced by distributing the pixels of a given pixet across the image, reasoning that in a natural image nearby pixels are more likely to be of the same value (FIG. 12D). The oligo sequence is converted into the structure of the minimal hairpin for oligo delivery. This initial image was distributed across 112 oligos with a total information content of ~879.3 bytes.

The oligos were pooled and electroporated into an arabinose-inducible T7 polymerase *E. coli* strain (BL21-AI)

containing a genomic array and overexpressing Cas1-Cas2 under the control of a T7 promoter with a lac operator. Following electroporation, the cells were allowed to recover, and the culture was passaged for overnight growth. The next day, a sample of the cells was lysed and their genomic arrays were amplified by PCR with adapters to permit library construction for multiplexed Illumina sequencing. After sequencing, new spacers were bioinformatically extracted from the arrays, and those that were not derived from the plasmid or genome were selected for analysis. Pixel values were assigned based on the most numerous new spacer with a given pixet. The images reconstructed from each of the replicates of this process are shown in FIG. 12E. With a sequencing depth of 655,360 reads, ~88% of pixet sequences were accurately recalled, on average (FIG. 12F). The read depth includes both the expanded and unexpanded arrays. Since each cell contains a single array, this is roughly equivalent to sequencing 655,360 individual cells. Accuracy of recall falls off steeply as fewer reads are sampled (FIG. 12F-12G). By electroporating subsets of the oligos, it was determined that the number of reads required to achieve similar levels of accuracy in recall is linearly related to the number of oligos electroporated (FIG. 12H). The image was reconstructed using the method described herein.

A second image having a more complex color scheme was used where flexibility was introduced into the encoding scheme to allow for sequence optimization. The second image was again a hand, slightly smaller than the first at 30×30 pixels in 21 colors (FIG. 14A). Rather than having each color paired to a single nucleotide, in this case, a nucleotide triplet table was generated whereby any given color could be encoded by three different nucleotide triplets (FIG. 14B) with each nucleotide being represented by two binary digits as shown in FIGS. 14C-1 and 14C-2. It is to be understood that methods of error-correction and compression known to those of skill in the art have application to the methods disclosed herein.

Similar to the first image, each protospacer begins with a PAM, followed by a four base pixet code, but then the rest of the protospacer can be constructed flexibly—adding nucleotide triplets in a way that keeps overall GC-content around 50%, eliminates mononucleotide repeats >3 bp, and disallows internal PAMs in either direction (FIGS. 14C-1 and 14C-2, 18A-18D). In the case of this image and encoding scheme, with nine pixels encoded by each protospacer, 100 total protospacers were required for a total information content of ~577.2 bytes.

Electroporation was performed as with the first image. In this case, with the additional flexibility in the protospacer code, at the same sequencing depth, one of the replicates (FIG. 14D) was perfectly reconstructed with an overall accuracy of ~96% (FIG. 14E). There was again a reduction in accuracy as fewer reads were sampled, but compared with the initial image, this encoding strategy was much more resistant to errors by under-sampling (FIG. 14E-14F). A linear relationship existed between the oligos delivered and the reads needed to accurately sequence the oligos (FIG. 14G). Compensating for a difference in information content between the images, it took far more reads per oligo protospacer to reach 80% accuracy in the initial image (~1,582 reads/protospacer) versus the second image (153 reads/protospacer).

The improvement in recall with a flexible code is likely driven primarily through an increased frequency of acquisition (FIG. 14H). When looking within both sets of protospacers, a similar range of acquisition frequencies is apparent among individual protospacer sequences (FIG. 14I).

Given this range, the sequences of the over-represented protospacers as compared with all sequences that were electroporated was analyzed. There was a significant motif identified as being present in the over-represented sequences in the final two nucleotides of the protospacer (FIG. 14J). A motif in the final two bases of the protospacer has been previously reported and termed the acquisition affecting motif (AAM) (see Yosef, I. et al. DNA motifs determining the efficiency of adaptation into the *Escherichia coli* CRISPR array. *Proc Natl Acad Sci USA* 110, 14396-14401, doi:10.1073/pnas.1300108110 (2013)), however the reported sequence of this motif differs from the identified motif.

To test whether this motif is primarily responsible for the difference in efficiency, individual protospacers were tested in isolation. One sequence based on nucleotides that were over-represented in the acquired spacers in one of the replicates, which ended in 'TGA' ($seq^{over}$) was created and another was created based on nucleotides that were under-represented in the acquired spacers from the same replicate, which ended in 'CCT' ($seq^{under}$). Two more protospacers were created that swapped the final three nucleotides from these two sequences ($seq^{over}$-CCT and $seq^{under}$-TGA) (FIG. 14K). When each of the sequences was delivered individually as minimal hairpin oligos, the final three nucleotides determined acquisition frequency, with 'TGA' yielding high efficiencies and 'CCT' yielding low efficiencies regardless of the sequence content in the rest of the oligo (FIG. 14L). Because these three nucleotides are in the loop region of the minimal hairpin, it was investigate whether their effect on acquisition efficiency was specific to the hairpin protospacer structure. Thus, these sequences were tested as complementary single stranded oligos (FIG. 15A) indicating an identical dependence on the final three nucleotides, ruling out a model based on hairpin stability (FIG. 15B).

Although the nucleotides at the end of the protospacer affect acquisition efficiency, the nature of optimized nucleotides was investigated. A minimal hairpin protospacer with random nucleotides (NNN) in the final three positions (FIG. 14M) was designed, and the protospacer mixture was electroporated into cells overexpressing Cas1-Cas2 to fully sample the sequence space. While acquisition events were observed with every possible NNN Cartesian product in the three variable nucleotides, there were clearly more efficient and less efficient sequences (FIG. 14N). The results are summarized by position in the protospacer in FIG. 14O.

To understand the kinetics of information capture as well as the fidelity of information maintenance over time (i.e., how well the information is maintained over time), another set of electroporations of the second (21 color) image was performed. Time-points were sampled throughout the initial minutes, hours, and days following the electroporation, with the bacterial culture under growth conditions for a week with daily passaging. Initial oligo-derived spacer acquisitions were detectable as early as ten minutes following the electroporation and reached a peak by 2 hours and 40 minutes—the same time at which the image from the bacterial population was first perfectly recalled (see FIG. 19A and FIG. 19B). Between 2 hours and forty minutes and 24 hours post-electroporation, the percentage of arrays expanded with oligo-derived spacers declined, then stabilized for the next six days. Presumably, some cells acquire spacers following the electroporation, but also lose viability and thus do not contribute to the bacterial population after outgrowth. All other sampling points occur at least 16 hours after the electroporation and therefore reflect the viable population of bacteria.

Aspects of the present disclosure are directed to presenting rules to optimize the sequences of the information-containing protospacers. According to one aspect, the GC percentage is greater than or equal to 20%, 30%, 40% or 50%. According to one aspect, mononucleotide repeats are lacking in pools of protospacers. According to one aspect, internal PAMs are lacking in pools of protospacers.

With respect to the flexible encoding scheme, three parameters were controlled that were uncontrolled in the initial image: GC content, the presence of mononucleotide repeats, and the presence of internal PAMs. Each was investigated separately to determine which, if any, of these parameters contribute to increase in acquisition efficiency. An additional 75 protospacer oligos were designed spanning a range of GC content in the pixel-color encoding bases—fifteen protospacers each at 0, 25, 50, 75, and 100% GC. These oligos as a single pool were electroporated, then the acquisition frequency of each individual oligo was quantified (see FIG. 20A). Protospacers with higher GC content were acquired at significantly higher frequencies than those with lower GC content. When the same oligos were electroporated in sub-pools within sets of a given GC percentage (see FIG. 20A), the same overall trend emerged—higher GC content, particularly over 50%—resulted in higher overall acquisition frequencies of the entire set.

The single pool showed very large differences between the high and low ends of the spectrum, with 0%, and 23% essentially not acquired and 50% acquired less frequently than either 75% or 100%. However, when the same sequences were sub-pooled within groups before electroporation, the differences were less substantial. Sequences with 0% GC were still almost never acquired, but, when sub-pooled, there was no significant difference between 50, 75, and 100% GC. A subset of 15 of these oligos was individually electroporated—three per GC group. No difference was found between any of the oligos in the 25, 50, 75, or 100% group—while the 0% GC oligos were rarely acquired (see FIG. 20B). GC percentage has a clear effect on acquisition frequency, with reductions in acquisition frequency at the extreme low end when oligos are supplied individually or pooled, and reaching up to 50% GC when supplied as pools of a similar GC content. Because of the steep effect of GC percentage in a pool of mixed percentages, it is beneficial to limit the range of GC percentages within a pool. Because the 50% pool was not significantly different than the 75, or 100% pool, and pushing GC content higher will reduce information density per protospacer, 50% appears to be a reasonable set point for a pool. The protospacers encoding the first image had an overall lower GC percentage than those encoding the second image (41.8±0.6% vs. 50.6±0.6%), which may largely account for the difference in acquisition frequency (and thus recall). Moreover, within each image, oligos with a higher GC percentage were acquired at a higher frequency. Because the GC percentage and the stability of the hairpin structure are related, there was also a slight trend toward acquisition of sequences with higher hairpin stability (see FIG. 20C).

For each of mononucleotide repeats and internal PAM sequences, 108 protospacer oligos were designed spread over four conditions (3, 4, 6, and 8 mononucleotide repeats; 0, 1, 3, and 5 internal PAMs). When each of these sets was electroporated as a single pool, no difference was found between the oligo acquisition frequencies as a function of the condition (see FIG. 20D and FIG. 20E). However, when sub-pooled by condition, a reduction was found in acquisition frequency at the high end (6 or 8 mononucleotide repeats; 5 internal PAMs) for each. Thus, when considering sequence design, it is advantageous to limit both the number of mononucleotide repeats and internal PAMs.

EXAMPLE X

Use of a CRISPR-Cas System for Time Dependent Recording of Protospacer Sequences Encoding Multiple Images Over Time into Bacterial Genomes to Generate a Short Movie or GIF The present disclosure provides a method of using a CRISPR-Cas system for time dependent recording of protospacer sequences encoding multiple images over time into bacterial genomes to generate a short movie or GIF. Multiple images were encoded and recorded over time in the same population of bacteria to generate a short movie, or GIF. The encoding strategy was redesigned to move the pixet code to the final nucleotides of the protospacer, where a reduced sequence space was employed, limiting the final three nucleotides to eight possible triplets drawn from the most efficient triplets found in FIG. 14N (FIG. 16A). Pixet codes, i.e. address barcodes, are used to address protospacers within an image. Pixet codes, i.e. address barcodes, could also be used to distinguish multiple images from one another. Five frames of Eadweard Muybridge's Horse in Motion were encoded at 36×26 pixels. Frames were each represented by a unique oligo set of 104 protospacers, for an overall information content of ~3 kilobytes. Pixet codes were reused between frames, and no nucleotides were used to identify frame order. In this manner, the timing of introduction of each set of protospacers representing each image is used to distinguish the images from one another. Each protospacer set (or frame) was electroporated successively over five days into a single population of bacteria (FIG. 16B). Because new spacers are nearly always acquired adjacent to the leader sequence in the CRISPR array, pushing previously acquired spacers away from the leader, the order of protospacers electroporated (and thus frames of the GIF) can be reconstructed based on the order of the spacers in the array.

The re-designed protospacers were efficiently acquired from each frame, populating the first three sequenced positions of the CRISPR array (FIG. 16C). Based on this information, it can be estimated how frequently positions further into the array that were not sequenced would be populated and how the arrays would expand with additional rounds of electroporation (FIG. 17A). To reconstruct the order of the frames, and thus the GIF, all new spacers from the sequenced arrays were extracted and those drawn from the plasmid or genome were set aside. Lists of five spacer sequences for each pixet were populated based on the most frequently acquired spacers with each pixet, assuming each pixet was represented in all five frames. Ordering the frames within a set of pixet spacers was a two-step process. Starting with the most numerous pixets, the positioning of spacers in arrays within the pixet were compared (FIGS. 17B-1 and 17B-2). If two oligos from the same pixet were found in a single array, their position should yield information about the order that they were electroporated. In fact, a list of ordering rules can be drawn based on the frequencies that pairs of spacers are found in the array in order relative to each other. Additionally, the order of spacers from a single pixet in pairs can be examined relative to spacers drawn from the plasmid and genome, which accumulate over the course of the experiment, again yielding reliable ordering rules. For each set of five spacers from a given pixet, all 120 order permutations were tested against these ordering rules (FIGS. 17B-1 and 17B-2). If any permutation satisfied all the ordering rules, the order of that permutation was used to definitively assign the spacers within a given pixel to their frame. This began to fill dictionaries of spacers by frame, starting with the most highly represented pixets and moving toward the least.

If no permutation of spacer order within a set satisfied all the initial ordering rules, a second set of tests was applied. In these, spacers of a given pixel were ordered by comparison to spacers that had already been assigned to a given frame. Again, based on pairs of spacers in any given array, reliable rules could be charted to describe the ordering of spacers if the electroporation order was correctly solved (FIGS. 17C and 17C-1). Again, all possible permutations of a set of five pixet spacers were tested against each of these rules. In this case, the permutation with the highest overall score was taken, and spacers were assigned to a frame. By beginning with pixets containing the most numerous new spacers, dictionaries of spacers by frame were populated with the best data first, then this data was leveraged to better assign spacers that were less frequently sampled.

Using these rules which allowed determination of the order of the spacers within the CRISPR array, each frame and the order of frames were constructed with high accuracy (FIG. 16D). An increasing read depth aided the accuracy of the reconstruction, although the returns on reads were diminishing as the reconstruction neared perfection (FIG. 16E). Surprisingly, although the sequence of the protospacer was optimized, a range of acquisition efficacies between the protospacers of any given frame was found (FIG. 16F). When the sequences of the over-represented protospacers was examined, a significant sequence motif at the end of the sequence was identified, which may indicate that a too large a range of nucleotide triplets in the final position was allowed for (FIG. 16G). Finally, since the protospacers themselves contain no code to specify frame position, the robustness of the reconstruction strategy was tested by electroporating the oligo frame sets in reverse order. The reversed GIF in this case was accurately reconstructed, showing definitively that the system is capable of recording and reconstructing an otherwise ambiguous signal based on timing of introduction of protospacers. Based on the methods described herein and using one or more of the optimized parameters described herein, a ~3 kilobyte GIF was reconstructed with reasonably high accuracy. Methods described herein allowed the tracking of the presence of 104 separately barcoded sequence elements over five timepoints (520 unique sequence elements).

According to the present disclosure, methods are provided for recording information, such as text, an image or images, a video format or an audio format into living cells that include a CRISPR array and using a Cas1 enzyme and a Cas2 enzyme. According to certain aspects, protospacer sequences can be optimized to facilitate effective transfer of data into the genome. According to certain aspects, the order of spacer sequences can be determined so as to determine the order of the oligonucleotide sequences encoding the format of information. A flexible encoding scheme is provided to allow optimization of sequence content. Exemplary protospacer sequences include controlled GC content, a lack of mononucleotide repeats, and/or no internal PAMs. Such optimized protospacer sequences outperform protospacer sequences which lack such optimization. According to certain aspects, the inclusion of invariant nucleotides at both the leading (AAG . . . ) and trailing ( . . . GA) end of the protospacer effects the frequency of acquisition.

According to certain aspects, methods are provided for tracking hundred elements over time in living cells with a CRISPR array and using a Cas1 enzyme and a Cas1 enzyme to introduce protospacers into the CRISPR array in a time dependent manner. Using the reconstruction algorithms described herein, the order in which the protospacer elements are present in a population of cells can be determined with no information other than the sequence of the arrays after the completion of the experiment.

EXAMPLE X

Analog Recording Device

Figure 6E:
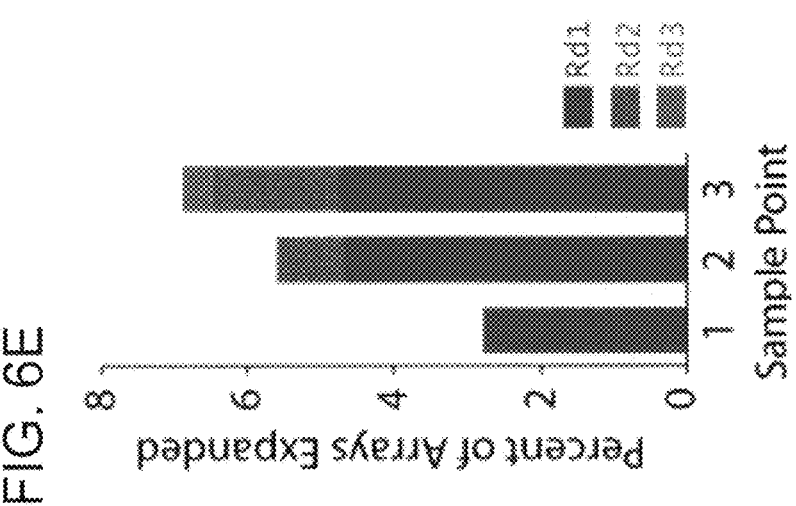
Figure 6F:
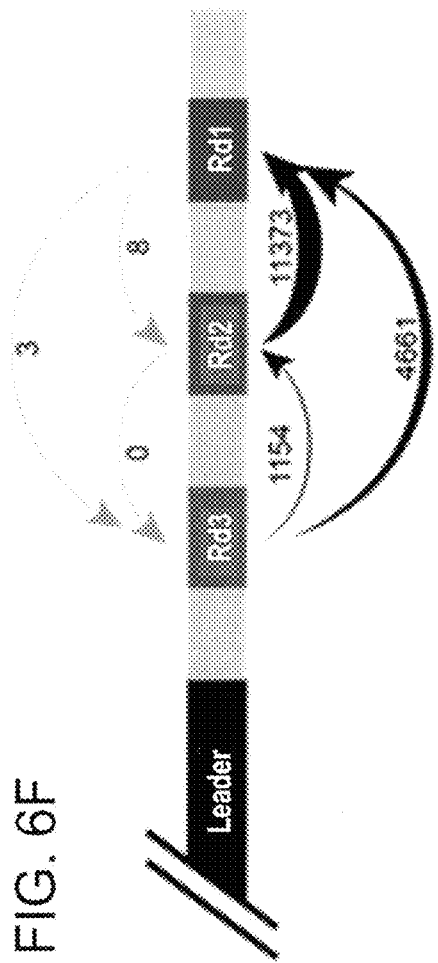
Figure 6G:
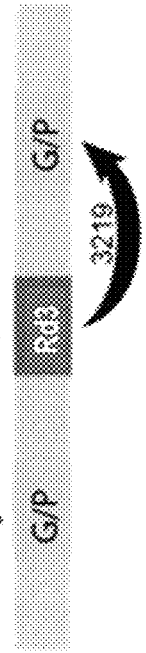
Figure 6H:
Figure 6I:
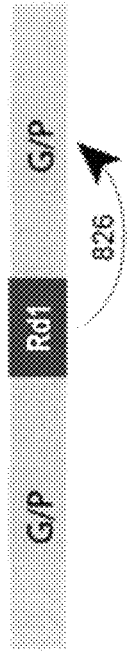

The molecular recording system using CRISPR-Cas described herein can also be used as an analogue recording device, so as to store or record the extent of gene expression from a natural or synthetic promoter over time. This is captured in the number of oligo-derived spacers present among the CRISPR arrays in a population of bacteria, where longer expression of Cas1 and Cas2 with oligo delivery will lead to increased numbers of oligo-derived spacers in the array over time (FIGS. 6E and 7C). Alternately, without oligo delivery, the number of genome- and/or plasmid-derived spacers can be used as a measure of the extent and duration of Cas1 and Cas2 expression (FIG. 16C). If Cas1 and Cas2 expression were to be driven by a promotor of interest, the number of newly acquired spacers could be used to estimate promoter activity.

EXAMPLE XI

Error Correction

The present disclosure provides error correction methods and considerations. Errors may result in the form of data that is wholly missing (a given pixet spacer is never found in the sequenced arrays); and data that is wrong (typically, the correct spacer is found, but under-sampled and therefore a different spacer or error-containing spacer is mis-assigned to the pixet). While the missing data is irrecoverable short of deeper sequencing, the second source of error (mis-assigned pixets) should be avoidable with error-correcting code. The number of nucleotides can be selected to implement error-correction. More nucleotides will yield a better correcting code, but the addition of those nucleotides means that the entire image must be distributed over more total protospacers. Because more reads are required to accurately reconstruct images encoded across more spacers, having more protospacers increases the probability of errors of the first type (missing data).

Error-correction may be introduced without adding any nucleotides. For instance, taking the flexible triplet code for 21 colors used in the second image and GIF, each of the three triplets that code for a color could be assigned to a different cluster (A, B, and X) (FIG. 18E) (see Blawat, M. et al. Forward Error Correction for DNA Data Storage. *Procedia Computer Science* 80, 1011-1022 (2016)). Rather than selecting triplets to optimize GC %, triplets could be chosen to implement an alternating cluster code (A, B, A, B, etc.) with swappable cluster X used to avoid internal PAMs and mononucleotide repeats (FIGS. 18F-18I). Although this scheme has no net nucleotide cost, it does reduce the overall flexibility of the sequence design. Moreover, it is not the most robust error-correction, as only a subset of single base mutations would lead to pattern disruption.

An example of a more robust error-correction scheme that does require additional nucleotides is a checksum. A subset of the nucleotides of a given spacer could be devoted to checking an aspect of the rest of the spacer—if the check is not passed, the spacer should be disregarded. For instance, one could devote two bases to represent the sum of all cytosines in the image encoding section of the spacer, two bases for the sum of all thymines, and two bases for the sum of all adenines (guanines can be inferred from the other three, and two bases, counting up to sixteen, would be sufficient to cover 21 bases of image space assuming that GC % is still being optimized for) (FIGS. 18J-18L). Thus, with six bases devoted to the checksum, the vast majority of errors would be identified. In the case of the second image, this would increase the total number of protospacers from 100 to 123. Variants of this checksum scheme, such as counting the AC % could be implemented using fewer nucleotides, although fewer errors would be caught.

Since robust error-correction increases the total nucleotide space required to encode the same image, one would likely employ some form of compression to counter this expansion. In terms of lossless compression, run-length encoding is one option. The code would specify a pixel value and then the number of adjacent pixels that are of the same value, rather than uniquely specifying each pixel value. Since adjacent pixels in our images are often the same value, this would achieve compression. However, the fact that each individual protospacer only encodes a small number of pixels reduces the effectiveness of run-length encoding within a protospacer. The greatest benefit would be run-length encoding spread across protospacers. Unfortunately, this strategy would be highly sensitive to missing data, which could potentially disrupt large sections of the image upon recall.

A more apt option for lossless compression would be the use of a dictionary algorithm (e.g. LZW/Huffman/Deflation) (see Welch, T. A. A technique for high-performance data compression. *Computer* 17, 8-19 (1984) and Huffman, D. A. A method for the construction of minimum-redundancy codes. *Proceedings of the IRE* 40, 1098-1101 (1952)) in which the most common pixel values are encoded using the fewest bits (nucleotides) which forces rare values to be encoded using more bits. An accompanying dictionary (also supplied via protospacers) would provide the lookup table to reconstruct the pixel values. Loss of the dictionary may be an issue, but this could be easily circumvented by providing redundancy in the form of multiple orthogonal dictionary protospacers. If some loss of fidelity is acceptable, a lossy compression method could be applied, such as transform coding.

Embodiments

The disclosure provides a method of recording information into a cell including converting a format of information into a plurality of bit sequences with the plurality of bit sequences comprising in series a bit stream representative of the format of information, converting the plurality of bit sequences to a set of corresponding oligonucleotide protospacer sequences, synthesizing the set of corresponding oligonucleotide protospacer sequences, introducing the set of corresponding oligonucleotide protospacer sequences into an engineered, non-naturally occurring cell including a nucleic acid sequence encoding a Cas1 protein and/or a Cas2 protein of a CRISPR adaptation system and a CRISPR array nucleic acid sequence including a leader sequence and at least one repeat sequence, wherein the CRISPR array nucleic acid sequence is inserted within genomic DNA of the cell or on a plasmid, wherein the cell expresses the Cas1 protein and/or the Cas 2 protein, and wherein the Cas1 protein and/or the Cas2 protein processes and inserts each member of the set of corresponding oligonucleotide protospacer sequences into the CRISPR array nucleic acid sequence adjacent a corresponding repeat sequence. According to one aspect, each member of the set of corresponding oligonucleotide protospacer sequences are introduced in series into an engineered, non-naturally occurring cell and wherein the Cas1 protein and/or the Cas2 protein processes and inserts each member of the set of corresponding oligonucleotide protospacer sequences separately and in series into the CRISPR array nucleic acid sequence adjacent a corresponding repeat sequence resulting in a. CRISPR array nucleic acid sequence representing the order in which protospacer sequences were introduced into the cell. According to one aspect, the plurality of bit sequences are converted to a set of corresponding oligonucleotide protospacer sequences wherein one or more bits represent a nucleotide. According to one aspect, the plurality of bit sequences are converted to a set of corresponding oligonucleotide protospacer sequences using one bit per base encoding or two bit per base encoding. According to one aspect, the protospacer sequence includes one or more or all of a data block sequence, a barcode sequence or flanking common sequences at each end of the protospacer sequence for amplification and sequencing. According to one aspect, the format of information is text, an image, a plurality of images, a video format or an audio format. According to one aspect, the format of information represented within the CRISPR array is retrieved by converting the spacer sequences to the format of information, and optionally, visualizing the format of information. According to one aspect, the format of information represented within the CRISPR array is retrieved by determining the sequence of spacer sequences within the CRISPR array, determining the ordering of the spacer sequences within the CRISPR array, converting the spacer sequences to the format of information, and optionally, visualizing the format of information. According to one aspect, the format of information represented within the CRISPR array is retrieved by determining the sequence of spacer sequences within the CRISPR array, determining the ordering of the spacer sequences within the CRISPR array, converting the spacer sequences to bit sequences, ordering the bit sequences based on the ordering of the spacer sequences, and converting the ordered bit sequences to the format of information, and optionally, visualizing the format of information. According to one aspect, the protospacer sequences including a first strand and a second strand complementary and hybridized thereto and further including a linker connecting the first strand and the second into a hairpin structure. According to one aspect, the protospacer sequences lack mononucleotide repeats. According to one aspect, the protospacer sequences lack an internal PAM sequence. According to one aspect, the protospacer sequences include controlled GC content.

The disclosure provides a method of recording an image into a cell including converting an image into a two dimensional array of rows and columns of pixels, wherein each pixel corresponds to a color of the image, wherein each color is represented by one or more nucleotides, and wherein each nucleotide is represented by one or more binary digits, identifying portions of the array of pixels as unique pixel sets and providing each pixel set with a unique pixel set identifier, converting each unique pixel set to a protospacer sequence to generate a set of protospacer sequences representative of the image, synthesizing the set of protospacer sequences, introducing the set of protospacer sequences into an engineered, non-naturally occurring cell including a nucleic acid sequence encoding a Cas1 protein and/or a Cas2 protein of a CRISPR adaptation system and a CRISPR array nucleic acid sequence including a leader sequence and at least one repeat sequence, wherein the CRISPR array nucleic acid sequence is inserted within genomic DNA of the cell or on a plasmid, wherein the cell expresses the Cas1 protein and/or the Cas 2 protein, and wherein the Cas1 protein and/or the Cas2 protein processes and inserts each member of the set of corresponding oligonucleotide protospacer sequences into the CRISPR array nucleic acid sequence adjacent a corresponding repeat sequence. According to one aspect, the protospacer sequence includes one or more or all of a data block sequence, a barcode sequence or flanking common sequences at each end of the protospacer sequence for amplification and sequencing. According to one aspect, the format of information represented within the CRISPR array is retrieved by converting the spacer sequences to the format of information. According to one aspect, the protospacer sequences including a first strand and a second strand complementary and hybridized thereto and further including a linker connecting the first strand and the second into a hairpin structure. According to one aspect, the protospacer sequences lack mononucleotide repeats. According to one aspect, the protospacer sequences lack an internal PAM sequence. According to one aspect, the protospacer sequences include controlled GC content.

The disclosure provides a method of recording multiple images into a cell in a series relationship including creating a set of protospacer sequences for each image wherein each set of protospacers sequences are separately and in series introduced into an engineered, non-naturally occurring cell including a nucleic acid sequence encoding a Cas1 protein and/or a Cas2 protein of a CRISPR adaptation system and a CRISPR array nucleic acid sequence including a leader sequence and at least one repeat sequence, wherein the CRISPR array nucleic acid sequence is inserted within genomic DNA of the cell or on a plasmid, wherein the cell expresses the Cas1 protein and/or the Cas 2 protein, and wherein the Cas1 protein and/or the Cas2 protein processes and inserts each member of the set of protospacer sequences into the CRISPR array nucleic acid sequence adjacent a corresponding repeat sequence, resulting in a CRISPR array nucleic acid sequence representing the order in which each set of protospacer sequences were introduced into the cell. According to one aspect, the protospacer sequence includes one or more or all of a data block sequence, a barcode sequence or flanking common sequences at each end of the protospacer sequence for amplification and sequencing. According to one aspect, the format of information represented within the CRISPR array is retrieved by determining the sequence of spacer sequences within the CRISPR array, determining the ordering of the spacer sequences within the CRISPR array, converting the spacer sequences to each of the multiple images. According to one aspect, the protospacer sequences including a first strand and a second strand complementary and hybridized thereto and further including a linker connecting the first strand and the second into a hairpin structure. According to one aspect, the protospacer sequences lack mononucleotide repeats. According to one aspect, the protospacer sequences lack an internal PAM sequence. According to one aspect, the protospacer sequences include controlled GC content.

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

What is claimed is:

1. A method of recording information into a bacterial cell comprising
    converting a format of information into a plurality of bit sequences with the plurality of bit sequences comprising in series a bit stream representative of the format of information,
    converting the plurality of bit sequences to a set of corresponding oligonucleotide protospacer sequences, wherein each of the protospacer sequences of the set includes one or more or all of a data block sequence, a barcode sequence or flanking common sequences at each end of the protospacer sequence for amplification and sequencing,
    synthesizing the set of corresponding oligonucleotide protospacer sequences,
    introducing the set of corresponding oligonucleotide protospacer sequences into a bacterial cell including a nucleic acid sequence encoding a Cas1 protein and/or a Cas2 protein of a CRISPR adaptation system and a CRISPR array nucleic acid sequence including a leader sequence and at least one repeat sequence, wherein the CRISPR array nucleic acid sequence is inserted within genomic DNA of the cell or on a plasmid,
    wherein the cell expresses the Cas1 protein and/or the Cas 2 protein, and
    wherein the Cas1 protein and/or the Cas2 protein processes and inserts each member of the set of corresponding oligonucleotide protospacer sequences into the CRISPR array nucleic acid sequence adjacent a corresponding repeat sequence.

2. The method of claim 1 wherein each member of the set of corresponding oligonucleotide protospacer sequences are introduced in series into a bacterial cell and wherein the Cas1 protein and/or the Cas2 protein processes and inserts each member of the set of corresponding oligonucleotide protospacer sequences separately and in series into the CRISPR array nucleic acid sequence adjacent a corresponding repeat sequence resulting in a CRISPR array nucleic acid sequence representing the order in which protospacer sequences were introduced into the cell.

3. The method of claim 2 wherein the format of information represented within the CRISPR array is retrieved by
    determining the sequence of spacer sequences within the CRISPR array,
    determining the ordering of the spacer sequences within the CRISPR array,
    converting the spacer sequences to the format of information, and
    optionally, visualizing the format of information.

4. The method of claim 2 wherein the format of information represented within the CRISPR array is retrieved by
    determining the sequence of spacer sequences within the CRISPR array,
    determining the ordering of the spacer sequences within the CRISPR array,
    converting the spacer sequences to bit sequences,
    ordering the bit sequences based on the ordering of the spacer sequences, and
    converting the ordered bit sequences to the format of information, and
    optionally, visualizing the format of information.

5. The method of claim 1 wherein the plurality of bit sequences are converted to a set of corresponding oligonucleotide protospacer sequences wherein one or more bits represent a nucleotide.

6. The method of claim 1 wherein the plurality of bit sequences are converted to a set of corresponding oligonucleotide protospacer sequences using one bit per base encoding or two bit per base encoding.

7. The method of claim 1 wherein the format of information is text, an image, a plurality of images, a video format or an audio format.

8. The method of claim 1 wherein the format of information represented within the CRISPR array is retrieved by
    converting the spacer sequences to the format of information, and
    optionally, visualizing the format of information.

9. The method of claim 1 wherein the protospacer sequences including a first strand and a second strand complementary and hybridized thereto and further including a linker connecting the first strand and the second into a hairpin structure.

10. The method of claim 1 wherein the protospacer sequences lack mononucleotide repeats.

11. The method of claim 1 wherein the protospacer sequences lack an internal PAM sequence.

12. The method of claim 1 wherein the protospacer sequences include controlled GC content.

13. A method of recording an image into a bacterial cell comprising
    converting an image into a two dimensional array of rows and columns of pixels, wherein each pixel corresponds to a color of the image, wherein each color is represented by one or more nucleotides, and wherein each nucleotide is represented by one or more binary digits,
    identifying portions of the array of pixels as unique pixel sets and providing each pixel set with a unique pixel set identifier,
    converting each unique pixel set to a protospacer sequence to generate a set of protospacer sequences representative of the image, wherein the protospacer sequence includes one or more or all of a data block sequence, a barcode sequence or flanking common sequences at each end of the protospacer sequence for amplification and sequencing,
    synthesizing the set of protospacer sequences,
    introducing the set of protospacer sequences into a bacterial cell including a nucleic acid sequence encoding a Cas1 protein and/or a Cas2 protein of a CRISPR adaptation system and a CRISPR array nucleic acid sequence including a leader sequence and at least one repeat sequence, wherein the CRISPR array nucleic acid sequence is inserted within genomic DNA of the cell or on a plasmid, wherein the cell expresses the Cas1 protein and/or the Cas 2 protein, and wherein the Cas1 protein and/or the Cas2 protein processes and inserts each member of the set of corresponding oligonucleotide protospacer sequences into the CRISPR array nucleic acid sequence adjacent a corresponding repeat sequence.

14. The method of claim 13 wherein the format of information represented within the CRISPR array is retrieved by converting the spacer sequences to the format of information.

15. The method of claim 13 wherein the protospacer sequences including a first strand and a second strand complementary and hybridized thereto and further including a linker connecting the first strand and the second into a hairpin structure.

16. The method of claim 13 wherein the protospacer sequences lack mononucleotide repeats.

17. The method of claim 13 wherein the protospacer sequences lack an internal PAM sequence.

18. The method of claim 13 wherein the protospacer sequences include controlled GC content.

19. A method of recording multiple images into a bacterial cell in a series relationship comprising creating a set of protospacer sequences for each image wherein each set of protospacers sequences are separately and in series introduced into a bacterial cell including a nucleic acid sequence encoding a Cas1 protein and/or a Cas2 protein of a CRISPR adaptation system and a CRISPR array nucleic acid sequence including a leader sequence and at least one repeat sequence, wherein each of the protospacer sequence includes one or more or all of a data block sequence, a barcode sequence or flanking common sequences at each end of the protospacer sequence for amplification and sequencing, wherein the CRISPR array nucleic acid sequence is inserted within genomic DNA of the cell or on a plasmid, wherein the cell expresses the Cas1 protein and/or the Cas 2 protein, and wherein the Cas1 protein and/or the Cas2 protein processes and inserts each member of the set of protospacer sequences into the CRISPR array nucleic acid sequence adjacent a corresponding repeat sequence, resulting in a CRISPR array nucleic acid sequence representing the order in which each set of protospacer sequences were introduced into the cell.

20. The method of claim 19 wherein the format of information represented within the CRISPR array is retrieved by determining the sequence of spacer sequences within the CRISPR array, determining the ordering of the spacer sequences within the CRISPR array, converting the spacer sequences to each of the multiple images.

21. The method of claim 19 wherein the protospacer sequences including a first strand and a second strand complementary and hybridized thereto and further including a linker connecting the first strand and the second into a hairpin structure.

22. The method of claim 19 wherein the protospacer sequences lack mononucleotide repeats.

23. The method of claim 19 wherein the proto spacer sequences lack an internal PAM sequence.

24. The method of claim 19 wherein the protospacer sequences include controlled GC content.

* * * * *